US008318731B2

(12) United States Patent
Diels et al.

(10) Patent No.: US 8,318,731 B2
(45) Date of Patent: Nov. 27, 2012

(54) PYRROLOPYRIMIDINES

(75) Inventors: Gaston Stanislas Marcella Diels, Ravels (BE); Peter Ten Holte, Beerse (BE); Eddy Jean Edgard Freyne, Rumst (BE); Thierry Andre Regis Grand-Perret, Brussels (BE); Kristof Van Emelen, Sint-Niklaas (BE); Werner Constant Johan Embrechts, Oud-Turnhout (BE); Pascal Ghislain André Bonnet, Berchem (BE)

(73) Assignee: Janssen Pharmaceutica NV, Beerse (BE)

( * ) Notice: Subject to any disclaimer, the term of this patent is extended or adjusted under 35 U.S.C. 154(b) by 227 days.

(21) Appl. No.: 12/670,670

(22) PCT Filed: Jul. 25, 2008

(86) PCT No.: PCT/EP2008/059833
§ 371 (c)(1),
(2), (4) Date: Jan. 26, 2010

(87) PCT Pub. No.: WO2009/016132
PCT Pub. Date: Feb. 5, 2009

(65) Prior Publication Data
US 2010/0204197 A1 Aug. 12, 2010

(30) Foreign Application Priority Data

Jul. 27, 2007 (EP) .................................. 07113297

(51) Int. Cl.
*C07D 487/08* (2006.01)
*C07D 498/08* (2006.01)
*A61K 31/529* (2006.01)
*A61P 35/02* (2006.01)
(52) U.S. Cl. ............... 514/232.8; 514/249; 514/255.05; 514/257; 540/458
(58) Field of Classification Search .................. 540/458; 514/232.8, 249, 255.05, 257
See application file for complete search history.

(56) References Cited

U.S. PATENT DOCUMENTS

| | | | |
|---|---|---|---|
| 4,067,726 A | 1/1978 | Sasse et al. | |
| 4,160,836 A | 7/1979 | Vandenberk et al. | |
| 4,442,278 A | 4/1984 | Giants | |
| 5,679,683 A | 10/1997 | Bridges et al. | |
| 5,721,237 A | 2/1998 | Myers et al. | |
| 5,770,599 A | 6/1998 | Gibson | |
| 5,821,240 A | 10/1998 | Himmelsbach et al. | |
| 6,002,008 A | 12/1999 | Wissner et al. | |
| 6,265,410 B1 | 7/2001 | Bridges et al. | |
| 6,288,082 B1 | 9/2001 | Wissner et al. | |
| 6,344,459 B1 | 2/2002 | Bridges et al. | |
| 6,414,148 B1 | 7/2002 | Thomas et al. | |
| 6,521,620 B1 | 2/2003 | Bridges et al. | |
| 6,602,863 B1 | 8/2003 | Bridges et al. | |
| 6,794,395 B1 | 9/2004 | Roth et al. | |
| 7,067,507 B2 | 6/2006 | Pulley et al. | |
| 7,312,225 B2 | 12/2007 | Luecking et al. | |
| 7,648,975 B2 | 1/2010 | Freyne et al. | |
| 7,655,642 B2 | 2/2010 | Freyne et al. | |
| 7,799,772 B2 | 9/2010 | Freyne et al. | |
| RE42,353 E | 5/2011 | Thomas et al. | |
| 2002/0173646 A1 | 11/2002 | Thomas et al. | |
| 2003/0087908 A1 | 5/2003 | Geuns-Meyer et al. | |
| 2003/0186987 A1 | 10/2003 | Bridges et al. | |
| 2004/0048880 A1 | 3/2004 | Himmelsbach et al. | |
| 2004/0116388 A1 | 6/2004 | Armistead et al. | |
| 2007/0078132 A1 | 4/2007 | Freyne et al. | |
| 2008/0219975 A1 | 9/2008 | Perera et al. | |
| 2009/0075999 A1 | 3/2009 | Blanchard et al. | |
| 2010/0029627 A1 | 2/2010 | Papanikos et al. | |
| 2010/0069424 A1 | 3/2010 | Freyne et al. | |
| 2010/0105668 A1 | 4/2010 | Freyne et al. | |
| 2010/0152174 A1 | 6/2010 | Freyne et al. | |
| 2010/0160310 A1 | 6/2010 | Freyne et al. | |
| 2010/0173913 A1 | 7/2010 | Freyne | |
| 2010/0190786 A1 | 7/2010 | Diels et al. | |
| 2010/0204197 A1 | 8/2010 | Diels et al. | |
| 2010/0222574 A1 | 9/2010 | Rombouts et al. | |
| 2011/0009404 A1 | 1/2011 | Buijnsters et al. | |

FOREIGN PATENT DOCUMENTS

| | | |
|---|---|---|
| GB | 807899 A | 1/1959 |
| GB | 1465451 A | 2/1977 |
| GB | 1542514 A | 3/1979 |
| WO | WO-95/19774 A1 | 7/1995 |
| WO | WO-96/07657 A1 | 3/1996 |
| WO | WO-96/09294 A1 | 3/1996 |
| WO | WO-96/33980 A1 | 10/1996 |
| WO | WO-96/39145 A1 | 12/1996 |
| WO | WO-97/32880 A1 | 9/1997 |
| WO | WO-97/38983 A1 | 10/1997 |
| WO | WO-98/13354 A1 | 4/1998 |
| WO | WO-98/43960 A1 | 10/1998 |
| WO | WO-99/33792 A2 | 7/1999 |
| WO | WO-99/33793 A2 | 7/1999 |

(Continued)

OTHER PUBLICATIONS

Barr, F., et al. "Polo-Like Kinases and the Orchestration of Cell Division", Molecular Cell Biology, Nature Reviews, vol. 5 (2004) pp. 429-440. Bettencourt-Dias, M., et al. "SAK/PLK4 is Required for Centriole Duplication and Flagella Development", Current Biology, vol. 15, (2005) pp. 2199-2207.
Burns, T., et al. "Silencing of the Novel p53 Target Gene *Sank/Plk2* Leads to Mitotic Catastrophe in Paclitaxel (Taxol)-Exposed Cells", Molecular and Cellular Biology, vol. 23, No. 6 (2003) pp. 5556-5571.
Cook, N., et al. "Scintillation Proximity Enzyme Assay. A Rapid and Novel Assay Technique Applied to HIV Proteinase", Structure and Function of the Aspartic Proteinases (1991) pp. 525-528.
Calderwood, D., et al. "Pyrrolo[2,3-d] pyrimidines Containing Diverse N-7 Substituents as Potent Inhibitors of Lck", Bioorganic & Medicinal Chemistry Letters (2002) pp. 1683-1686.

(Continued)

*Primary Examiner* — Bruck Kifle

(57) ABSTRACT

The present invention relates to compounds or pharmaceutically-acceptable salts thereof, processes for preparing them, pharmaceutical compositions containing them and their use in therapy. The invention particularly relates to compounds that are polo-like kinase (PLKs) inhibitors useful for the treatment of disease states mediated by PLK, especially PLK4, in particular such compounds that are useful in the treatment of pathological processes which involve an aberrant cellular proliferation, such as tumor growth, rheumatoid arthritis, restenosis and atherosclerosis.

10 Claims, No Drawings

FOREIGN PATENT DOCUMENTS

| | | |
|---|---|---|
| WO | WO-99/33795 A1 | 7/1999 |
| WO | WO-99/33815 A1 | 7/1999 |
| WO | WO-00/18761 A1 | 4/2000 |
| WO | WO-00/55159 A2 | 9/2000 |
| WO | WO-01/16130 A1 | 3/2001 |
| WO | WO-02/20479 A1 | 3/2002 |
| WO | WO-02/083654 A1 | 10/2002 |
| WO | WO 03/072062 A2 | 9/2003 |
| WO | WO-03/072062 A2 | 9/2003 |
| WO | WO-03/082290 A1 | 10/2003 |
| WO | WO-2004/009562 A1 | 1/2004 |
| WO | WO-2004/014899 A1 | 2/2004 |
| WO | WO 2004/014899 A1 | 2/2004 |
| WO | WO-2004/026829 A2 | 4/2004 |
| WO | WO-2004/026881 A1 | 4/2004 |
| WO | WO-2004/037814 A1 | 5/2004 |
| WO | WO-2004/043936 A1 | 5/2004 |
| WO | WO 2004/043936 A1 | 6/2004 |
| WO | WO-2004/074224 A1 | 9/2004 |
| WO | WO 2004/074224 A1 | 9/2004 |
| WO | WO-2004/078682 A2 | 9/2004 |
| WO | WO-2004/105765 A1 | 12/2004 |
| WO | WO 2004/105765 A1 | 12/2004 |
| WO | WO 2005/058318 A1 | 6/2005 |
| WO | WO-2005/058318 A1 | 6/2005 |
| WO | WO-2005/058913 A1 | 6/2005 |
| WO | WO 2005/058913 A1 | 6/2005 |
| WO | WO 2006/061415 A1 | 6/2006 |
| WO | WO-2006/061415 A1 | 6/2006 |
| WO | WO-2006/061417 A2 | 6/2006 |
| WO | WO 2006/061417 A2 | 6/2006 |
| WO | WO-2007/003525 A2 | 1/2007 |
| WO | WO 2007/003525 A2 | 1/2007 |
| WO | WO-2007/058267 A1 | 5/2007 |
| WO | WO-2007/058627 A1 | 5/2007 |
| WO | WO-2007/058628 A1 | 5/2007 |
| WO | WO-2008/006884 A2 | 1/2008 |
| WO | WO-2008/049902 A2 | 5/2008 |
| WO | WO-2008/155421 A2 | 12/2008 |
| WO | WO-2009/016132 A1 | 2/2009 |
| WO | WO-2009/112439 A1 | 9/2009 |

OTHER PUBLICATIONS

Carvajal, R., et al. "Aurora Kinases: New Targets for Cancer Therapy", Clinical Cancer Research, vol. 12, No. 23 (2006) pp. 6869-6875.

Fode, C., et al. "Sak, a Murine Protein-Serine/Threonine Kinase that is Related to the *Drosophila* Polo Kinase and Involved in Cell Proliferation", Proc. Natl. Acad., Sci, vol. 9, (1994) pp. 6388-6392.

Karn, T., et al. "Human SAK Related to the PLK/polo Family of Cell Cycle Kinases Shows High mRNA Expression in testis", Oncology Reports, vol. 5 (1997) pp. 505-510.

Li, J., et al. SAK, A New Polo-Like Kinase, is Transcriptionally Repressed by p53 and Induces Apoptosis upon RNAi Silencing, Neoplasia, vol. 7, No. 4 (2005) pp. 312-323.

Nagamatsu, T., et al. "General Syntheses of 1-Alkyltoxoflavin and 8-Alkylfervenulin Derivatives of Biological Significance by the Regioselective Alkylation of Reumycin Derivatives and the Rates of Transalkylation from 1-Alkyltoxoflavins into Nucleophiles", J. Chemic. So., Perkin Trans., vol. 1 (2001) pp. 130-137.

Nagamatsu, T., et al. "Syntheses of 3-Subsitutred 1-Methyl-6-phenylprimido[5,4-e]-1,2,4-triazine-5,7(1H,6H)-dines (6-Phenyl Analogs of Toxoflavin) and their 4-Oxides, and Evaluation of Antimicrobial Activity of Toxoflavins and Their Analogs", Chem. Pharm. Bull. vol. 41, No. 2 (1993) pp. 362-368.

Pleixats, R., et al. "The Search for New Biochemical Photoprobes. The Nucleophilic Photosubstitution of 2-Fluoro-4-Nitronisole", Tetrahedron, vol. 45, No. 24, pp. 7817-7826, (1989).

Spankuch-Schmitt, B., et al. "Downregulaton of Human Polo-Like Kinase Activity by Antisense Oligonucleotides Induces Growth Inhibitor in Cancer Cells", Oncogene (2002) pp. 3162-3171.

Wang, Q., et al., "Cell Cycle Arrest and Apoptosis Induced by Human Polo-Like Kinase 3 Is Mediated through Perturbation of Microtubule Integrity", Molecular and Cellular Biology, (2002) pp. 3450-3459.

Yuan, J., et al. "Efficient Internalization of the Polo-Box of Polo-Like Kinase 1 Fused to an Antennapedia Peptide Results in Inhibition of Cancer Cell Proliferation", Cancer Research, vol. 62 (2002) pp. 4186-4190.

Pyrimidotriazines, "Heterocyclic Compounds", vol. 24, Part IV, pp. 261-304, (1986).

International Search Report mailed Oct. 23, 2008 for corresponding Application No. PCT/EP2008/059833.

In the U.S. Patent and Trademark Office U.S. Appl. No. 10/558,007 Non-Final Office Action dated Apr. 28, 2008, 5 pages.

In the U.S. Patent and Trademark Office U.S. Appl. No. 10/558,007 Non-Final Office Action dated Nov. 25, 2008, 5 pages.

In the U.S. Patent and Trademark Office U.S. Appl. No. 10/596,509 Non-Final Office Action dated Nov. 26, 2008, 6 pages.

In the U.S. Patent and Trademark Office U.S. Appl. No. 11/720,681 Non-Final Office Action dated Mar. 3, 2011, 6 pages.

In the U.S. Patent and Trademark Office U.S. Appl. No. 11/720,681 Non-Final Office Action dated Sep. 14, 2010, 7 pages.

In the U.S. Patent and Trademark Office U.S. Appl. No. 11/875,288 Final Office Action dated Sep. 24, 2009, 8 pages.

In the U.S. Patent and Trademark Office U.S. Appl. No. 11/875,288 Non-Final Office Action dated Apr. 15, 2009, 8 pages.

In the U.S. Patent and Trademark Office U.S. Appl. No. 11/993,237 Final Office Action dated Jul. 21, 2011, 5 pages.

In the U.S. Patent and Trademark Office U.S. Appl. No. 11/993,237 Non-Final Office Action dated Dec. 10, 2010, 7 pages.

In the U.S. Patent and Trademark Office U.S. Appl. No. 12/373,404 Final Office Action dated Jun. 28, 2011, 47 pages.

In the U.S. Patent and Trademark Office U.S. Appl. No. 12/373,404 Non-Final Office Action dated Oct. 27, 2010, 12 pages.

In the U.S. Patent and Trademark Office U.S. Appl. No. 12/624,637 Non-Final Office Action dated Feb. 2, 2012, 5 pages.

In the U.S. Patent and Trademark Office U.S. Appl. No. 12/670,670 Final Office Action dated Mar. 9, 2012, 5 pages.

In the U.S. Patent and Trademark Office U.S. Appl. No. 12/670,670 Non-Final Office Action dated Nov. 9, 201, 10 pages.

In the U.S. Patent and Trademark Office U.S. Appl. No. 11/720,693 Non-Final Office Action dated Jul. 21, 2010, 5 pages.

In the U.S. Patent and Trademark Office U.S. Appl. No. 11/720,693 Final Office Action dated Nov. 4, 2011, 6 pages.

Arora et al., "Role of Tyrosine Kinase Inhibitors in Cancer Therapy," *Perspectives in Pharmacology*, 2005; 315: 971-979.

Bagrov et al., "N-[Hydroxy(amino)alkyl]amides of Amino(nitro)benzoic Acids", *Russian Journal of Organic Chemistry*, 2000; 36: 674-678.

Barr et al. "Polo-Like Kinases and The Orchestration of Cell Division", *Molecular Cell Biology, Nature Reviews*, 2004; 5: 429-440.

Bettencourt-Dias, et al. "SAK/PLK4 is Required for Centriole Duplication and Flagella Development", *Current Biology*, 2005; 15:2199-2207.

Burke, "Protein-Tyrosine Kinase Inhibitors", *Drugs of the Future*, 1992; 17: 119-131.

Burns, et al. "Silencing of the Novel p53 Target Gene Sank/P1k2 Leads to Mitotic Catastrophe in Paclitaxel (Taxol)-Exposed Cells", *Molecular and Cellular Biology*, 2003; 23: 5556-5571.

Carvajal et al., "Aurora Kinases: New Targets for Cancer Therapy", *Clinical Cancer Research*, 2006; vol. 12, No. 23: (6869-6875).

Castedo et al., "Cell death by mitotic catastrophe: a molecular definition." *Oncogene*, 2004; 23: 2825-2837.

Coghlan et al., "Selective small molecule inhibitors of glycogen synthase kinase-3 modulate glycogen metabolism and gene transcription", *Chemistry & Biology*, 2000; 7: 793-803.

Collins et al., "The Chemotherapy of Schistosomiasis. Part IV. Some Ethers of 4-Amino-2-methoxyphenol", *Journal of the Chemical Society*, 1961: 1863-1879.

Cross et al., "Selective small-molecule inhibitors of glycogen synthase kinase-3 activity protect primary neurons from death", *Journal of Neurochemistry*, 2001; 77: 94-102.

Dai et al., "Tyrosine Kinase Etk/BMX is Up-Regulated in Human Prostate Cancer and Its Overexpression Induces Prostate Intraepithelial Neoplasia in Mouse", *Cancer Research*, 2006; 66: 8058-8064.

Delia et al., "Fused Pyrimidines Part Four: Miscellaneous Fused Pyrimidines", *The Chemistry of Heterocyclic Compounds, A Series of Monographs*, 1992: 261-305.

Elder et al., "Overexpression of Transforming Growth Factor α in Psoriatic Epidermis", *Science*, 1989; 243: 811-814.

Embi et al., "Glycogen Synthase Kinase-3 from Rabbit Skeletal Muscle Separation from Cyclic-AMP-Dependent Protein Kinase and Phosporylase Kinase", *Eur. J. Biochem.*, 1980; 107: 519-527.

Fode et al. "Sak, a Murine Protein-Serine/Threonine Kinase that is Related to the *Drosophila* Polo Kinase and Involved in Cell Proliferation", *Proc. Natl. Acad. Sci.*, 1994; 9: 6388-6392.

Furuta et al, "Molecular Design of Glutathione-Derived Biochemical Probes Targeting the GS-X Pump", *Tetrahedron*, 1999; 55: 7529-7540.

He et al., "Suppression of Tumor Lymphangiogenesis and Lymph Node Metastasis by Blocking Vascular Endothelial Growth Factor Receptor 3 Signaling", *Journal of the National Cancer Institute*, 2002; 94:819-825.

Hennequin et al., "Novel-4 Anilinoquinazolines with C-7 Basic Side Chains: Design and Structure Activity Relationship of a Series of Potent, Orally Active, VEGF Receptor Tyrosine Kinase Inhibitors", *Journal of Medicinal Chemistry*, 2002; 45: 1300-1312.

International Search Report from PCT/EP2004/005621, dated Oct. 27, 2004.

International Search Report from PCT/EP2004/053497, dated Apr. 12, 2005.

International Search Report from PCT/EP2004/053501, dated Apr. 28, 2005.

International Search Report from PCT/EP2005/056606, dated Apr. 3, 2006.

International Search Report from PCT/EP2005/056609, dated May 26, 2005.

International Search Report from PCT/EP2007/061499, dated Jul. 30, 2008.

International Search Report from PCT/EP2008/059833, dated Oct. 23, 2008.

International Search Report from PCT/EP2009/052692, dated Jun. 9, 2009.

International Search Report from PCT/EP2006/063555, dated Feb. 21, 2008.

Kaipainen et al. "Expression of the fms-Like Tyrosine Kinase 4 Gene Becomes Restricted to Lymphatic Endothelium During Development", *Pro. Natl. Acad. Sci.*, 1995; 92: 3566-70.

Karkkainen et al. "Lymphatic Endothelial Regulation, Lymphoedema, and Lymph Node Metastasis", *Cell & Developmental Biology*, 2002; 13: 9-18.

Kawato et al., "Novel Pepitdomimetics of the Antifungal Cyclic Peptide Rhodopeptin: Synthesis of Mimetics and Their Antifungal Activity", *Organic Letters*, 2001; 3: 3451-3454.

Kuo et al., Synthesis and Identification of [1,3,5]Triazine-pyridine Biheteroaryl as a Novel Series of Potent Cyclin-Dependent Kinase Inhibitors, *J. Med. Chem.*, 2005; 48: 4535-4546.

Li, et al., "SAK, A New Polo-Like Kinase, is Transcriptionally Repressed by p53 and Induces Apoptosis upon RNAi Silencing", *Neoplasia*, 2005; 7: 312-323.

Morin, "Oncogene to Drug: Development of Small Molecule Tyrosine Kinase Inhibitors as Anti-Tumor and Anti-Angiogenic Agents", *Oncogene*, 2000; 19: 6574-6583.

Murphy et al., "Intramolecular Termination of Radical-Polar Crossover Reactions", *Journal of the Chemical Society Perkin Transactions 1*, 1998; 15: 2331-2339.

Nagamatsu et al., "General Syntheses of 1-Alkyltoxoflavin and 8-Alkylfervenulin Derivatives of Biological Significance by the Regioselective Alkylation of Reumycin Derivatives and the Rates of Transalkylation From 1-Alkyltoxoflavins Into Nucleophiles", *J. Chem. Soc., Perkin Trans.* 1, 2001: 130-137.

Nagamatsu et al., "Syntheses of 3-Substituted 1-Methyl-6-Phenylprimido[5,4-e]-1,2,4-Triazine-5,7(1H,6H)-Diones (6-Phenyl Analogs of Toxoflavin) and Their 4-Oxides, and Evaluation of Antimicrobial Activity of Toxoflavins and Their Analogs", *Chem. Pharm. Bull*, 1993; 41: 362-368.

Palmer et al., "Tyrosine Kinase Inhitors. II. Soluble Analogues of Pyrrolo- and Pyrazoloquinazolines as Epidermal Growth Factor Receptor Inhibitors: Synthesis, Biological Evaluation, and Modeling of the Mode of Binding", *Journal of Medicinal Chemistry*, 1997; 40: 1519-1529.

Rusnak et al., "The characterization of novel, dual ErbB-2/EGFR, tyrosine kinase inhibitors: potential therapy for cancer", *Cancer Research*, 2001; 61: 7196-7203.

Saito et al., "Fyn: A Novel Molecular Target in Prostate Cancer", *Cancer*, 2010; 116:1629-1637.

Spankuch-Schmitt et al., "Downregulaton of Human Polo-Like Kinase Activity by Antisense Oligonucleotides Induces Growth Inhibitor in Cancer Cells", *Oncogene*, 2002: 3162-3171.

Stacker et al., "The Role of Tumor Lymphangiogenesis in Metastatic Spread", *FASEB J.*, 2002; 16: 922-34.

Table of Contents, *Chemical Reviews*, 1996; vol. 96, No. 8.

Von Pawel, "Gefitinib (Iressa, ZD1839): a novel targeted approach for the treatment of solid tumors," *Bull. Cancer*, 2004; 91(5): E70-E76.

Wang et al., "Cell Cycle Arrest and Apoptosis Induced by Human Polo-Like Kinase 3 Is Mediated through Perturbation of Microtubule Integrity", *Molecular and Cellular Biology*, 2002: 22:3450-3459.

Wedge et al. "ZD6474 Inhibits Vascular Endothelial Growth Factor Signaling, Angiogenesis, and Tumor Growth Following Oral Administration", *Cancer Research*, 2002; vol. 62: (4645).

Yuan et al. "Efficient Internalization of the Polo-Box of Polo-Like Kinase 1 Fused to an Antennapedia Peptide Results in Inhibition of Cancer Cell Proliferation", *Cancer Research*, 2002; 62: 4186-4190.

Zeneca Ltd., "4-Anilinoquinazoline Derivatives", *Expert Opinion on Therapeutic Patents*, 1998; 8: 475-478.

Brown et al., "FlashPlate™ Technology—Principles and Characteristics of Flashplate Scintillation Counting", *High Throughput Screening, The Discovery of Bioactive Substances*, 1997; 317-328.

Calderwood et al., "Pyrrolo[2,3-d]pyrimidines Containing Diverse N-7 Substituents as Potent Inhibitors of Lck", *Bioorganic & Medicinal Chemistry Letters*, 2002; 12: 1683-1686.

Cardiello et al., Epidermal Growth Factor Receptor Tyrosine Kinase Inhibitors in Late Stage Clinical Trials, *Oncologic, Endocrine & Metabolic, Expert Opinion*, 2003; 8(2): 501-514.

Cohen et al., "The renaissance of GSK3", *Nature Reviews: Molecular Cell Biology*, 2001; 2: 769-776.

Cook et al., "Scintillation Proximity Enzyme Assay. A Rapid and Novel Assay Technique Applied to HIV Proteinase", *Structure and Function of the Aspartic Proteinases*, 1991: 525-528.

Dumont et al. "Cardiovascular Failure in Mouse Embryos Deficient in VEGF Receptor-3", *Science*, 1998; 282:946-949.

Grimminger et al., "Targeting non-malignant disorders with tyrosine kinase inhibitors", *Nature Review: Drug Discovery*, 2010; 9: 856-870.

Kaidanovich et al. "The role of glycogen synthase kinase-3 in insulin resistance and Type 2 diabetes", *Expert Opinion on Therapeutic Targets*, 2002; 6: 555-561.

Karn et al. "Human SAK Related to the PLK/polo Family of Cell Cycle Kinases Shows High mRNA Expression in testis", *Oncology Reports*, 1997; 5: 505-10 (Abstract Only).

Kypta, "GSK-3 inhibitors and their potential in the treatment of Alzheimer's disease", *Expert Opinion on Therapeutic Patents*, 2005; 15: 1315-1331.

Liotta et al. "Tumor Invasion and Metastases: Biochemical Mechanisms", *Cancer Treatment and Research*, 1988; 40: 223-238.

Makinen et al., "Inhibition of Lymphangiogenesis with Resulting Lymphedema in Transgenic Mice Expressing Soluble VEGF Receptor-3", *Nature Medicine*, 2001; 7: 199-205.

Nicolson et al., "Cancer Metastasis: Tumor Cell and Host Organ Properties Important in Metastasis to Specific Secondary Sites", *Biochimica et Biophysica Acta*, 1988; 948: 175-224.

Norman, "Emerging Fundamental Themes in Modern Medicinal Chemistry", *Drug News Perspect*, 2001; 14: 242-247.

Ny et al., "A Genetic Xenopus Laevis Tadpole Model to Study Lymphangiogenesis", *Nature Medicine*, 2005; 11: 998-1004.

Pleixats et al., "The Search for New Biochemical Photoprobes. The Nucleophilic Photosubstitution of 2-Fluoro-4-Nitronisole", *Tetrahedron*, 1989; 45: 7817-7826.

Prichard et al., "The prevention of breast cancer," *British Journal of Surgery*, 2003; 90: 772-783.

Skobe et al. "Induction of Tumor Lymphangiogenesis by VEGF-C Promotes Breast Cancer Metastasis", *Nature Medicine*, 2001; 7: 192-198.

Underiner et al., "Development of Vascular Endothelial Growth Factor Receptor (VEGFT) Kinase Inhibitors as Anti-Angiogenic Agents in Cancer Therapy", *Current Medicinal Chemistry*, 2004; 11: 731-745.

Wissner et al., "4-Anilino-6,7-dialkoxyquinoline-3-carbonitrile Inhibitors of Epidermal Growth Factor Receptor Kinase and Their Bioisosteric Relationship to the 4-Anilino-6,7-dialkoxyquinazoline Inhibitors", *Journal of Medicinal Chemistry*, 2000; 43: 3244-3256.

Wright et al., "Anilinoquinazoline Inhibitors of Fructose 1,6-Bisphosphate Bind at a Nove Allosteric Site: Synthesis, in vitro Characterizations, and X-ray Crystallography", *J. Med. Chem.*, 2002; 45: 3865-3877.

Yang et al., "Inhibition of Epidermal Growth Factore Receptor Tyrosine Kinase by Chalcone Derivatives," *Biochimica et Biophysica Acta*, 2001; 1550: 144-152.

Zetter et al., "The Cellular Basis of Site-Specific Tumor Metastasis", *N. Engl. J. Med.*, 1990; 322: 605-12.

PYRROLOPYRIMIDINES

CROSS REFERENCE TO RELATED APPLICATIONS

This application is a national stage application of PCT Application No. PCT/EP2008/059833, filed Jul. 25, 2008, which application claims priority from EP Patent Application No. 07113297.1, filed Jul. 27, 2007, all of which are hereby incorporated by reference in their entirety.

The present invention relates to pyrrolopyrimidines or pharmaceutically acceptable salts thereof, processes for preparing them, pharmaceutical compositions containing them and their use in therapy. The invention particularly relates to compounds that are polo-like kinase (PLKs) inhibitors useful for the treatment of disease states mediated by PLK, in particular such compounds that are useful in the treatment of pathological processes which involve an aberrant cellular proliferation, such as tumour growth, rheumatoid arthritis, restenosis and atherosclerosis.

BACKGROUND OF THE INVENTION

The majorities of human cancers show no obvious inheritance pattern, but appear to develop through a multistep process in which genetic changes alter the normal control over cell division. A multitude of factors, including viruses, exposure to ultraviolet radiation and carcinogens, may contribute to a weakening of checkpoint controls in cell division. Also the aging process involves cumulative oxidative damage to gene promoters and a selective reduction in expression of mitotic regulators and centrosome proteins including cyclins A, B, F and PLKs. In combination, an incremental loss of checkpoint controls increases the probability of mitotic errors over multiple cell divisions that in combination with activating mutations in proto-oncogenes and loss of tumour suppressors lead to the progression of benign lesions into malignant tumours.

Polo-like kinases (PLKs) are key enzymes that control mitotic entry of proliferating cells and regulate many aspects of mitosis necessary for successful cytokinesis, including centrosome duplication and maturation; DNA damage checkpoint activation; bipolar spindle formation; Golgi fragmentation and assembly; and chromosome segregation (Barr, F. A. et al., Nat. Rev. Mol. Cell Biol. 2004, 5, 429-441). PLKs are found in organisms as diverse as yeast and human and contain two conserved domains, the N-terminal catalytic kinase domain and a C-terminal region composed of the so-called polo-boxes. In yeasts a single PLK exist, whereas four distinct PLKs have been identified to date in mammals. Whereas PLK1, PLK2 and PLK3 are expressed in all tissues and structurally homologous in that they comprise the N-terminal catalytic kinase domain and two polo-boxes, PLK 4 differs not only in structure, compared to the other PLKs it has only one polo-box, but also in the distribution of PLK4 mRNA in adults that is restricted to certain tissues such as testes and thymus (Karn, T. et al., Oncol. Rep. 1997, 4, 505-510; Fode, C. et al., Proc. Natl. Acad. Sci. USA 1994, 91, 6388-6392). It is still under investigation whether these differences also result in a unique physiological role for PLK4.

Given the established role of PLKs as mitotic regulators, they have been regarded as validated mitotic cancer targets for a number of years. In addition, recent studies demonstrate that changes of intracellular levels of PLKs are involved in the control of cell growth. For example, PLK1 when fused to an antennapedia peptide and efficiently internalized into cells caused an inhibition of cancer cell proliferation (Yuan, J., et al., Cancer Res. 62, 2002, 4186-4190), whereas downregulation of PLK1 by antisense induced the growth inhibition of cancer cells (Spankuch-Schmitt, B., et al., Oncogene 21, 2002, 3162-3171). PLK2 was recently found to be a novel p53 target gene and RNAi silencing of PLK2 leads to mitotic catastrophe in taxol-exposed cells (Burns, T F., et al., Mol Cell Biol. 23, 2003, 5556-5571). For PLK3 it was found that it induces cell cycle arrest and apoptosis through perturbation of microtubule integrity (Wang, Q., et al., Mol Cell Biol. 22, 2002, 3450-3459) and PLK4 was shown to be transcriptionally repressed by p53 and induces apoptosis upon RNAi silencing (Li, J., et al., Neoplasia 7, 2005, 312-323). PLK4 was also found to be required for centriole duplication and flagella development. The absence of centrioles, and hence basal bodies, compromises the meiotic divisions and the formation of sperm axonemes (Bettencourt-Dias M., et al., Current Biology 15, 2005, 2199-2207).

All of this confirms that targeting PLKs with conventional small-molecule agents may be a valid and effective anticancer strategy with potential to synergize with established DNA-damage and antimitotic chemotherapies.

Relatively few reports of selective small-molecule PLK inhibitors have appeared to date.

Kyowa Hakko Kogyu has disclosed trisubstituted diaminopyrimidine compounds as PLK1 inhibitors (PCT Int. Pat. Appl. Publ. WO 2004043936). Active compounds contain either a tetrazole group or a nitrile function at the pyrimidine C-5 position. A variety of (hetero)arylalkylamino groups are tolerated at C-2, whereas the C-4 substituent does not appear to be critical for PLK1 inhibitory activity.

A closely related pharmacophore, 5-nitro-N2,N4-diarylpyrimidine-2,4-diamines, was disclosed by GlaxoSmithKline (PCT Int. Pat. Appl. Publ. WO 2004074244). Again a variety of pyrimidine C-2 and C4 arylamine substituents were tolerated and the C-5 nitro group was a determinant of activity.

GlaxoSmithKline has also reported on a different pharmacophore, the 5-benzimidazol-1-yl-3-aryloxy-thiophene-2-carboxylic acid amides (PCT Int. Pat. Appl. Publ. WO 2004014899). Different substituents on the benzimidazole benzene ring were tolerated and a range of aryl ethers are present in the active compounds.

Onconova are developing amino-substituted 1(E)-2,6-dialkoxystyryl 4-substituted benzyl sulfones as cell-cycle agents with CDK inhibitory properties (PCT Int. Pat. Appl. Publ. WO 2003072062). Although reported as ATP-non-competitive kinase inhibitors, the relevant tumour cell target appears to be PLK1.

Certain macrocyclic compounds have been disclosed by the Applicants as inhibitors of tyrosine kinases (PCT Int. Pat. Appl. Publ. WO2004105765, WO2005058318, WO2005058913, WO2006061415 and WO2006061417) and as glycogen synthase kinase inhibitors (PCT Int. Pat. Appl. Publ. WO 2007003525).

It is accordingly an object of the present invention to provide selective small-molecule PLK inhibitors useful in the treatment of cell proliferative disorders.

DESCRIPTION OF THE INVENTION

The present invention concerns macrocyclic pyrrolopyrimidines having PLK inhibitory activity, particularly against PLK4. The invention further relates to methods for their preparation and pharmaceutical compositions comprising them. The invention also relates to the use of the macrocyclic pyrrolopyrimidines for the manufacture of a medicament for the treatment of cell proliferative disorders, including cancer, rheumatoid arthritis, restenosis and atherosclerosis. In the treatment of cancers, said cancers include lung cancer (especially non small-cell lung cancer), breast cancer, liver cancer, ovarian cancer, prostate cancer, pancreatic cancer, colorectal cancer, gastrointestinal cancer such as colon, rectal or stomach cancer and papillary carcinomas (such as papillary thyroid cancer) as well as in squamous cell cancers of the head and neck and in oesophageal cancers including oropharyngeal cancer.

The compounds of the present invention are distinguishable from the above cited prior art because of their structure and their pharmacological activity as PLK inhibitors, in particular their activity against PLK4.

In addition to their activity against PLK4 certain of the compounds according to the invention have been found to have activity against Aurora B kinase. Aurora B is required for chromosome alignment, kinetochore-microtubule biorientation, activation of the spindle assembly checkpoint and cytokinesis. Aurora B is upregulated in various cancers such as colorectal cancer and high-grade gliomas, and Aurora B overexpression in CHO cells results in an increased invasiveness, suggesting a role for Aurora B in tumourigenesis (Carvajal, R. D. et al., Clin. Cancer Res. (2006) 12(23), 6869-6875).

The present invention relates to compounds of formula:

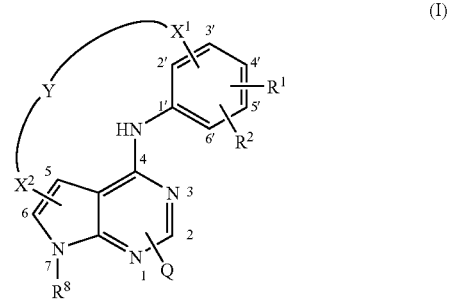

(I)

the N-oxide forms, the pharmaceutically acceptable addition salts, the quaternary amines and the stereochemically isomeric forms thereof, wherein Y represents —$C_{1-6}$alkyl-$NR^3$—CO—$C_{1-6}$alkyl-; —$C_{1-6}$alkyl-CO-$Het^1$-$C_{1-6}$alkyl-; —$C_{1-6}$alkyl-$Het^2$-CO—$NR^4$—$C_{1-6}$alkyl-; or —$C_{1-6}$alkyl-$NR^3$—CO—$C_{1-6}$alkyl-$NR^4$—CO—$C_{1-6}$alkyl-; wherein each —$C_{1-6}$alkyl-in any of —$C_{1-6}$alkyl-$NR^3$—CO—$C_{1-6}$alkyl-; —$C_{1-6}$alkyl-CO-$Het^1$-$C_{1-6}$alkyl-; —$C_{1-6}$alkyl-$Het^2$-CO—$NR^4$—$C_{1-6}$alkyl-; or —$C_{1-6}$alkyl-$NR^3$—CO—$C_{1-6}$alkyl-$NR^4$—CO—$C_{1-6}$alkyl-is optionally and independently substituted with a substituent selected from hydroxy, phenyl or $Het^3$;

$X^1$ represents a direct bond, —O—; —$NR^5$— or —$C_{1-4}$alkyl-$NR^6$— where the —$C_{1-4}$alkyl-moiety is directly attached to the phenyl ring;

$X^2$ represents a direct bond or —$C_{1-4}$alkyl-$NR^7$— where the —$C_{1-4}$alkyl-moiety is directly attached to the pyrrolopyrimidine ring system Q represents hydrogen, halogen, $C_{1-6}$alkyl, $C_{3-6}$cycloalkyl, $Het^5$, —$NR^9R^{10}$, $C_{1-4}$alkyl-O—, $C_{3-6}$cycloalkyl-O—, $Het^6$-O—, $Ar^1$—O, $C_{1-4}$alkyl-$S(O)_{1-2}$—, $C_{3-6}$cycloalkyl-$S(O)_{1-2}$—, $Het^7$-$S(O)_{1-2}$—, $Ar^2$—$S(O)_{1-2}$, $C_{1-4}$alkyl-S— or $C_{3-6}$cycloalkyl-S—;

$R^1$ and $R^2$ each independently represent hydrogen; halo; hydroxy; $C_{1-6}$alkyl; $C_{3-6}$cycloalkyl; $C_{1-4}$alkyl-O—; $C_{3-6}$cycloalkyl-O—; $Het^4$; cyano; $C_{1-6}$alkyl substituted with one or where possible two, three or more substituents selected from halo, hydroxy or $C_{1-4}$alkyl-O—; $C_{1-4}$alkyl-O— substituted with one or where possible two, three or more substituents selected from halo, hydroxy, $C_{1-4}$alkyl-O—, $C_{1-4}$alkyl-O—$C_{1-4}$alkyl-O—, phenyl, $C_{3-6}$cycloalkyl, $C_{3-6}$cycloalkyl-O—, $C_{3-6}$cycloalkyl-NH—CO—, $Het^8$-O—, $Het^9$-CO—, $Ar^3$—O—, $Ar^4$—NH—CO-$Het$-S—, $Ar^6$—S—, $HetAr^1$—S—, thiazolyl-$NR^{11}$—, pyridinyl-$NR^{12}$—, pyrazinyl-NH—, $C_{1-4}$alkyl-O—$C_{1-4}$alkyl-$NR^{13}$—, $Ar^7$—NH—, $HetAr^2$—NH—; $C_{3-6}$cycloalkyl-O— substituted with one or where possible two, three or more substituents selected from halo, hydroxy or $C_{1-4}$alkyl-O—; pyranyl-O—; tetrahydrofuran-O—; $Ar^8$—NH—CO—NH—; $C_{1-6}$alkyl-NH—CO—NH—; $C_{3-6}$cycloalkyl-NH—CO—NH—; $C_{3-6}$cycloalkyl-$C_{1-4}$alkyl-NH—CO—$NR^{14}$—, $C_{1-4}$alkyl-O—$NR^{15}$—, $Ar^5$—NH—;

$R^3$ and $R^4$ each independently represent hydrogen, $C_{1-4}$alkyl, $C_{1-4}$alkyl substituted with $C_{1-4}$alkyl-O—, morpholinyl or piperazinyl; or $C_{3-6}$cycloalkyl;

$R^5$, $R^6$ and $R^7$ each independently represent hydrogen, $C_{1-4}$alkyl, $C_{3-6}$cycloalkyl or $C_{1-4}$alkyl substituted with $C_{1-4}$alkyl-O—, $C_{3-6}$cycloalkyl, phenyl or pyridyl;

$R^8$ represents hydrogen, $C_{1-6}$alkyl or $C_{3-6}$cycloalkyl;

$R^9$, $R^{10}$, $R^{11}$, $R^{12}$ and $R^{13}$ each independently represent hydrogen, $C_{1-6}$alkyl, $C_{3-6}$cycloalkyl;

$R^{14}$ and $R^{15}$ each independently represent hydrogen, $C_{1-4}$alkyl, $C_{3-6}$cycloalkyl or benzyl;

$Ar^1$, $Ar^2$, $Ar^3$, $Ar^4$, $Ar^5$, $Ar^6$, $Ar^7$ and $Ar^8$ each independently represent phenyl optionally substituted with one or where possible two or more substituents selected from halo, cyano, amino, $C_{1-4}$alkyl, $C_{1-4}$alkyl-O—, halo-$C_{1-4}$alkyl, polyhalo-$C_{1-4}$alkyl, $C_{3-6}$cycloalkyl, hydroxy-$C_{1-4}$alkyl, $C_{1-4}$alkyloxy$C_{1-4}$alkyl or polyhydroxy-$C_{1-4}$alkyl;

$Het^1$ and $Het^2$ each independently represent piperidinyl, piperazinyl, pyrrolidinyl or azetidinyl;

$Het^3$, $Het^4$, $Het^5$, $Het^6$, $Het^7$, $Het^8$ and $Het^9$ each independently represent morpholinyl, pyrrolidinyl, piperazinyl or piperidinyl wherein said $Het^3$, $Het^4$, $Het^5$, $Het^6$, $Het^7$, $Het^8$ and $Het^9$ is independently and optionally substituted with one or where possible two or more substituents selected from halo, cyano, amino, $C_{1-4}$alkyl, halo-$C_{1-4}$alkyl, polyhalo-$C_{1-4}$alkyl, $C_{3-6}$cycloalkyl, phenyl, hydroxy-$C_{1-4}$alkyl, $C_{1-4}$alkyloxy$C_{1-4}$alkyl or polyhydroxy-$C_{1-4}$alkyl;

$HetAr^1$ and $HetAr^2$, each independently represent an aryl or heteroaryl ring system selected from the group consisting of phenyl, naphthyl, quinolinyl, benzoxazolyl, pyridyl, pyrazinyl, furanyl, thienyl, pyrimidinyl, isoxazolyl, isothiazolyl, oxazolyl, thiazolyl, pyrrolyl, pyrazolyl, indolyl, pyridazinyl, benzimidazolyl, benzothienyl and benzothiazolyl.

In an alternative embodiment, the invention relates to compounds of formula:

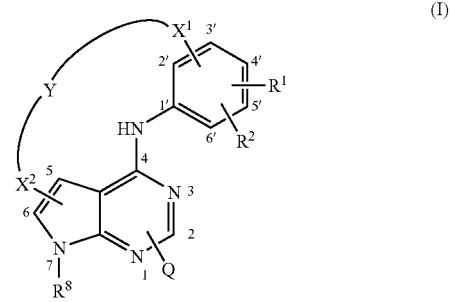

(I)

the N-oxide forms, the pharmaceutically acceptable addition salts, the quaternary amines and the stereochemically isomeric forms thereof, wherein Y represents —$C_{1-6}$alkyl-$NR^3$—CO—$C_{1-6}$alkyl-; —$C_{1-6}$alkyl-CO-$Het^1$-$C_{1-6}$alkyl-; —$C_{1-6}$alkyl-$Het^2$-CO—$NR^4$—$C_{1-6}$alkyl-; or —$C_{1-6}$alkyl-$NR^3$—CO—$C_{1-6}$alkyl-$NR^4$—CO—$C_{1-6}$alkyl-; wherein each —$C_{1-6}$alkyl- in any of —$C_{1-6}$alkyl-$NR^3$—CO—$C_{1-6}$alkyl-; —$C_{1-6}$alkyl-CO-$Het^1$-$C_{1-6}$alkyl-; —$C_{1-6}$alkyl-$Het^2$-CO—$NR^4$—$C_{1-6}$alkyl-; or —$C_{1-6}$alkyl-$NR^3$—CO—$C_{1-6}$alkyl-$NR^4$—CO—$C_{1-6}$alkyl- is optionally and independently substituted with a substituent selected from hydroxy, phenyl or $Het^3$;

$X^1$ represents a direct bond, —O—; —$NR^5$— or —$C_{1-4}$alkyl-$NR^6$— where the —$C_{1-4}$alkyl-moiety is directly attached to the phenyl ring;

$X^2$ represents a direct bond or —$C_{1-4}$alkyl-$NR^7$— where the —$C_{1-4}$alkyl-moiety is directly attached to the pyrrolopyrimidine ring system;

Q represents hydrogen, halogen, $C_{1-6}$alkyl, $C_{3-6}$cycloalkyl, $Het^5$, —$NR^9R^{10}$, $C_{1-4}$alkyl-O—, $C_{3-6}$cycloalkyl-O—, $Het^6$-O—, $Ar^1$—O, $C_{1-4}$alkyl-S(O)$_{1-2}$—, $C_{3-6}$cycloalkyl-S(O)$_{1-2}$—, $Het^7$-S(O)$_{1-2}$—, $Ar^2$—S(O)$_{1-2}$, $C_{1-4}$alkyl-S— or $C_{3-6}$cycloalkyl-S—;

$R^1$ and $R^2$ each independently represent hydrogen; halo; $C_{1-6}$alkyl; $C_{3-6}$cycloalkyl; $C_{1-4}$alkyl-O—; $C_{3-6}$cycloalkyl-O—; $Het^4$; cyano; $C_{1-6}$alkyl substituted with one or where possible two, three or more substituents selected from halo, hydroxy or $C_{1-4}$alkyl-O—; $C_{1-4}$alkyl-O— substituted with one or where possible two, three or more substituents selected from halo, hydroxy, $C_{1-4}$alkyl-O—, phenyl or $C_{3-6}$cycloalkyl; $C_{3-6}$cycloalkyl-O— substituted with one or where possible two, three or more substituents selected from halo, hydroxy or $C_{1-4}$alkyl-O—; —NH—CO—NH—$Ar^1$; —NH—CO—NH—$C_{1-6}$alkyl; or —NH—CO—NH—$C_{3-6}$cycloalkyl;

$R^3$ and $R^4$ each independently represent hydrogen, $C_{1-4}$alkyl, $C_{1-4}$alkyl substituted with $C_{1-4}$alkyl-O—, morpholinyl or piperazinyl; or $C_{3-6}$cycloalkyl;

$R^5$, $R^6$ and $R^7$ each independently represent hydrogen, $C_{1-4}$alkyl, $C_{3-6}$cycloalkyl or $C_{1-4}$alkyl substituted with $C_{1-4}$alkyl-O—, $C_{3-6}$cycloalkyl, phenyl or pyridyl;

$R^8$ represents hydrogen, $C_{1-6}$alkyl or $C_{3-6}$cycloalkyl;

$R^9$ and $R^{10}$ each independently represent hydrogen, $C_{1-6}$alkyl or $C_{3-6}$cycloalkyl;

$Ar^1$ and $Ar^2$ each independently represent phenyl optionally substituted with one or where possible two or more substituents selected from halo, cyano, amino, $C_{1-4}$alkyl, $C_{1-4}$alkyl-O—, halo-$C_{1-4}$alkyl, polyhalo-$C_{1-4}$alkyl, $C_{3-6}$cycloalkyl, hydroxy-$C_{1-4}$alkyl, $C_{1-4}$alkyloxy$C_{1-4}$alkyl or polyhydroxy-$C_{1-4}$alkyl;

$Het^1$ and $Het^2$ each independently represent piperidinyl, piperazinyl, pyrrolidinyl or azetidinyl;

$Het^3$ represents morpholinyl, pyrrolidinyl, piperazinyl or piperidinyl wherein said $Het^3$ is optionally substituted with one or where possible two or more substituents selected from halo, cyano, amino, $C_{1-4}$alkyl, halo-$C_{1-4}$alkyl, polyhalo-$C_{1-4}$alkyl, $C_{3-6}$cycloalkyl, hydroxy-$C_{1-4}$alkyl, $C_{1-4}$alkyloxy$C_{1-4}$alkyl or polyhydroxy-$C_{1-4}$alkyl;

$Het^4$ represents morpholinyl, pyrrolidinyl, piperazinyl or piperidinyl wherein said $Het^4$ is optionally substituted with one or where possible two or more substituents selected from halo, cyano, amino, $C_{1-4}$alkyl, halo-$C_{1-4}$alkyl, polyhalo-$C_{1-4}$alkyl, $C_{3-6}$cycloalkyl, hydroxy-$C_{1-4}$alkyl, $C_{1-4}$alkyloxy$C_{1-4}$alkyl or polyhydroxy-$C_{1-4}$alkyl;

$Het^5$, $Het^6$ and $Het^7$ each independently represents morpholinyl, pyrrolidinyl, piperazinyl or piperidinyl wherein each said $Het^5$, $Het^6$ and $Het^7$ is independently and optionally substituted with one or where possible two or more substituents selected from halo, cyano, amino, $C_{1-4}$alkyl, halo-$C_{1-4}$alkyl, polyhalo-$C_{1-4}$alkyl, $C_{3-6}$cycloalkyl, hydroxy-$C_{1-4}$alkyl, $C_{1-4}$alkyloxy$C_{1-4}$alkyl or polyhydroxy-$C_{1-4}$alkyl.

In an embodiment the present invention provides compounds of formula (I) and the N-oxide forms, the pharmaceutically acceptable addition salts, the quaternary amines and the stereochemically isomeric forms thereof, wherein one or more of the following restrictions apply:

Y represents —$C_{1-6}$alkyl-$NR^3$—CO—$C_{1-6}$alkyl-; —$C_{1-6}$alkyl-CO-$Het^1$-$C_{1-6}$alkyl-; —$C_{1-6}$alkyl-$Het^2$-CO—$NR^4$—$C_{1-6}$alkyl-; or —$C_{1-6}$alkyl-$NR^3$—CO—$C_{1-6}$alkyl-$NR^4$—CO—$C_{1-6}$alkyl-; wherein each —$C_{1-6}$alkyl- in any of —$C_{1-6}$alkyl-$NR^3$—CO—$C_{1-6}$alkyl-; —$C_{1-6}$alkyl-CO-$Het^1$-$C_{1-6}$alkyl-; —$C_{1-6}$alkyl-$Het^2$-CO—$NR^4$—$C_{1-6}$alkyl-; or —$C_{1-6}$alkyl-$NR^3$—CO—$C_{1-6}$alkyl-$NR^4$—CO—$C_{1-6}$alkyl- is optionally and independently substituted with a substituent selected from hydroxy or phenyl;

$X^1$ represents a direct bond, —O—; or —$C_{1-4}$alkyl-$NR^6$— where the —$C_{1-4}$alkyl-moiety is directly attached to the phenyl ring;

$X^2$ represents a direct bond or —$C_{1-4}$alkyl-$NR^7$— where the —$C_{1-4}$alkyl-moiety is directly attached to the pyrrolopyrimidine ring system;

Q represents hydrogen;

$R^1$ and $R^2$ each independently represent hydrogen; halo; $C_{1-4}$alkyl-O—; $Het^4$; $C_{1-6}$alkyl substituted with one or where possible two, three halo; $C_{1-4}$alkyl-O— substituted with one or where possible two, three or more substituents selected from, phenyl or $C_{3-6}$cycloalkyl; —NH—CO—NH—$Ar^1$; or —NH—CO—NH—$C_{3-6}$cycloalkyl;

$R^3$ and $R^4$ each independently represent hydrogen, $C_{1-4}$alkyl; or $C_{3-6}$cycloalkyl;

$R^5$, $R^6$ and $R^7$ each independently represent hydrogen, $C_{1-4}$alkyl or $C_{1-4}$alkyl substituted with $C_{1-4}$alkyl-O—, $C_{3-6}$cycloalkyl, phenyl or pyridyl;

$R^8$ represents hydrogen;

$Ar^1$ represents phenyl optionally substituted with one or where possible two or more substituents selected from halo or $C_{1-4}$alkyl-O—;

$Het^1$ and $Het^2$ each independently represent piperidinyl or pyrrolidinyl;

$Het^4$ represents morpholinyl, wherein said $Het^4$ is optionally substituted with one or where possible two or more substituents selected from halo, cyano, amino, $C_{1-4}$alkyl, halo-$C_{1-4}$alkyl, polyhalo-$C_{1-4}$alkyl, $C_{3-6}$cycloalkyl, hydroxy-$C_{1-4}$alkyl, $C_{1-4}$alkyloxy$C_{1-4}$alkyl or polyhydroxy-$C_{1-4}$alkyl.

In a further embodiment the present invention provides compounds of formula (I) and the N-oxide forms, the pharmaceutically acceptable addition salts, the quaternary amines and the stereochemically isomeric forms thereof, wherein one or more of the following restrictions apply:

Y represents —$C_{1-6}$alkyl-$NR^3$—CO—$C_{1-6}$alkyl; wherein each —$C_{1-6}$alkyl- in —$C_{1-6}$alkyl-$NR^3$—CO—$C_{1-6}$alkyl- is optionally and independently substituted with a substituent selected from hydroxy or phenyl;

$X^1$ represents —O—;

$X^2$ represents —$C_{1-4}$alkyl-$NR^7$— where the —$C_{1-4}$alkyl-moiety is directly attached to the pyrrolopyrimidine ring system;

Q represents hydrogen;

R$^1$ and R$^2$ each independently represent hydrogen or halo; C$_{1-4}$alkyl-O—; C$_{1-6}$alkyl substituted with one or where possible two or three halo; C$_{1-4}$alkyl-O— substituted with phenyl; —NH—CO—NH—Ar$^1$; or —NH—CO—NH—C$_{3-6}$cycloalkyl;

R$^3$ represents hydrogen, C$_{1-4}$alkyl; or C$_{3-6}$cycloalkyl;

R$^7$ represents hydrogen, C$_{1-4}$alkyl or C$_{1-4}$alkyl substituted with C$_{3-6}$cycloalkyl or phenyl;

R$^8$ represents hydrogen;

Ar$^1$ represents phenyl optionally substituted with one or more C$_{1-4}$alkyl-O—.

In a further embodiment the present invention provides compounds of formula (I) and the N-oxide forms, the pharmaceutically acceptable addition salts, the quaternary amines and the stereochemically isomeric forms thereof, wherein one or more of the following restrictions apply:

Y represents —C$_{1-6}$alkyl-NR$^3$—CO—C$_{1-6}$alkyl-; wherein each —C$_{1-6}$alkyl-in —C$_{1-6}$alkyl-NR$^3$—CO—C$_{1-6}$alkyl-is optionally and independently substituted with a substituent selected from hydroxy or phenyl;

X$^1$ represents —O—;

X$^2$ represents —C$_{1-4}$alkyl-NR$^7$— where the —C$_{1-4}$alkyl-moiety is directly attached to the pyrrolopyrimidine ring system;

Q represents hydrogen;

R$^1$ and R$^2$ each independently represent hydrogen; halo; or C$_{1-4}$alkyl-O—;

R$^3$ represents hydrogen, C$_{1-4}$alkyl; or C$_{3-6}$cycloalkyl;

R$^7$ represents hydrogen, C$_{1-4}$alkyl or C$_{1-4}$alkyl substituted with C$_{3-6}$cycloalkyl or phenyl;

R$^8$ represents hydrogen.

In a further embodiment the present invention provides compounds of formula (I) and the N-oxide forms, the pharmaceutically acceptable addition salts, the quaternary amines and the stereochemically isomeric forms thereof, wherein one or more of the following restrictions apply:

Y represents —C$_{1-6}$alkyl-NR$^3$—CO—C$_{1-6}$alkyl-; wherein each —C$_{1-6}$alkyl-in —C$_{1-6}$alkyl-NR$^3$—CO—C$_{1-6}$alkyl-is unsubstituted;

X$^1$ represents —O—;

X$^2$ represents —C$_{1-4}$alkyl-NR$^7$—;

Q represents hydrogen;

R$^1$ and R$^2$ each independently represent hydrogen; halo; or C$_{1-4}$alkyl-O—;

R$^3$ represents C$_{1-4}$alkyl;

R$^7$ represents C$_{1-4}$alkyl;

R$^8$ represents hydrogen.

In the compounds of formula (I) the —X$^2$—Y—X$^1$— linkage is advantageously attached to the 5-position of the pyrrolopyrimidine ring system and to the 3'-position of the phenyl ring.

Specific compounds according to the invention include:
7,11-metheno-11H-12-oxa-2,3,5,6,15,19-hexaazacyclooctadec[1,2,3-cd]inden-14(13H)-one, 2,3,15,16,17,18,19,20-octahydro-10-methoxy-15,19-dimethyl-3H-11,7-metheno-12-oxa-2,3,5,6,15,18-hexaazacycloheptadec[1,2,3-cd]inden-14(13H)-one, 2,15,16,17,18,19-hexahydro-15,18-dimethyl-7,11-metheno-11H-12-oxa-2,3,5,6,15,19-hexaazacyclooctadec[1,2,3-cd]inden-14(13H)-one, 2,3,15,16,17,18,19,20-octahydro-10-methoxy-15-methyl-19-(phenylmethyl)-
N-(2,3,13,14,15,16,17,18,19,20-decahydro-15,19-dimethyl-14-oxo-11,7-metheno-7H-12-oxa-2,3,5,6,15,19-hexaazacyclooctadec[1,2,3-cd]inden-10-yl)-N'-(4-methoxyphenyl)-urea,
10-ethoxy-2,3,15,16,17,18,19,20-octahydro-15,19-dimethyl-7,11-metheno-11H-12-oxa-2,3,5,6,15,19-hexaazacyclooctadec[1,2,3-cd]inden-14(13H)-one,
2,3,15,16,17,18,19,20-octahydro-15,19-dimethyl-10-(phenylmethoxy)-7,11-metheno-11H-12-oxa-2,3,5,6,15,19-hexaazacyclooctadec[1,2,3-cd]inden-14(13H)-one,
2,3,15,16,17,18,19,20-octahydro-10-methoxy-19-methyl-15-(1-methylethyl)-7,11-metheno-11H-12-oxa-2,3,5,6,15,19-hexaazacyclooctadec[1,2,3-cd]inden-14(13H)-one,
2,3,15,16,17,18,19,20-octahydro-10-methoxy-15-methyl-7,11-metheno-11H-12-oxa-2,3,5,6,15,19-hexaazacyclooctadec[1,2,3-cd]inden-14(13H)-one,
N-cyclopentyl-N'-(2,3,13,14,15,16,17,18,19,20-decahydro-15,19-dimethyl-14-oxo-11,7-metheno-7H-12-oxa-2,3,5,6,15,19-hexaazacyclooctadec[1,2,3-cd]inden-10-yl)-urea,
N-(3-chlorophenyl)-N'-(2,3,13,14,15,16,17,18,19,20-decahydro-15,19-dimethyl-14-oxo-11,7-metheno-7H-12-oxa-2,3,5,6,15,19-hexaazacyclooctadec[1,2,3-cd]inden-10-yl)-urea,
10-chloro-2,3,15,16,17,18,19,20-octahydro-15,19-dimethyl-7,11-metheno-11H-12-oxa-2,3,5,6,15,19-hexaazacyclooctadec[1,2,3-cd]inden-14(13H)-one,
N-cyclohexyl-N'-(2,3,13,14,15,16,17,18,19,20-decahydro-15,19-dimethyl-14-oxo-11,7-metheno-7H-12-oxa-2,3,5,6,15,19-hexaazacyclooctadec[1,2,3-cd]inden-10-yl)-urea,
10-(cyclopropylmethoxy)-2,3,15,16,17,18,19,20-octahydro-15,19-dimethyl-7,11-metheno-11H-12-oxa-2,3,5,6,15,19-hexaazacyclooctadec[1,2,3-cd]inden-14(13H)-one,
10-(cyclopentyloxy)-2,3,15,16,17,18,19,20-octahydro-15,19-dimethyl-7,11-metheno-11H-12-oxa-2,3,5,6,15,19-hexaazacyclooctadec[1,2,3-cd]inden-14(13H)-one,
N-cyclopentyl-2-[(2,3,13,14,15,16,17,18,19,20-decahydro-15,19-dimethyl-14-oxo-7,11-metheno-11H-12-oxa-2,3,5,6,15,19-hexaazacyclooctadec[1,2,3-cd]inden-10-yl)oxy]-acetamide,
10-[2-(cyclopentyloxy)ethoxy]-2,3,15,16,17,18,19,20-octahydro-15,19-dimethyl-11,7-metheno-7H-12-oxa-2,3,5,6,15,19-hexaazacyclooctadec[1,2,3-cd]inden-14(13H)-one,
10-(2-ethoxyethoxy)-2,3,15,16,17,18,19,20-octahydro-15,19-dimethyl-11,7-metheno-7H-12-oxa-2,3,5,6,15,19-hexaazacyclooctadec[1,2,3-cd]inden-14(13H)-one,
2,3,15,16,17,18,19,20-octahydro-15,19-dimethyl-10-(1-methylethoxy)-11,7-metheno-7H-12-oxa-2,3,5,6,15,19-hexaazacyclooctadec[1,2,3-cd]inden-14(13H)-one,
2,3,15,16,17,18,19,20-octahydro-15,19-dimethyl-10-propoxy-11,7-metheno-7H-12-oxa-2,3,5,6,15,19-hexaazacyclooctadec[1,2,3-cd]inden-14(13H)-one,
N-(4-chlorophenyl)-N'-(2,3,13,14,15,16,17,18,19,20-decahydro-15,19-dimethyl-14-oxo-11,7-metheno-7H-12-oxa-2,3,5,6,15,19-hexaazacyclooctadec[1,2,3-cd]inden-10-yl)-urea,
4-[[(2,3,13,14,15,16,17,18,19,20-decahydro-15,19-dimethyl-14-oxo-11,7-metheno-7H-12-oxa-2,3,5,6,15,19-hexaazacyclooctadec[1,2,3-cd]inden-10-yl)oxy]acetyl]-morpholine,
N-cyclohexyl-2-[(2,3,13,14,15,16,17,18,19,20-decahydro-15,19-dimethyl-14-oxo-7,11-metheno-11H-12-oxa-2,3,5,6,15,19-hexaazacyclooctadec[1,2,3-cd]inden-10-yl)oxy]-acetamide,
2,3,15,16,17,18,19,20-octahydro-10-(2-methoxyethoxy)-15,19-dimethyl-7,11-metheno-11H-12-oxa-2,3,5,6,15,19-hexaazacyclooctadec[1,2,3-cd]inden-14(13H)-one,
2,3,15,16,17,18,19,20-octahydro-15,19-dimethyl-11,7-metheno-7H-12-oxa-2,3,5,6,15,19-hexaazacyclooctadec[1,2,3-cd]inden-14(13H)-one, N-cyclopropyl-2-[(2,3,13,14,15,16,17,18,19,20-decahydro-15,19-dimethyl-14-oxo-11,7-metheno-7H-12-oxa-2,3,5,6,15,19-hexaazacyclooctadec[1,2,3-cd]inden-10-yl)oxy]-acetamide, N-(cyclopropylmethyl)-N'-(2,3,13,14,15,16,17,18,19,20-decahydro-15,19-dimethyl-14-oxo-11,7-metheno-7H-12-oxa-2,3,5,6,15,19-hexaazacyclooctadec[1,2,3-cd]inden-10-yl)-urea, 2,3,15,16,17,18,19,20-octahydro-10-[2-(2-methoxyethoxy)ethoxy]-15,19-dimethyl-11,7-metheno-7H-12-oxa-2,3,5,6,15,19-hexaazacyclooctadec[1,2,3-cd]inden-14(13H)-one, 2,3,15,16,17,18,19,20-octahydro-10-(2-methoxyethoxy)-15-methyl-11,7-metheno-7H-12-oxa-2,3,5,6,15,19-hexaazacyclooctadec[1,2,3-cd]inden-14(13H)-one, 2-[(2,3,13,14,15,16,17,18,19,20-decahydro-15,19-dimethyl-14-oxo-11,7-metheno-7H-12-oxa-2,3,5,6,15,19-hexaazacyclooctadec[1,2,3-cd]inden-10-yl)oxy]-N-(4-methoxyphenyl)-acetamide, 10-(3-ethoxypropoxy)-2,3,15,16,17,18,19,20-octahydro-15,19-dimethyl-11,7-metheno-7H-12-oxa-2,3,5,6,15,19-hexaazacyclooctadec[1,2,3-cd]inden-14(13H)-one, 2-[(2,5,13,14,15,16,17,18,19,20-decahydro-15,19-dimethyl-14-oxo-11,7-metheno-7H-12-oxa-2,3,5,6,15,19-hexaazacyclooctadec[1,2,3-cd]inden-10-yl)oxy]-N-(3,4,5-trimethoxyphenyl)-acetamide, 10-(difluoromethoxy)-2,3,15,16,17,18,19,20-octahydro-15,19-dimethyl-11,7-metheno-7H-12-oxa-2,3,5,6,15,19-hexaazacyclooctadec[1,2,3-cd]inden-14(13H)-one, 10-bromo-2,3,15,16,17,18,19,20-octahydro-15,19-dimethyl-11,7-metheno-7H-12-oxa-2,3,5,6,15,19-hexaazacyclooctadec[1,2,3-cd]inden-14(13H)-one, 2,3,15,16,17,18,19,20-octahydro-15,19-dimethyl-10-[2-(1-methylethoxy)ethoxy]-7,11-metheno-11H-12-oxa-2,3,5,6,15,19-hexaazacyclooctadec[1,2,3-cd]inden-14(13H)-one, 2,3,15,16,17,18,19,20-octahydro-10-(3-methoxypropoxy)-15,19-dimethyl-7,11-metheno-11H-12-oxa-2,3,5,6,15,19-hexaazacyclooctadec[1,2,3-cd]inden-14(13H)-one, 10-[2-[ethyl(2-methoxyethyl)amino]ethoxy]-2,3,15,16,17,18,19,20-octahydro-15,19-dimethyl-11,7-metheno-7H-12-oxa-2,3,5,6,15,19-hexaazacyclooctadec[1,2,3-cd]inden-14(13H)-one, 2,3,15,16,17,18,19,20-octahydro-10-[3-(4-methoxyphenoxy)propoxy]-15,19-dimethyl-11,7-metheno-7H-12-oxa-2,3,5,6,15,19-hexaazacyclooctadec[1,2,3-cd]inden-14(13H)-one, 10-[2-[(4-chlorophenyl)amino]ethoxy]-2,3,15,16,17,18,19,20-octahydro-15,19-dimethyl-11,7-metheno-7H-12-oxa-2,3,5,6,15,19-hexaazacyclooctadec[1,2,3-cd]inden-14(13H)-one, 2,3,15,16,17,18,19,20-octahydro-10-[2-[(2-methoxyethyl)(phenylmethyl)amino]ethoxy]-15,19-dimethyl-7,11-metheno-11H-12-oxa-2,3,5,6,15,19-hexaazacyclooctadec[1,2,3-cd]inden-14(13H)-one, 2,3,15,16,17,18,19,20-octahydro-10-(2-hydroxyethoxy)-15,19-dimethyl-11,7-metheno-7H-12-oxa-2,3,5,6,15,19-hexaazacyclooctadec[1,2,3-cd]inden-14(13H)-one, N-(4-chlorophenyl)-2-[(2,3,13,14,15,16,17,18,19,20-decahydro-15,19-dimethyl-14-oxo-11,7-metheno-7H-12-oxa-2,3,5,6,15,19-hexaazacyclooctadec[1,2,3-cd]inden-10-yl)oxy]-acetamide, 10-[2-(4-chlorophenoxy)ethoxy]-2,3,15,16,17,18,19,20-octahydro-15,19-dimethyl-11,7-metheno-7H-12-oxa-2,3,5,6,15,19-hexaazacyclooctadec[1,2,3-cd]inden-14(13H)-one, 10-(2-ethoxyethoxy)-2,3,15,16,17,18,19,20-octahydro-15-methyl-7,11-metheno-11H-12-oxa-2,3,5,6,15,19-hexaazacyclooctadec[1,2,3-cd]inden-14(13H)-one, 10-[3-[(4-chlorophenyl)amino]propoxy]-2,3,15,16,17,18,19,20-octahydro-15,19-dimethyl-7,11-metheno-11H-12-oxa-2,3,5,6,15,19-hexaazacyclooctadec[1,2,3-cd]inden-14(13H)-one, 2,3,15,16,17,18,19,20-octahydro-15,19-dimethyl-10-(1-pyrrolidinyl)-11,7-metheno-7H-12-oxa-2,3,5,6,15,19-hexaazacyclooctadec[1,2,3-cd]inden-14(13H)-one, 2,3,15,16,17,18,19,20-octahydro-15,19-dimethyl-10-[2-[(1-methyl-1H-imidazol-2-yl)thio]ethoxy]-7,11-metheno-11H-12-oxa-2,3,5,6,15,19-hexaazacyclooctadec[1,2,3-cd]inden-14(13H)-one, 10-(2-ethoxyethoxy)-2,3,15,16,17,18,19,20-octahydro-2,15,19-trimethyl-7,11-metheno-11H-12-oxa-2,3,5,6,15,19-hexaazacyclooctadec[1,2,3-cd]inden-14(13H)-one, and the N-oxide forms, the pharmaceutically acceptable addition salts, the quaternary amines and the stereochemically isomeric forms of such compounds.

Other specific compounds according to the invention include:

2,6,13,14,15,16,18,19,20,21,22,23-dodecahydro-10-methoxy-18,22-dimethyl-17H-7,11-metheno-12-oxa-2,3,5,6,18,22-hexaazacycloheneicos[1,2,3-cd]inden-17-one, 2,6,14,15,17,18,19,20,21,22-decahydro-10-methoxy-17,21-dimethyl-7,11-metheno-11H-12-oxa-2,3,5,6,17,21-hexaazacycloeicos[1,2,3-cd]inden-16(13H)-one, 10-chloro-2,6,14,15,17,16,17,19,20,21,22,23,24-dodecahydro-19,23-dimethyl-7,11-metheno-11H-12-oxa-2,3,5,6,19,23-hexaazacyclodocos[1,2,3-cd]inden-18(13H)-one, 2,6,15,16,17,18,19,20-octahydro-10-methoxy-15,19-dimethyl-7,11-metheno-11H-12-oxa-2,3,5,6,15,19-hexaazacyclooctadec[1,2,3-cd]inden-14(13H)-one, 2,14,15,17,18,19,20,21-octahydro-10-methoxy-17,20-dimethyl-6H-11,7-metheno-12-oxa-2,3,5,6,17,20-hexaazacyclononadec[1,2,3-cd]inden-16(13H)-one, 19-ethyl-2,6,15,16,17,18,19,20-octahydro-10-methoxy-15-methyl-7,11-metheno-11H-12-oxa-2,3,5,6,15,19-hexaazacyclooctadec[1,2,3-cd]inden-14(13H)-one, 2,6,15,16,17,18,19,20-octahydro-15,19-dimethyl-9-(trifluoromethyl)-11,7-metheno-7H-12-oxa-2,3,5,6,15,19-hexaazacyclooctadec[1,2,3-cd]inden-14(13H)-one, 2,15,16,17,18,19-hexahydro-15,18-dimethyl-6H-11,7-metheno-12-oxa-2,3,5,6,15,18-hexaazacycloheptadec[1,2,3-cd]inden-14(13H)-one, 2,15,16,17,18,19-hexahydro-10-methoxy-15,18-dimethyl-6H-7,11-metheno-12-oxa-2,3,5,6,15,18-hexaazacycloheptadec[1,2,3-cd]inden-14(13H)-one, 10-chloro-2,6,15,16,17,18,19,20-octahydro-15,19-dimethyl-7,11-metheno-11H-12-oxa-2,3,5,6,15,19-hexaazacyclooctadec[1,2,3-cd]inden-14(13H)-one, 10-ethoxy-2,6,15,16,17,18,19,20-octahydro-15,19-dimethyl-7,11-metheno-11H-12-oxa-2,3,5,6,15,19-hexaazacyclooctadec[1,2,3-cd]inden-14(13H)-one, 2,6,15,16,17,18,19,20-octahydro-15,19-dimethyl-10-(phenylmethoxy)-7,11-metheno-11H-12-oxa-2,3,5,6,15,19-hexaazacyclooctadec[1,2,3-cd]inden-14(13H)-one, 2,6,15,16,17,18,19,20-octahydro-10-methoxy-15-methyl-7,11-metheno-11H-12-oxa-2,3,5,6,15,19-hexaazacyclooctadec[1,2,3-cd]inden-14(13H)-one, 2,6,15,16,17,18,19,20-octahydro-10-methoxy-15-methyl-19-(phenylmethyl)-7,11-metheno-11H-12-oxa-2,3,5,6,15,19-hexaazacyclooctadec[1,2,3-cd]inden-14(13H)-one, 19-(cyclopropylmethyl)-2,6,15,16,17,18,19,20-octahydro-10-methoxy-15-methyl-7,11-metheno-11H-12-oxa-2,3,5,6,15,19-hexaazacyclooctadec[1,2,3-cd]inden-14(13H)-one, N-(2,6,13,14,15,16,17,18,19,20-decahydro-15,19-dimethyl-14-oxo-11,7-metheno-7H-12-oxa-2,3,5,6,15,19-hexaazacyclooctadec[1,2,3-cd]inden-10-yl)-N'-(4-methoxyphenyl)-urea, 2,6,15,16,17,18,19,20-octahydro-10-methoxy-19-methyl-15-(1-methylethyl)-7,11-metheno-11H-12-oxa-2,3,5,6,15,19-hexaazacyclooctadec[1,2,3-cd]inden-14(13H)-one, 15-cyclohexyl-2,6,15,16,17,18,19,20-octahydro-10-methoxy-19-methyl-7,11-metheno-11H-12-oxa-2,3,5,6,15,19-hexaazacyclooctadec[1,2,3-cd]inden-14(13H)-one, N-cyclohexyl-N'-(2,6,13,14,15,16,17,18,19,20-decahydro-15,19-dimethyl-14-oxo-11,7-metheno-7H-12-oxa-2,3,5,6,15,19-hexaazacyclooctadec[1,2,3-cd]inden-10-yl)-urea, N-(3-chlorophenyl)-N'-(2,6,13,14,15,16,17,18,19,20-decahydro-15,19-dimethyl-14-oxo-11,7-metheno-7H-12-oxa-2,3,5,6,15,19-hexaazacyclooctadec[1,2,3-cd]inden-10-yl)-urea, N-cyclopentyl-N'-(2,6,13,14,15,16,17,18,19,20-decahydro-15,19-dimethyl-14-oxo-11,7-metheno-7H-12-oxa-2,3,5,6,15,19-hexaazacyclooctadec[1,2,3-cd]inden-10-yl)-urea and 10-(cyclopropylmethoxy)-2,6,15,16,17,18,19,20-octahydro-15,19-dimethyl-7,11-metheno-11H-12-oxa-2,3,5,6,15,19-hexaazacyclooctadec[1,2,3-cd]inden-14(13H)-one, and the N-oxide forms, the pharmaceutically acceptable addition salts, the quaternary amines and the stereochemically isomeric forms of such compounds.

A more specific group of compounds according to the invention includes:

2,6,15,16,17,18,19,20-octahydro-10-methoxy-15,19-dimethyl-7,11-metheno-11H-12-oxa-2,3,5,6,15,19-hexaazacyclooctadec[1,2,3-cd]inden-14(13H)-one, 2,15,16,17,18,19-hexahydro-15,18-dimethyl-6H-11,7-metheno-12-oxa-2,3,5,6,15,18-hexaazacycloheptadec[1,2,3-cd]inden-14(13H)-one, 10-chloro-2,6,15,16,17,18,19,20-octahydro-15,19-dimethyl-7,11-metheno-11H-12-oxa-2,3,5,6,15,19-hexaazacyclooctadec[1,2,3-cd]inden-14(13H)-one, 10-ethoxy-2,6,15,16,17,18,19,20-octahydro-15,19-dimethyl-7,11-metheno-11H-12-oxa-2,3,5,6,15,19-hexaazacyclooctadec[1,2,3-cd]inden-14(13H)-one, 2,6,15,16,17,18,19,20-octahydro-15,19-dimethyl-10-(phenylmethoxy)-7,11-metheno-11H-12-oxa-2,3,5,6,15,19-hexaazacyclooctadec[1,2,3-cd]inden-14(13H)-one, 2,6,15,16,17,18,19,20-octahydro-10-methoxy-15-methyl-7,11-metheno-11H-12-oxa-2,3,5,6,15,19-hexaazacyclooctadec[1,2,3-cd]inden-14(13H)-one, 2,6,15,16,17,18,19,20-octahydro-10-methoxy-15-methyl-19-(phenylmethyl)-7,11-metheno-11H-12-oxa-2,3,5,6,15,19-hexaazacyclooctadec[1,2,3-cd]inden-14(13H)-one, N-(2,6,13,14,15,16,17,18,19,20-decahydro-15,19-dimethyl-14-oxo-11,7-metheno-7H-12-oxa-2,3,5,6,15,19-hexaazacyclooctadec[1,2,3-cd]inden-10-yl)-N'-(4-methoxyphenyl)-urea, 2,6,15,16,17,18,19,20-octahydro-10-methoxy-19-methyl-15-(1-methylethyl)-7,11-metheno-11H-12-oxa-2,3,5,6,15,19-hexaazacyclooctadec[1,2,3-cd]inden-14(13H)-one, N-cyclohexyl-N'-(2,6,13,14,15,16,17,18,19,20-decahydro-15,19-dimethyl-14-oxo-11,7-metheno-7H-12-oxa-2,3,5,6,15,19-hexaazacyclooctadec[1,2,3-cd]inden-10-yl)-urea, N-(3-chlorophenyl)-N'-(2,6,13,14,15,16,17,18,19,20-decahydro-15,19-dimethyl-14-oxo-11,7-metheno-7H-12-oxa-2,3,5,6,15,19-hexaazacyclooctadec[1,2,3-cd]inden-10-yl)-urea, N-cyclopentyl-N'-(2,6,13,14,15,16,17,18,19,20-decahydro-15,19-dimethyl-14-oxo-11,7-metheno-7H-12-oxa-2,3,5,6,15,19-hexaazacyclooctadec[1,2,3-cd]inden-10-yl)-urea and 10-(cyclopropylmethoxy)-2,6,15,16,17,18,19,20-octahydro-15,19-dimethyl-7,11-metheno-11H-12-oxa-2,3,5,6,15,19-hexaazacyclooctadec[1,2,3-cd]inden-14(13H)-one, and the N-oxide forms, the pharmaceutically acceptable addition salts, the quaternary amines and the stereochemically isomeric forms of such compounds.

Two particular compounds according to the invention comprise:

10-ethoxy-2,6,15,16,17,18,19,20-octahydro-15,19-dimethyl-7,11-metheno-11H-12-oxa-2,3,5,6,15,19-hexaazacyclooctadec[1,2,3-cd]inden-14(13H)-one, and N-(2,6,13,14,15,16,17,18,19,20-decahydro-15,19-dimethyl-14-oxo-11,7-metheno-7H-12-oxa-2,3,5,6,15,19-hexaazacyclooctadec[1,2,3-cd]inden-10-yl)-N'-(4-methoxyphenyl)-urea, and the N-oxide forms, the pharmaceutically acceptable addition salts, the quaternary amines and the stereochemically isomeric forms of such compounds.

As used herein;

$C_{1-4}$alkyl as a group or part of a group defines straight or branched chain saturated hydrocarbon radicals having from 1 to 4 carbon atoms such as methyl, ethyl, propyl, 1-methylethyl, butyl;

$C_{1-6}$alkyl as a group or part of a group defines straight or branched chain saturated hydrocarbon radicals having from 1 to 6 carbon atoms such as the groups defined for $C_{1-4}$alkyl and pentyl, hexyl, 2-methylbutyl and the like;

$C_{3-6}$cycloalkyl as a group or part of a group defines cyclic saturated hydrocarbon radicals having from 3 to 6 carbon atoms such as cyclopropyl, cyclobutyl, cyclopentyl or cyclohexyl;

halo is generic to fluoro, chloro, bromo and iodo.

CO represents a carbonyl moiety;

$S(O)_{1-2}$ represents either a sulfoxide moiety when only one oxygen atom is attached to a sulfur atom and a sulfonyl moiety when two of said oxygen atoms are attached to a sulfur atom.

Lines drawn into ring systems indicate that the bond may be attached to any suitable ring atom.

When any variable occurs more than one time in any constituent, each definition is independent.

It will be appreciated that some of the compounds of formula (I) and their N-oxides, addition salts, quaternary amines and stereochemically isomeric forms may contain one or more centers of chirality and exist as stereochemically isomeric forms.

The term "stereochemically isomeric forms" as used hereinbefore or hereinafter defines all the possible stereoisomeric forms which the compounds of formula (I) and their N-oxides, addition salts, quaternary amines or physiologically functional derivatives may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms of formula (I) and their N-oxides, salts, solvates, quaternary amines substantially free, i.e. associated with less than 10%, preferably less than 5%, in particular less than 2% and most preferably less than 1% of the other isomers. Stereochemically isomeric forms of the compounds of formula (I) are obviously intended to be embraced within the scope of this invention.

For therapeutic use, salts of the compounds of formula (I) are those wherein the counter ion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove or hereinafter are meant to comprise the therapeutically active non-toxic acid and base addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, tromethamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

The term addition salt as used hereinabove also comprises the solvates which the compounds of formula (I), as well as the salts thereof, are able to form. Such solvates are for example hydrates, alcoholates and the like.

The term "quaternary amine" as used hereinbefore defines the quaternary ammonium salts which the compounds of formula (I) are able to form by reaction between a basic nitrogen of a compound of formula (I) and an appropriate quaternizing agent, such as, for example, an optionally substituted alkyl halide, aryl halide or arylalkyl halide, e.g. methyl iodide or benzyl iodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include for example chloro, bromo, iodo, trifluoroacetate and acetate. The counterion of choice can be made using ion exchange resin columns.

The N-oxide forms of the present compounds are meant to comprise the compounds of formula (I) wherein one or several tertiary nitrogen atoms are oxidized to the so-called N-oxide.

Some of the compounds of formula (I) may also exist in their tautomeric form. Such forms although not explicitly indicated in the above formula are intended to be included within the scope of the present invention.

The compounds of this invention can be prepared by any of several standard synthetic processes commonly used by those skilled in the art of organic chemistry and described for instance in the following references; "Heterocyclic Compounds"—Vol. 24 (part 4), p 261-304, Fused Pyrimidines, Wiley-Interscience; Chem. Pharm. Bull., Vol 41(2), 362-368 (1993); and J. Chem. Soc., Perkin Trans. 1, 2001, 130-137. The compounds are generally prepared from starting materials which are either commercially available or prepared by standard means obvious to those skilled in the art.

In general the compounds of formula (I) can be prepared as shown in Scheme 1 below wherein a pyrrolopyrimidine of formula (II) is converted, directly (for example by reaction with a compound of formula $X^4$—$Y^2$—$X^2$—H (III)) or indirectly, into a compound of formula (IV) which is then reacted with an aniline of formula (V) to form a compound of formula (VI). The compound of formula (VI) can then be optionally deprotected if desired before cyclisation to form a compound of formula (I).

Scheme 1

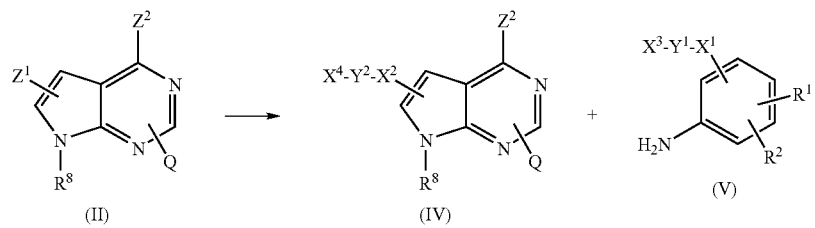

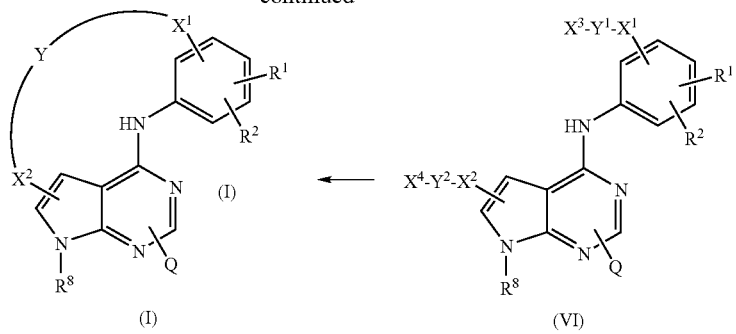

(I) ← (VI)

In the above Scheme:

$Z^1$ and $Z^2$ each independently represent suitable leaving or functional groups;

$Y^1$ and $Y^2$ each independently represent groups which together form the group Y in formula (I) upon cyclisation, for example —$C_{1-6}$alkyl-$NR^3$—, —$C_{1-6}$alkyl-CO—, —$NR^4$—$C_{1-6}$alkyl-CO—, —$C_{1-6}$alkyl-$NR^3$—CO—$C_{1-6}$alkyl-$NR^4$—, -$Het^1$-$C_{1-6}$alkyl-, -$Het^2$-CO— or —$NR^4$—$C_{1-6}$alkyl-; and $X^3$ and $X^4$ together with the functional moiety to which they are attached represent a protected functional group, such as for example a protected carboxy group for example tert-butoxy carbonyl (Boc) or a protected primary or secondary amine, which upon reaction (after deprotection) produce together with the $Y^1$ respectively $Y^2$ substituent to which they are attached, the bivalent Y radical as defined in the general formula I.

In the above reaction of the compound of formula (II) with the compound of formula (III) the leaving group $Z^2$ is advantageously a halo group such as a chlorine group and the group $Z^1$ is advantageously an aldehyde (—CHO) group. The reaction can be effected by reductive amination for example by treating the compound of formula (II) in an organic solvent such as THF/DMF with an appropriate amine using a reducing agent such as for example sodium triacetoxyborohydride in an organic solvent for example dichloromethane, at r.t.

The reaction of the resulting compound of formula (IV) with the aniline compound of formula (V) is advantageously effected under acidic conditions for example with 4N hydrochloric acid in dioxane, the reaction being effected in an organic solvent such as acetonitrile or tert-butanol at an elevated temperature for example under reflux.

The resulting compound of formula (VI) can optionally be treated to remove any desired protecting groups for example ester groups such as tert-butyloxy-carbonyl ester groups can be converted to the parent free carboxy group, or an amide group such as a tert-butyloxycarbonylamino group can be converted to the free amino group. Such deprotection can be effected in conventional manner for example by treatment under acidic conditions for example using aqueous hydrochloric acid in dioxane at an elevated temperature for example about 60° C. Alternatively deprotection of a carboxy group can be effected under basic conditions for example using a base such as lithium hydroxide in THF/$H_2O$ 1/1 at r.t., followed by deprotection of an amino group by addition of aqueous hydrochloric acid in an appropriate solvent such as for example dioxane, or by addition of trifluoroacetic acid in an appropriate solvent such as dichloromethane.

The cyclisation of the compound of formula (VI) can be effected by treatment with a cyclising agent such as 1-benzotriazolyloxytripyrrolidinylphosphonium hexafluorophosphate (PyBOP) in the presence of a base such as triethylamine and in an organic solvent such as dimethylformamide at r.t.

Other cyclisation agents which may be employed include 1,3-dicyclohexyl-carbodiimide (DCC), N,N'-carbonyldiimidazole (CDI), 1-[bis(dimethylamino)-methylene]-1H-benzotriazoliumhexafluorophophate-(1-)3-oxide (HBTU) or 1-(3-dimethylaminopropyl)-3-ethylcarbodiimide (EDCI) in the presence or absence of hydroxybenzotriazole (HOBt).

The above general process is illustrated by the following more specific processes which describe the preparation of various classes of compounds of formula (I) above.

In these processes, illustrated by reaction Schemes 2-6, the various reaction stages, namely reductive amination, reaction of the pyrrolopyrimidine and the aniline compound, deprotection and cyclisation are all conducted in conventional manner for example using the reactions conditions and reagents described above for the general process illustrated in Scheme 1.

The compounds of formula (I) in which the —$X^2$—Y—$X^1$ grouping is —$CH_2$—$NR^7$—$C_{1-6}$alkyl-$NR^3$—CO—$C_{1-6}$alkyl-$X^1$, represented by formula (Ia), can be prepared as described below in Scheme 2 in which $Y^{2a}$ is —$C_{1-6}$alkyl-$NR^3$— and $Y^{1a}$ is —CO—$C_{1-6}$alkyl- such that —$Y^{2a}$—$Y^{1a}$— is —$C_{1-6}$alkyl-$NR^3$—CO—$C_{1-6}$alkyl-, $P^1$ is an amino protecting group and $P^2$ is a carboxy protecting group:

Scheme 2

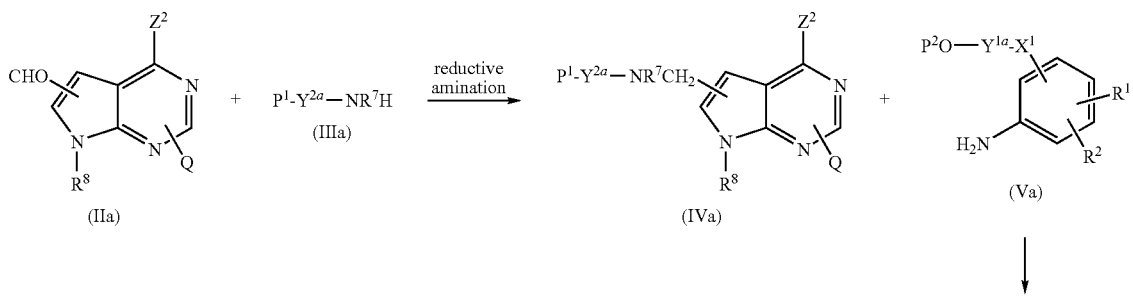

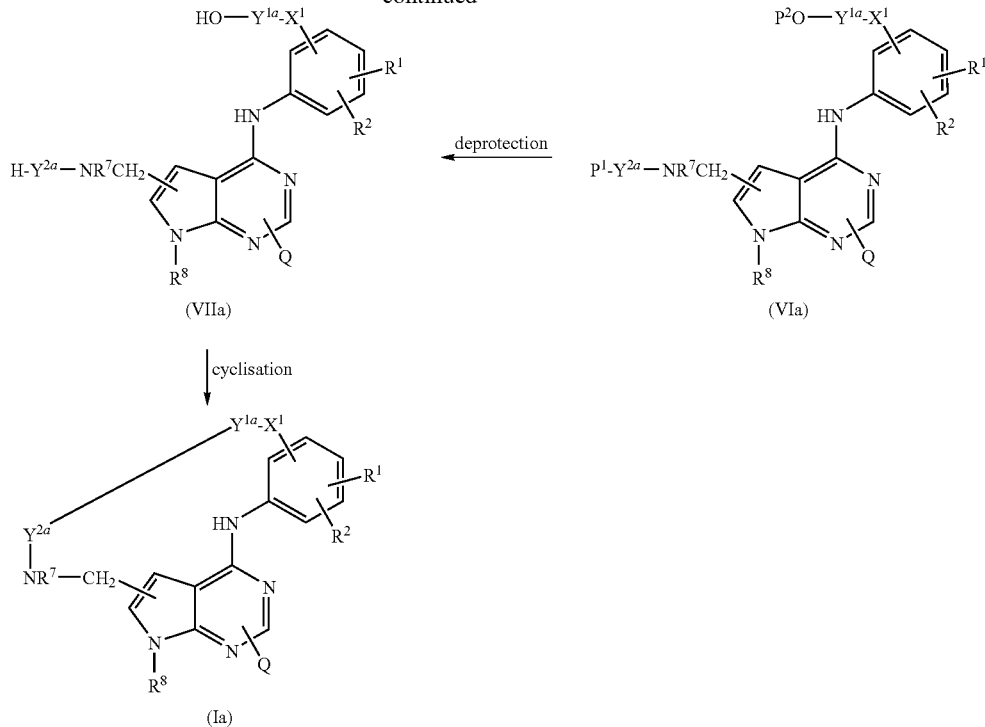

In the above scheme $P^1$ is an amino protecting group such as tert-butoxycarbonyl (Boc) and $P^2$ is a carboxy protecting group such as a $C_{1-6}$alkyl group for example an ethyl group. Both protecting groups can be removed in one step by hydrolysis under acidic conditions for example using aqueous hydrochloric acid in an organic solvent such as dioxane. Alternatively the groups can be removed separately for example as described above using basic conditions to deprotect the carboxy group and then acidic conditions to deprotect the amino group.

The compounds of formula (I) in which $-X^2-Y-X^1-$ grouping is $-CH_2-NR^7-C_{1-6}alkyl-CO-NR^3-C_{1-6}alkyl-X^1-$, represented by formula (Ib), can be prepared as described below in Scheme 3 in which $Y^{1b}$ is $-NR^3-C_{1-6}alkyl-$ and $Y^{2b}$ is $-C_{1-6}alkyl-CO-$ such that $-Y^{2b}-Y^{1b}-$ is $-C_{1-6}alkyl-CO-NR^3-C_{1-6}alkyl-$:

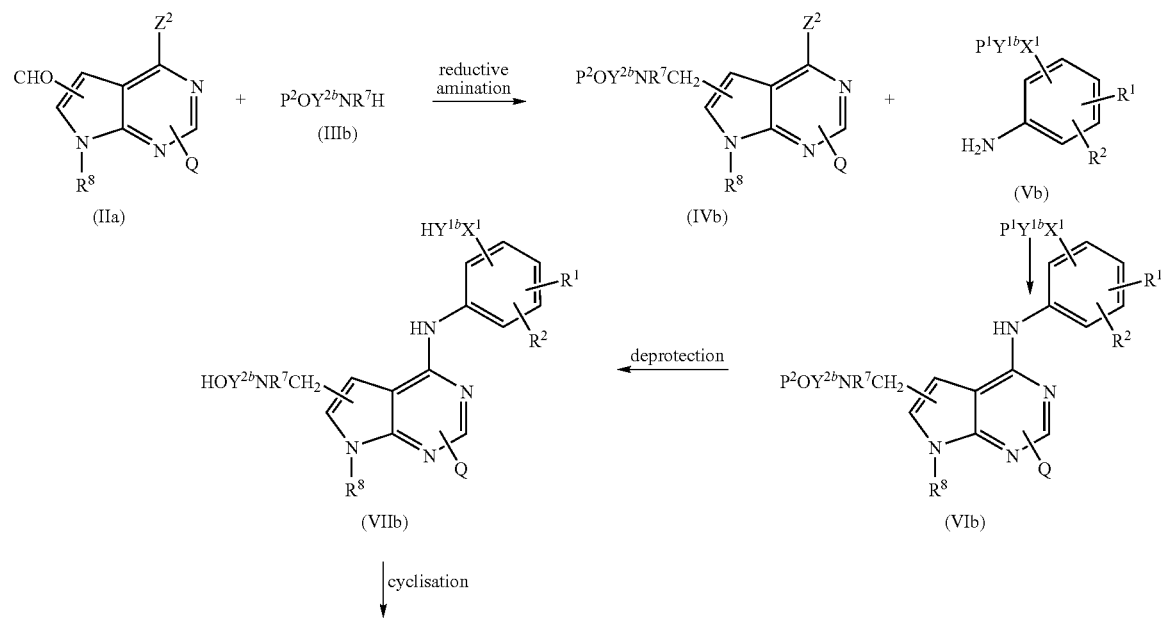

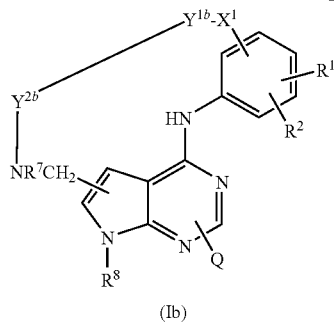
The compounds of formula (I) containing a —X²—Y— grouping in which a C₃ or C₄alkyl group is directly attached to the pyrrolopyrimidine ring system may be prepared using an acetylenic intermediate as described in Scheme 4 below in which $R^y$ is a $R^3$, $R^4$ or $R^7$ group, $R^z$ is a —CH₂OH, —OCH₂-phenyl or —OCH₂COOP² group and $P^3$ is an N-protecting group:
Scheme 4
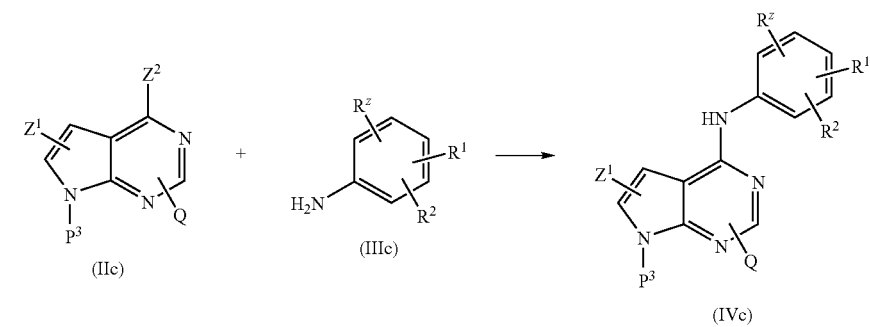
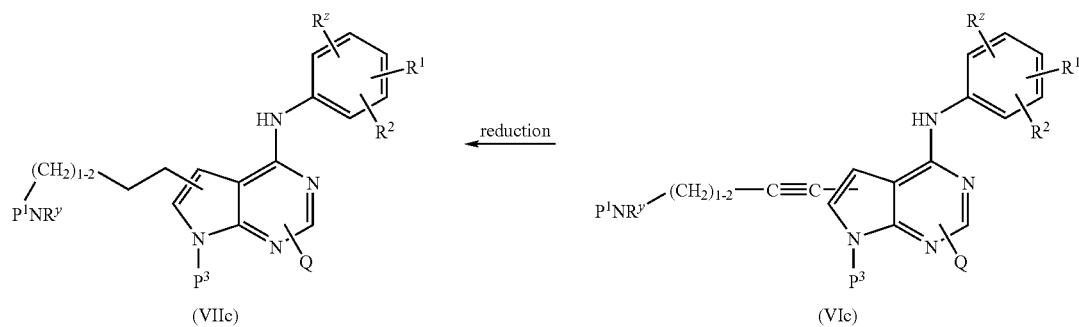

In the above Scheme the Sonogashira reaction of the compound of formula (IVc) and the acetylenic compound of formula (Vc) is generally carried out in the presence of Pd(Ph$_3$P)$_2$Cl$_2$ and cuprous iodide (CuI) and a base such as triethylamine or diethylamine, in an organic solvent such as dimethylacetamide or dimethylformamide, for example at r.t. The subsequent reduction may be effected for example by hydrogenation in the presence of a nickel catalyst in an organic solvent such as tetrahydrofuran.

The compounds of formula (I) in which the —X$^2$—Y—X$^1$— grouping is —(CH$_2$)$_{3\ or\ 4}$—NR$^3$—CO—C$_{1-6}$alkyl-NR$^6$—CH$_2$—, represented by formula (Ic), can be prepared as described in Scheme 4a below using a compound of formula (VIIc) in which R$^z$ is —CH$_2$OH, R$^y$ is R$^3$, Y$^{2c}$ is —(CH$_2$)$_{3\ or\ 4}$—NR$^3$— and Y$^{1c}$ is —CO—C$_{1-6}$alkyl- such that —Y$^{2c}$—Y$^{1c}$— is —(CH$_2$)$_{3\ or\ 4}$—NR$^3$—CO—C$_{1-6}$alkyl-:

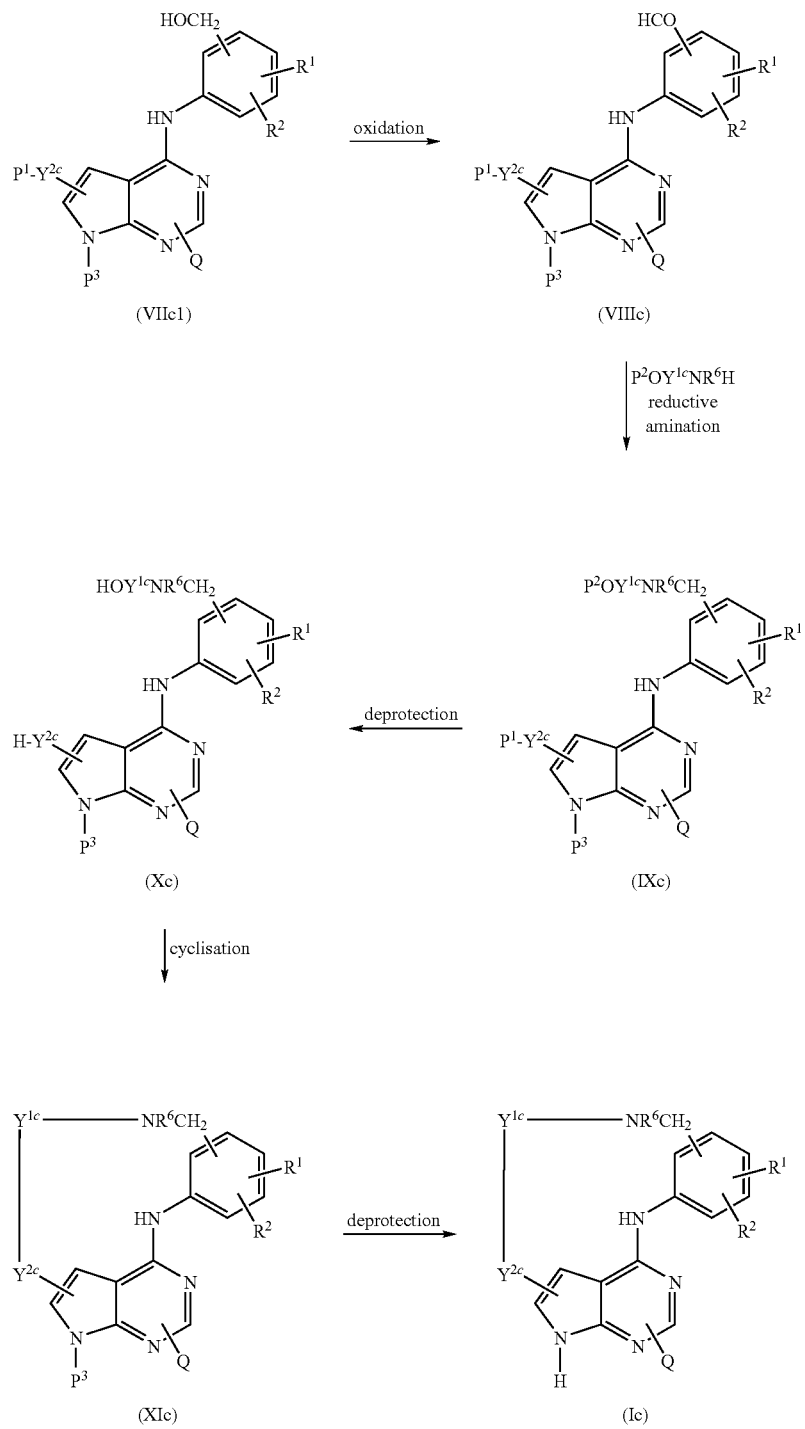

In the above Scheme the oxidation of the compound of formula (VIIc1) may be effected for example by treatment with manganese dioxide in an organic solvent such as tetrahydrofuran at r.t. The deprotection of the compound of formula (IXc) can be effected for example by treatment with a base such as aqueous sodium hydroxide in an appropriate solvent such as tetrahydrofuran or methanol, at r.t.

The procedure described in Scheme 4a can also be used to prepare compounds of formula (I) in which —$X^2$—Y—$X^1$— is —$(CH_2)_{3 \text{ or } 4}$—$NR^4$—CO-$Het^2$-$CH_2$—, represented by formula (Id), as described in Scheme 4b below in which $Y^{2d}$ is —$(CH_2)_{3 \text{ or } 4}$—$NR^4$— and $Y^{1d}$ is —CO-$Het^2$- such that —$Y^{2d}$—$Y^{1d}$— is —$(CH_2)_{3 \text{ or } 4}$—$NR^4$—CO-$Het^2$-:

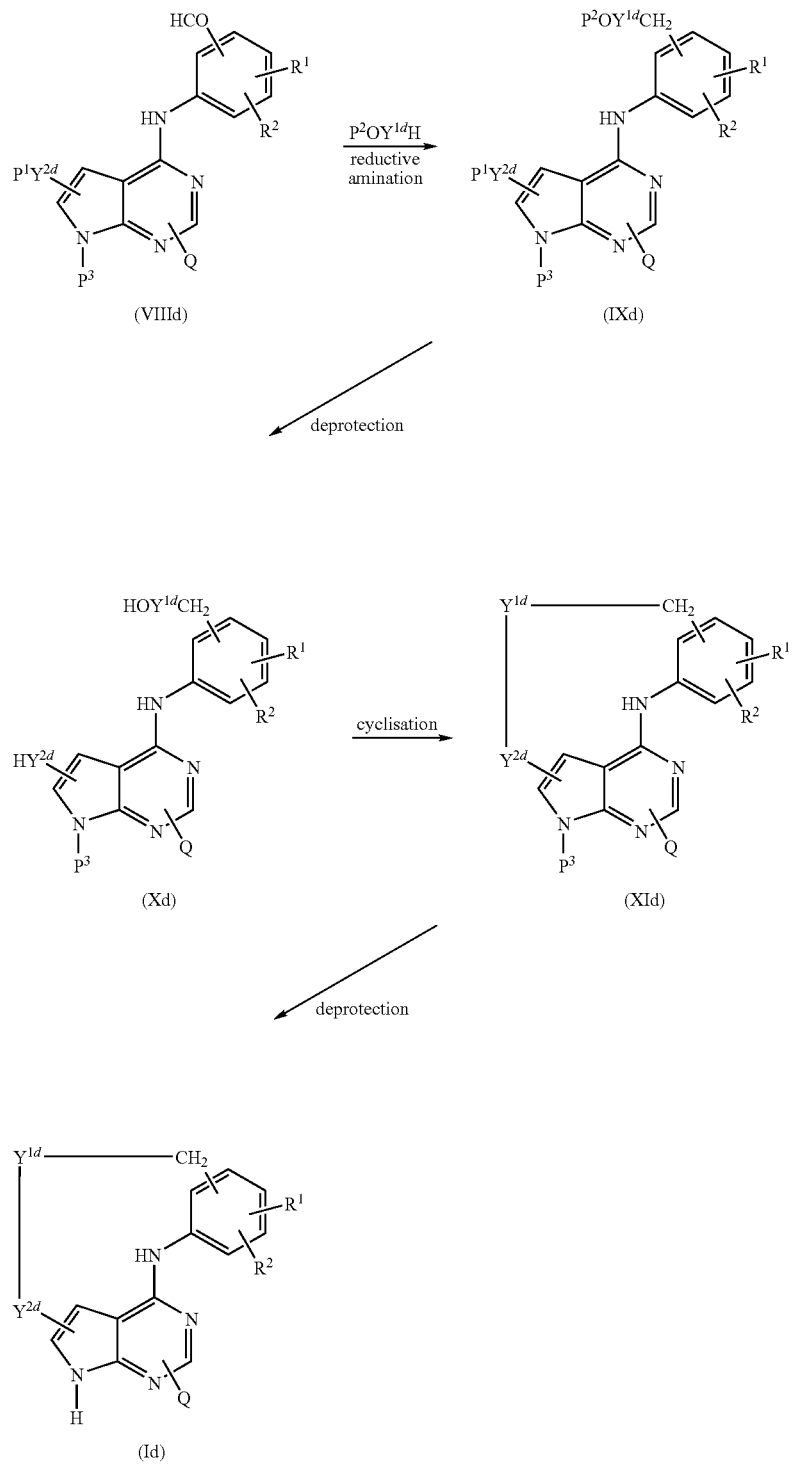

Compounds of formula I in which the —X²—Y—X¹— grouping is —(CH₂)₃ ₒᵣ ₄—NR⁷—C₁₋₆alkyl-NR³CO—CH₂—O—, represented by formula (Ie), can be prepared as described in Scheme 4c below using a compound of formula (VIIc) in which R$^z$ is a protected —OCH₂COOP² group, R$^y$ is R⁷, Y$^{2e}$ is —C₁₋₆alkyl-NR³— and Y$^{1e}$ is —CO—CH₂— such that —Y$^{2e}$—Y$^{1e}$— is —C₁₋₆alkyl-NR³—CO—CH₂—:
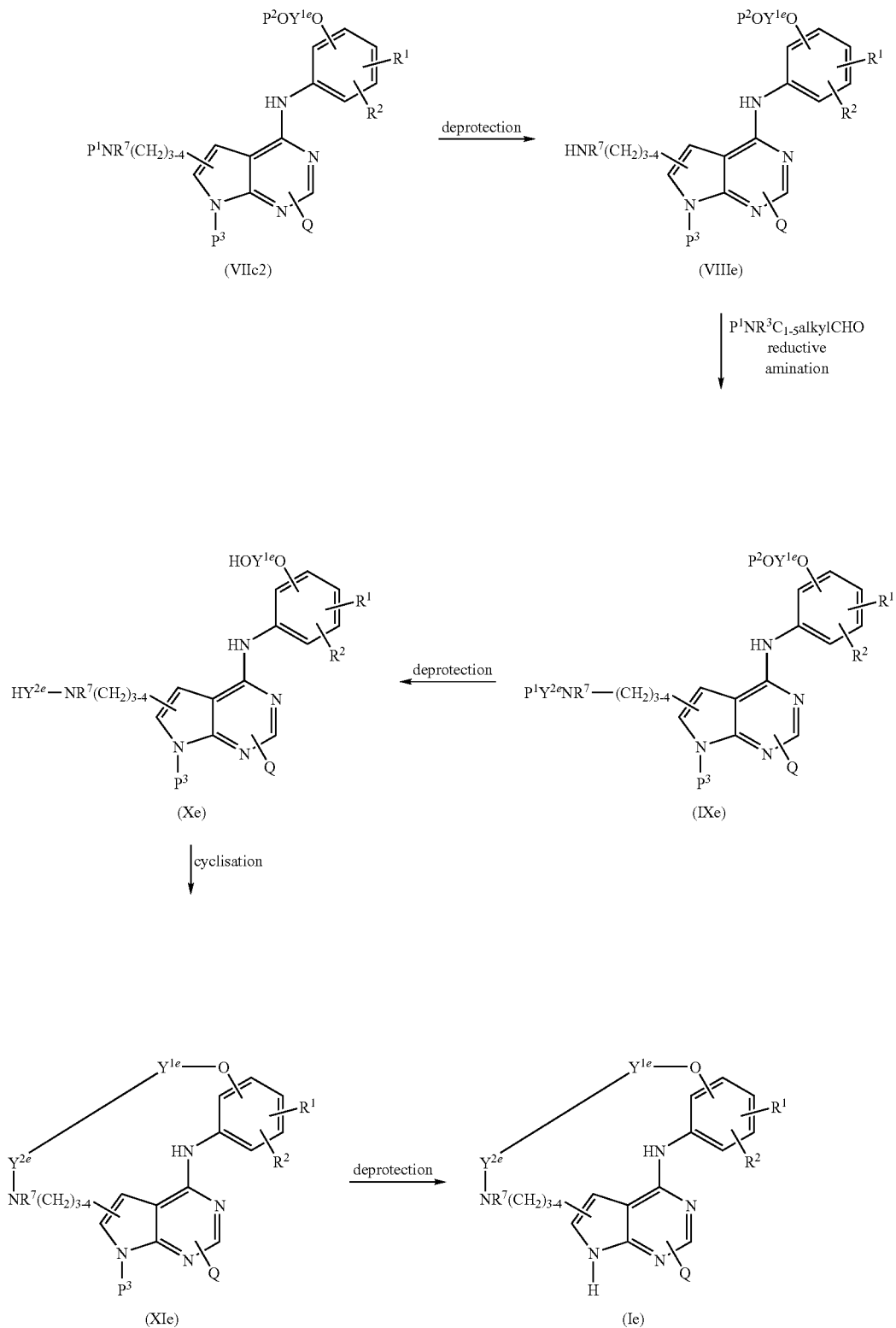

The procedure described in Scheme 4c can be used to prepare compounds of formula (I) in which —X²—Y—X¹— is —(CH₂)₃ or 4—NR⁷—C₁₋₆alkyl-Het¹-CO—CH₂—O—, represented by formula (If), as described in Scheme 4d below in which $Y^{2f}$ is —CH₂-Het¹- and $Y^{1f}$ is —CO—CH₂— such that —$Y^{2f}$—$Y^{1f}$— is —CH₂-Het¹-CO—CH₂—:
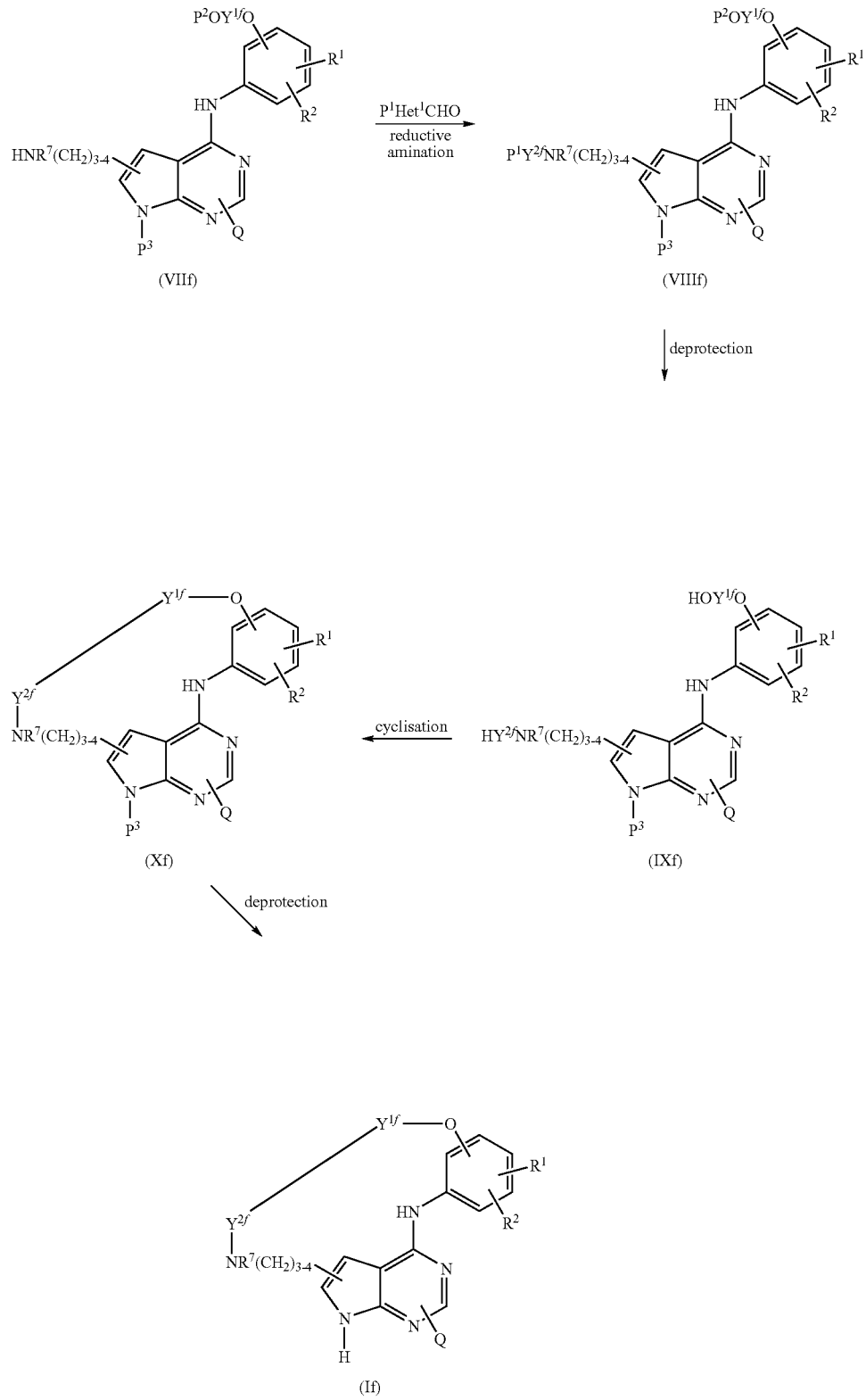

Compounds of formula (I) in which the —X²—Y—X¹— grouping is —(CH₂)₂—NR⁷—C₁₋₆alkyl-NR³—CO—CH₂O—, represented by formula (Ig) below, may be prepared as described in Scheme 5 below in which in which Y²ᵍ is —C₁₋₆alkyl-NR³— and Y¹ᵍ is —CO—CH₂— such that —Y²ᵍ—Y¹ᵍ— is —C₁₋₆alkyl-NR³—CO—CH₂—:
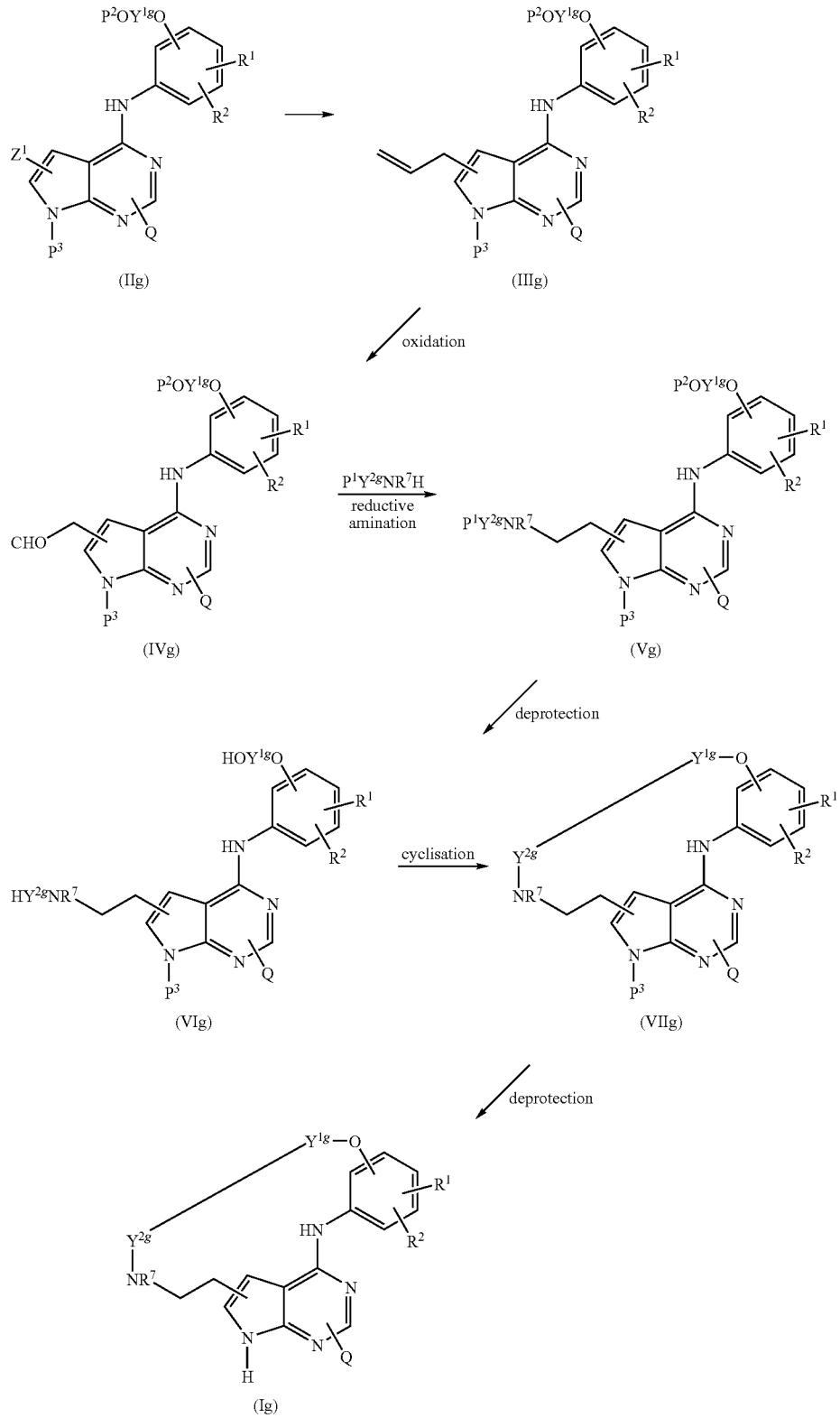
Scheme 5

In the above Scheme the compound of formula (IIg) in which $Z^1$ is an iodine atom may be subjected to a Stille reaction using $(CH_3(CH_2)_3)_3SnCH_2CHCH_2$ and $Pd(Ph_3P)_4$, in an organic solvent such as toluene at an elevated temperature for example at reflux. The resulting compound of formula (IIIg) can then be oxidised for example using osmium tetroxide, 4-methylmorpholine 4-oxide (NMO) and $NaIO_4$ in an aqueous system, or by ozonolysis.

Compounds of formula (I) in which the $X^2$—Y—$X^1$—grouping is —$CH_2$—$NR^7$—$C_{1-6}$alkyl-$NR^3$—CO—$C_{1-6}$alkyl-$NR^4$—CO—$C_{1-6}$alkyl-, represented by formula (Ih), may be prepared as described in Scheme 6 below in which $Y^{1h}$ is —CO—$C_{1-6}$alkyl-, $Y^{2h}$ is —$C_{1-6}$alkyl-$NR^3$— and $Y^{3h}$ is —CO—$C_{1-6}$alkylNR$^4$— such that —$Y^{2h}$—$Y^{3h}$—$Y^{1h}$ is —$C_{1-6}$alkyl-$NR^3$—CO—$C_{1-6}$alkyl-$NR^4$—CO—$C_{1-6}$alkyl-:

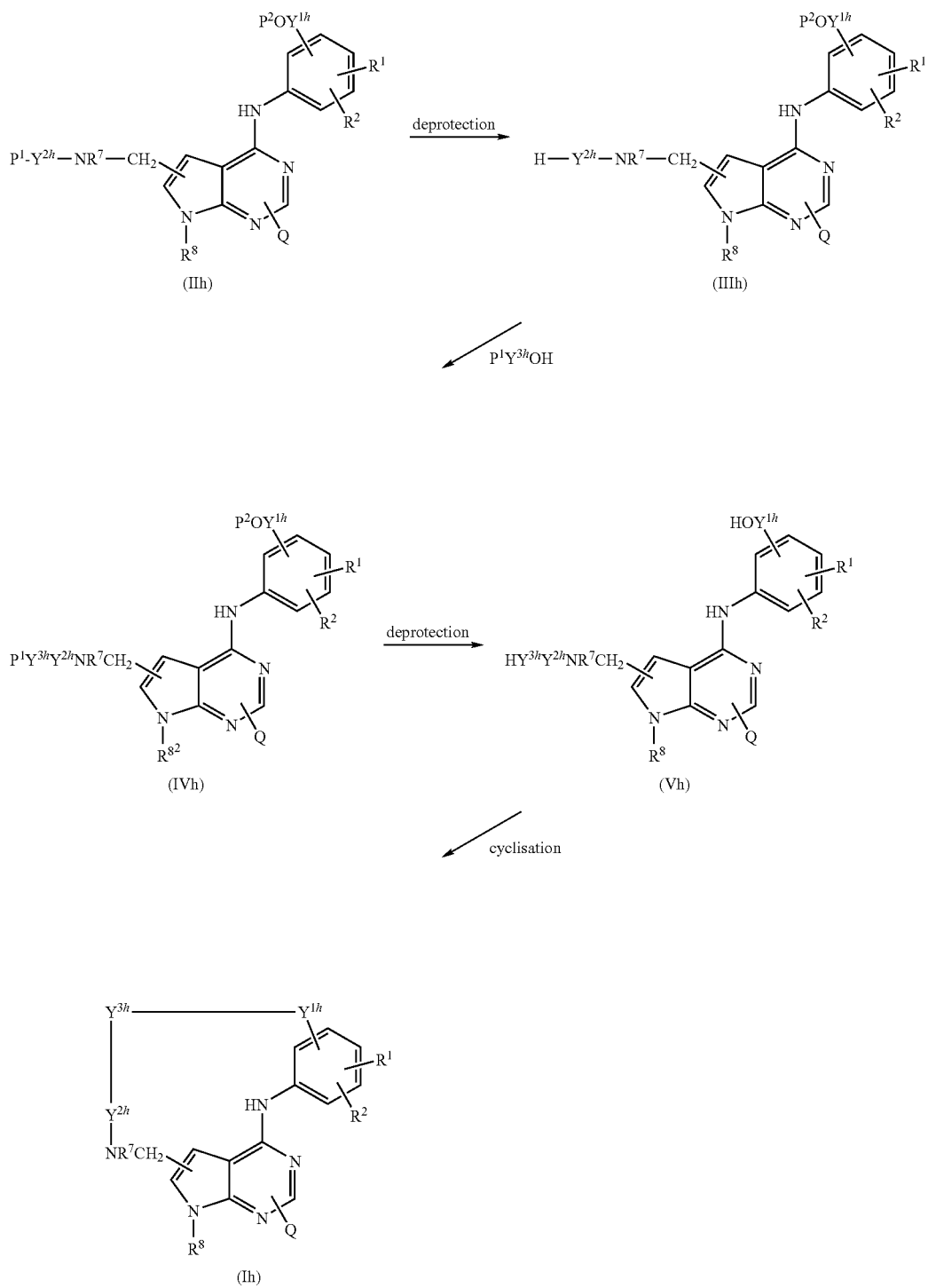

Scheme 6

In the above Scheme the initial deprotection of the amino function in the compound of formula (IIh) can be effected by treatment with anhydrous 4N hydrochloric acid in dioxane in an organic solvent such as ethanol. The reaction of the compound of formula (IIIb) with the compound of formula $P^1Y^{3h}OH$ can be effected using the same reagents and reaction conditions described above for the cyclisation reaction for example using PyBOP in the presence of a base such as triethylamine for example at 25° C.

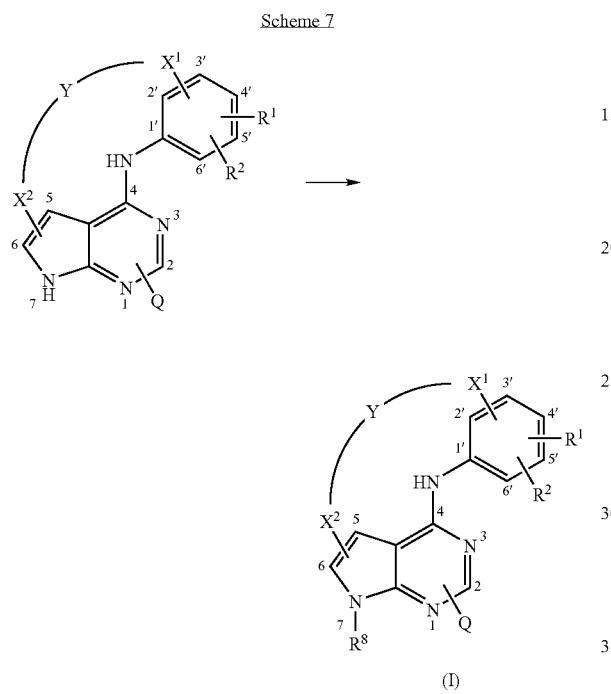

In the above scheme compounds of formula (I) can be effected by for example alkylation reactions with for example alkylhalides in an organic solvent as for example dimethylformamide in the presence of a base such as cesium carbonate.

The starting materials used in the above syntheses may be prepared in conventional manner or are available commercially.

For the preparation of the starting materials of formula (IIa) above the following process can be used:

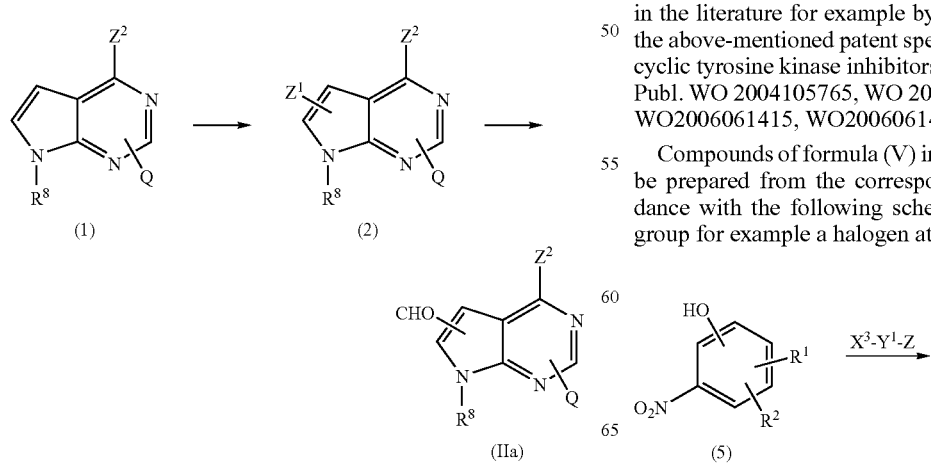

In the above Scheme the $Z^2$ leaving group is preferably a halogen atom such as a chlorine atom and $Z^1$ is generally a leaving group such as a halogen atom for example a bromine atom which is introduced by treating a compound of formula (1) with N-bromosuccinimide in an organic solvent such as dichloromethane and then reacting the resulting compound of formula (2) with butyllithium in an organic solvent such as tetrahydrofuran at −78° C. and subsequently quenching the resulting reaction product with dimethylformamide in an organic solvent such as tetrahydrofuran, also at −78° C.

For the preparation of the N-protected pyrrolopyrimidine starting materials of formula (IIc), used for example in Scheme 4, these can prepared in accordance with the following reaction Scheme:

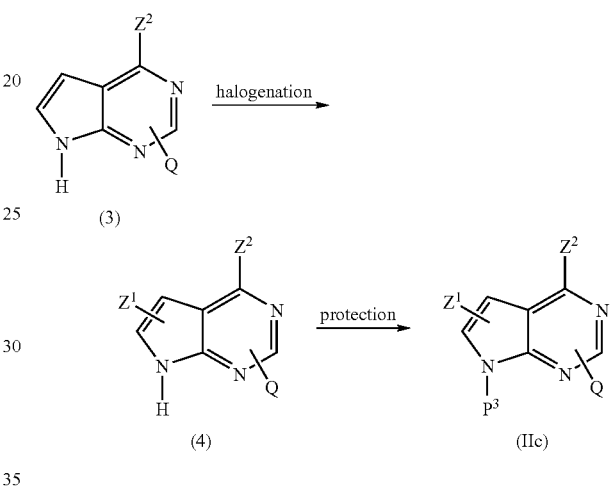

In the above reaction scheme the $Z^2$ leaving group is preferably a halogen atom such as a chlorine atom and the leaving group $Z^1$ is generally an iodine atom which is introduced by treating the compound of formula (3) with N-iodosuccinimide in an organic solvent for example dichloromethane at r.t. for about one hour, and then reacting the resulting compound of formula (4) with sodium hydride and introduction of an appropriate $P^3$ protecting group which is preferably an organosulphonyl group such as benzenesulphonyl for example by treatment with benzenesulphonyl chloride at a temperature between r.t. and 0° C.

The aniline starting materials can be prepared as described in the literature for example by the procedures described in the above-mentioned patent specifications relating to macrocyclic tyrosine kinase inhibitors, namely PCT Int. Pat. Appl. Publ. WO 2004105765, WO 2005058318, WO 2005058913, WO2006061415, WO2006061417 and WO 2007003525.

Compounds of formula (V) in which —$X^1$— is —O— can be prepared from the corresponding nitrophenol in accordance with the following scheme in which Z is a leaving group for example a halogen atom such as chlorine:

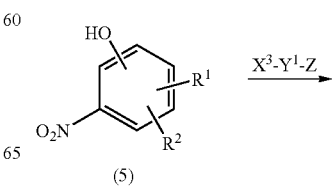

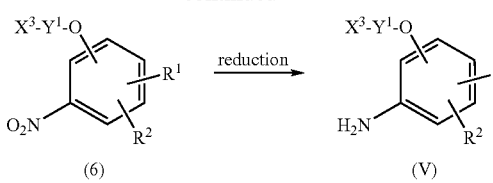

The reaction of the compounds of formulae (5) and (6) can be effected under alkaline conditions for example in the presence of a base such cesium carbonate in an organic solvent for example dimethylformamide. The resulting compound of formula (6) can then be reduced in conventional manner to the aniline compound of formula (V), for example by hydrogenation with palladium/carbon in the presence of a 4% thiophene solution in diisopropyl ether and in an organic solvent such as tetrahydrofuran.

For the preparation of such compounds in which $X^1$ is —$NR^5$— the corresponding nitro compound can be obtained for example in accordance with the procedure described in Tetrahedron Vol. 45, No. 24, pp 7817-7826, 1989.

Compounds of formula (V) in which —$Y^1$—$X^1$— is —$C_{1-6}$ alkyl-$NR^3$—$CH_2$— may be prepared for example by reductive amination of a corresponding commercially available 2-nitrobenzaldehyde in accordance with the following scheme:

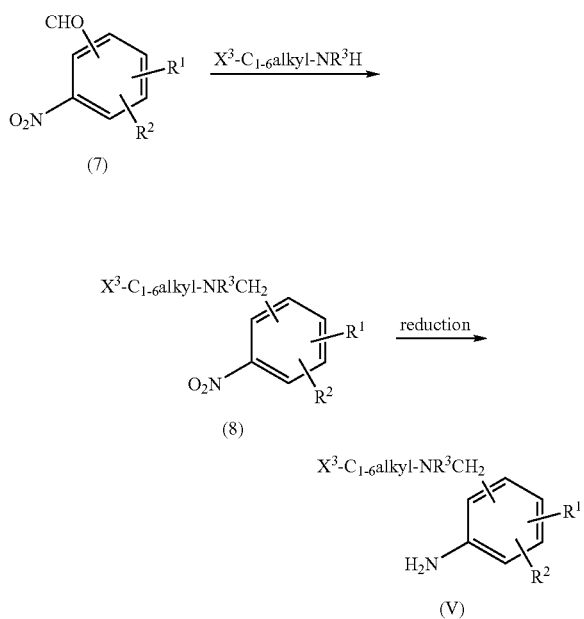

The compound of formula (7) is subjected to reductive amination in conventional manner for example as described above to form a nitro compound of formula (8) which is then reduced under conventional conditions for example as described above to form the desired aniline of formula (V).

Compounds of formula (V) in which —$Y^1$—$X^1$— is —CO—$C_{1-6}$alkyl-may be prepared for example by subjecting a 2-nitrobenzaldehyde of formula (9) to a Wittig reaction to obtain a compound of formula (10) which is then reduced in accordance with the following scheme in which n is 0 to 4:

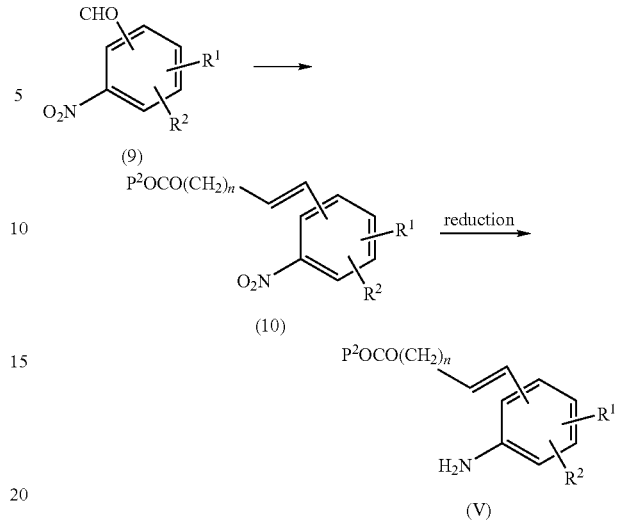

The compound of formula (9) is reacted with a (triphenylphosphorylidene)alkanoic acid ester in an organic solvent such as tetrahydrofuran and the resulting compound of formula (10) is then reduced under conventional conditions for example as described above to form the desired aniline of formula (V).

Where necessary or desired, any one or more of the following further steps in any order may be performed:

(i) removing any remaining protecting group(s);
(ii) converting a compound of formula (I) or a protected form thereof into a further compound of formula (I) or a protected form thereof;
(iii) converting a compound of formula (I) or a protected form thereof into a N-oxide, a salt, a quaternary amine or a solvate of a compound of formula (I) or a protected form thereof;
(iv) converting a N-oxide, a salt, a quaternary amine or a solvate of a compound of formula (I) or a protected form thereof into a compound of formula (I) or a protected form thereof;
(v) converting a N-oxide, a salt, a quaternary amine or a solvate of a compound of formula (I) or a protected form thereof into another N-oxide, a pharmaceutically acceptable addition salt a quaternary amine or a solvate of a compound of formula (I) or a protected form thereof;
(vi) where the compound of formula (I) is obtained as a mixture of (R) and (S) enantiomers resolving the mixture to obtain the desired enantiomer.

Compounds of formula (I), N-oxides, addition salts, quaternary amines and stereochemical isomeric forms thereof can be converted into further compounds according to the invention using procedures known in the art.

It will be appreciated by those skilled in the art that in the processes described above the functional groups of intermediate compounds may need to be blocked by protecting groups.

Functional groups, which are desirable to protect, include hydroxy, amino and carboxylic acid. Suitable protecting groups for hydroxy include trialkylsilyl groups (e.g. tert-butyldimethylsilyl, tert-butyldiphenylsilyl or trimethylsilyl), benzyl and tetrahydropyranyl. Suitable protecting groups for amino include tert-butyloxycarbonyl or benzyloxycarbonyl. Suitable protecting groups for carboxylic acid include $C_{1-6}$alkyl or benzyl esters.

The protection and deprotection of functional groups may take place before or after a reaction step.

Additionally, the N-atoms in compounds of formula (I) can be methylated by art-known methods using $CH_3$—I in a suitable solvent such as, for example 2-propanone, tetrahydrofuran or dimethylformamide. Alternatively N-atoms can be alkylated by treatment with an appropriate aldehyde and a reducing agent such as $NaBH(OAc)_3$.

Compounds of formula (I) in which $R^8$ is hydrogen, obtained in certain of the synthetic routes described above, can be converted into compounds of formula (I) in which $R^8$ is other than hydrogen in conventional manner for example by reaction with sodium hydride in dimethylformamide and treatment with an appropriate $R^8$ derivative for example an organosulphonyl derivative such as benzenesulfonyl chloride, or a halo alkyl derivative such as methyl iodide. Alternatively the conversion can be effected using an appropriate $R^8$ derivative such as $R^8OH$ in a Mitsunobu reaction with for example $Ph_3P$ and DEAD in an appropriate organic solvent such as tetrahydrofuran. Such conversions are further described by D. J. Calderwood et al, Bioorg. Med. Chem. Lett. 12, (2002), 1683-1686.

The compounds of formula (I) can also be converted into each other following art-known procedures of functional group transformation of which some examples are mentioned hereinafter.

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with 3-phenyl-2-(phenylsulfonyl)oxaziridine or with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t-butyl hydroperoxide. Suitable solvents are, for example, water, lower alkanols, e.g. ethanol and the like, hydro-carbons, e.g. toluene, ketones, e.g. 2-butanone, halogenated hydrocarbons, e.g. dichloromethane, and mixtures of such solvents.

Pure stereochemically isomeric forms of the compounds of formula (I) may be obtained by the application of art-known procedures. Diastereomers may be separated by physical methods such as fractional crystallization and chromatographic techniques, e.g. counter-current distribution, liquid chromatography and the like.

Some of the compounds of formula (I) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as fractional crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, fractional rystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I) and intermediates involves liquid chromatography, in particular liquid chromatography using a chiral stationary phase.

Some of the intermediates and starting materials as used in the reaction procedures mentioned hereinabove are known compounds and may be commercially available or may be prepared according to art-known procedures.

We have now surprisingly found that, the pyrrolopyrimidines defined hereinbefore possess potent anti-tumour activity. Without wishing to imply that the compounds disclosed in the present invention possess pharmacological activity only by virtue of an effect on a single biological process, it is believed that the compounds provide an anti-tumour effect by way of inhibition of one or more of protein kinases that are involved in the regulation of cellular mitosis and which lead to cytogenetic catastrophe in case of abberant activity.

It is thus an object of the present invention to provide the compounds of the present invention for use as a medicine. As used herein the compounds of the present invention includes the compounds of formula (I) as defined hereinbefore, including all subgroups and combinations thereof In one aspect, the compounds of the present invention may be useful for the treatment or prevention of cell proliferative disorders, including cancer, rheumatoid arthritis, restenosis and atherosclerosis. In the treatment of cancers said cancers include lung cancer (especially non small-cell lung cancer), breast cancer, liver cancer, ovarian cancer, prostate cancer, pancreatic cancer, colorectal cancer, gastrointestinal cancer such as colon, rectal or stomach cancer and papillary carcinomas (such as papillary thyroid cancer), squamous cell cancers of the head and neck, oesophageal cancers including oropharyngeal cancer, and fast-dividing leukaemias such as acute myelogenous leukaemia (AML).

The compounds of the present invention may be administered alone or in combination with one or more additional therapeutic agents. Combination therapy includes administration of a single pharmaceutical dosage formulation which contains a compound of formula (I) and one or more additional therapeutic agents, as well as administration of the compound of formula (I) and each additional therapeutic agents in its own separate pharmaceutical dosage formulation. For example, a compound of formula (I) and a therapeutic agent may be administered to the patient together in a single oral dosage composition such as a tablet or capsule, or each agent may be administered in separate oral dosage formulations.

Where separate dosage formulations are used, the compounds of the present invention and one or more additional therapeutic agents may be administered at essentially the same time (e.g., concurrently) or at separately staggered times (e.g., sequentially).

For example the compounds of the present invention could be used in combination with other anti-cancer agents. Examples of anti-cancer agents are:
- platinum coordination compounds for example cisplatin, carboplatin or oxalyplatin;
- taxane compounds for example paclitaxel or docetaxel;
- topoisomerase I inhibitors such as camptothecin compounds for example irinotecan or topotecan;
- topoisomerase II inhibitors such as anti-tumour podophyllotoxin derivatives for example etoposide or teniposide;

anti-tumour vinca alkaloids for example vinblastine, vincristine or vinorelbine;

anti-tumour nucleoside derivatives for example 5-fluorouracil, gemcitabine or capecitabine;

alkylating agents such as nitrogen mustard or nitrosourea for example cyclophosphamide, chlorambucil, carmustine or lomustine;

anti-tumour anthracycline derivatives for example daunorubicin, doxorubicin, idarubicin or mitoxantrone;

HER2 antibodies for example trastuzumab;

estrogen receptor antagonists or selective estrogen receptor modulators for example tamoxifen, toremifene, droloxifene, faslodex or raloxifene;

aromatase inhibitors such as exemestane, anastrozole, letrazole and vorozole;

differentiating agents such as retinoids, vitamin D and retinoic acid metabolism blocking agents (RAMBA) for example accutane;

DNA methyl transferase inhibitors for example azacytidine;

kinase inhibitors for example flavoperidol, imatinib mesylate or gefitinib;

farnesyltransferase inhibitors for example tipifarnib;

Histone Deacetylase (HDAC) inhibitors for example sodium butyrate, suberoylanilide hydroxamide acid (SAHA) and trichostatin A;

Inhibitors of the ubiquitin-proteasome pathway for example PS-341, MLN 0.41 or bortezomib;

Yondelis;

Telomerase inhibitors for example telomestatin;

Matrix metalloproteinase inhibitors for example batimastat, marimastat, prinostat and metastat.

The term "platinum coordination compound" is used herein to denote any tumour cell growth inhibiting platinum coordination compound which provides platinum in the form of an ion.

The term "taxane compounds" indicates a class of compounds having the taxane ring system and related to or derived from extracts from certain species of yew (Taxus) trees.

The term "topisomerase inhibitors" is used to indicate enzymes that are capable of altering DNA topology in eukaryotic cells. They are critical for important cellular functions and cell proliferation. There are two classes of topoisomerases in eukaryotic cells, namely type I and type II. Topoisomerase I is a monomeric enzyme of approximately 100,000 molecular weight. The enzyme binds to DNA and introduces a transient single-strand break, unwinds the double helix (or allows it to unwind) and subsequently reseals the break before dissociating from the DNA strand. Topisomerase II has a similar mechanism of action which involves the induction of DNA strand breaks or the formation of free radicals.

The term "camptothecin compounds" is used to indicate compounds that are related to or derived from the parent camptothecin compound which is a water-insoluble alkaloid derived from the Chinese tree Camptothecin acuminata and the Indian tree Nothapodytes foetida.

The term "podophyllotoxin compounds" is used to indicate compounds that are related to or derived from the parent podophyllotoxin, which is extracted from the mandrake plant.

The term "anti-tumour vinca alkaloids" is used to indicate compounds that are related to or derived from extracts of the periwinkle plant (Vinca rosea).

The term "alkylating agents" encompass a diverse group of chemicals that have the common feature that they have the capacity to contribute, under physiological conditions, alkyl groups to biologically vital macromolecules such as DNA. With most of the more important agents such as the nitrogen mustards and the nitrosoureas, the active alkylating moieties are generated in vivo after complex degradative reactions, some of which are enzymatic. The most important pharmacological actions of the alkylating agents are those that disturb the fundamental mechanisms concerned with cell proliferation in particular DNA synthesis and cell division. The capacity of alkylating agents to interfere with DNA function and integrity in rapidly proliferating tissues provides the basis for their therapeutic applications and for many of their toxic properties.

The term "anti-tumour anthracycline derivatives" comprise antibiotics obtained from the fungus *Strep. peuticus var. caesius* and their derivatives, characterised by having a tetracycline ring structure with an unusual sugar, daunosamine, attached by a glycosidic linkage.

Amplification of the human epidermal growth factor receptor 2 protein (HER 2) in primary breast carcinomas has been shown to correlate with a poor clinical prognosis for certain patients. Trastuzumab is a highly purified recombinant DNA-derived humanized monoclonal IgG1 kappa antibody that binds with high affiniity and specificity to the extracellular domain of the HER2 receptor.

Many breast cancers have estrogen receptors and growth of these tumours can be stimulated by estrogen. The terms "estrogen receptor antagonists" and "selective estrogen receptor modulators" are used to indicate competitive inhibitors of estradiol binding to the estrogen receptor (ER). Selective estrogen receptor modulators, when bound to the ER, induces a change in the three-dimensional shape of the receptor, modulating its binding to the estrogen responsive element (ERE) on DNA.

In postmenopausal women, the principal source of circulating estrogen is from conversion of adrenal and ovarian androgens (androstenedione and testosterone) to estrogens (estrone and estradiol) by the aromatase enzyme in peripheral tissues. Estrogen deprivation through aromatase inhibition or inactivation is an effective and selective treatment for some postmenopausal patients with hormone-dependent breast cancer.

The term "antiestrogen agent" is used herein to include not only estrogen receptor antagonists and selective estrogen receptor modulators but also aromatase inhibitors as discussed above.

The term "differentiating agents" encompass compounds that can, in various ways, inhibit cell proliferation and induce differentiation. Vitamin D and retinoids are known to play a major role in regulating growth and differentiation of a wide variety of normal and malignant cell types. Retinoic acid metabolism blocking agents (RAMBA's) increase the levels of endogenous retinoic acids by inhibiting the cytochrome P450-mediated catabolism of retinoic acids.

DNA methylation changes are among the most common abnormalities in human neoplasia. Hypermethylation within the promotors of selected genes is usually associated with inactivation of the involved genes. The term "DNA methyl transferase inhibitors" is used to indicate compounds that act through pharmacological inhibition of DNA methyl transferase and reactivation of tumour suppressor gene expression.

The term "kinase inhibitors" comprises potent inhibitors of kinases that are involved in cell cycle progression and programmed cell death (apoptosis).

The term "farnesyltransferase inhibitors" is used to indicate compounds that were designed to prevent farnesylation of Ras and other intracellular proteins. They have been shown to have effect on malignant cell proliferation and survival.

The term "histone deacetylase inhibitor" or "inhibitor of histone deacetylase" is used to identify a compound, which is capable of interacting with a histone deacetylase and inhibiting its activity, more particularly its enzymatic activity. Inhibiting histone deacetylase enzymatic activity means reducing the ability of a histone deacetylase to remove an acetyl group from a histone.

The term "other inhibitors of the ubiquitin-proteasome pathway" is used to indentify compounds that inhibit the targeted destruction of cellular proteins in the proteasome, including cell cycle regulatory proteins.

The term "telomerase inhibitor" refers to compounds which target, decrease or inhibit the activity of telomerase, especially compounds which inhibit the telomerase receptor.

The term "matrix metalloproteinase inhibitor" includes but is not limited to, collagen peptidomimetic and non-peptidomimetic inhibitors.

The compounds of the present invention can be used as "radiosensitizer" and/or "chemosensitizer".

Radiosensitizers are known to increase the sensitivity of cancerous cells to the toxic effects of ionizing radiation. Several mechanisms for the mode of action of radiosensitizers have been suggested in the literature including: hypoxic cell radiosensitizers (e.g., 2-nitroimidazole compounds, and benzotriazine dioxide compounds) mimicking oxygen or alternatively behave like bioreductive agents under hypoxia; non-hypoxic cell radiosensitizers (e.g., halogenated pyrimidines) can be analogs of DNA bases and preferentially incorporate into the DNA of cancer cells and thereby promote the radiation-induced breaking of DNA molecules and/or prevent the normal DNA repair mechanisms; and various other potential mechanisms of action have been hypothesized for radiosensitizers in the treatment of disease. Many cancer treatment protocols currently employ radiosensitizers in conjunction with radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumour with or without additional radiation; or other therapeutically effective compounds for treating cancer or other disease. Examples of additional therapeutic agents that may be used in conjunction with radiosensitizers include, but are not limited to: 5-fluorouracil, leucovorin, 5'-amino-5'deoxythymidine, oxygen, carbogen, red cell transfusions, perfluorocarbons (e.g., Fluosol 10 DA), 2,3-DPG, BW12C, calcium channel blockers, pentoxyfylline, antiangiogenesis compounds, hydralazine, and LBSO. Examples of chemotherapeutic agents that may be used in conjunction with radiosensitizers include, but are not limited to: adriamycin, camptothecin, carboplatin, cisplatin, daunorubicin, docetaxel, doxorubicin, interferon (alpha, beta, gamma), interleukin 2, irinotecan, paclitaxel, topotecan, and therapeutically effective analogs and derivatives of the same.

Chemosensitizers may be administered in conjunction with a therapeutically effective amount of one or more other compounds, including but not limited to: compounds which promote the incorporation of chemosensitizers to the target cells; compounds which control the flow of therapeutics, nutrients, and/or oxygen to the target cells; chemotherapeutic agents which act on the tumour or other therapeutically effective compounds for treating cancer or other disease.

In view of the above described pharmacological properties, the compounds of formula (I) or any subgroup thereof, their N-oxides, pharmaceutically acceptable addition salts, quaternary amines and stereochemically isomeric forms, may be used as a medicine. In particular, the present compounds can be used for the manufacture of a medicament for treatment of any one of the disease conditions mentioned hereinbefore, in particular for the manufacture of a medicament for the treatment of cancer including lung cancer (especially non small-cell lung cancer), breast cancer, liver cancer, ovarian cancer, prostate cancer, pancreatic cancer, colorectal cancer, gastrointestinal cancer such as colon, bladder, rectal or stomach cancer and papillary carcinomas (such as papillary thyroid cancer), squamous cell cancers of the head and neck, oesophageal cancers including oropharyngeal cancer, and fast-dividing leukaemias such as acute myelogenous leukaemia (AML).

In view of the utility of the compounds of formula (I) there is provided a method of treating warm-blooded animals, including humans, suffering from or a method of preventing warm-blooded animals, including humans, to suffer from any one of the diseases mentioned hereinbefore, such as cancer including lung cancer (especially non small-cell lung cancer), breast cancer, liver cancer, ovarian cancer, prostate cancer, pancreatic cancer, colorectal cancer, gastrointestinal cancer such as colon, bladder, rectal or stomach cancer and papillary carcinomas (such as papillary thyroid cancer) as well as in squamous cell cancers of the head and neck and in oesophageal cancers including oropharyngeal cancer. Said methods comprise the administration, i.e. the systemic or topical administration, preferably oral administration, of an effective amount of a compound of formula (I), a N-oxide form, a pharmaceutically acceptable addition salt, a quaternary amine or a possible stereoisomeric form thereof, to warm-blooded animals, including humans.

One skilled in the art will recognize that a therapeutically effective amount of the compounds of the present invention is the amount sufficient to have anti-tumour activity and that this amount varies inter alias, depending on the type of disease, the concentration of the compound in the therapeutic formulation, and the condition of the patient. Generally, the amount of a compound of the present invention to be administered as a therapeutic agent for treating cell proliferative disorders such as cancer, rheumatoid arthritis, restenosis and atherosclerosis will be determined on a case by case by an attending physician.

Generally, a suitable dose is one that results in a concentration of the compounds of the present invention at the treatment site in the range of 0.5 nM to 200 µM, and more usually 5 nM to 50 µM. To obtain these treatment concentrations, a patient in need of treatment likely will be administered between 0.01 mg/kg to 250 mg/kg body weight, in particular from 0.1 mg/kg to 50 mg/kg body weight. The amount of a compound according to the present invention, also referred to here as the active ingredient, which is required to achieve a therapeutically effect will be, of course vary on case-by-case basis, for example with the particular compound, the route of administration, the age and condition of the recipient, and the particular disorder or disease being treated. A method of treatment may also include administering the active ingredient on a regimen of between one and four intakes per day. In these methods of treatment the compounds according to the invention are preferably formulated prior to admission. As described herein below, suitable pharmaceutical formulations are prepared by known procedures using well known and readily available ingredients.

The present invention also provides compositions for preventing or treating cell proliferative diseases, such as cancer, rheumatoid arthritis, restenosis and atherosclerosis. Said compositions comprising a therapeutically effective amount of a compound of formula (I) and a pharmaceutically acceptable carrier or diluent.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof The pharmaceutical compositions of this invention may be prepared by any methods well known in the art of pharmacy, for example, using methods such as those described in Gennaro et al. Remington's Pharmaceutical Sciences (18$^{th}$ ed., Mack Publishing Company, 1990, see especially Part 8: Pharmaceutical preparations and their Manufacture). A therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The present compounds can be used for systemic administration such as oral, percutaneous or parenteral administration; or topical administration such as via inhalation, a nose spray, eye drops or via a cream, gel, shampoo or the like. The compounds are preferably orally administered. The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

The following examples illustrate the present invention.

Experimental Part

In obtaining the compounds described in the examples below, the following experimental protocols were followed unless otherwise indicated.

Unless otherwise stated, reaction mixtures were magnetically stirred at r.t. Where solutions were "dried," they were generally dried over a drying agent such as $Na_2SO_4$ or $MgSO_4$. Where mixtures, solutions, and extracts were "concentrated", they were typically concentrated on a rotary evaporator under reduced pressure.

Hereinafter, the term "DMA" means N,N-dimethylacetamide, "DIPEA" means N-ethyl-N-(1-methylethyl)-2-propanamine, "DCM" means dichloromethane, "MeOH" means methanol, "EtOAc" means ethyl acetate, "HBTU" means 1-[bis(dimethylamino)methylene]-1H-benzotriazolium-hexafluorophosphate(1-)3-oxide, "DMF" means N,N-dimethylformamide, "TFA" means trifluoroacetic acid, "PyBOP" means 1-benzotriazolyloxytripyrrolidinylphosphonium hexafluorophosphate, "EtOH" means ethanol, "DIPE" means diisopropyl ether, "THF" means tetrahydrofuran, "LCMS" means Liquid Chromatography/Mass spectrometry, "eq." means equivalent, "t-BuOH" means t-butanol, "HPLC" means high-performance liquid chromatography, "HOAc" acetic acid, "BOC-anhydride" means di-tert-butyl dicarbonate, "DMAP" means N,N-Dimethyl-4-pyridinamine, "DIAD" means diisopropyl diazodicarboxylate, "DMSO" means dimethyl sulfoxide, "$CH_3CN$" means acetonitrile, "r.t." means room temperature, "p.a." means pro analyse, "aq." means aqueous, "$(Ph)_3P$" means triphenylphosphine and "$Et_2O$" means diethyl ether.

For some compounds that were purified by reversed phase high-performance liquid chromatography (HPLC) the used method is described below (indicated in the compound procedure with HPLC method A, HPLC method B, HPLC method C). When necessary, these methods can be slightly adjusted by a person skilled in the art to obtain a more optimal result for the separation.

HPLC Method A

The product was purified by reversed-phase HPLC (Shandon Hyperprep® C18 BDS (Base Deactivated Silica) 8 μm, 250 g, I.D. 5 cm). Three mobile phases were used (phase A: a 0.25% NH$_4$HCO$_3$ solution in H$_2$O; phase B: CH$_3$OH; phase C: CH$_3$CN). First, 75% A and 25% B with a flow rate of 40 ml/min was hold for 0.5 minutes. Then a gradient was applied to 100% B in 41 minutes with a flow rate of 80 ml/min. Then a gradient was applied to 100% C in 20 minutes with a flow rate of 80 ml/min and hold for 4 minutes.

HPLC Method B

The product was purified by reversed-phase HPLC (Shandon Hyperprep® C18 BDS (Base Deactivated Silica) 8 μm, 250 g, I.D. 5 cm). Two mobile phases were used (phase A: a 0.25% NH$_4$HCO$_3$ solution in H$_2$O; phase B: CH$_3$CN). First, 85% A and 15% B with a flow rate of 40 ml/min was hold for 0.5 minutes. Then a gradient was applied to 10% A and 90% B in 41 minutes with a flow rate of 80 ml/min. Then a gradient was applied to 100% C in 20 minutes with a flow rate of 80 ml/min and hold for 4 minutes.

HPLC Method C

The product was purified by reversed-phase HPLC (Shandon Hyperprep® C18 BDS (Base Deactivated Silica) 8 μm, 250 g, I.D. 5 cm). Three mobile phases were used (phase A: a 0.25% NH$_4$HCO$_3$ solution in H$_2$O; phase B: CH$_3$OH; phase C: CH$_3$CN). First, 75% A and 25% B with a flow rate of 40 ml/min was hold for 0.5 minutes. Then a gradient was applied to 50% B and 50% C in 41 minutes with a flow rate of 80 ml/min. Then a gradient was applied to 100% C in 20 minutes with a flow rate of 80 ml/min and hold for 4 minutes.

A. Preparation of the Intermediates

Example A1 a) Preparation of Intermediate 1

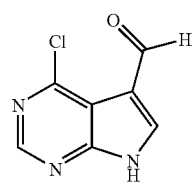

Reaction under N$_2$ atmosphere. A mixture of 5-bromo-4-chloro-7H-pyrrolo[2,3-d]pyrimidine (0.010 mol) in THF (65 ml; dry) was stirred at −78° C. BuLi (0.022 mol; 2.5 M) was added dropwise at −78° C. Then the mixture was stirred for 30 minutes at −78° C. DMF (2 ml; dry) was added dropwise at −78° C. and the reaction mixture was stirred at r.t. for 1 hour. An aq. NH$_4$Cl solution was added (decomposition). This mixture was extracted with EtOAc. The separated organic layer was dried, filtered and the solvent was evaporated. The residue (1.9 g) was stirred in DIPE, filtered off and dried. Yield: 1.420 g of intermediate 1.

b) Preparation of Intermediate 2

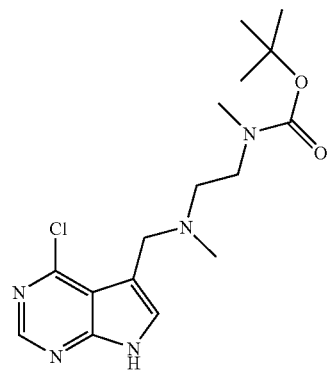

A mixture of N-(2-aminoethyl)-N-methylcarbamic acid 1,1-dimethylethyl ester (1.044 g, 0.0060 mol) and NaBH(OAc)$_3$ (3.2 g, 0.015 mol) in DCM (50 ml) was stirred at r.t. A solution of intermediate 1 (0.905 g, 0.0050 mol) in THF/DMF 1/1 (70 ml) was added dropwise. Stirring was continued for 16 hours. Then more NaBH(OAc)$_3$ (3.2 g, 0.015 mol) was added. Formaldehyde (2 ml; 40%) dissolved in THF (10 ml) was added dropwise. Stirring was continued for 16 hours The reaction mixture was poured into H$_2$O, basified with K$_2$CO$_3$ and extracted with DCM. The organic layer was dried (MgSO$_4$), filtered and the solvent was evaporated. The residue was purified on silica (eluent: DCM/(MeOH/NH$_3$) 90/10. Yield: 1.6 g of intermediate 2 (90.6%).

Example A2 a) Preparation of Intermediate 3

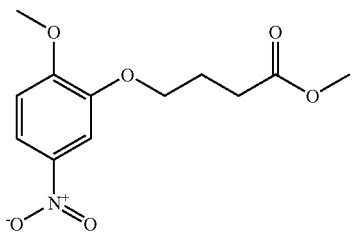

A mixture of 2-methoxy-5-nitrophenol (0.001 mol), 4-chlorobutanoic acid methyl ester (0.0013 mol) and Cs$_2$CO$_3$ (1.63 g) in DMF (30 ml) was stirred at r.t. When the reaction was finished, the solvent was evaporated. The residue was partitioned between H$_2$O and toluene (3×). The organic layers were combined, dried (MgSO$_4$), filtered and the solvent was evaporated. Yield: 0.250 g of intermediate 3.

b) Preparation of Intermediate 4

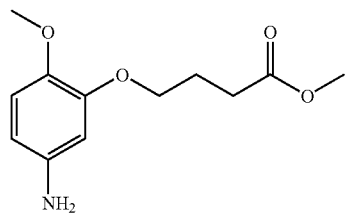

A mixture of intermediate 3 (0.0008 mol) in MeOH (40 ml) was hydrogenated with Pd/C 10% (1 g) as a catalyst in the presence of a thiophene solution (0.1 ml; 4% in DIPE). After uptake of $H_2$ (3 eq.), the catalyst was filtered off and the filtrate was evaporated. Yield: 0.158 g of intermediate 4.

Example A3 a) Preparation of Intermediate 5

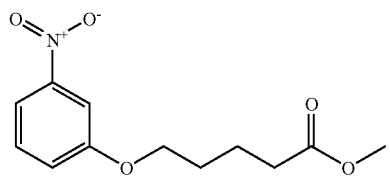

3-Nitrophenol (5 g, 0.036 mol) was dissolved in DMA (70 ml). 5-Bromopentanoic acid methyl ester (7.7 g, 0.0395 mol) was added. $K_2CO_3$ (5.5 g, 0.0395 mol) was added to the stirred solution and the mixture was stirred overnigth at 60° C. After completion of the reaction (TLC monitoring), the mixture was partitioned between EtOAc and brine. The layers were separated and the organic layer dried ($MgSO_4$), filtered and concentrated. The resulting product was dried under high vacuum. Yield: 9.3 g of intermediate 5 (used as such in next reaction step).

b) Preparation of Intermediate 6

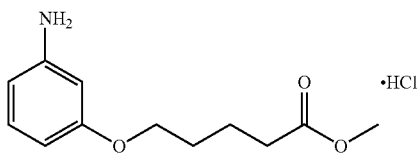

Intermediate 5 (9.3 g., 0.036 mol) was dissolved in EtOH (175 ml). A thiophene solution (4 ml; 2% in DIPE) was added, followed by addition of Pd/C 10% as catalyst. After a $N_2$ purge, $H_2$ was introduced through a gas-bag. The reaction mixture was hydrogenated for 40 hours at r.t. The catalyst was filtered off over a Celite-pad. HCl in dioxane (13 ml; 4 N) was added to the filtrate and the mixture was concentrated under reduced pressure. THF was added to the residue and the resulting solid was filtered off, washed with DIPE and dried. Yield: 7.0 g of intermediate 6 (.HCl).

Example A4 a) Preparation of Intermediate 7

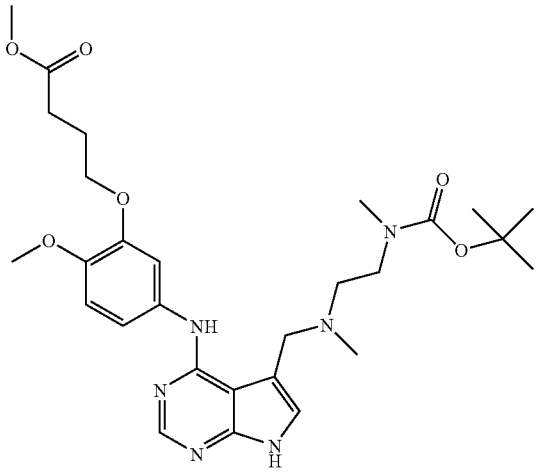

First intermediate 4 was converted into its HCl-salt.

A mixture of intermediate 2 (0.00042 mol) and the HCl-salt of intermediate 4 (1.1 eq.; 0.00046 mol) in $CH_3CN$/2-propanol 3/1 (2 ml) and HCl/2-propanol (q.s.) was heated for 4 hours at 80° C. The solvent was evaporated and the crude residue was purified by flash column chromatography over silica gel (eluent: DCM/MeOH gradient). The product fractions were collected and the solvent was evaporated, yielding intermediate 7.

b) Preparation of Intermediate 8

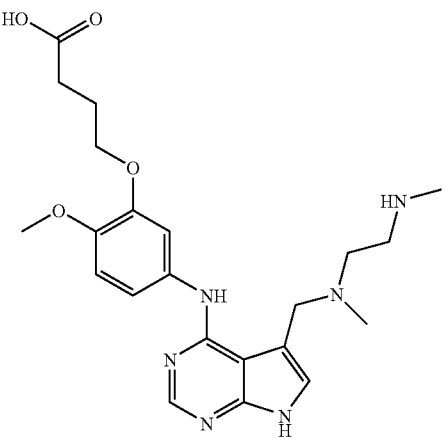

A mixture of intermediate 7 (max. 0.00042 mol) and LiOH (3 eq.) was stirred in $THF/H_2O$ 1/1 (5 ml) at r.t. for 6 hours. HOAc (q.s.) was added until pH=6-7. The reaction mixture was extracted with DCM (3×5 ml). The organic layers were combined, dried, filtered and the solvent was evaporated. The residue was stirred in TFA/DCM 1/1 (5 ml) for 6 hours at r.t. The solvent was evaporated. Yield: intermediate 8 (used in next reaction step, without further purification).

Example A5 a) Preparation of Intermediate 9

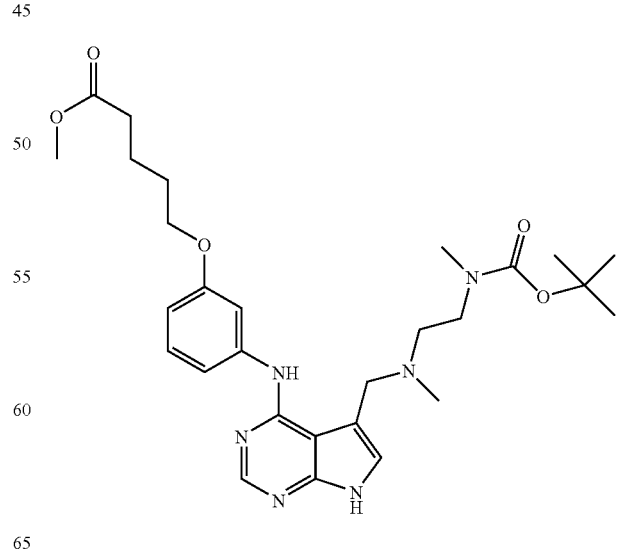

A mixture of intermediate 2 (0.00042 mol) and intermediate 6 (1.1 eq.; 0.00046 mol) in $CH_3CN$/2-propanol (2 ml) and HCl/2-propanol (q.s.) was heated for 4 hours at 80° C. The solvent was evaporated and the crude residue was purified by flash column chromatography over silica gel (eluent: DCM/MeOH gradient). The product fractions were collected and the solvent was evaporated. Yield: intermediate 9.

b) Preparation of Intermediate 10

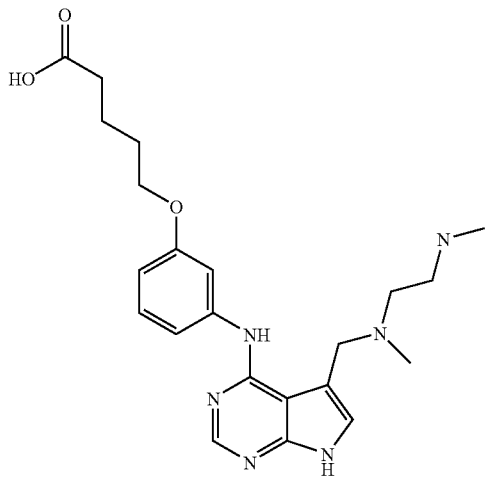

A mixture of intermediate 9 (max. 0.00042 mol) and LiOH (3 eq.) was stirred in THF/H$_2$O 1/1 (5 ml) at r.t. for 6 hours. HOAc (q.s.) was added until pH 6-7. The reaction mixture was extracted with DCM (3×5 ml). The organic layers were combined, dried, filtered and the solvent was evaporated. The residue was stirred in TFA/DCM 1/1 (5 ml) for 6 hours at r.t. The solvent was evaporated. Yield: intermediate 10 (used in next reaction step, without further purification).

Example A6 a) Preparation of intermediate 11

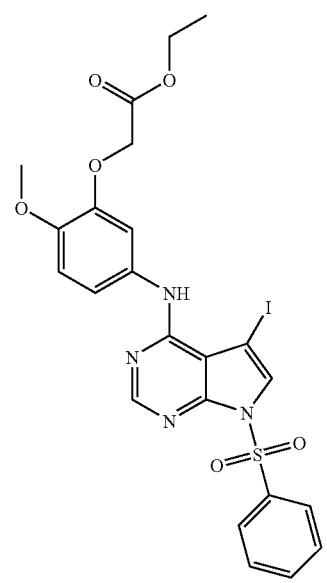

A mixture of 4-chloro-5-iodo-7-(phenylsulfonyl)-7H-Pyrrolo[2,3-d]pyrimidine (0.005 mol), (5-amino-2-methoxyphenoxy)acetic acid ethyl ester (0.0055 mol) and HCl/dioxane (0.5 ml) in t-BuOH (100 ml) was stirred for 40 hours at 80° C. The mixture was purified by HPLC. Three product fraction groups were collected and the solvent was evaporated. The main product fraction group yielded 1.5 g of intermediate 11.

b) Preparation of Intermediate 12

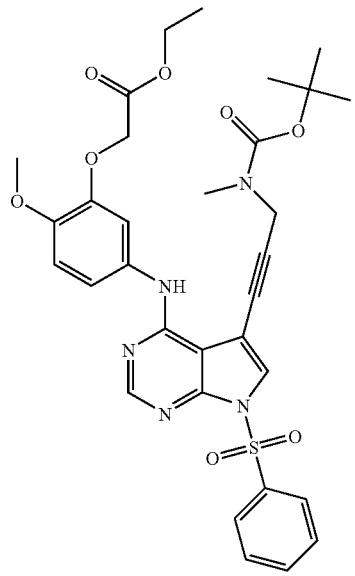

A mixture of intermediate 11 (0.0246 mol), dichlorobis(triphenylphosphine)palladium (0.00246 mol) and CuI (0.00246 mol) in Et$_3$N (250 ml) and DMA (250 ml) was stirred at r.t. A solution of N-methyl-N-2-propyn-1-yl-carbamic acid 1,1-dimethylethyl ester (0.0492 mol) in DMA (q.s.) was added dropwise and the resultant reaction mixture was stirred for 2 hours at r.t. The mixture was poured out into H$_2$O and was extracted 3× with EtOAc. The combined organic layers were washed with H$_2$O (2×), dried, filtered and the solvent was evaporated. The residue was purified by column chromatography over silica gel (eluent: EtOAc/hexane from 30/70 to 70/30). The desired product fractions were collected and the solvent was evaporated. The residue was stirred in DIPE, filtered off and dried. Yield: 11.8 g of intermediate 12 (79.9%).

c) Preparation of Intermediate 13

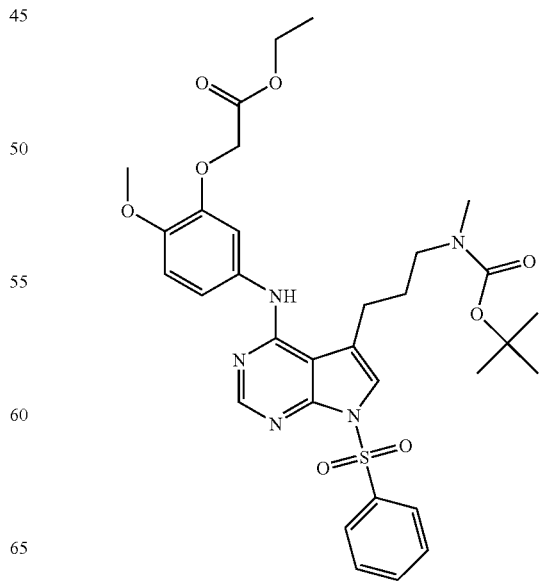

A mixture of intermediate 12 (0.019 mol) in THF (250 ml) was hydrogenated with Raney Nickel (1 g) as a catalyst. After uptake of $H_2$ (2 eq.), the catalyst was filtered off and the filtrate was evaporated. Yield: 12.8 g of intermediate 13 (quantitative yield; used in next reaction step, without further purification).

d) Preparation of Intermediate 14

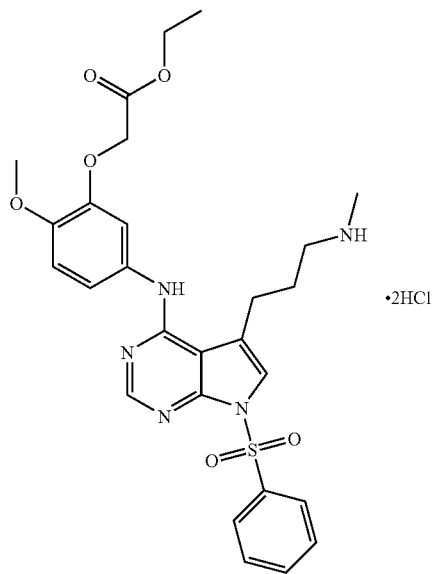

A mixture of intermediate 13 (0.019 mol) in EtOH (700 ml; p.a.) and HCl/dioxane (60 ml; 4 N) was stirred for 4 days at r.t. and then for 16 hours at 50° C. The solvent was evaporated. The residue was taken up in DIPE. The precipitate was filtered off and dried. Yield: 10.6 g of intermediate 14 (0.2 HCl; 89.5%).

e) Preparation of Intermediate 15

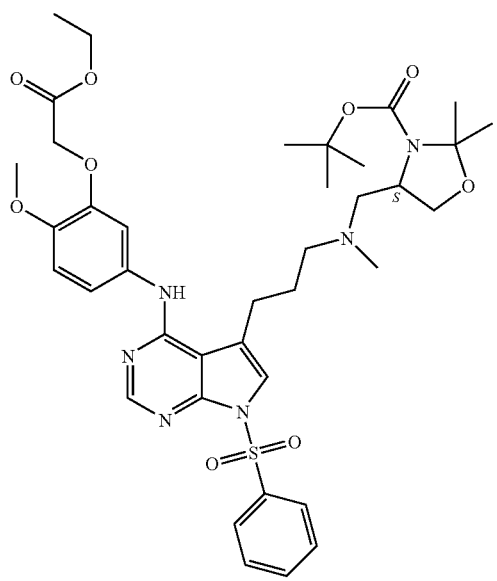

A mixture of intermediate 14 (0.001 mol) and $Et_3N$ (0.0003 mol) in DCM (50 ml) was stirred at r.t. NaBH(OAc)$_3$ (0.003 mol) was added portionwise. 4R-4-formyl-2,2-dimethyl-3-oxazolidinecarboxylic acid 1,1-dimethylethyl ester (0.0015 mol) was added portionwise. The resultant reaction mixture was stirred for 16 hours at r.t. The mixture was poured out into $H_2O$ and was then alkalized with $K_2CO_3$. This mixture was extracted with DCM. The separated organic layer was dried, filtered and the solvent evaporated. Yield: intermediate 15 (quantitative yield; used in next reaction step, without further purification).

f) Preparation of Intermediate 16

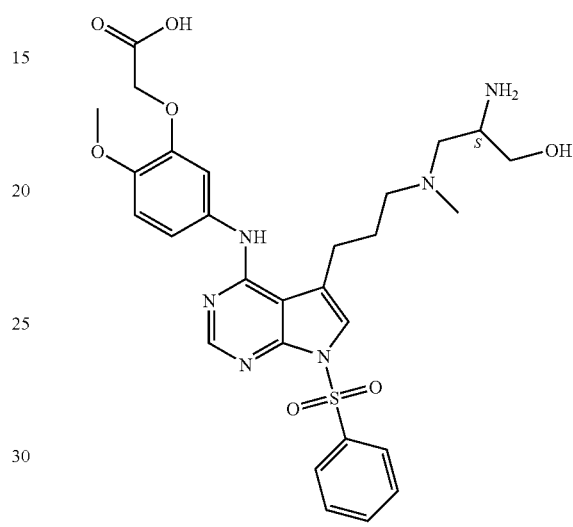

A mixture of intermediate 15 (0.001 mol) in dioxane (30 ml), $H_2O$ (30 ml) and HCl (15 ml; 36%) was stirred for 2 hours at 60° C. The solvent was evaporated. The residue was purified by HPLC. The product fractions were collected and the solvent was evaporated. $CH_3CN$ was added and was then evaporated again (2×). Yield: 0.458 g of intermediate 16 (76.6%; S-enantiomer).

g) Preparation of Intermediate 17

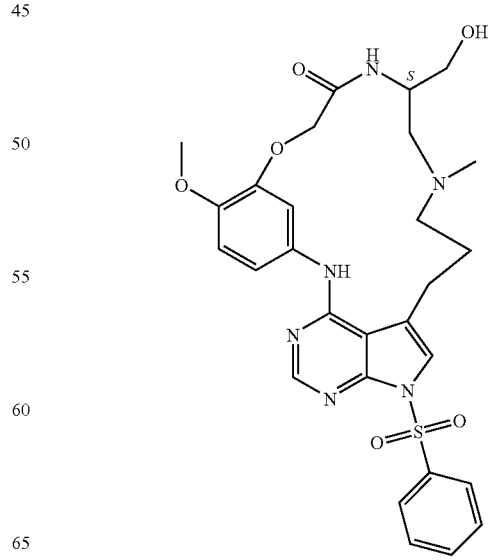

A mixture of PyBOP (2.600 g) and Et₃N (0.300 g) in DMF (50 ml) was stirred at r.t. under N₂ atmosphere. A solution of intermediate 16 (0.00076 mol) in DMF (50 ml) was added dropwise. The resultant reaction mixture was stirred for one hour at r.t. H₂O was added (decomposition). The solvent was evaporated. The residue was purified by HPLC. The product fractions were collected and the solvent was evaporated, yielding intermediate 17 (S-enantiomer).

Example A7 a) Preparation of Intermediate 18

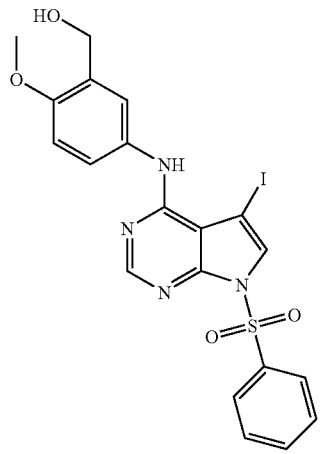

A mixture of 4-chloro-5-iodo-7-(phenylsulfonyl)-7H-Pyrrolo[2,3-d]pyrimidine (0.005 mol), 5-amino-2-methoxy-benzenemethanol (0.0051 mol) and HCl/dioxane (0.5 ml; 1 N) in t-BuOH (100 ml) was stirred for 3 days at 80° C. The solvent was evaporated. The residue was purified by HPLC. The product fractions were collected and the solvent was evaporated. The residue was taken up into H₂O. This mixture was extracted with DCM. The separated organic layer was dried, filtered and the solvent evaporated. Yield: 1.85 g of intermediate 18 (69%).

b) Preparation of Intermediate 19

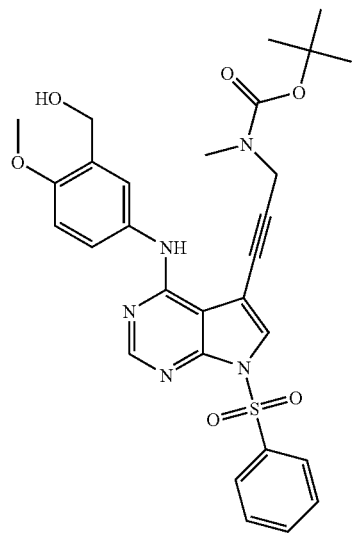

Reaction mixture (I): A mixture of intermediate 18 (0.0003 mol), dichlorobis(triphenylphosphine)palladium (0.00006 mol) and CuI (0.00006 mol) in Et₃N (5 ml) and DMA (5 ml) was stirred at r.t. A solution of N-methyl-N-2-propyn-1-yl-carbamic acid, 1,1-dimethylethyl ester (0.00075 mol) in DMA (2 ml) was added dropwise. The reaction mixture was stirred for one hour at r.t. Reaction mixture (II): A mixture of A (0.003 mol), dichlorobis(triphenylphosphine)palladium (0.0006 mol) and CuI (0.0006 mol) in Et₃N (50 ml) and DMA (50 ml) was stirred at r.t. A solution of N-methyl-N-2-propyn-1-yl-carbamic acid, 1,1-dimethylethyl ester (0.0075 mol) in DMA (20 ml) was added dropwise. The reaction mixture was stirred for one hour at r.t. Reaction mixtures (I) and (II) were combined and combined mixture was poured out into H₂O. This mixture was extracted with EtOAc (3×). The separated organic layer was washed with H₂O (3×), dried, filtered and the solvent evaporated. The residue was purified by HPLC. The product fractions were collected and the solvent was evaporated. The residue was taken up into H₂O, then extracted with EtOAc. The separated organic layer was dried, filtered and the solvent evaporated. Yield: 0.7 g of intermediate 19 (35.7%).

c) Preparation of Intermediate 20

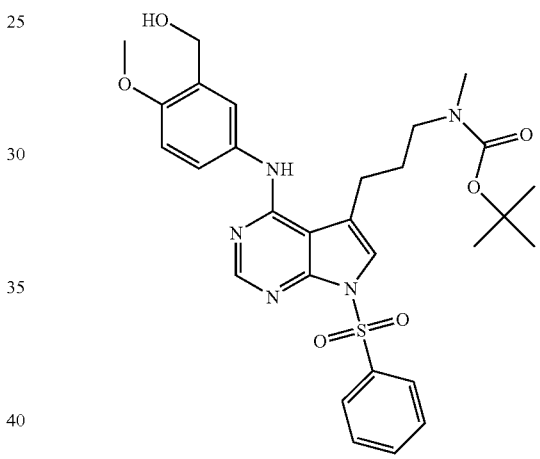

A mixture of intermediate 19 (0.0012 mol) in THF (50 ml) was hydrogenated with Raney Nickel (catalytic quantity) as a catalyst. After uptake of H₂ (2 eq.), the catalyst was filtered off and the filtrate was evaporated. Yield: 0.7 g of intermediate 20 (quantitative yield; used in next reaction step, without further purification).

d) Preparation of Intermediate 21

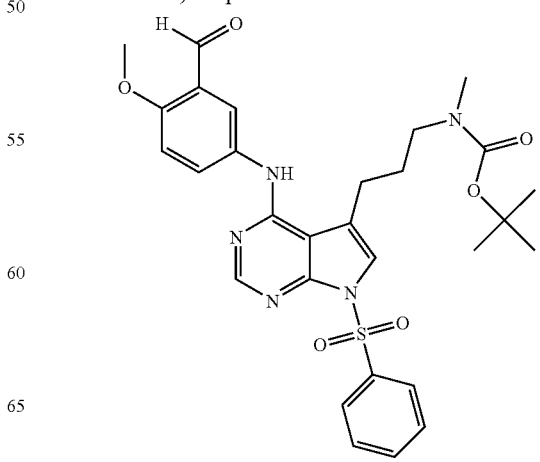

A mixture of intermediate 20 (0.0012 mol) and MnO$_2$ (7 g; activated) in THF (100 ml) was stirred for 2 hours at r.t. The catalyst was filtered off and the filtrate was evaporated. Yield: 0.550 g of intermediate 21 (78.6%).

Example A8 a) Preparation of Intermediate 22

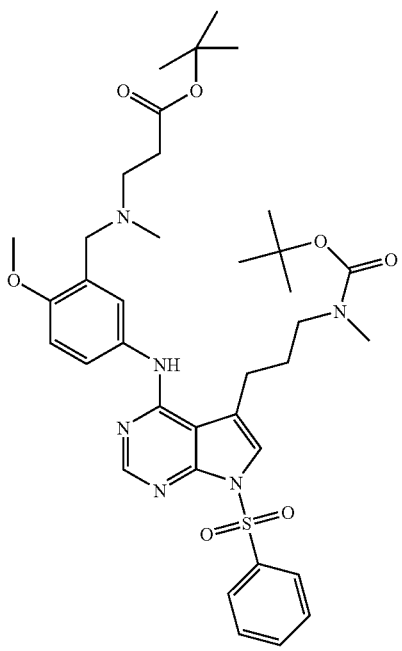

A mixture of intermediate 21 (0.001 mol), N-methyl-β-alanine 1,1-dimethylethyl ester hydrochloride (0.001 mol) and NaBH(OAc)$_3$ (0.003 mol) in DCM (50 ml) and Et$_3$N (0.2 g) was stirred overnight at r.t. More N-methyl-β-alanine 1,1-dimethylethyl ester hydrochloride (0.0005 mol) was added and the reaction mixture was stirred overnight at r.t. The mixture was purified by column chromatography over silica gel (eluent: DCM/(MeOH/NH$_3$) 95/5). The product fractions were collected and the solvent was evaporated. Yield: 0.950 g of intermediate 22 (oil).

b) Preparation of Intermediate 23

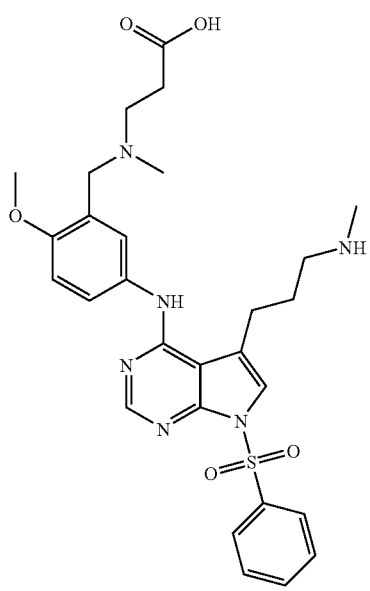

A mixture of intermediate 22 (0.001 mol) in dioxane (20 ml), H$_2$O (20 ml) and HCl (20 ml; 36%) was stirred for one hour at 60° C. The solvent was evaporated. CH$_3$CN was added, then evaporated again (3×), yielding intermediate 23 (quantitative yield; used in next reaction step, without further purification).

c) Preparation of Intermediate 24

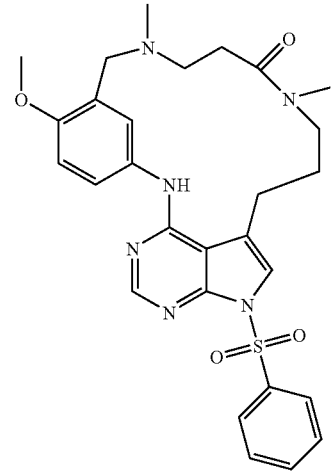

A mixture of PyBOP (0.005 mol) and Et$_3$N (0.010 mol) in DMF (50 ml) was stirred at r.t. under N$_2$ atmosphere. A solution of intermediate 23 (0.001 mol) in DMF (50 ml) was added dropwise. The resultant reaction mixture was stirred for 1 hour at r.t. H$_2$O was added. The solvent was evaporated. The residue was purified by HPLC. The product fractions were collected and the solvent was evaporated. Yield: 0.106 g of intermediate 24.

Example A9 a) Preparation of Intermediate 25

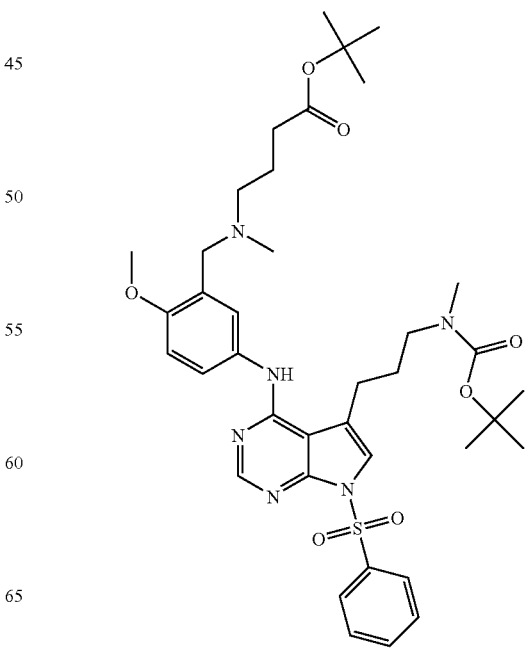

A mixture of intermediate 21 (0.00024 mol), 4-(methylamino)-butanoic acid 1,1-dimethylethyl ester hydrochloric acid (0.00036 mol) and NaBH(OAc)₃ (0.00072 mol) in DCM (10 ml) and Et₃N (0.036 g) was stirred for 16 hours at r.t. The reaction mixture was poured out into H₂O and this mixture was extracted with DCM. The separated organic layer was dried, filtered and the solvent evaporated. The residue was purified by HPLC. The product fractions were collected and the solvent was evaporated. Yield: 0.075 g of intermediate 25.

b) Preparation of Intermediate 26

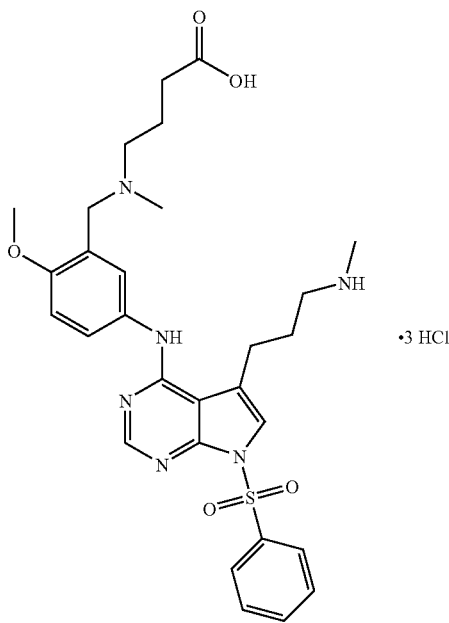

·3 HCl

A mixture of intermediate 25 (0.0001 mol) in dioxane (20 ml), H₂O (20 ml) and HCl (10 ml; 36%) was stirred for one hour at 60° C. The solvent was evaporated. CH₃CN was added and was evaporated again (3×). Yield: intermediate 26 as a hydrochloric acid salt form (0.3 HCl) (quantitative yield; used in next reaction step, without further purification).

c) Preparation of Intermediate 27

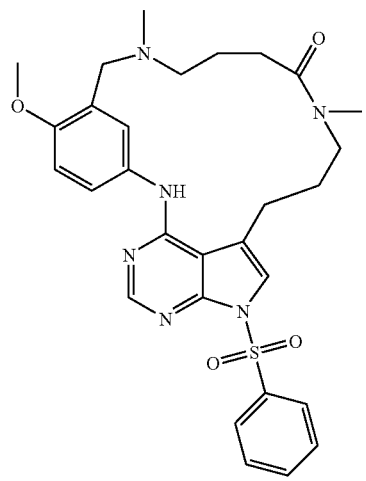

A mixture of PyBOP (0.0005 mol) and Et₃N (0.0010 mol) in DMF (20 ml) was stirred at r.t. under N₂ atmosphere. A solution of intermediate 26 (0.0001 mol) in DMF (20 ml) was added dropwise. The resultant reaction mixture was stirred for one hour at r.t. H₂O was added (decomposition). The solvent was evaporated. The residue was purified by HPLC. The product fractions were collected and the solvent was evaporated. Yield: 0.044 g of intermediate 27.

Example A10 a) Preparation of Intermediate 29

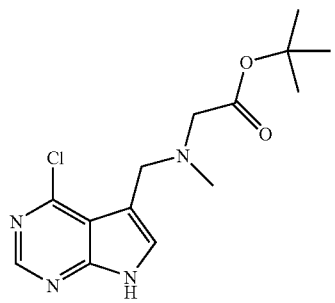

A mixture of glycine 1,1-dimethylethyl ester hydrochloride (0.0056 mol) and NaBH(OAc)₃ (3.535 g) in DCM (55 ml) and Et₃N (0.84 g) was stirred at r.t. A solution of intermediate 1 (0.0056 mol) in THF (22 ml) and DMF (22 ml) was added dropwise. The reaction mixture was stirred for 5 hours. Formaldehyde (2 ml) and NaBH(OAc)₃ were added. The reaction mixture was stirred overnight. The mixture was poured out into H₂O, alkalized with K₂CO₃ and then extracted with DCM. The organic layer was separated, dried, filtered and the solvent was evaporated. The residue was purified by HPLC. The product fractions were collected and the solvent was evaporated. Yield: 0.857 g of intermediate 29 (49%).

b) Preparation of Intermediate 30

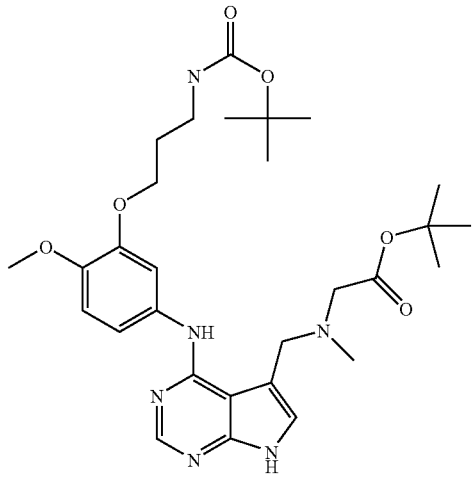

A mixture of intermediate 29 (0.00032 mol), [3-(5-amino-2-methoxyphenoxy)propyl]-carbamic acid 1,1-dimethylethyl ester (0.000358 mol) and HCl/dioxane (5 drops; 4 N) in CH₃CN (2 ml) was stirred for 3 hours at 75° C. The solvent was evaporated. The residue was purified by HPLC. The product fractions were collected and the solvent was evaporated. Yield: 0.097 g of intermediate 30 (53.2%).

c) Preparation of Intermediate 31

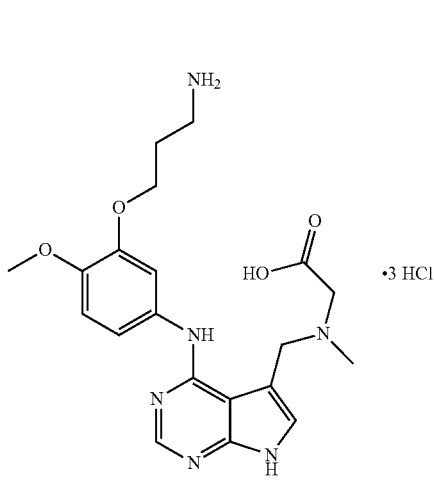

A mixture of intermediate 30 (0.00017 mol) in dioxane (10 ml), H₂O (10 ml) and HCl (5 ml; 36%) was stirred for one hour at 60° C. The solvent was evaporated. CH₃CN was added, then evaporated again (3×). The residue was dried (vacuum, 50° C., 16 hours). Yield: intermediate 31 as a HCl-salt (0.3 HCl) (quantitative yield; used in next reaction step, without further purification).

Example A11 a) Preparation of Intermediate 32

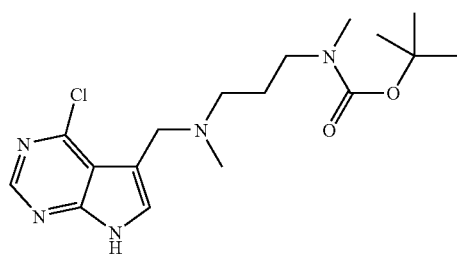

A mixture of intermediate 1 (0.008 mol) in DCM (100 ml) and THF (100 ml) was stirred at r.t. NaBH(OAc)₃ (0.024 mol) was added portionwise. A solution of methyl[3-(methylamino)propyl]carbamic acid 1,1-dimethylethyl ester (0.008 mol) in DCM (q.s.) was added dropwise. The reaction mixture was stirred overnight at r.t. The mixture was purified by HPLC. The product fractions were collected and the solvent was evaporated. The residue was taken up into H₂O, then extracted with DCM. The separated organic layer was dried, filtered and the solvent evaporated. Yield: 0.800 g of intermediate 32.

b) Preparation of Intermediate 33

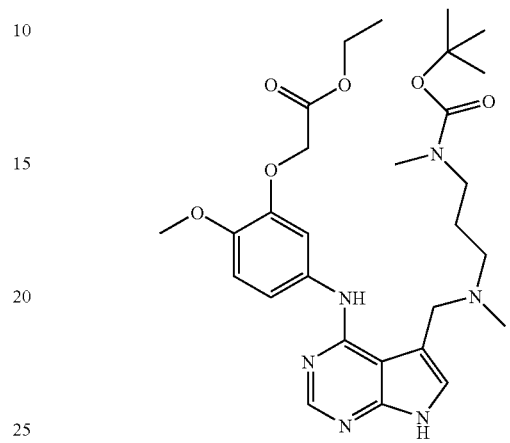

A mixture of intermediate 32 (0.00027 mol), (5-amino-2-methoxyphenoxy)acetic acid ethyl ester (0.0003 mol) and HCl/2-propanol (3 drops) in CH₃CN (2 ml) was stirred for 3 hours at 80° C. The solvent was evaporated. The residue was purified by HPLC. The product fractions were collected and the solvent was evaporated. Yield: 0.059 g of intermediate 33 (39.3%).

c) Preparation of Intermediate 34

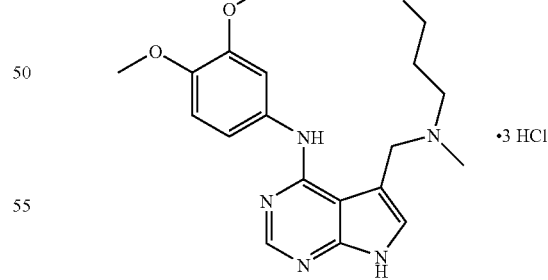

A mixture of intermediate 33 (0.00010 mol) in dioxane (10 ml), H₂O (10 ml) and HCl (5 ml; 36%) was stirred for 2 hours at 60° C. The solvent was evaporated. CH₃CN was added, then evaporated again (3×). Yield: intermediate 34 as a HCl-salt (0.3 HCl)(quantitative yield; used in next reaction step, without further purification).

Example A12 a) Preparation of Intermediate 35

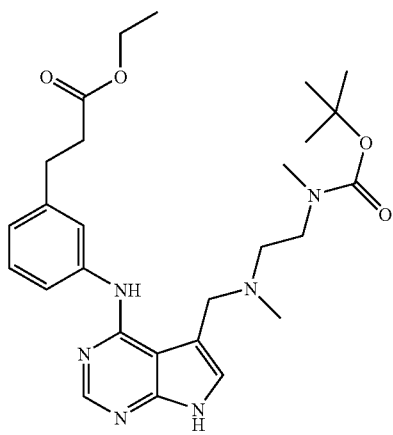

(Reaction mixture I): A mixture of intermediate 2 (0.00026 mol) and 3-amino-benzenepropanoic acid ethyl ester hydrochloride (0.00026 mol) in CH$_3$CN (5 ml) was stirred for 3 hours at 80° C. (Reaction mixture II): A mixture of intermediate 2 (0.00052 mol) and 3-amino-benzenepropanoic acid ethyl ester hydrochloride (0.00052 mol) in CH$_3$CN (10 ml) was stirred for 5 hours at 80° C. Reaction mixture (I) and (II) were combined. The solvent was evaporated. The residue was purified by HPLC. Yield: 0.217 g of intermediate 35 (54.6%).

b) Preparation of Intermediate 36

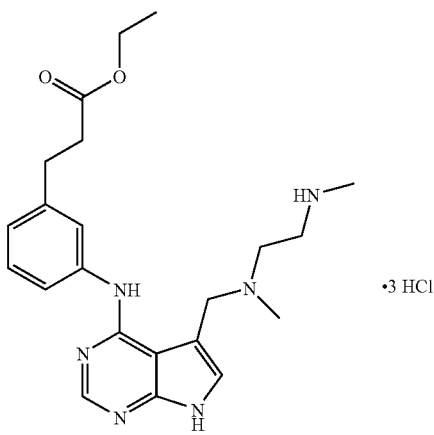

A mixture of intermediate 35 (0.00025 mol) in EtOH (20 ml; p.a.) and HCl/2-propanol (5 ml) was stirred for 32 hours at 25° C. The solvent was evaporated. The residue was stirred in DIPE. The resulting precipitate was filtered off and dried. Yield: 0.099 g of intermediate 36 as a HCl-salt (0.3 HCl) (96.6%).

c) Preparation of Intermediate 37

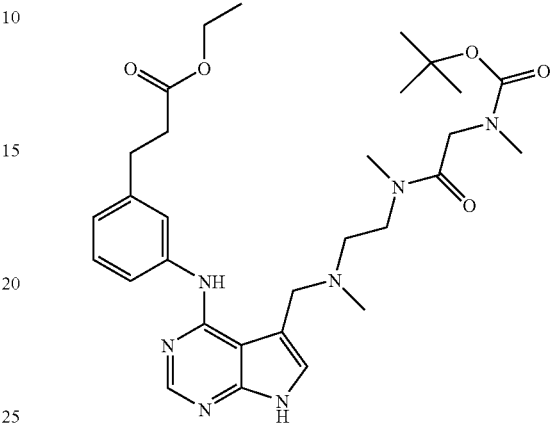

Reaction under N$_2$ atmosphere. A mixture of intermediate 36 (0.00019 mol) and PyBOP (0.00038 mol) and Et$_3$N (0.0019 mol) in DMF (10 ml) was stirred at r.t. under N$_2$ flow. A solution of N-[(1,1-dimethylethoxy)carbonyl]-N-methylglycine (0.00019 mol) in Et$_3$N (10 ml) was added dropwise and the resultant reaction mixture was stirred for 30 minutes at r.t. The mixture was decomposed with H$_2$O. The solvent was evaporated. The residue was purified by HPLC. The product fractions were collected and the solvent was evaporated. Yield: 0.052 g of intermediate 37 (47.1%).

d) Preparation of Intermediate 38

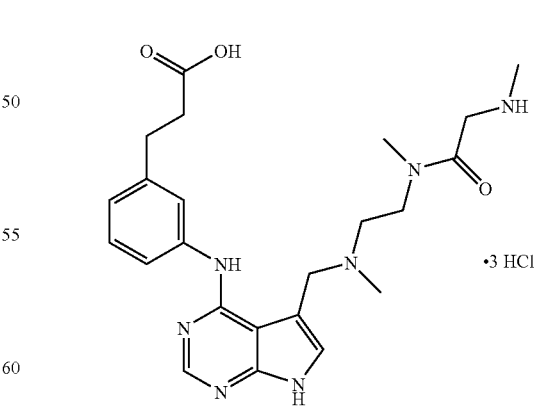

A mixture of intermediate 37 (0.00009 mol) in dioxane (10 ml), H$_2$O (10 ml) and HCl/2-propanol (5 ml) was stirred for 2 hours at 60° C. The solvent was evaporated. CH$_3$CN was added, then evaporated again (3×). The residue was dried (vacuum, 50° C., 3 hours). Yield: intermediate 38 as a HCl-salt (0.3 HCl) (quantitative yield; used in next reaction step, without further purification).

Example A13 a) Preparation of Intermediate 39

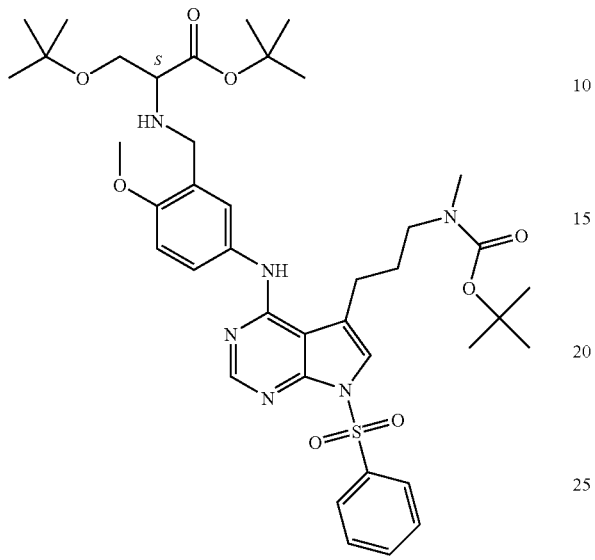

A mixture of intermediate 21 (0.001 mol), O-(1,1-dimethylethyl)-L-Serine 1,1-dimethylethyl ester hydrochloride (0.0015 mol), Et$_3$N (0.002 mol) and NaBH(OAc)$_3$ (0.003 mol) in DCM (50 ml) was stirred for 16 hours at r.t. Extra O-(1,1-dimethylethyl)-L-Serine 1,1-dimethylethyl ester hydrochloride (0.00075 mol) and NaBH(OAc)$_3$ (0.0015 mol) were added and the mixture was stirred overnight at r.t. Then the mixture was poured out into H$_2$O. This mixture was extracted with DCM. The separated organic layer was dried, filtered and the solvent evaporated. Yield: intermediate 39 (S-enantiomer) (crude; used in next reaction step, without further purification).

b) Preparation of Intermediate 40

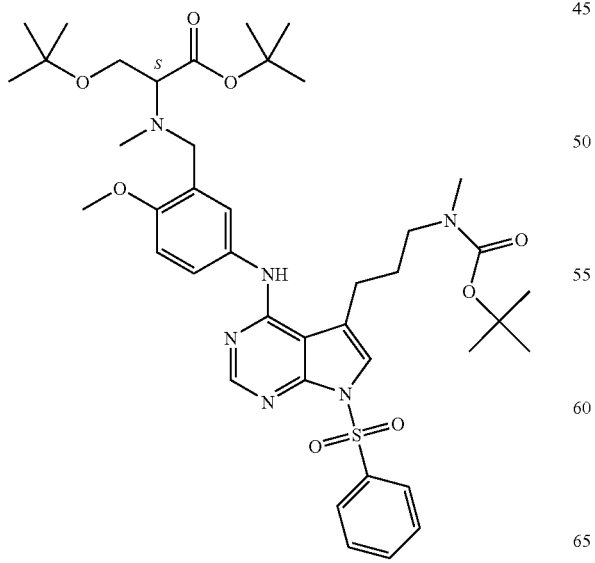

A mixture of intermediate 39 (max. 0.001 mol), formaldehyde (5 ml; 40%) and NaBH(OAc)$_3$ (0.003 mol) in THF (50 ml) was stirred for 16 hours at r.t. The mixture was poured out into H$_2$O. This mixture was extracted with DCM. The separated organic layer was dried, filtered and the solvent evaporated. Yield: intermediate 40 (S-enantiomer) (crude, used in next reaction step, without further purification).

c) Preparation of Intermediate 41

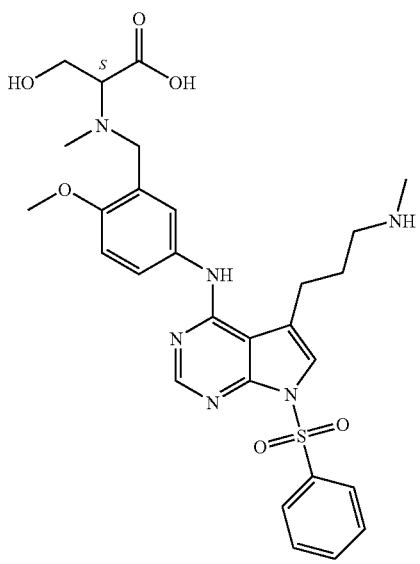

A mixture of intermediate 40 (max. 0.001 mol) in H$_2$O (30 ml), dioxane (30 ml) and HCl (15 ml; 36%) was stirred for 6 hours at 60° C. The solvent was evaporated. The residue was purified by reversed-phase HPLC (Shandon Hyperprep® C18 BDS (Base Deactivated Silica) 8 µm, 250 g, I.D. 5 cm). The mentioned mobile phases were used to apply a gradient (phase A: 0.25% NH$_4$HCO$_3$ solution in H$_2$O; phase B: CH$_3$OH (optional); phase C: CH$_3$CN). The product fractions were collected and the solvent was evaporated. Yield: 0.185 g of intermediate 41 (S-enantiomer).

d) Preparation of Intermediate 42

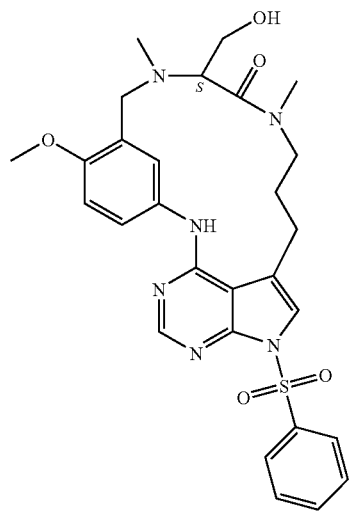

Reaction under N₂ atmosphere. A mixture of PyBOP (0.00160 mol) and Et₃N (0.00160 mol) in DMF (25 ml; p.a.) was stirred at r.t. A solution of intermediate 41 (0.000317 mol) in DMF (25 ml; p.a.) was added dropwise. The resultant reaction mixture was stirred for one hour. The solvent was evaporated. Yield: intermediate 42 (S-enantiomer) (quantitative yield; used in next reaction step, without further purification).

Example A14 a) Preparation of Intermediate 43

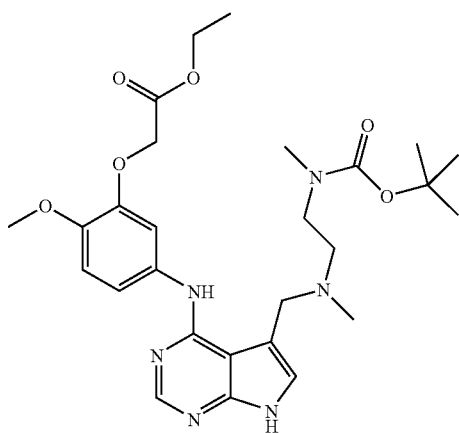

A mixture of intermediate 2 (1.6 g, 0.0045 mol) and (5-amino-2-methoxyphenoxy)acetic acid ethyl ester (1.237 g, 0.0055 mol) in t-BuOH (35 ml) and HCl/dioxane (2 ml; 4 N) was stirred at 75° C. for 5 hours. The reaction mixture with intermediate 43 was used as such in the next step.

b) Preparation of Intermediate 44

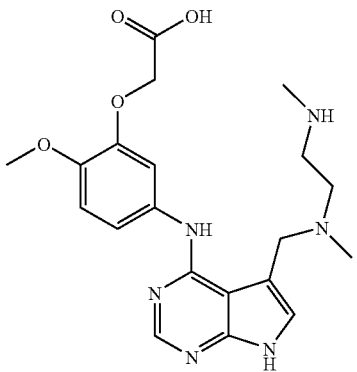

A mixture of intermediate 43 (0.0045 mol; crude mixture from previous reaction step), t-BuOH (35 ml), H₂O (35 ml) and HCl/dioxane (17.5 ml; 4 N) was stirred at 60° C. for 2 hours. The reaction mixture was evaporated to dryness. The residue was purified by HPLC method B. Yield: 0.69 g of intermediate 44 (37%).

Example A15 a) Preparation of Intermediate 45

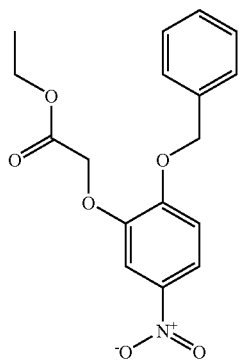

2-Bromoacetic acid ethyl ester (15 g, 0.0897 mol) and then K₂CO₃ (25 g, 0.0179 mol) were added to a solution of 2-(benzyloxy)-5-nitro-phenol (22 g, 0.0897 mol) in DMF (300 ml). The reaction mixture was stirred at r.t. for 12 hours. H₂O and ether were added. The separated organic layer was washed with a K₂CO₃ aq. solution (10%) and with brine, and was then dried (MgSO₄), filtered and the solvent was evaporated. The residue was purified by column chromatography over silica (eluent: petroleum ether/DCM 15:1). The product fractions were collected and the solvent was evaporated. Yield: 15 g of intermediate 45 (51%).

b) Preparation of Intermediate 46

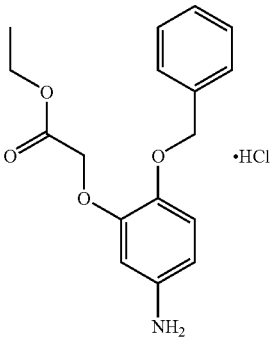

NH₄Cl (2.1 g, 0.0398 mol) in H₂O (100 ml) was added to a solution of intermediate 45 (11 g, 0.0332 mol) and Fe (9.3 g, 0.1660 mol) in THF (200 ml) and stirred for 25 hours at 85° C. Then, the reaction mixture was cooled to r.t. and filtered through Celite. The solvent was evaporated. The residue was partitioned between EtOAc and a Na₂CO₃ aq. solution (2 M). The separated organic layer was washed with brine, dried (MgSO4), filtered and the solvent was evaporated. The residue was acidified with HCl in dioxane and the precipitate was filtered off. The product was dissolved in H₂O (200 ml) and then extracted with ether. The aq. layer was lyophilized to obtain the residue. Yield: 10 g of intermediate 46 (.HCl; 91%).

Example A16 a) Preparation of Intermediate 47

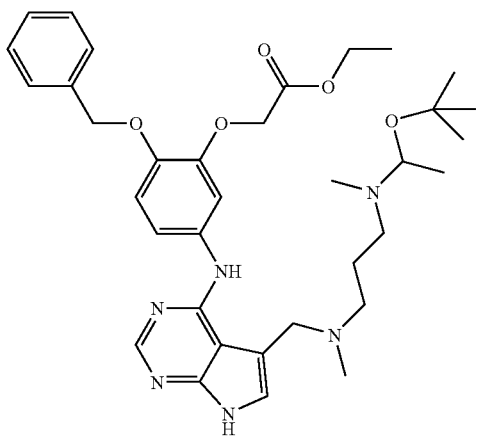

A mixture of intermediate 32 (0.400 g, 0.0011 mol), intermediate 46 (0.432 g, 0.0013 mol), t-BuOH (8 ml) and HCl/1,4-dioxane (0.4 ml; 4 N) was stirred for 5 hours at 75° C. The reaction mixture with intermediate 47 was used as such in the next reaction step.

b) Preparation of Intermediate 48

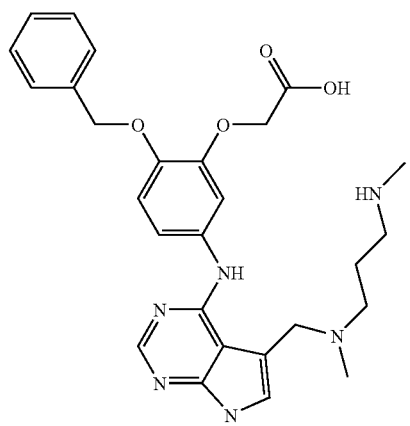

A mixture of intermediate 47 (0.0011 mol; crude mixture from precious reaction step), t-BuOH (8 ml), H$_2$O (8 ml) and HCl (4 ml; 36%) was stirred for 2 hours at 60° C. The reaction mixture was evaporated to dryness and purified by HPLC method B. Yield: 0.045 g of intermediate 48 (8.2%).

Example A17 a) Preparation of Intermediate 49

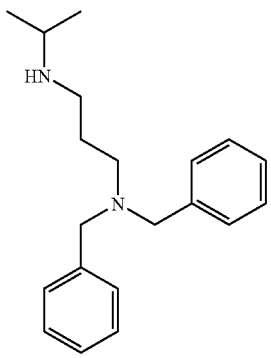

Pd/C 10% (2 g) was suspended in MeOH (125 ml) under N$_2$ flow. A thiophene solution (1 ml; 4% in DIPE) was added. N,N-bis(phenylmethyl)-1,3-propanediamine (20 g, 0.0790 mol) and acetone (13.8 g, 0.2370 mol) in MeOH (125 ml) was added. The reaction mixture was stirred under H$_2$ atmosphere until 1 eq. of H$_2$ was absorbed. The catalyst was removed by filtration over Dicalite and the solvent was evaporated. Yield: intermediate 49 (97.0%).

b) Preparation of Intermediate 50

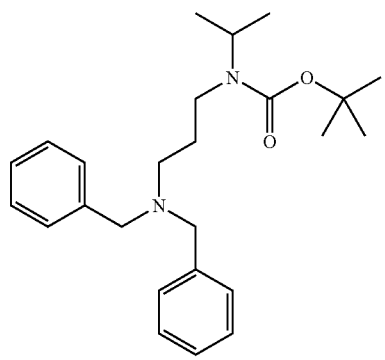

Intermediate 49 (22.6 g, 0.0760 mol) was dissolved in DCM (225 ml) and stirred. DMAP (catalytic amount) was added. BOC-anhydride (17.5 g, 0.0800 mol) was dissolved in DCM (75 ml) and added dropwise. The reaction mixture was stirred at r.t. (CO$_2$ gas development). When the reaction was finished, the solvent was evaporated and the residue was purified by column chromatography (eluent: DCM/MeOH from 100/0 till 92/8. The product fractions were collected and the solvent was evaporated and co-evaporated with toluene. Yield: 27.9 g of intermediate 50 (92.6%).

c) Preparation of Intermediate 51

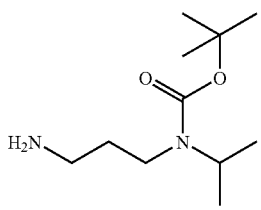

Pd/C 10% (2.5 g) was suspended in MeOH (125 ml). Intermediate 50 (27.8 g, 0.0700 mol) in MeOH (125 ml) was added (under N$_2$ flow). The reaction mixture was stirred under H$_2$ atmosphere until 2 eq. of H$_2$ were absorbed. The catalyst was removed by filtration over Dicalite and the solvent was evaporated. Yield: 14.3 g of intermediate 51 (94.3%).

Example A18 a) Preparation of Intermediate 52

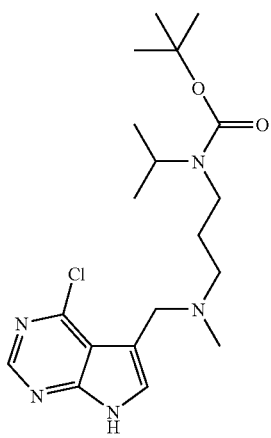

A mixture of intermediate 51 (1.30 g, 0.0060 mol), NaBH(OAc)$_3$ (3.2 g, 0.0150 mol) and DCM was stirred at r.t. Intermediate 1 (0.905 g, 0.0050 mol) dissolved in THF/DMF 1/1 (70 ml) was added dropwise. Stirring was continued for 16 hours. Another portion of NaBH(OAc)$_3$ (3.2 g, 0.0150 mol) was added. Formaldehyde (2 ml; 40%) dissolved in THF (10 ml) was added dropwise. Stirring was continued for 16 hours The reaction mixture was poured into H$_2$O, basified with K$_2$CO$_3$ and extracted with DCM. The organic layer was dried with MgSO$_4$, filtered off and the solvent was evaporated. The residue was purified over silica gel (eluent: DCM/(MeOH/NH$_3$) 90/10) Yield: 1.8 g of intermediate 52 (91%).

b) Preparation of Intermediate 53

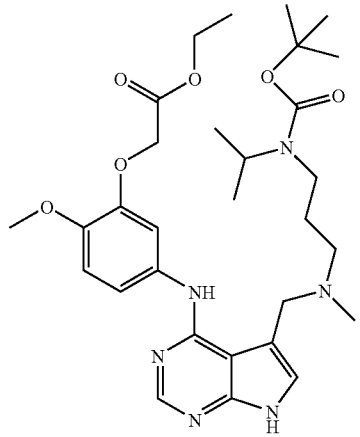

A mixture of intermediate 52 (1.8 g, 0.0045 mol), (5-amino-2-methoxyphenoxy)acetic acid ethyl ester, t-BuOH (35 ml) and HCl/dioxane (2 ml; 4 N) was stirred for 5 hours at 75° C. The reaction mixture with intermediate 53 was used as such in the next reaction step.

c) Preparation of Intermediate 54

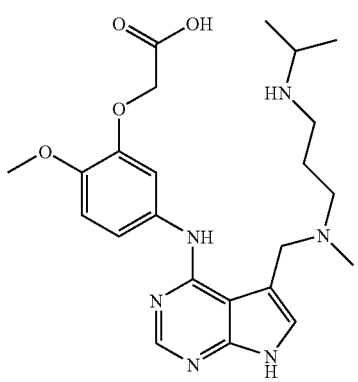

A mixture of intermediate 53 (0.0045 mol; crude reaction mixture from previous reaction step), t-BuOH (35 ml), H$_2$O (35 ml) and HCl (17.5 ml; 36%) was stirred for 2 hours at 60° C. The reaction mixture was evaporated to dryness and the residue was purified on HPLC. Yield: 0.714 g of intermediate 54 (34.8%).

Example A19 a) Preparation of Intermediate 55

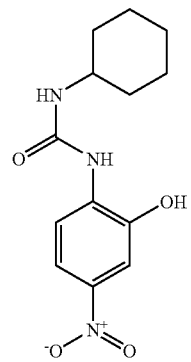

A mixture of 2-amino-5-nitrophenol (7.7 g, 0.05 mol), isocyanatocyclohexane (6.3 g, 0.05 mol) and THF (100 ml) was stirred for 16 hours at r.t. The solvent was evaporated. The residue was stirred in DIPE, filtered off and dried. Yield: 13.44 g of intermediate 55 (96.2%).

b) Preparation of Intermediate 56

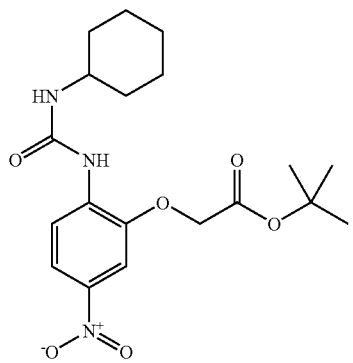

A mixture of intermediate 55 (13.4 g, 0.0480 mol), 2-bromo acetic acid 1,1-dimethylethyl ester (10.3 g, 0.0530 mol), $K_2CO_3$ (8 g, 0.0580 mol) and DMF (130 ml) was stirred at r.t. for 5 hours. The reaction mixture was poured into $H_2O$ and extracted with EtOAc (3×). The organic layer was washed with $H_2O$ (2×), filtered over Dicalite, dried ($MgSO_4$), filtered and the solvent was evaporated. The residue was stirred in DIPE and the solid was filtered off and dried. Yield: 9.2 g of intermediate 56 (LCMS 99%). (More but impure intermediate 56 can be obtained by evaporation of the solvent (DIPE) of the filtrate and by stirring the residue in DIPE again. After filtration and drying of the solid, 6.3 g of less pure intermediate 56 (LCMS 91%) was obtained. Total yield: 82.1%)

c) Preparation of Intermediate 57

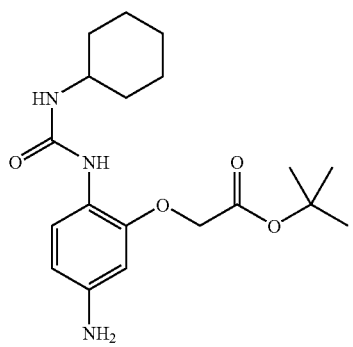

Pd/C 10% (1.5 g) was suspended in THF (75 ml). Under $N_2$ flow, a thiophene solution (1 ml; 4% in DIPE) was added. Then intermediate 56 (5 g, 0.0127 mol) in THF (75 ml) was added. The reaction mixture was stirred under $H_2$ atmosphere until 3 eq. of $H_2$ were absorbed (3 eq.). The catalyst was removed by filtration over Dicalite and the solvent was evaporated, yielding 5.2 g of the crude product. The crude product was purified by HPLC. Yield: 3.3 g of intermediate 57 (71.5%; LC-MS 98%).

Example A20 a) Preparation of Intermediate 58

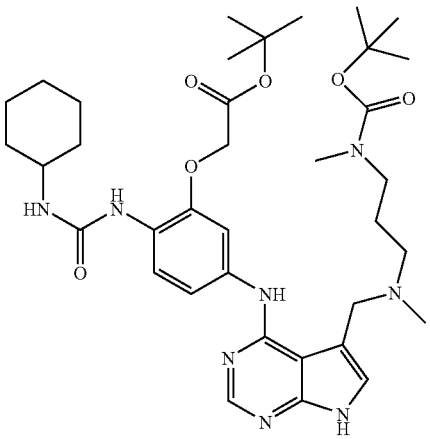

A mixture of intermediate 32 (0.700 g, 0.0019 mol) and intermediate 57 (0.889 g, 0.0025 mol) in t-BuOH (14 ml) and HCl/1,4-dioxane (0.7 ml; 4 N) was stirred for 5 hours at 75° C. The reaction mixture with intermediate 58 was used as such in the next reaction step.

b) Preparation of Intermediate 59

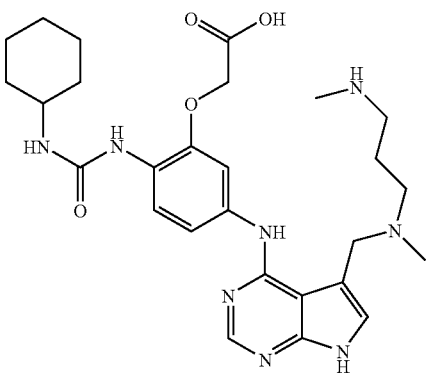

A mixture of intermediate 58 (0.0019 mol; crude mixture from previous reaction step) in $H_2O$ (14 ml) and HCl (7 ml; 36%) was stirred for 2 hours at 60° C. The mixture was evaporated to dryness and the residue was purified by HPLC method B. The pure fractions were collected, evaporated to dryness and 3 times co-evaporated with CH₃CN. Yield: 0.380 g of intermediate 59 (38%).

Example A21 a) Preparation of Intermediate 67

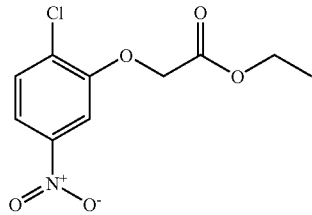

2-Chloro-5-nitrophenol (10.0 g, 0.058 mol), bromoacetic acid ethyl ester (9.7 g, 0.058 mol) and K₂CO₃ (16.0 g, 0.116 mol) were suspended in DMF (150 ml). The reaction mixture was stirred overnight at r.t. H₂O (200 ml) and Et₂O (200 ml) were added. The organic layer was washed with 10% K₂CO₃ and saturated brine, and was then dried (Na₂SO₄). The mixture was filtered. The filtrate was concentrated in vacuo. The residue was suspended in petroleum ether (100 ml). The precipitate was filtered off and dried in vacuo to give 11.0 g of intermediate 67 (73%).

b) Preparation of Intermediate 60

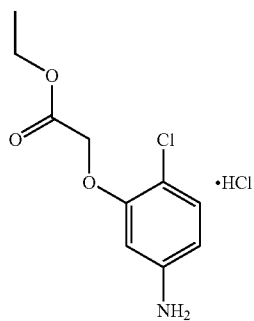

Intermediate 67 (11.0 g, 0.042 mol) and Raney Nickel (2.2 g) were suspended in THF (350 ml) and hydrogenated (under H₂ atmosphere) for 2 hours. Then the mixture was filtered. The filtrate was concentrated in vacuo. The residue was dissolved in 4 N HCl/dioxane (35 ml). Then Et₂O (100 ml) was added. The precipitate was filtered off and dried in vacuo to give 7.0 g of intermediate 60 (.HCl; 62%).

c) Preparation of Intermediate 61

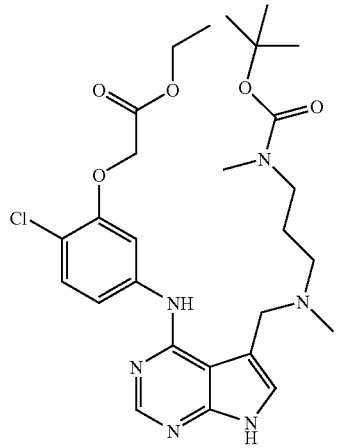

A mixture of intermediate 32 (3 g, 0.0080 mol), intermediate 60 (2.1 g, 0.0080 mol), t-BuOH (60 ml) and HCl/dioxane (3 ml; 4 N) was stirred for 6 hours at 75° C. The reaction mixture with intermediate 61 was used as such in the next reaction step.

d) Preparation of Intermediate 67

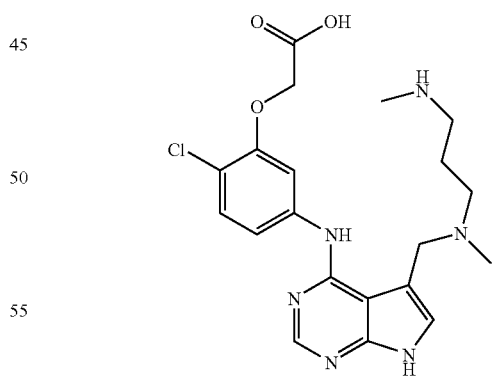

A mixture of intermediate 61 (0.0080 mol; crude reaction mixture from previous reaction step), H₂O (60 ml) and HCl (30 ml; 36%) was stirred for 2 hours at 60° C. The reaction mixture was evaporated to dryness and the residue was purified by HPLC method B. The pure fractions were evaporated to dryness and evaporated 2 times with CH₃CN Yield: 0.340 g of intermediate 62. The residue was dried in vacuum at 50° C. for 16 hours.

Example A22 a) Preparation of Intermediate 63

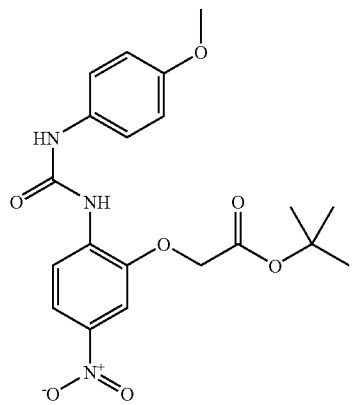

A mixture of N-(2-hydroxy-4-nitrophenyl)-N-(4-methoxyphenyl)urea (3.85 g, 0.0127 mol), 2-bromo acetic acid 1,1-dimethylethyl ester (2.73 g, 0.0140 mol) and K₂CO₃ (2.11 g, 0.0152 mol) in DMF (40 ml) was stirred at r.t. The reaction mixture was poured into H₂O and extracted with EtOAc (3×). The organic layer was washed with H₂O (1×). The EtOAc-layer was dried (MgSO₄) and filtered. The solvent was evaporated. The crude product (6.18 g) was purified over silica gel (eluent: 25% EtOAc/hexane). The product fractions were collected and the solvent was evaporated. Yield: 4.99 g of intermediate 63 (94.1%).

b) Preparation of Intermediate 64

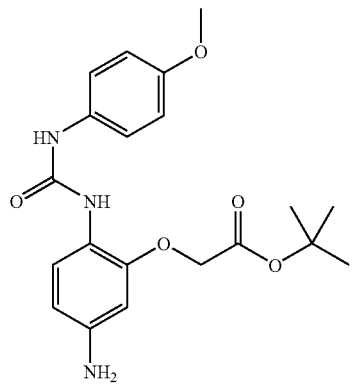

Pd/C 10% (1 g) was suspended in THF (q.s.) under N₂ flow. A thiophene solution (1 ml; 4% in DIPE) was added. Intermediate 63 (5.0 g, 0.0120 mol) in THF (q.s.) was added. The reaction mixture was stirred under H₂ atmosphere until 3 eq. of H₂ were absorbed. The catalyst was removed by filtration over Dicalite and the solvent was evaporated. The crude product (5.5 g) was purified by HPLC. The desired fractions were collected and the solvent was evaporated, yielding 2.6 g residue. This residue was stirred in DIPE and filtered off. Yield: 2.32 g of intermediate 64 (49.9%).

Example A23 a) Preparation of Intermediate 65

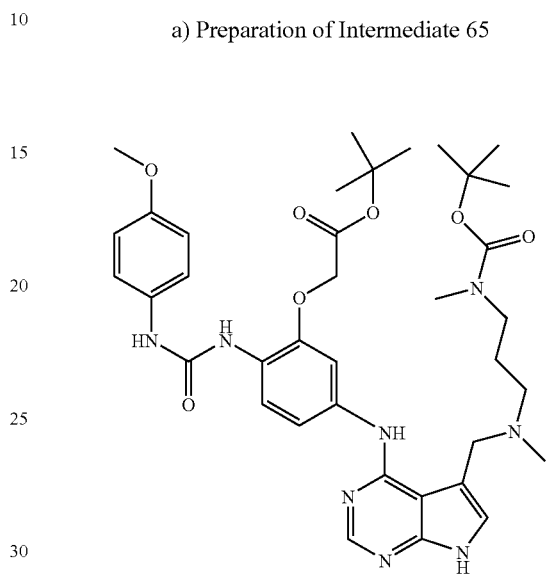

Intermediate 32 (0.700 g, 0.0019 mol) and intermediate 64 (0.950 g, 0.0025 mol) in t-BuOH (14 ml) and HCl/1,4-dioxane (0.7 ml; 4 N) was stirred at 75° C. for 5 hours. The reaction mixture with intermediate 65 was used as such in the next step.

b) Preparation of Intermediate 66

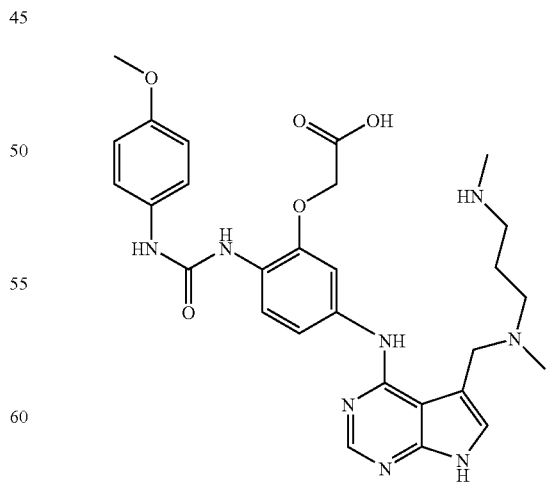

A mixture of intermediate 65 (0.0019 mol; crude reaction mixture from previous reaction step), t-BuOH (14 ml), H₂O (14 ml) and HCl (7 ml; 36%) was stirred at 60° C. for 2 hours.

The reaction mixture was evaporated to dryness and the residue was purified by HPLC method B. The product fractions were collected and the solvent was evaporated. Yield: 0.285 g of intermediate 66.

Example A24 a) Preparation of Intermediate 68

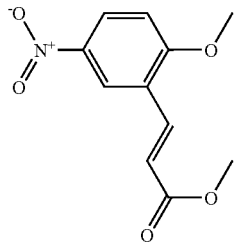

A mixture of 2-methoxy-5-nitrobenzaldehyde (0.058 mol) in DCM (200 ml) was stirred at r.t. 2-(triphenylphosphoranylidene)acetic acid, methyl ester (0.058 mol) was added portionwise. The reaction mixture was stirred at r.t. More 2-(triphenylphosphoranylidene)acetic acid, methyl ester (6 g) was added and the reaction mixture was stirred overnight at r.t. The solvent was evaporated. The residue was purified by column chromatography over silica gel (eluent: DCM/MeOH 99/1). The product fractions were collected and the solvent was evaporated. Yield: 9.7 g of intermediate 68.

b) Preparation of Intermediate 69

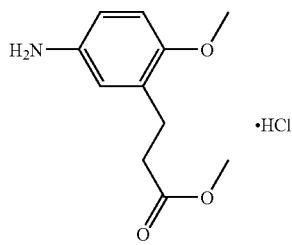

A mixture of intermediate 68 (0.041 mol) in THF (250 ml) was hydrogenated with Raney Nickel as a catalyst. After uptake of $H_2$ (4 eq.), the catalyst was filtered off and the filtrate was evaporated. The residue was taken up into 2-propanone and treated with 4 N HCl/dioxane. The solvent was evaporated. The residue was stirred in DIPE, filtered off and dried, and was then taken up into MeOH (150 ml). This mixture was treated with 4 N HCl/dioxane. The mixture was stirred for 3 hours at 65° C. The mixture was cooled and the solvent was evaporated. The residue was stirred in DIPE. The precipitate was filtered off and dried. Yield: 7.6 g of intermediate 69 (.HCl).

c) Preparation of Intermediate 70

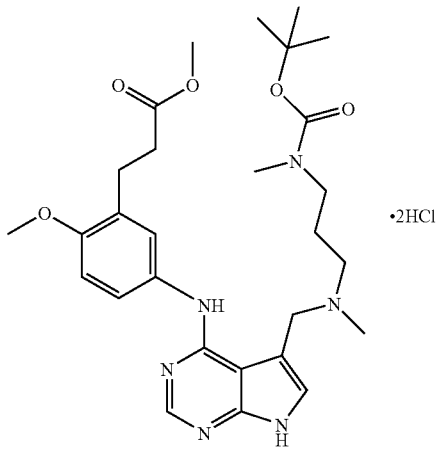

A mixture of intermediate 32 (0.001 mol) and intermediate 69 (0.001 mol) in $CH_3CN$ (3 ml) with HCl/dioxane (0.1 ml) was stirred for 4 hours at 80° C. The mixture was cooled. The solvent was evaporated to give residue (I). The reaction was repeated, without addition of the acid. The reaction mixture was stirred for 4 hours at 80° C. The mixture was cooled. The solvent was evaporated to give residue (II). Residues (I) and (II) were combined to give intermediate 70 (.2HCl) (used in next reaction step without further purification).

d) Preparation of Intermediate 71

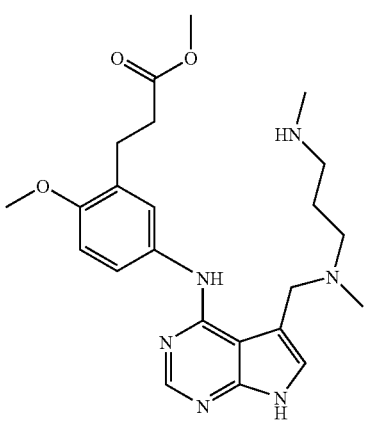

A mixture of crude intermediate 70 (max. 0.002 mol) in MeOH (60 ml) and HCl/dioxane (20 ml) was stirred for one hour at 60° C. The solvent was evaporated. The residue was purified by HPLC. The product fractions were collected and worked-up. Yield: intermediate 71 (used in the next reaction step without further purification).

e) Preparation of Intermediate 72

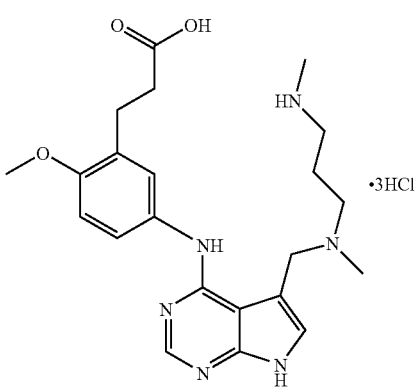

A mixture of crude intermediate 71 (max. 0.002 mol) in dioxane (20 ml), H$_2$O (20 ml) and HCl (10 ml;

36%) was stirred for 2 hours at 60° C. The solvent was evaporated. CH$_3$CN was added (3×) and was evaporated each time. Yield: 0.184 g of intermediate 72 (.3HCl) (used in the next reaction step without further purification).

Example A25 a) Preparation of Intermediate 73

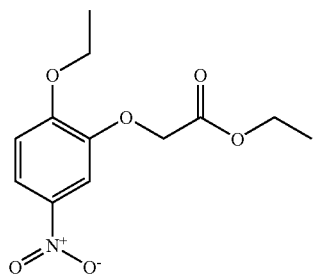

K$_2$CO$_3$ (32 g, 0.2292 mol) was added to a solution of 2-ethoxy-5-nitrophenol (21 g, 0.1146 mol) and 2-bromoacetic acid ethyl ester (19 g, 0.1146 mol) in DMF (400 ml) and the reaction mixture was stirred at r.t. for 12 hours. The reaction mixture was extracted with H$_2$O and ether. The separated organic layer was washed with an aq. K$_2$CO$_3$ solution (10%), washed with brine, dried (MgSO$_4$), filtered and the solvent was evaporated. The residue was purified by column chromatography over silica gel (eluent: petroleum ether/ EtOAc 8/1). The desired fractions were collected and the solvent was evaporated. Yield: 13 g of intermediate 73 (42%).

b) Preparation of Intermediate 74

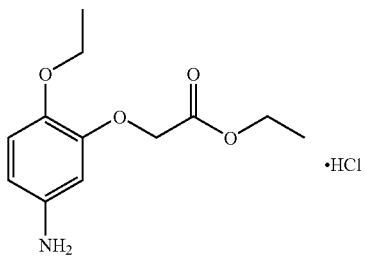

A solution of NH$_4$Cl (2.9 g, 0.0535 mol) in H$_2$O (100 ml) was added to a solution of intermediate 73 (12 g, 0.0446 mol) and Fe (12.5 g, 0.2230 mol) in THF (200 ml) and stirred at 85° C. for 150 minutes. The reaction mixture was cooled to r.t., filtered over Celite and the filtrate's solvent was evaporated. The residue was partitioned between EtOAc and an aq. solution of Na$_2$CO$_3$ (2 M). The separated organic layer was washed with brine, dried (MgSO$_4$), filtered and the filtrate's solvent was evaporated. The residue was acidified with HCl in dioxane. Yield: 10 g of intermediate 74 (81%; .HCl).

c) Preparation of Intermediate 75

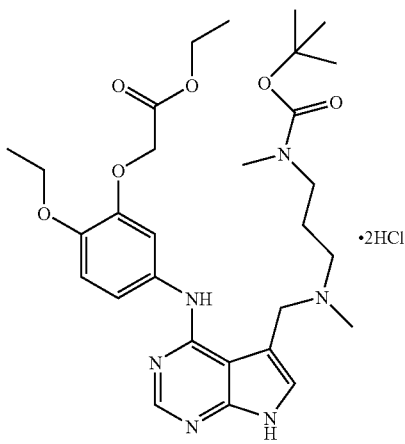

A mixture of intermediate 32 (0.40 g, 0.0011 mol) and intermediate 74 (0.352 g, 0.0013 mol) in t-BuOH (8 ml) and 4 N HCl/1,4-dioxane (0.4 ml) was stirred at 75° C. for 5 hours. The reaction mixture which contained intermediate 75 (0.2HCl) was used as such in the next step.

d) Preparation of Intermediate 76

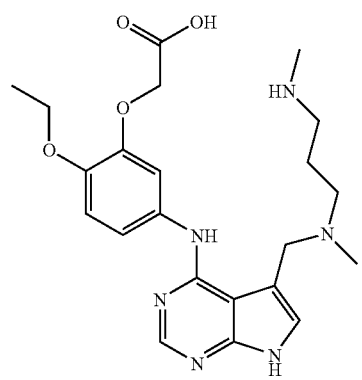

A mixture of intermediate 75 (crude; approximately 0.0011 mol) in t-BuOH (8 ml), H₂O (8 ml) and HCl (4 ml; 36%) was stirred at 60° C. for 2 hours. The reaction mixture was evaporated to dryness and the residue was purified by HPLC method B. The product fractions were collected and the solvent was evaporated. Yield: 0.210 g of intermediate 76 (44%).

Example A26 a) Preparation of Intermediate 77

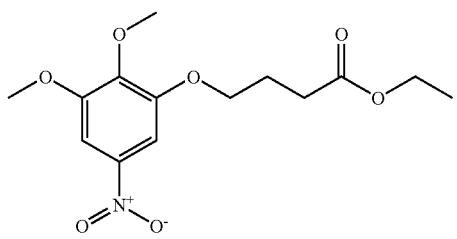

2,3-Dimethoxy-5-nitrophenol (0.0182 mol) was dissolved in CH₃CN (55 ml). Then 4-bromobutanoic acid ethyl ester (0.0219 mol) was added followed by the addition of K₂CO₃ (0.0273 mol). The reaction mixture was stirred overnight at 80° C. The solid was filtered off and washed with CH₃CN. EtOAc (50 ml) was added and the mixture was washed with brine, dried (MgSO₄), filtered and concentrated to dryness. The residue was purified by flash column chromatography on silica gel, using as eluents a mixture of hexanes:EtOAc (ratios: 30:1-25:1-20:1-15:1-10:1). The product fractions were collected and the solvent was evaporated. The product was dried (vacuum, r.t.) yielding a pale yellow solid. Yield: 2.50 g of intermediate 77 (44%).

b) Preparation of Intermediate 78

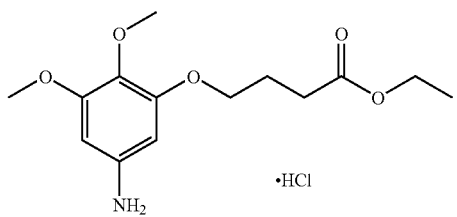

Intermediate 77 (0.0080 mol) was dissolved in THF (30 ml). Then, Pt/C 5% (0.50 g) was added and the mixture was stirred at r.t. under H₂ atmosphere for 15 hours. The reaction mixture was filtered through a Celite pad and the Celite was washed with THF. The filtrate was evaporated under reduced pressure. The product was dried (vacuum, r.t.) yielding 2.25 g of a brown oil. The hydrochloric salt was obtained by purging HCl gas into a solution of the aniline in Et₂O. Yield: 2.20 g of intermediate 78 (.HCl).

c) Preparation of Intermediate 79

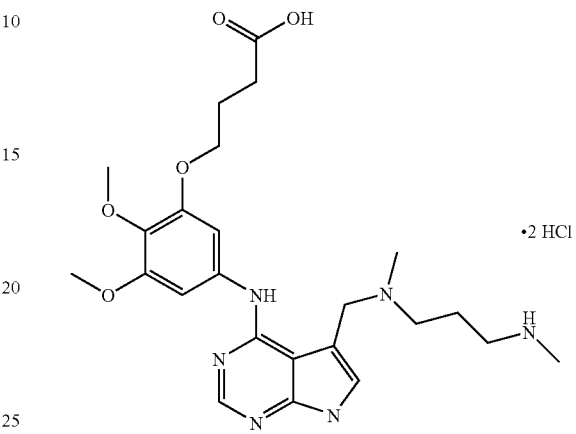

Intermediate 32 (0.0019 mol) was dissolved in a mixture of CH₃CN (4 ml) and 2-propanol (2 ml). Then, intermediate 78 (0.0023 mol) was added followed by the addition of HCl in 1,4-dioxane (1 ml; 4 N). The reaction mixture was heated at 80° C. for 2 hours. The solvent was evaporated and the residue was dried (vacuum, r.t.) yielding intermediate 79 (0.2 HCl) as a brown foam that was used a such in the next reaction step.

Example A27 a) Preparation of Intermediate 80

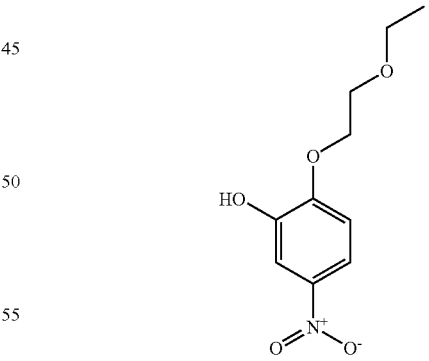

Na (5.2 g, 0.226 mol) was added portionwise to 2-ethoxyethanol (90 ml). This mixture was stirred for 1 hour under N₂ atmosphere at r.t. Subsequently, 1,2-(methylenedioxy)-4-nitrobenzene (15 g, 0.090 mol) and DMSO (180 ml) were added and the reaction mixture was stirred overnight at r.t. First H₂O (250 ml) was added and then a NaOH solution (150 ml; 10%) was added dropwise. The mixture was washed 2 times with DIPE (200 ml). The aq. layer was acidified (to pH 5). The precipitate was filtered off and washed with H₂O to yield 17.8 g of intermediate 80 (87%).

b) Preparation of Intermediate 81

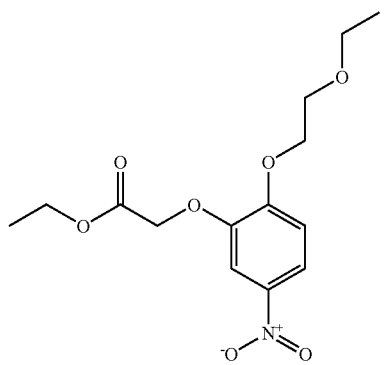

A mixture of intermediate 80 (17.8 g, 0.078 mol), ethyl 2-bromoacetate (14.4 g, 0.086 mol), K₂CO₃ (13.0 g, 0.094 mol) and DMF (300 ml) was stirred overnight at r.t. H₂O was added and the product precipitated. The solid was filtered off, washed with H₂O and dried. Yield: 22.0 g of intermediate 81 (90%).

c) Preparation of Intermediate 82

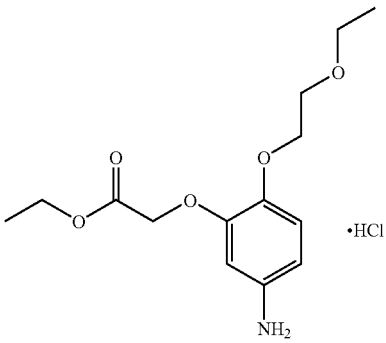

Raney Nickel (catalytical amount) was suspended in THF (350 ml) under N₂ flow. Intermediate 81 (22.0 g, 0.0702 mol) was added and the reaction mixture was stirred under H₂ atmosphere until 3 eq. of H₂ were absorbed. Then the catalyst was filtered over Dicalite and the solvent was evaporated. THF and HCl/dioxane (20 ml; 4 N) were added to the residue.

The solvent was evaporated. The residue was stirred in DIPE, filtered off and dried. Yield: 19.5 g of intermediate 82 (86.9%; .HCl).

d) Preparation of Intermediate 83

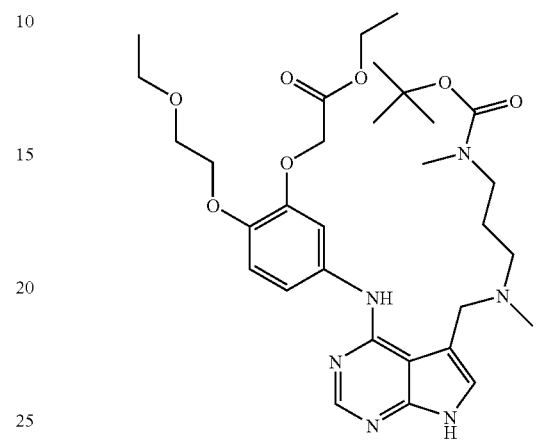

A mixture of intermediate 32 (1.84 g; crude, max 0.005 mol), intermediate 82 (1.60 g, 0.005 mol), HCl/dioxane (2 ml; 4 N) and t-BuOH (40 ml) was stirred for 5 hours at 75° C. Then the solvent was evaporated and the crude intermediate 83 was used as such in the next reaction step.

e) Preparation of Intermediate 84

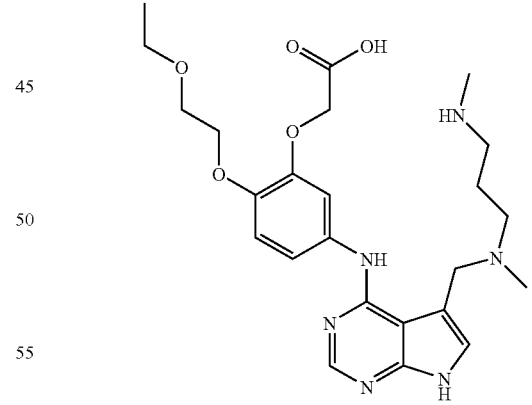

A mixture of intermediate 83 (crude, max. 0.005 mol), HCl (0.5 ml) and H₂O (30 ml) was stirred for 5 hours at 60° C. The solvent was evaporated and the residue (3.8 g) was purified by reversed-phase HPLC (Shandon Hyperprep® C18 BDS (Base Deactivated Silica) 8 μm, 250 g, I.D. 5 cm). A gradient with 2 mobile phases was applied. Phase A: a 0.25% NH₄HCO₃ solution in H₂O; phase B: CH₃CN). The desired fractions were collected. After removal of the solvent, 0.51 g of intermediate 84 was obtained.

Example A28 a) Preparation of Intermediate 85

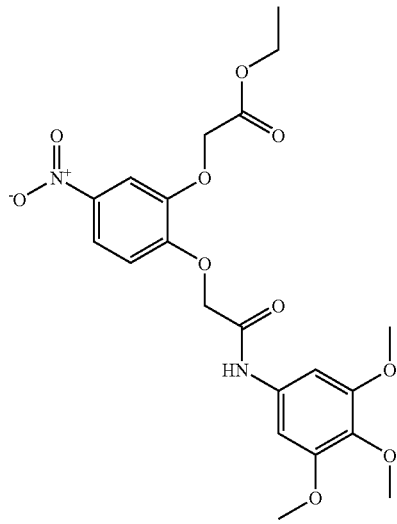

A mixture of (2-hydroxy-5-nitrophenoxy)acetic acid ethyl ester (4.82 g, 0.020 mol) and $K_2CO_3$ (3.04 g, 0.022 mol) was stirred in DMF (75 ml) at r.t. 2-Bromo-N-(3,4,5-trimethoxyphenyl)acetamide (6.08 g, 0.020 mol) in DMF (75 ml) was added dropwise and the reaction mixture was stirred for 6 hours. Then $H_2O$ (300 ml) was added. The compound was filtered off, washed ($H_2O$) and dried. Yield: 7.3 g of intermediate 85 (78.6%).

b) Preparation of Intermediate 86

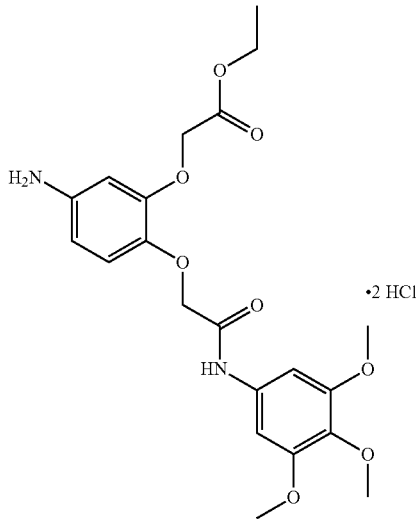

Raney Nickel (0.5 g) was suspended in THF (300 ml) under $N_2$ flow. Intermediate 85 (7.3 g, 0.0157 mol) was added and the reaction mixture was stirred under $H_2$ atmosphere until 3 eq. of $H_2$ were absorbed. The catalyst was filtered off over Dicalite and the filtrate was evaporated. EtOH and HCl/dioxane (20 ml; 4 N) were added and this mixture was stirred. The solvent was evaporated and the residue was stirred in DIPE. The compound was filtered off and dried. Yield: 6.6 g of intermediate 86 (89.3%; 0.2HCl).

c) Preparation of Intermediate 87

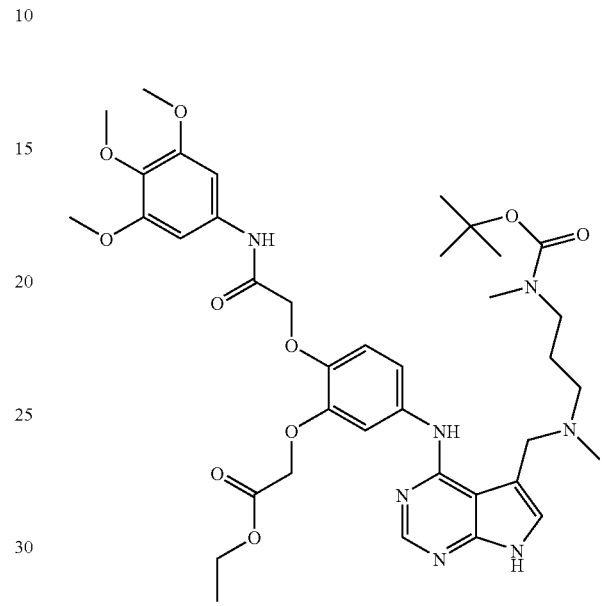

A mixture of intermediate 32 (1.84 g, 0.005 mol), intermediate 86 (3.53 g, 0.0075 mol), dioxane/HCl (2.5 ml; 4 N) and t-BuOH was stirred for 5 hours at 75° C. The solvent was evaporated and the crude residue (with intermediate 87) was used as such in the next reaction step.

d) Preparation of Intermediate 88

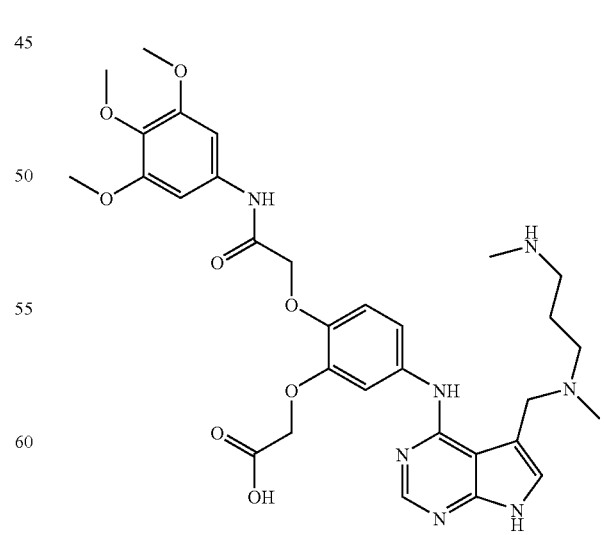

A mixture of intermediate 87 (crude; max. 0.005 mol), dioxane/HCl (2 ml; 4 N) and $H_2O$ (40 ml) was stirred for 5 hours at 60° C. The solvent was evaporated and the residue (7.1 g) was purified by HPLC. After workup, 0.30 g of intermediate 88 was obtained.

Example A29 a) Preparation of Intermediate 89

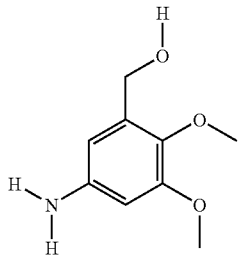

A mixture of 2,3-dimethoxy-5-nitro-benzenemethanol (0.0375 mol) in MeOH (150 ml) was hydrogenated at r.t. for 20 hours with Pt/C 5% (2 g) as a catalyst in the presence of a thiophene solution (1 ml; 4% in DIPE). After uptake of $H_2$ (3 eq.), the catalyst was filtered off and the filtrate was evaporated. The residue was suspended in DIPE. The precipitate was filtered off, washed with DIPE and dried (vacuo). Yield: 5.5 g of intermediate 89 (80%).

b) Preparation of Intermediate 90

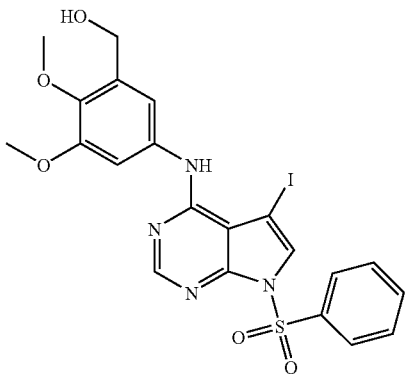

A mixture of 4-chloro-5-iodo-7-(phenylsulfonyl)-7H-pyrrolo[2,3-d]pyrimidine (0.014 mol), intermediate 89 (0.015 mol) and HCl (1.40 ml; 4 N in 1,4-dioxane) in t-BuOH (278 ml) was stirred for 72 hours at 80° C. The solvent was evaporated. $H_2O$ was added and the mixture was alkalized with $Et_3N$. The mixture was extracted with DCM (3×). The organic layers were combined, dried ($MgSO_4$), filtered and the solvent was evaporated. Yield: 6.45 g of intermediate 90 (81%).

c) Preparation of Intermediate 91

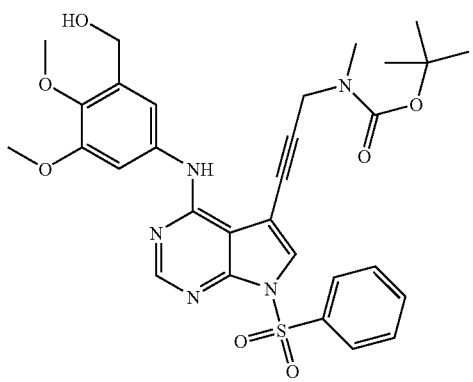

Intermediate 90 (0.0104 mol) was dissolved in $Et_3N$ (100 ml) and DMA (100 ml), and the solution was purged with $N_2$. Then, bis(triphenylphosphine)dichloropalladium (0.001 mol) and CuI (0.001 mol) were added. This mixture was purged again with $N_2$ and a solution of N-methyl-N-2-propyn-1-yl-carbamic acid, 1,1-dimethylethyl ester (0.0209 mol) in DMA (15 ml) was added dropwise over 30 minutes. The reaction mixture was stirred under $N_2$ over the weekend. The reaction mixture was poured into $H_2O$ and was extracted with EtOAc (3×100 ml). The organic layer was washed with $H_2O$ (2×100 ml), dried and concentrated to dryness. The residue was purified by column chromatography on silica gel eluting with EtOAc/hexane 3/1, 2/1, 3/2 and 1/1. The product fractions were collected and the solvent was evaporated. Yield: 6.9 g of intermediate 91 (100%).

d) Preparation of Intermediate 92

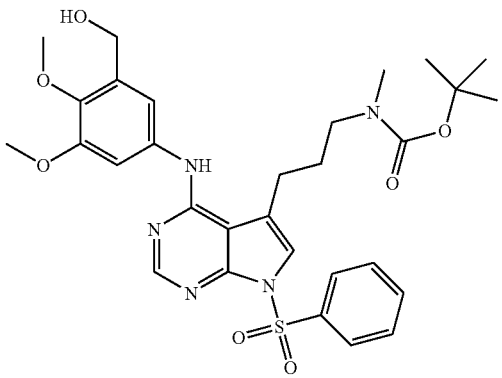

Intermediate 91 (0.011 mol) was dissolved in THF (120 ml), and Raney Nickel (2 g) was added to the solution. The reaction mixture was purged with $H_2$ and it was stirred at r.t. overnight under $H_2$ atmosphere. The reaction mixture was filtered through Celite and the filtrate was concentrated to dryness. The crude intermediate 92 (6.9 g; 99% yield) was used as such in the next reaction step.

e) Preparation of Intermediate 93

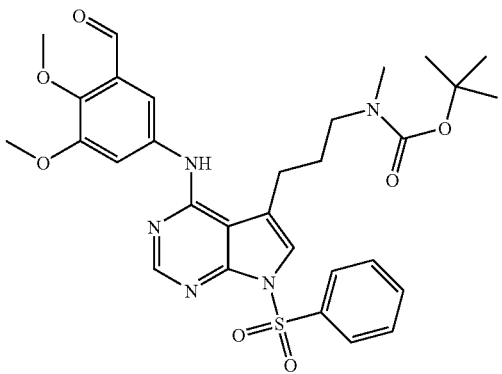

Intermediate 92 (0.0112 mol) was dissolved in THF (250 ml) and the solution was purged with $N_2$. Then, $MnO_2$ (0.245 mol) was added and the reaction mixture was purged with $N_2$. The reaction mixture was stirred overnight at r.t. under $N_2$ atmosphere. Then the mixture was filtered through Celite and the Celite was washed with THF, then with THF/MeOH and with MeOH/DCM. The filtrate was concentrated to dryness. The product was purified by column chromatography on silica eluting with DCM/MeOH (95/5). The product fractions were collected and the solvent was evaporated. Yield: 3.8 g of intermediate 93 (96%).

f) Preparation of Intermediate 94

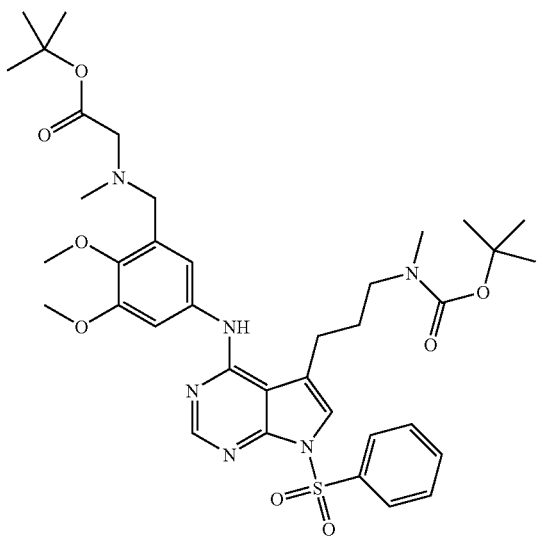

A mixture of intermediate 93 (0.00205 mol), N-methylglycine 1,1-dimethylethyl ester hydrochloride (0.003075 mol) and Et₃N (0.0041 mol) in DCM (102.5 ml) was stirred at r.t. NaBH(OAc)₃ (0.00615 mol) was added portionwise. The reaction mixture was stirred for 16 hours at r.t. The reaction mixture was poured out into H₂O and this mixture was extracted 2 times with DCM. The organic layers were combined, dried (MgSO₄), filtered and concentrated to dryness. The residue was dried (vacuum, r.t.) yielding 1.37 g of intermediate 94 as a yellow solid (90% yield).

g) Preparation of Intermediate 95

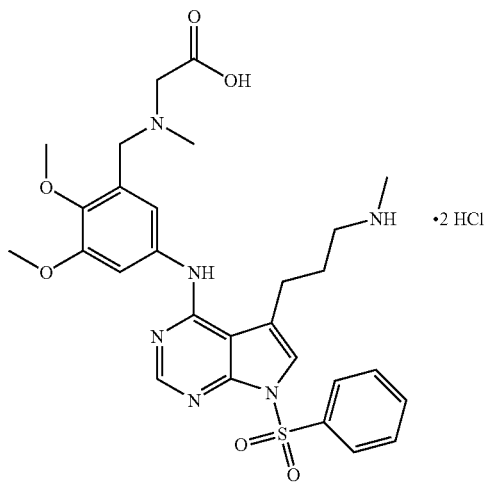

A mixture of intermediate 94 (0.0024 mol) in 1,4-dioxane (48 ml), H₂O (48 ml) and HCl (24 ml; 37%) was stirred for 2 hours at 60° C. Then the solvent was evaporated, and co-evaporated 3 times with CH₃CN. After drying at high vacuum, the obtained residue (with intermediate 95 as a HCl-salt) was used as such in the next reaction step.

h) Preparation of Intermediate 96

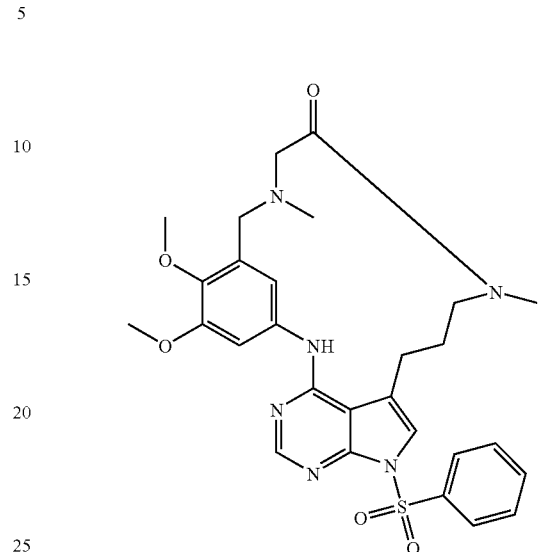

A solution of intermediate 95 (0.0024 mol) in DMF (190 ml) was added very slowly (over 1 hour, using a Marlow peristaltic pump) to a solution of HBTU (0.00576 mol) and DIPEA (0.060 mol) in DMF (190 ml). After the addition was completed, the reaction mixture was stirred for an additional hour. Then the mixture was quenched by addition of 7 N NH₃ in MeOH (5 ml) and the solvents were evaporated. The reaction mixture was concentrated to dryness and the residue was partitioned between DCM and a saturated aq. K₂CO₃ solution. The aq. layer was extracted with more DCM. The organic extracts were washed with a saturated aq. K₂CO₃ solution, then dried, filtered and the filtrate was concentrated to dryness. Yield: Intermediate 96 (quantitative yield; used as a crude in the next reaction step without further purification).

Example A30 a) Preparation of Intermediate 97

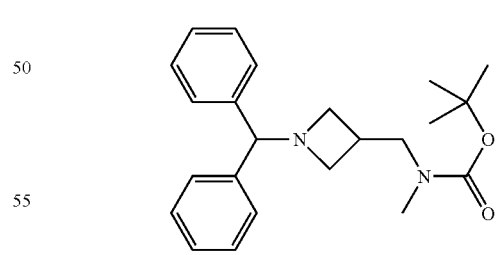

A mixture of [[1-(diphenylmethyl)-3-azetidinyl]methyl]-carbamic acid 1,1-dimethylethyl ester (8 g, 0.0227 mol) and THF (100 ml) was stirred under N₂ atmosphere. NaH (1 g, 0.025 mol; 60%) was added and the reaction mixture was stirred for 30 minutes. Dimethylsulphate (3.16 g, 0.025 mol) was added dropwise and the mixture was stirred for 16 hours. More NaH (1 g, 0.025 mol; 60%) and dimethylsulphate (3.16 g, 0.025 mol) were added and stirring was continued for 16 hours. Then, the reaction mixture was decomposed with H₂O and the mixture was extracted with DCM. The separated organic layer was dried and the solvent was evaporated. The residue was purified by HPLC. Yield: 4.9 g of intermediate 97. A mixture of intermediate 97 (4.9 g, 0.0135 mol) in THF (50 ml) was hydrogenated at r.t. with Pd/C 10% (1 g) as a catalyst. After uptake of H$_2$ (1 eq.), the catalyst was filtered off and the filtrate containing intermediate 98 was used as such in the next reaction step.

c) Preparation of Intermediate 99

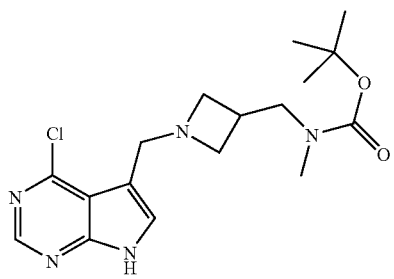

A mixture of the filtrate from the previous reaction step containing intermediate 98 (0.0135 mol) and NaBH(OAc)$_3$ (8.6 g, 0.040 mol) was stirred at r.t. A mixture of intermediate 1 (2 g, 0.011 mol) and THF/DMF (50 ml/50 ml) was added dropwise to the first mixture and the reaction mixture was stirred for 3 hours. Then, the mixture was poured out into H$_2$O and the aq. mixture was extracted with DCM. The organic layer was dried and evaporated to dryness. The residue was purified over silica gel (eluent: DCM/MeOH 90/10). The desired fractions were collected and the solvent was evaporated. Yield: 1.5 g of intermediate 99.

d) Preparation of Intermediate 100

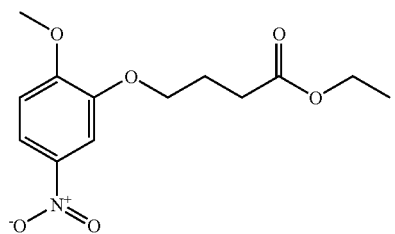

A mixture of 2-methoxy-5-nitrophenol (10 g, 0.0590 mol), K$_2$CO$_3$ (9 g, 0.0650 mol) and 4-chlorobutanoic acid ethyl ester (10 g, 0.0660 mol) in DMF (120 ml) was stirred at 60° C. until the reaction was finished. Then, the mixture was poured out into H$_2$O. The precipitate was filtered off and dried (vacuum). Yield: 8.05 g of intermediate 100.

e) Preparation of Intermediate 101

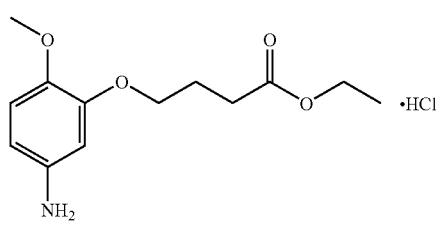

A mixture of intermediate 100 (14 g, 0.0494 mol) in EtOH (250 ml) was hydrogenated at r.t. with Pd/C 10% (2 g) as a catalyst in the presence of a thiophene solution (2 ml; 4% in DIPE). After uptake of H$_2$ (3 eq.), the catalyst was filtered off and the filtrate was acidified with HCl/2-propanol. The mixture was evaporated and the residue was stirred in DIPE. The precipitate was filtered off and dried. Yield: 13.3 g of intermediate 101 (.HCl).

f) Preparation of Intermediate 102

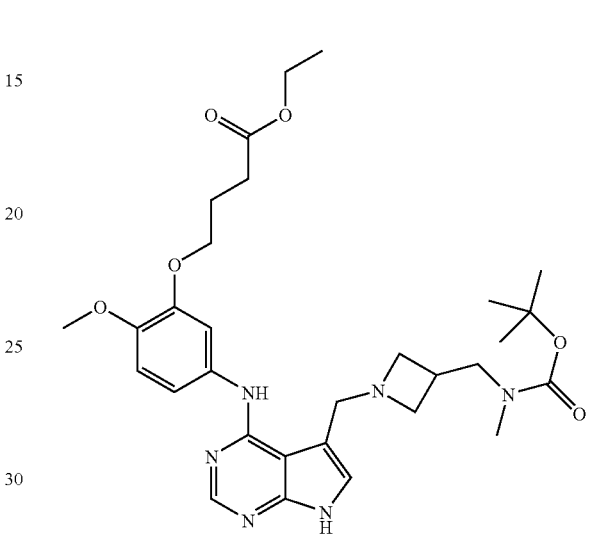

A mixture of intermediate 99 (0.750 g, 0.002 mol) and intermediate 101 (0.575 g, 0.002 mol) in HCl/dioxane (0.750 ml; 4 N) and t-BuOH (15 ml) was stirred for 5 hours at 75° C. This reaction mixture (containing intermediate 102) was used as such in the next reaction step.

g) Preparation of Intermediate 103

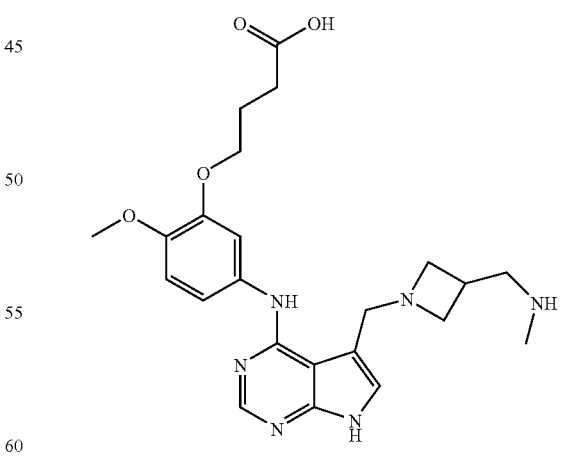

The reaction mixture of the previous reaction step containing crude intermediate 102 (max. 0.002 mol) was heated together with H$_2$O (20 ml) and HO/dioxane (4 ml; 4 N) for 8 hours at 50° C. Then the reaction mixture was cooled, neutralized with Et$_3$N and evaporated to dryness. The residue was purified by reversed-phase HPLC (Shandon Hyperprep®

C18 BDS (Base Deactivated Silica) 8 μm, 250 g, I.D. 5 cm). A gradient with 2 mobile phases was applied. Phase A: a 0.25% NH₄HCO₃ solution in H₂O; phase B: CH₃CN). The desired fractions were collected. After workup, 0.180 g of intermediate 103 was obtained.

Example A31 a) Preparation of Intermediate 104

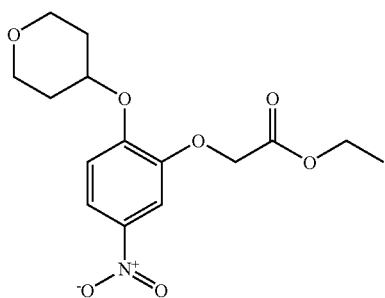

A solution of (2-hydroxy-5-nitrophenoxy)acetic acid ethyl ester (2 g, 0.0083 mol), tetrahydro-2H-pyran-4-ol (1.13 g, 0.0111 mol) and (Ph)₃P (4.35 g, 0.0166 mol) in THF (80 ml) was stirred at r.t. DIAD (3.3 ml, 0.0166 mol) was added dropwise and the reaction mixture was stirred for 3 hours. The solvent was evaporated and the residue was purified over silica gel (eluent: DCM/MeOH 100/0-98/2). The desired fractions were collected and the solvent was evaporated. The crude intermediate 104 was used as such in the next reaction step (quantitative yield).

b) Preparation of Intermediate 105

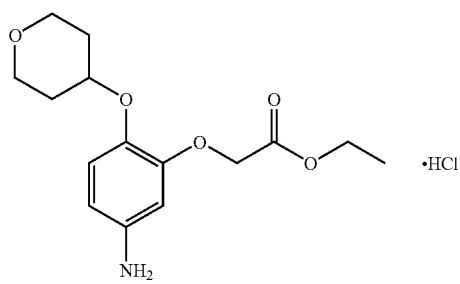

A mixture of intermediate 104 (2.6 g, 0.008 mol) in THF (120 ml) was hydrogenated at r.t. with Raney Nickel (1 g) as a catalyst. After uptake of H₂ (3 eq.), the catalyst was filtered off and the filtrate was evaporated. The residue was treated with DIPE and a few drops of HCl/2-propanol. The mixture was stirred for 1 hour. The solvent was evaporated and the crude residue was used as such in the next reaction step. Yield: 3.2 g of intermediate 105 (crude HCl-salt).

c) Preparation of Intermediate 106

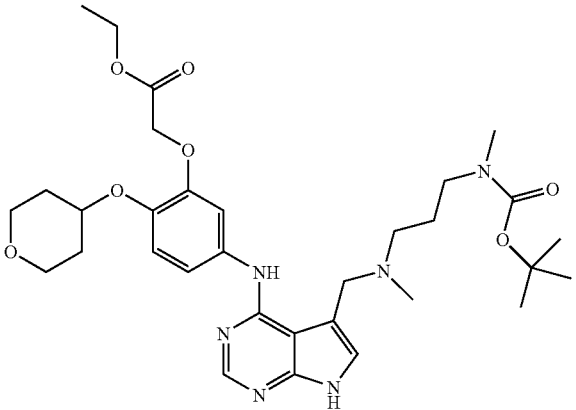

A solution of intermediate 105 (1.6 g, 0.0048 mol), intermediate 32 (1.7 g, 0.0046 mol) and HCl/dioxane (2 ml; 4 N) in t-BuOH (38 ml) was stirred for 6 hours at 75° C. The reaction mixture (with intermediate 106) was used as such in the next reaction step.

d) Preparation of Intermediate 107

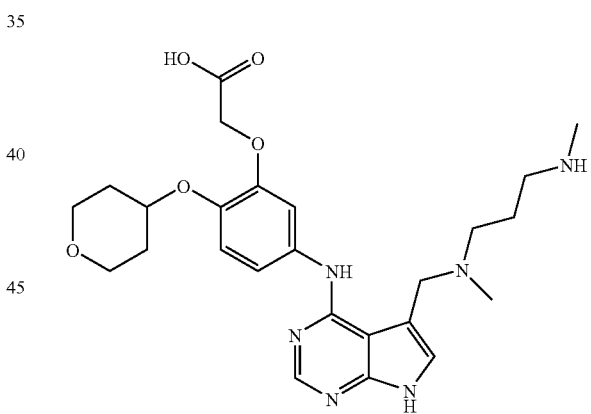

The crude reaction mixture from the previous reaction step containing intermediate 106 (approx. 0.0046 mol) was treated with concentrated HCl (1 ml) and H₂O (2 ml). The solution was heated for 2 hours to 60° C. Then the solvent was evaporated and the residue was purified by HPLC (RP-18; eluent: (0.25% NH₄HCO₃ in H₂O)/CH₃CN v/v 100/0-0/100). The desired fractions were collected and the solvent was evaporated. The residue was repurified under the same HPLC conditions. The desired fractions were collected and the solvent was evaporated and co-evaporated with toluene. The residue was used as such in the next reaction step. Yield: 0.26 g of intermediate 107.

Example A32 a) Preparation of Intermediate 108

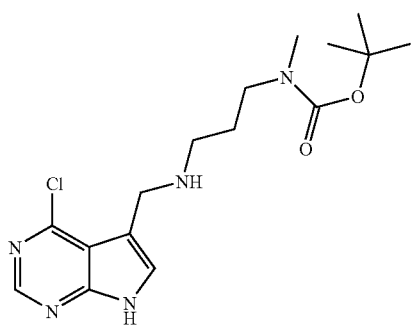

A solution of intermediate 1 (0.91 g, 0.005 mol) in THF/DMF (40 ml/40 ml) was added dropwise at r.t. to a stirred solution of N-(3-Aminopropyl)-N-(methyl)carbamic acid tert-butyl ester (1.13 g, 0.006 mol) and NaBH(OAc)$_3$ (3.2 g, 0.015 mol) in DCM (40 ml). The reaction mixture was stirred for 19 hours and was then poured out into ice-water. The mixture was basified with K$_2$CO$_3$, extracted with DCM, dried (MgSO$_4$), filtered and the solvent was evaporated to yield crude intermediate 108 as an oil that was used as such in the next reaction step.

b) Preparation of Intermediate 109

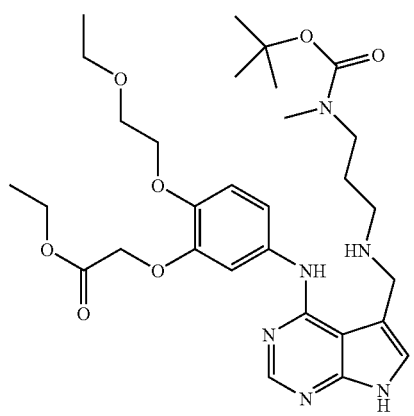

A solution of intermediate 108 (crude; max. 0.005 mol) and intermediate 82 (0.006 mol) in HCl/dioxane (2 ml; 4 N) and t-BuOH (40 ml) was stirred for 6 hours at 75° C. The reaction mixture (containing intermediate 109) was used as such in the next reaction step.

c) Preparation of Intermediate 110

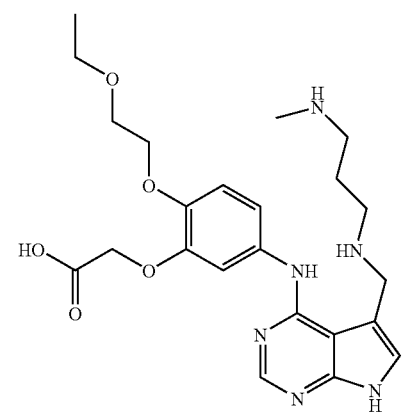

A mixture of intermediate 109 (crude; max. 0.005 mol), HCl (20 ml; 36%) and H$_2$O (40 ml) was stirred for 2 hours at 60° C. Then the solvent was evaporated and the residue was purified by HPLC (Shandon Hyperprep® C18 HS BDS; 8 µm, 50 mm by 16.5 cm). A gradient with 2 mobile phases was applied: (0.25% NH$_4$HCO$_3$ in H$_2$O)/CH$_3$CN from 100/0 to 80/20 in 35 minutes; then 0/100 for 10 minutes and finally 100/0 for 12 minutes. The desired fractions were collected and the solvent was evaporated. Yield: 0.750 g of intermediate 110 (32% yield).

Example A33 a) Preparation of Intermediate 111

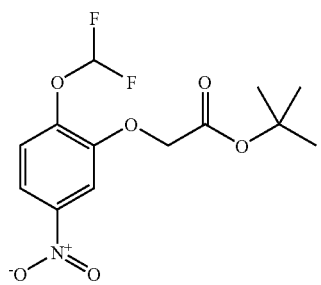

2-(Difluoromethoxy)-5-nitrophenol (1.68 g, 0.0082 mol) and K$_2$CO$_3$ (2.26 g, 0.0164 mol) were stirred in DMA (20 ml). Then, 2-bromoacetic acid tert-butyl ester (1.32 ml, 0.0090 mol) was added and the resulting reaction mixture was stirred overnight at 60° C. The reaction mixture was cooled and H$_2$O was added. This mixture was extracted with EtOAc (3×300 ml). The combined organic layers were washed with H$_2$O (2×200 ml), dried (MgSO$_4$), filtered and concentrated to dryness. Yield: 3 g of crude intermediate 111 (used as such in the next reaction step).

b) Preparation of Intermediate 112

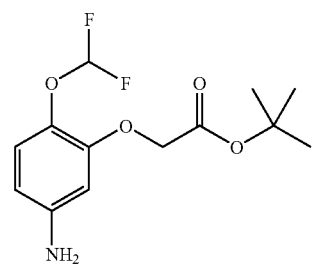

Intermediate 111 (crude; max. 0.0082 mol) was dissolved in EtOAc (q.s.) and the solution was purged using vacuum and N$_2$. Then Pd/C ((catalytic quantity) was added and the reaction mixture was purged with N$_2$. The reaction mixture was stirred overnight at r.t. under H$_2$ atmosphere. The reaction mixture was filtered through Celite and the Celite was washed with more EtOAc, THF/MeOH and with MeOH/DCM. The filtrate was concentrated to dryness. Yield: 2.4 g of intermediate 112 (99%).

c) Preparation of Intermediate 113

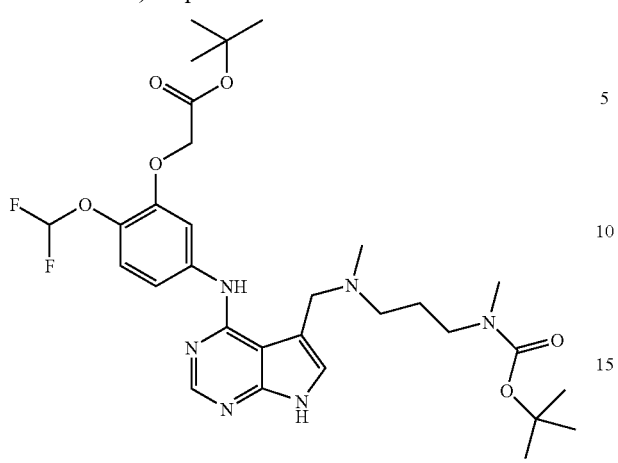

A mixture of intermediate 32 (1.26 g, 0.0034 mol), intermediate 112 (1.2 g, 0.0041 mol) and HCl (1 ml; 4 N in 1,4-dioxane) in CH$_3$CN (25 ml) was stirred for 2 hours at 80° C. The reaction mixture was concentrated to dryness and the residue was re-dissolved in DCM and filtered. After washing with H$_2$O, the organic phase was filtered and concentrated to dryness. Yield: 1.4 g of intermediate 113.

d) Preparation of Intermediate 114

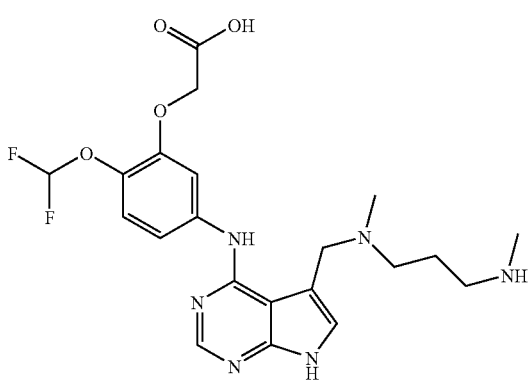

Intermediate 113 (0.00226 mol) was dissolved in HCl (25 ml; 36%) and 1,4-dioxane (3 ml), and the reaction mixture was stirred at r.t. for 3 hours. The solvent was evaporated. The residue was stirred in DIPE, filtered off and dried (vacuum, r.t.). Intermediate 114 was used as such in the next reaction step (quantitative yield).

Example A34 a) Preparation of Intermediate 115

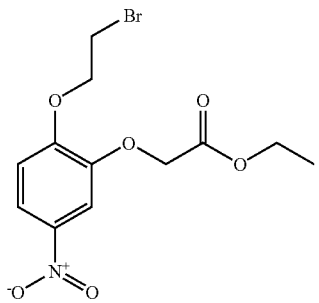

A mixture of (2-hydroxy-5-nitrophenoxy)acetic acid ethyl ester (5 g, 0.0207 mol) and K$_2$CO$_3$ (4.3 g, 0.03105 mol) in DMF (150 ml) was stirred for 20 minutes at r.t. Then 1,2-dibromoethane (17.9 ml) was added and the mixture was heated to 60° C. for 18 hours. The mixture was quenched with ice-water and the product was extracted with toluene. The organic layer was dried (MgSO$_4$), filtered and the solvent was evaporated. Yield: 6.7 g of intermediate 115.

b) Preparation of Intermediate 116

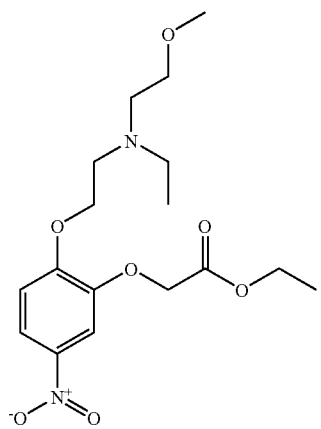

A solution of intermediate 115 (1.4 g, 0.0042 mol) and N-ethyl-2-methoxyethanamine (1 g, 0.010 mol) in DMF (50 ml) was heated up to 100° C. for 18 hours. The solvent was evaporated and the residue was dissolved in DCM. This organic solution was washed with H$_2$O and was then dried (MgSO$_4$), filtered and the solvent was evaporated. The crude intermediate 116 (1.6 g) was used as such in the next reaction step.

c) Preparation of Intermediate 117

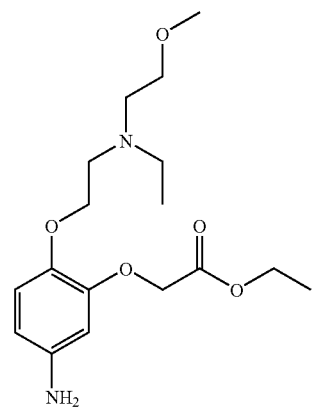

A mixture of intermediate 116 (1.6 g; crude) in THF (120 ml) was hydrogenated at r.t. with Raney Nickel as a catalyst. After uptake of H$_2$ (3 eq.), the catalyst was filtered off and the filtrate was evaporated. The residue was treated with HCl (2 ml; 4 N in dioxane) and this mixture was stirred for 15 minutes. The solvent was evaporated and the crude intermediate 117 (1.6 g; 0.2 HCl) was used as such in the next reaction step.

d) Preparation of Intermediate 118

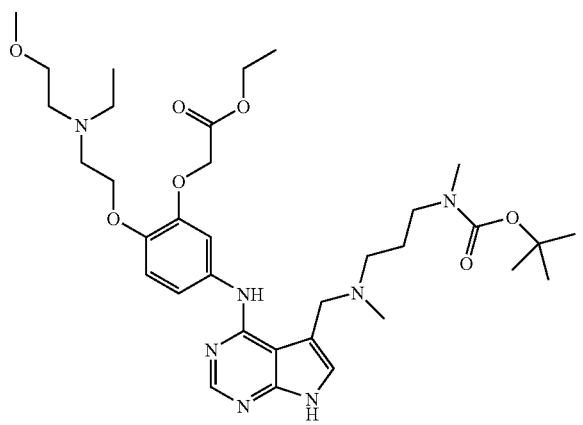

A solution of intermediate 32 (0.96 g, 0.0026 mol) and intermediate 117 (1.6 g, 0.0037 mol) in HCl/dioxane (2 ml; 4 N), t-BuOH (20.8 ml) and DMF (20 ml) was stirred for 6 hours at 75° C. This reaction mixture (containing intermediate 118) was used as such in the next reaction step.

e) Preparation of Intermediate 119

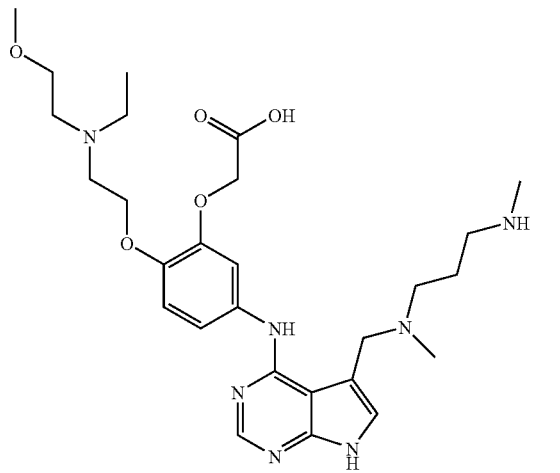

The reaction mixture from the previous reaction step containing intermediate 118 (max. 0.0026 mol) was treated with concentrated HCl (1 ml) and H$_2$O (2 ml). The solution was heated up to 60° C. for 2 hours. Then the solvent was evaporated and the residue was purified by HPLC (RP-18; eluent: (0.25% NH$_4$HCO$_3$ in H$_2$O)/CH$_3$CN v/v 100/0-0/100). The desired fractions were collected and the solvent was evaporated and co-evaporated with toluene. The crude intermediate 119 (0.1 g) was used as such in the next reaction step.

Example A35 a) Preparation of Intermediate 120

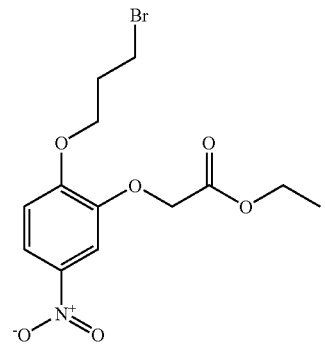

A mixture of (2-hydroxy-5-nitrophenoxy)acetic acid ethyl ester (10 g, 0.0414 mol) and K$_2$CO$_3$ (8.6 g, 0.0621 mol) in DMF (300 ml) was stirred for 1 hour at r.t. Then 1,3-dibromopropane (42 ml, 0.414 mol) was added and the mixture was heated to 60° C. for 18 hours. The mixture was quenched with ice-water and the product was extracted with toluene (3×). The organic layer was dried (MgSO$_4$), filtered and the solvent was evaporated. The residue was purified by flash column chromatography over silica (eluent: DCM). The desired fractions were collected and the solvent was evaporated. Yield: 8.40 g of intermediate 120 (55% yield).

b) Preparation of Intermediate 121

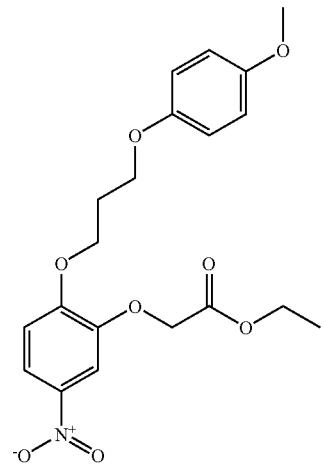

A solution of 4-methoxyphenol (1.56 g, 0.0126 mol) and K$_2$CO$_3$ (1.73 g, 0.0126 mol) in DMF (70 ml) was heated at 60° C. for 1 hour till the appearance of a strong violet pigmentation. Then intermediate 120 (3.5 g, 0.0097 mol) was added and the mixture was heated for 24 hours. The reaction mixture was poured in ice-water and the product was extracted with toluene (3×). The organic layer was dried (MgSO$_4$), filtered and the solvent was evaporated to yield an oil. This oil was purified by flash column chromatography over silica gel (eluent: heptane/EtOAc 4/1). The desired fractions were collected and the solvent was evaporated. Yield: 2.28 g of intermediate 121 (58%).

c) Preparation of Intermediate 122

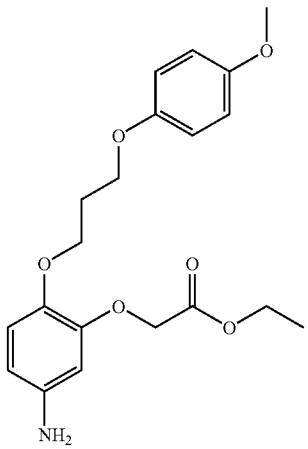

A mixture of intermediate 121 (2.28 g, 0.0056 mol) in EtOH (60 ml) was hydrogenated at r.t. with Pd/C 10% (0.5 g) as a catalyst in the presence of a thiophene solution (0.3 ml; 4% in DIPE). After uptake of $H_2$ (3 eq.), the catalyst was filtered off and the filtrate was evaporated. The residue was dissolved in DCM and treated with HCl gas for 5 minutes. The solvent was evaporated to obtain crude intermediate 122 (2.12 g; .HCl) as a purple solid that was used a such in the next reaction step.

d) Preparation of Intermediate 123

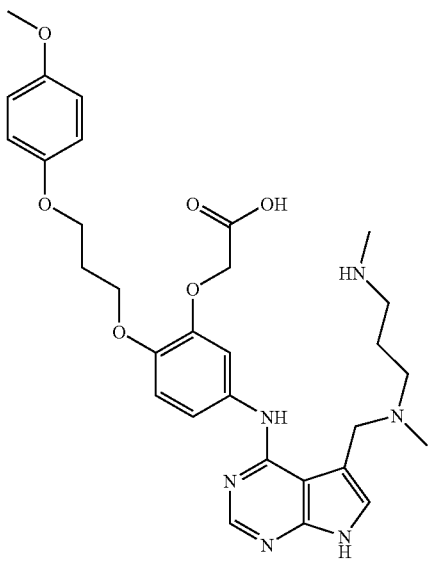

A solution of intermediate 122 (1 g, 0.002664 mol), intermediate 32 (1.176 g, 0.003196 mol) and HCl/dioxane (1.1 ml; 4 N) in 1-butanol (22 ml) was heated for 30 minutes at 100° C. This mixture was added to a solution of HCl (13 ml; 36%) in $H_2O$ (26 ml). The mixture was stirred for 2 hours at 60° C. and was then heated to 80° C. for 20 hours. The mixture was concentrated under reduced pressure and a mixture of LiOH.$H_2O$ (0.559 g, 0.01332 mol), THF (20 ml) and $H_2O$ (5 ml) was added. The reaction mixture was heated for 30 minutes at 50° C. The solvent was evaporated and the residue was purified by HPLC method C. The desired fractions were collected and the solvent was evaporated and co-evaporated with MeOH. Yield: 0.287 g of intermediate 123 (18.6%).

Example A36 a) Preparation of Intermediate 124

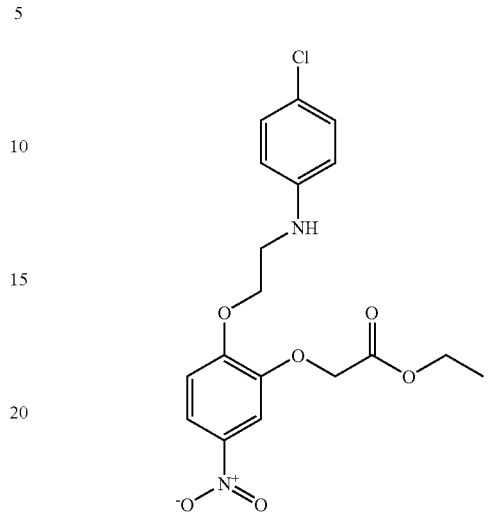

A solution of intermediate 115 (1.25 g, 0.0036 mol) and 4-chlorobenzenamine (1.37 g, 0.0108 mol) in DMF (30 ml) was heated in the microwave to 125° C. for 90 minutes. After cooling, the reaction mixture was poured into ice-water and the product was extracted with EtOAc (3×). The organic layer was washed with $H_2O$, dried (MgSO$_4$), filtered and the solvent was evaporated to yield an oil. This oil was purified by flash column chromatography over silica gel (eluent: heptane/EtOAc 4/1). The desired fractions were collected and the solvent was evaporated. Yield: 0.7 g of intermediate 124 (50% yield).

b) Preparation of Intermediate 125

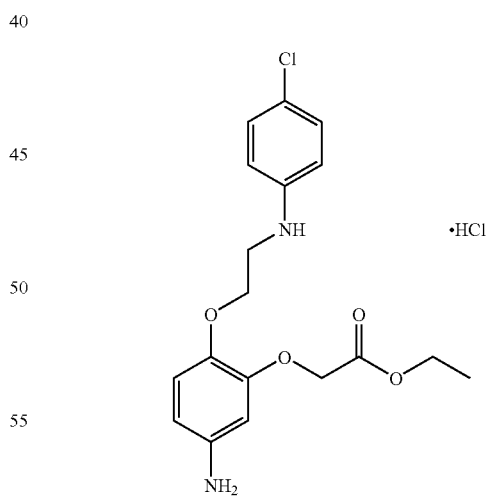

A mixture of intermediate 124 (0.66 g, 0.0017 mol) in THF (50 ml) was hydrogenated at r.t. with Pd/C 5% (0.2 g) as a catalyst in the presence of a thiophene solution (4% in DIPE). After uptake of $H_2$ (3 eq), the catalyst was filtered off and the filtrate was evaporated. The residue was dissolved in DCM and treated with HCl gas for 5 minutes. Then the solvent was evaporated to yield 0.749 g of intermediate 125 (.HCl) as a brown solid that was used as such in the next reaction step.

c) Preparation of Intermediate 126

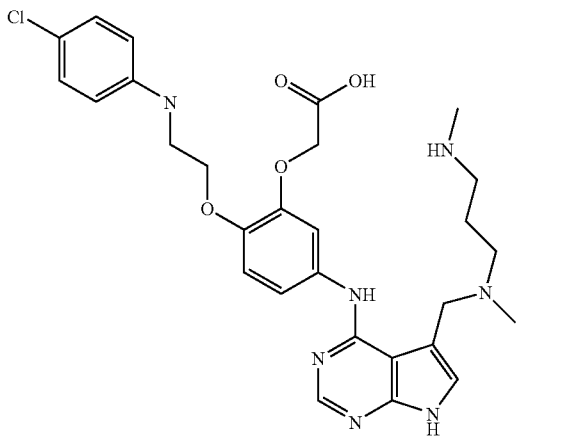

A solution of intermediate 125 (0.749 g, 0.002053 mol), intermediate 32 (0.906 g, 0.002464 mol) and HCl/dioxane (0.8 ml; 4 N) in 1-butanol (18 ml) was heated for 30 minutes at 100° C. This mixture was added to a solution of HCl (0.8 ml, 36%) in $H_2O$ (16 ml) and the reaction mixture was stirred for 24 hours at 80° C. Then the solvent was evaporated. A mixture of $LiOH.H_2O$ (0.43 g, 0.01025 mol) and THF (15 ml) in $H_2O$ (3 ml) was added to the residue and the mixture was heated overnight at 50° C. The solvent was evaporated and the residue was purified by HPLC method C. The desired fractions were collected and the solvent was evaporated and co-evaporated with MeOH. Yield: 0.1 g of intermediate 126 (7.3% yield).

Example A37 a) Preparation of Intermediate 127

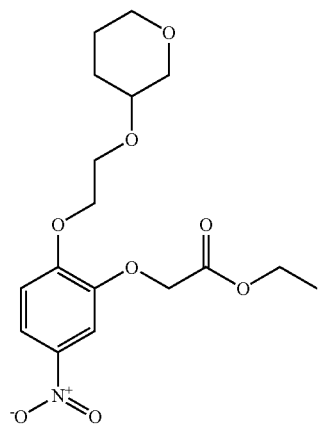

NaH (1.5 g, 0.0375 mol) was stirred in DMF (80 ml; dry) under $N_2$ at r.t. 2-[(Tetrahydro-2H-pyran-2-yl)oxy]ethanol (5.09 ml, 0.0375 mol) was added dropwise and the mixture was stirred for 1 hour. 5-Nitro-1,3-benzodioxole (4.178 g, 0.025 mol) was added portionwise and the reaction mixture was stirred for 5 hours. Ethyl 2-bromoacetate (4.158 ml, 0.0375 mol) in DMF (20 ml; dry) was added dropwise and the mixture was stirred overnight. Subsequently, $H_2O$ was added and the product was extracted with EtOAc (3×). The organic layer was washed with $H_2O$, dried and the solvent was evaporated. Yield: 9.5 g of intermediate 127.

b) Preparation of Intermediate 128

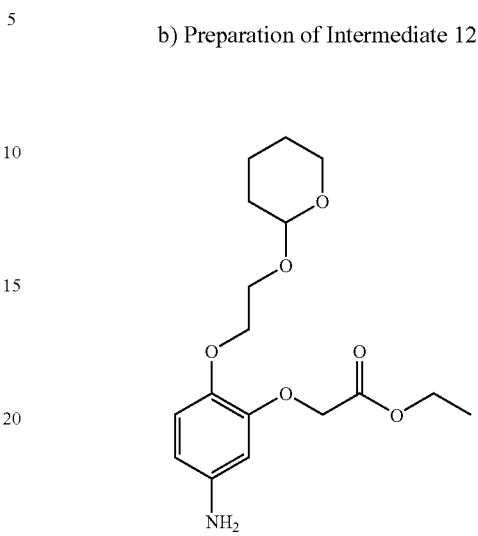

Pd/C (2 g, 0.001879 mol) was suspended in EtOH (300 ml) under $N_2$ flow. Intermediate 127 (9.234 g, 0.025 mol) and a thiophene solution (0.025 mol; 4% in DIPE) was added and the reaction mixture was stirred under $H_2$ atmosphere until 3 eq. of $H_2$ were absorbed. Then the catalyst was filtered off over Dicalite and the solvent was evaporated. The residue was stirred in DIPE and the precipitate was filtered off and dried, yielding crude intermediate 128 (8.8 g).

c) Preparation of Intermediate 129

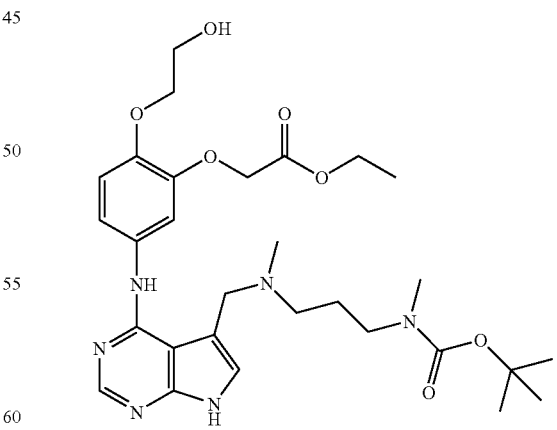

A mixture of intermediate 32 (1.839 g, 0.005 mol), intermediate 128 (3.636 g, 0.006 mol), HCl/dioxane (2.5 ml; 4 M) and t-BuOH (40 ml) was stirred overnight at 75° C. The solvent was evaporated the crude intermediate 129 was used as such in the next reaction step.

d) Preparation of Intermediate 130

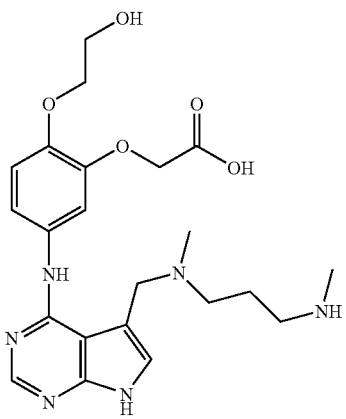

A mixture of intermediate 129 (2.933 g, 0.005 mol), HCl/dioxane (2.5 ml; 4 N) and H₂O (40 ml) was stirred for 5 hours at 60° C. The solvent was evaporated and the residue was purified by HPLC. The solvent was evaporated, yielding 0.16 g of intermediate 130 (6.7%).

Example A38 a) Preparation of Intermediate 131

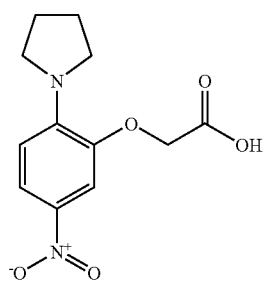

A mixture of 2-chloro-5-nitrophenoxyacetic acid (2 g, 0.0086 mol), pyrrolidine (0.92 ml, 0.011 mol), Cu powder (catalytic amount; dendritic, 3 micron) and K₂CO₃ (1.5 g, 0.011 mol) in DMF (5 ml) was heated for 2 hours at 150° C. The solvent was evaporated and the residue was stirred in a mixture of MeOH/DCM 5/95. The precipitate was filtered off, washed and dried. The product was dissolved in H₂O and treated with HCl (1 N). The formed precipitate was filtered off and washed. Yield: 1.6 g of crude intermediate 131 that was used as such in the next reaction step b) Preparation of Intermediate 132

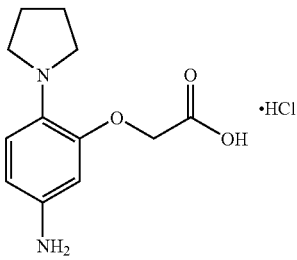

A mixture of intermediate 131 (1.6 g, 0.006 mol) in THF (120 ml) was hydrogenated at r.t. with Raney Nickel (1 g) as a catalyst. After uptake of H₂ (3 eq.), the catalyst was filtered off and the filtrate was evaporated. The residue was treated with HCl (4 N) in dioxane (2 ml) and this mixture was stirred for 15 minutes. The solvent was evaporated and the crude intermediate 132 (.HCl) was used as such in the next reaction step.

c) Preparation of Intermediate 133

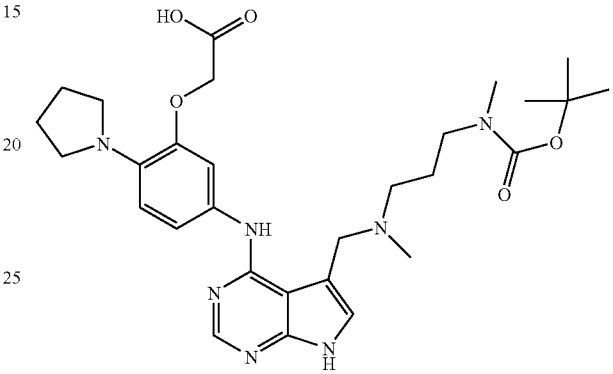

A solution of intermediate 32 (1.58 g, 0.0043 mol), intermediate 132 (1.6 g, 0.0043 mol) and HCl/dioxane (2 ml; 4 N) in t-BuOH (20 ml) was stirred for 18 hours at 75° C. This reaction mixture containing intermediate 133 was used as such in the next reaction step.

d) Preparation of Intermediate 134

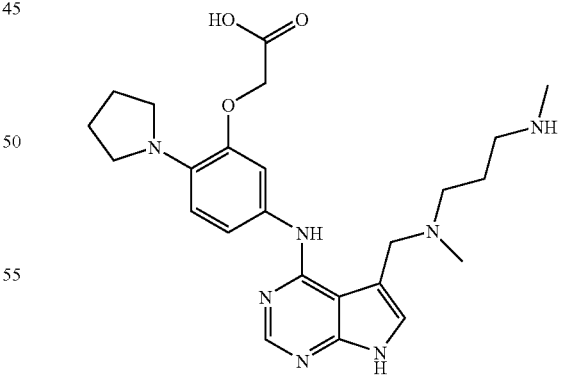

The crude reaction mixture from the previous reaction step containing intermediate 133 (max. 0.0043 mol) was treated with concentrated HCl (3 ml) and H₂O (5 ml). The solution was heated up to 60° C. for 2 hours. The solvent was evaporated and the residue was purified by HPLC (RP-18; eluent: (0.25% NH₄HCO₃ in H₂O)/CH₃CN v/v 100/0-0/100). The desired fractions were collected and the solvent was evaporated. The crude intermediate 134 (0.030 g) was used as such in the next reaction step.

Example A39 a) Preparation of Intermediate 135

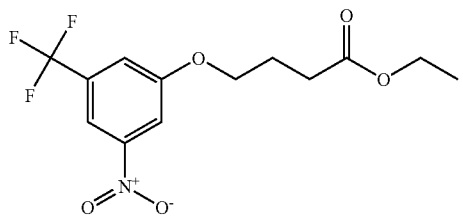

3-Nitro-5-trifluoromethylphenol (3.20 g, 0.0154 mol) was dissolved in CH$_3$CN (46 ml). 4-Bromobutanoic acid ethyl ester (2.6 ml, 0.0185 mol) was added to the solution, followed by the addition of K$_2$CO$_3$ (3.20 g, 0.0232 mol). The reaction mixture was heated at 80° C. overnight. The solid was filtered off and washed with CH$_3$CN. EtOAc (20 ml) was added and the mixture was washed with brine, dried (MgSO$_4$), filtered and concentrated to dryness. The residue was purified by flash column chromatography on silica gel, using as eluent a mixture of hexanes:EtOAc (ratio 40/1). The product fractions were collected and the solvent was evaporated. The product was dried (vacuum, r.t.) yielding a pale yellow solid. Yield: 4.40 g of intermediate 135 (89%).

b) Preparation of Intermediate 136

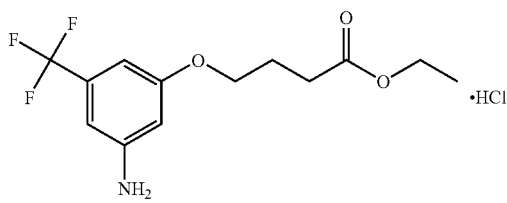

Intermediate 135 (4.40 g, 0.0137 mol) was dissolved in THF (48 ml) at r.t. Pt/C 5% (0.88 g) was added and the mixture was stirred at r.t. under H$_2$ atmosphere for 15 hours. The mixture was filtered through a Celite pad. The Celite was washed with THF. The solvent was evaporated. The product was dried (vacuum, r.t.), yielding 3.96 g of a brown oil. The hydrochloric salt was obtained purging HCl gas into a solution of the aniline in Et$_2$O. Yield: 3.86 g of intermediate 136 (86%; .HCl).

c) Preparation of Intermediate 137

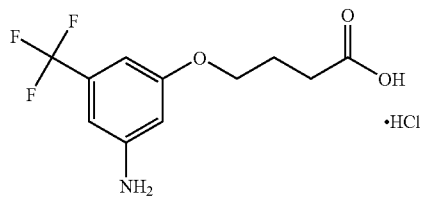

Intermediate 136 (3.86 g, 0.0118 mol) was dissolved in HCl/1,4-dioxane (30 ml; 4 N). The solution was heated at 60° C. overnight. The solvent was evaporated and the residue was stirred in Et$_2$O and filtered off. The product was dried (vacuum, r.t.) yielding 3.40 g of intermediate 137 (96%; .HCl) as a grey solid.

d) Preparation of Intermediate 138

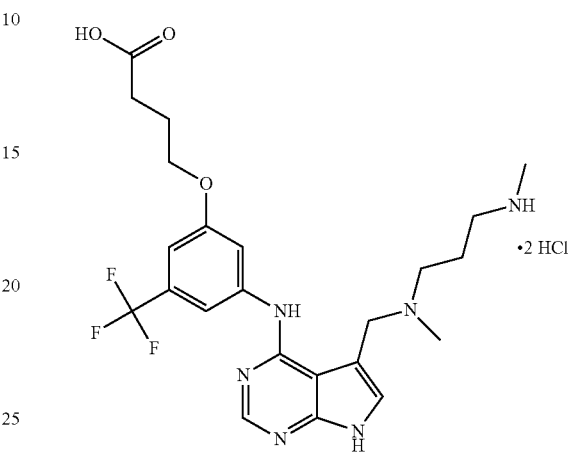

Intermediate 32 (0.70 g, 0.0019 mol) was dissolved in a mixture of CH$_3$CN (4 ml) and 2-propanol (2 ml). Then intermediate 137 (0.69 g, 0.0023 mol) was added, followed by the addition of HCl (1 ml; 4 N in 1,4-dioxane). The reaction mixture was heated at 80° C. for 2 hours. The solvent was evaporated and the residue was dried (vacuum, r.t.), yielding crude intermediate 138 (0.2HCl) as a brown foam. This compounds was used as such in the next reaction step.

Example A40 a) Preparation of Intermediate 139

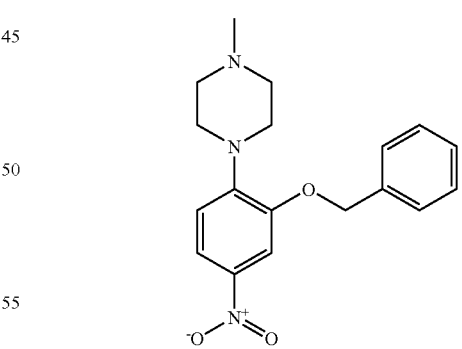

A mixture of 1-chloro-4-nitro-2-(phenylmethoxy)benzene (26.29 g, 0.0997 mol) in 1-methyl-1,4-piperazine (50 ml) was heated at 100° C. overnight. The mixture was partitioned between EtOAc and a saturated aq. NaHCO$_3$ solution. The aq. phase was extracted with EtOAc several times. The combined organic layers were washed first with brine, then with 200 ml of HOAc (1%), again with brine and finally with a saturated aq. NaHCO$_3$ solution. Subsequently, the organic layer was dried (MgSO$_4$), filtered and concentrated to dryness. The product was dried (vacuum, r.t.) yielding 23.90 g of intermediate 139 (73%) as a brown syrup.

b) Preparation of Intermediate 140

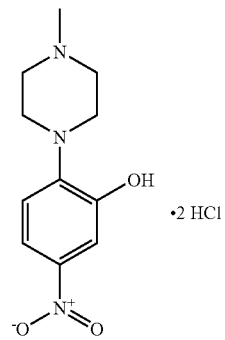

Intermediate 139 (1.5 g, 0.0045 mol) was suspended in 4 N HCl in 1,4-dioxane (15 ml) and the reaction mixture was heated at 100° C. in a sealed tube overnight. The reaction mixture was concentrated to dryness and the residue was triturated with DIPE, filtered off and dried, giving 1 g of a yellow solid. Yield: 1 g of intermediate 140 (0.2 HCl; 91%).

c) Preparation of Intermediate 141

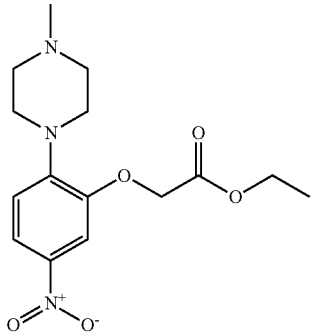

Intermediate 140 (4.23 g, 0.0136 mol) was dissolved in a mixture of toluene (70 ml) and $H_2O$ (30 ml). $NaHCO_3$ (4.0 g, 0.0477 mol) and N,N,N-tributyl-1-butanaminium bromide (0.22 g, 0.0007 mol) were added, followed by the addition of ethyl 2-bromoacetate (1.8 ml, 0.0164 mol). The reaction mixture was heated at 80° C. overnight. The phases were separated and the aq. phase was extracted with EtOAc (3×20 ml). The organic layers were combined, dried ($MgSO_4$), filtered and concentrated to dryness. The residue was purified by flash column chromatography on silica gel, eluent: a mixture of DCM/MeOH (ratios: 80/1-70/1-60/1-50/1). The product fractions were collected and the solvent was evaporated. The product was dried (vacuum, r.t.) yielding a pale yellow solid. Yield: 0.75 g of intermediate 141 (17%).

d) Preparation of Intermediate 142

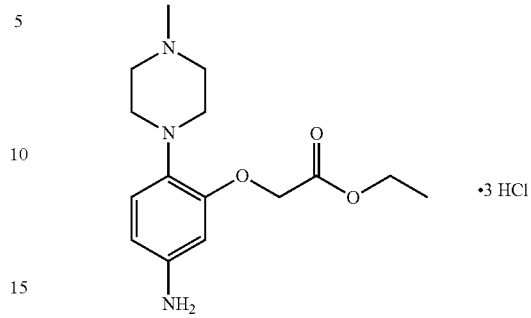

Intermediate 141 (0.75 g, 0.0023 mol) was dissolved in THF (10 ml) at r.t. Then, Pt/C 5% (0.15 g) was added and the mixture was stirred at r.t. under $H_2$ atmosphere for 15 hours. The mixture was filtered through a Celite pad. The Celite was washed with THF. The solvent was evaporated. The residue was dried (vacuum, r.t.), yielding 0.72 g of a brown oil. The hydrochloric acid salt was obtained by purging HCl gas into a solution of the aniline in $Et_2O$. Yield: 0.86 g of intermediate 142 (0.3 HCl; 92%).

e) Preparation of Intermediate 143

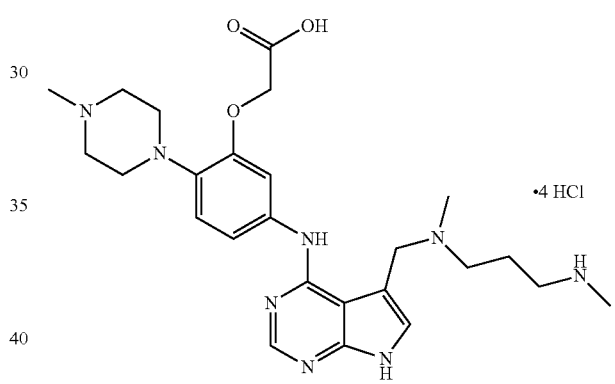

Intermediate 32 (0.70 g, 0.0019 mol) was dissolved in a mixture of $CH_3CN$ (4 ml) and 2-propanol (2 ml). Then, HCl (1 ml; 4 N in 1,4-dioxane) was added followed by the addition of intermediate 142 (0.53 g, 0.0023 mol). The reaction mixture was heated at 80° C. for 2 hours. The solvent was evaporated and the crude intermediate 143 (0.4 HCl) was used as such in the next reaction step. The product was dried (vacuum, r.t.), yielding a brown foam.

Example A41 a) Preparation of Intermediate 144

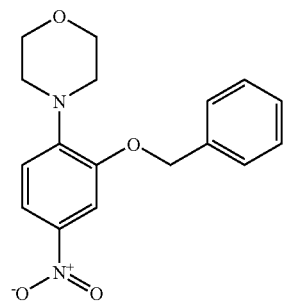

A mixture of 1-chloro-4-nitro-2-(phenylmethoxy)benzene (26.29 g, 0.0997 mol) in morpholine (50 ml) was heated at 100° C. overnight. The mixture was partitioned between EtOAc and a saturated aq. NaHCO₃ solution. The aq. phase was extracted with EtOAc several times. The combined organic layers were washed with brine, with 200 ml of HOAc (1%), with brine and finally with a saturated aq. NaHCO₃ solution. The organic layer was dried (MgSO₄), filtered and concentrated to dryness. The residue was dried (vacuum, r.t.) yielding a brown syrup. Yield: 26.47 g of intermediate 144 (85%).

b) Preparation of Intermediate 145

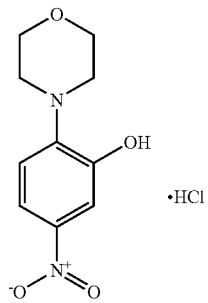

Intermediate 144 (26.47 g, 0.0842 mol) was dissolved in HCl (185 ml; 4 N in 1,4-dioxane). The solution was stirred at 100° C. overnight in a sealed tube. The solvent was evaporated and the residue was dried (vacuum, r.t.), yielding a brown oil. The product was used as such in the next reaction step. Yield: 21.95 g of intermediate 145 (.HCl).

c) Preparation of Intermediate 146

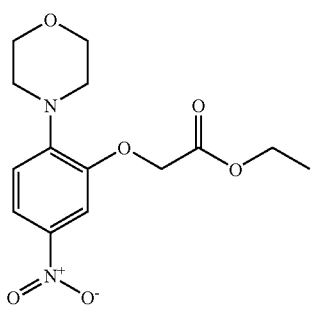

Intermediate 145 (6.0 g, 0.0230 mol) was dissolved in CH₃CN (70 ml) and then ethyl 2-bromoacetate (3.1 ml, 0.0276 mol) was added, followed by the addition of K₂CO₃ (4.77 g, 0.0345 mol). The reaction mixture was heated at 80° C. overnight. The solid was filtered off and washed with CH₃CN. EtOAc (50 ml) was added and the mixture was washed with brine, dried (MgSO₄), filtered and concentrated to dryness. The residue was purified by flash column chromatography over silica gel (eluent: a mixture of hexanes/EtOAc (ratios: 10/1-8/1-5/1-3/1). The product fractions were collected and the solvent was evaporated. The product was dried (vacuum, r.t.) yielding a pale yellow solid. Yield: 5.88 g of intermediate 146 (82%).

d) Preparation of Intermediate 147

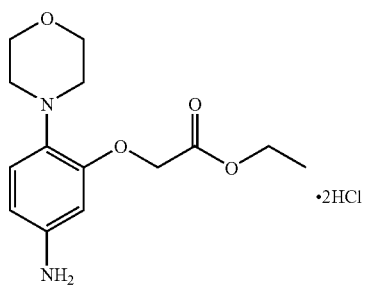

Intermediate 146 (5.88 g, 0.0189 mol) was dissolved in THF (66 ml) and the solution was stirred at r.t. Then, Pt/C 5% (1.18 g) was added and the mixture was stirred at r.t. under H₂ atmosphere for 15 hours. The mixture was filtered through a Celite pad. The Celite was washed with THF. The solvent was evaporated. The residue was dried (vacuum, r.t.) yielding 4.67 g of a brown oil. The hydrochloric salt was obtained by purging HCl gas into a solution of the aniline in Et₂O. Yield: 3.71 g of compound 147 (55%).

e) Preparation of Intermediate 148

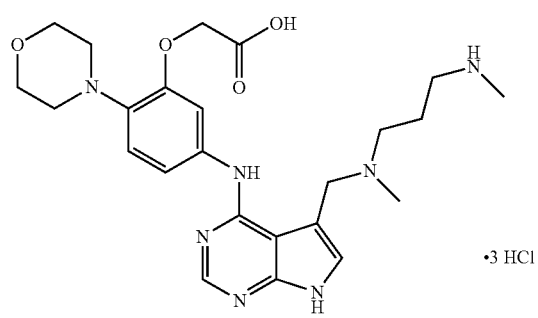

Intermediate 32 (0.70 g, 0.0019 mol) was dissolved in a mixture of CH₃CN (4 ml) and 2-propanol (2 ml). Then, HCl (1 ml; 4 N in 1,4-dioxane) was added followed by the addition of intermediate 147 (0.53 g, 0.0023 mol). The reaction mixture was heated at 80° C. for 2 hours. The solvent was evaporated and the residue was dried (vacuum, r.t.), yielding crude intermediate 148 (0.3 HCl) as a brown foam.

Example A42 a) Preparation of Intermediate 149

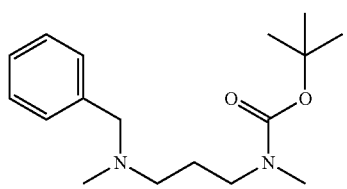

Pd/C 10% (4 g) was suspended in MeOH (200 ml) under N₂ atmosphere. A 4% thiophene solution (4 ml) was added. The mixture was stirred at 25° C. under H₂ atmosphere for pre-hydrogenation. First N-(3-aminopropyl)-N-methylcarbamic acid 1,1-dimethylethyl ester (0.106 mol) and then benzaldehyde (0.106 mol) was added. The reaction mixture was stirred and hydrogenated at 25° C. under H₂ atmosphere. After uptake of H₂ (1 equiv), formaldehyde (0.106 mol) was added and the reaction mixture was hydrogenated further. After uptake of H₂ (1 equiv), the catalyst was filtered off over dicalite and the filtrate was evaporated. The residue was purified over silica gel (eluent: DCM/CH₃OH 95/5). The product fractions were collected and the solvent was evaporated to give an oil, yielding 26.5 g (71.7%) of intermediate 149.

b) Preparation of Intermediate 150

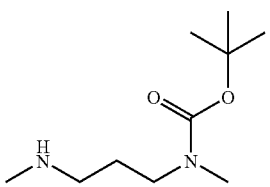

Pd/C 10% (2 g, catalyst) was suspended in MeOH (150 ml) under N₂ flow. intermediate 149 (0.092 mol) was added. The reaction mixture was stirred under H₂ atmosphere until 1 equivalent of H₂ was taken up. The catalyst was removed by filtration over dicalite. The filtrate's solvent was evaporated under reduced pressure, yielding 18.4 g (98.9%) of intermediate 150.

Example A43 a) Preparation of Intermediate 151

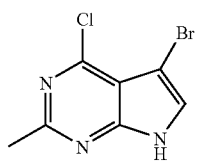

A mixture of 4-chloro-2-methyl-1H-pyrrolo[2,3-d]pyrimidine (0.0298 mol) in DCM (150 ml) was stirred at r.t. 1-bromo-2,5-pyrrolidinedione (0.0471 mol) was added portionwise. The reaction mixture was stirred for one hour. The precipitate was filtered off, washed with DIPE, then dried in vacuo at 50° C., yielding 2.5 g (34%) of intermediate 151.

b) Preparation of Intermediate 152

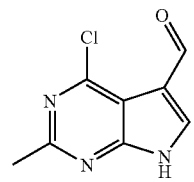

A solution of intermediate 151 (0.01014 mol) in THF (50 ml) was stirred under N₂— flow at −78° C. and a solution of n-BuLi 2.5M (0.0305 mol) in THF (10 ml) was added dropwise. After addition, the reaction was continued for one hour at −78° C. A solution of DMF (0.02029 mol) in THF (10 ml) was added dropwise. The reaction mixture was stirred for 30 min at −78° C. The reaction mixture was allowed to reach −30° C., and H₂O (10 ml) was added dropwise. The reaction mixture was stirred for 30 min. The organic layer was separated and filtered over silica gel (eluent: THF). The collected fractions were concentrated under reduced pressure and the residue was stirred in a mixture of 2% CH₃OH and 98% DCM. The precipitate was filtered off, washed and dried under vacuo, yielding 0.85 g (42.8%) of intermediate 152.

c) Preparation of Intermediate 153

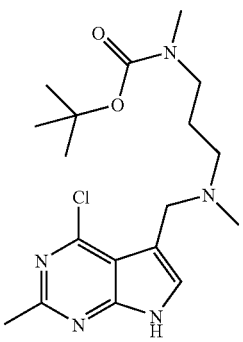

A mixture of intermediate 150 (0.00515 mol) and Na(OAc)₃ BH (0.01288 mol) in DCM (q.s.) was stirred at r.t. A mixture of intermediate 152 (0.00429 mol) in THF (q.s.) was added dropwise. After addition, stirring was continued for 18 hours. The reaction mixture was treated with H₂O. The layers were separated and the water layer was further extracted with DCM. The combined organic layers were concentrated under reduced pressure. The crude residual fraction was purified by high-performance liquid chromatography over an RP-18 column (eluent:(0.25% NH₄HCO₃ in H₂O)/CH₃CN/v/v 50/50-0/100). The product fractions were collected, evaporated to dryness and the residue was dried in vacuo at 50° C., yielding 0.87 g (49.3%) of intermediate 153. A mixture of intermediate 153 (0.000655 mol) and the free base of intermediate 82 (0.000655 mol) in HCl/Dioxane (4N) (1 ml) and n-Butanol (20 ml) was heated under microwave conditions for 2 hours at 100° C. The reaction solution was concentrated under reduced pressure. The crude residual fraction (0.43 g; 66.1%) was used as intermediate 154 (0.2HCl) in the next step.

e) Preparation of Intermediate 155

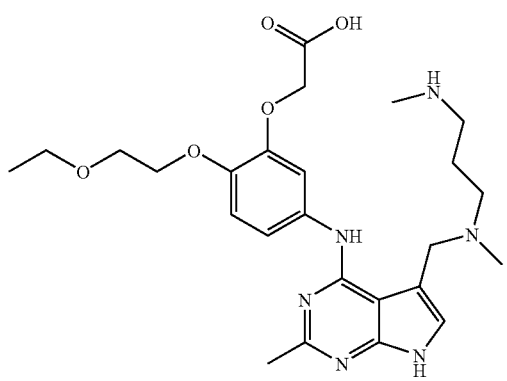

A solution of intermediate 154 (0.00079 mol) and LiOH (0.002371 mol) in THF (20 ml) and H₂O (2 ml) was heated to 50° C. and stirred for 1.5 hours. The solvent was removed under reduced pressure. The crude residue was purified by high-performance liquid chromatography over RP-18 (eluent:(0.25% NH₄HCO₃ in H₂O)/CH₃CN/CH₃OH/v/v 100/0/0-60/40/0-0/50/50). The product fractions were collected and evaporated to dryness. The residue was dried in vacuo at 50° C., yielding 0.130 g (32.8%) of intermediate 155.

Example A44 a) Preparation of Intermediate 156

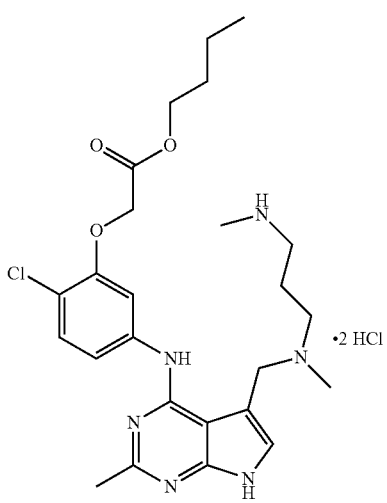

A mixture of intermediate 153 (0.000655 mol) and the free base of intermediate 60 (0.000655 mol) in HCl/Dioxane (4N) (1 ml) and n-butanol (20 ml) was heated under microwave conditions for 2 hours at 100° C. The solution was concentrated under reduced pressure. The crude residual fraction (0.660 g; 60.1%) was used as intermediate 156(0.2HCl) in the next step.

b) Preparation of Intermediate 157

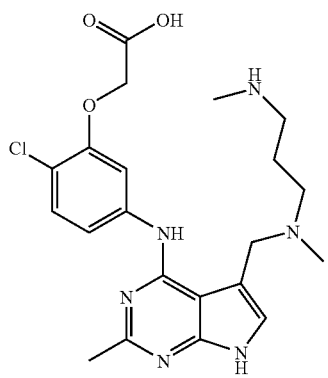

A solution of intermediate 156 (0.000497 mol) and LiOH (0.001491 mol) in THF (20 ml) and H$_2$O (2 ml) was heated to 50° C. and stirred for 90 min. The solvent was removed under reduced pressure. The crude residue was purified by high-performance liquid chromatography over RP-18 (eluent: (0.25% NH$_4$HCO$_3$ in H$_2$O)/CH$_3$CN/v/v 100/0-50/50-0/100).

The product fractions were collected and evaporated to dryness. The residue was dried in vacuo at 50° C., yielding 0.030 g (13.5%) of intermediate 157.

Example A45 a) Preparation of Intermediate 158

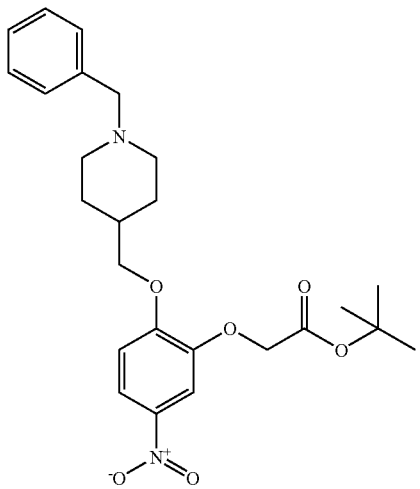

Reaction under N$_2$ atmosphere. NaH (0.004488 mol) was added to DMF (12 ml), and the mixture was stirred at r.t. A solution of 1-(phenylmethyl)-4-piperidinemethanol (0.004488 mol) in DMF (4 ml) was added dropwise. The mixture was stirred for one hour. Then a solution of 5-nitro-1,3-benzodioxole (0.002992 mol) in DMF (4 ml) was added dropwise to the reaction mixture and stirring was continued for one hour. A solution of 2-bromoacetic acid 1,1-dimethylethyl ester (0.004488 mol) in DMF (4 ml) was added dropwise and the reaction mixture was stirred for one hour. The reaction mixture was poured out into ice water. The product was extracted with EtOAc (×2). The separated organic layer was dried, filtered and the solvent evaporated, yielding 1.78 g (96.4%) of intermediate 158 used as such in the next step b) Preparation of Intermediate 159

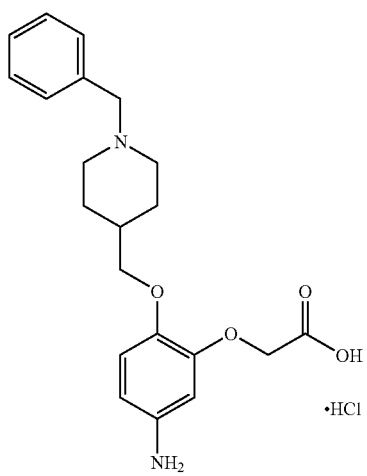

The catalyst Pt/C 5% (0.5 g) was suspended in THF (100 ml), under N₂ flow. A 4% thiophene solution (1 ml) was added. Intermediate 158 (0.002885 mol) was added. The reaction mixture was stirred at 25° C. under H₂ atmosphere until 3 equivalents of hydrogen were taken up. The catalyst was removed by filtration over dicalite. The filtrate was evaporated under reduced pressure. The residue was dissolved in DCM and treated with HCl gas for 5 minutes. The solvent was removed in vacuo to give a powder, yielding 2.11 g of intermediate 159(.HCl) used in the next reaction step.

c) Preparation of Intermediate 160

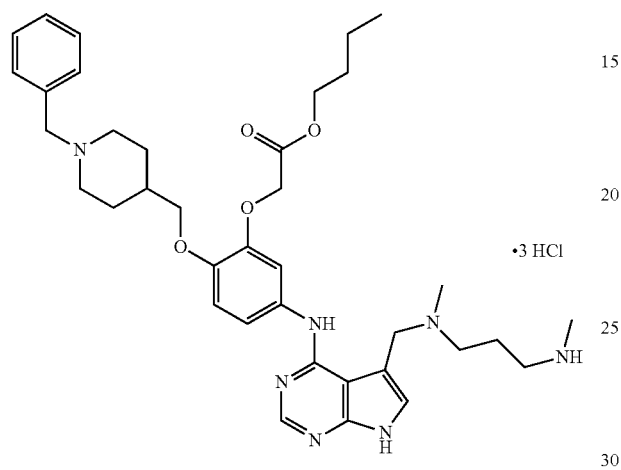

A solution of intermediate 32 (0.002556 mol), intermediate 159 (0.005112 mol) and HCl/Dioxane (4N) (2 ml) in 1-butanol (40 ml) was stirred and heated at 100° C. for one hour, then the resulting mixture was used as intermediate 160(0.3HCl) in the next reaction step.

d) Preparation of Intermediate 161

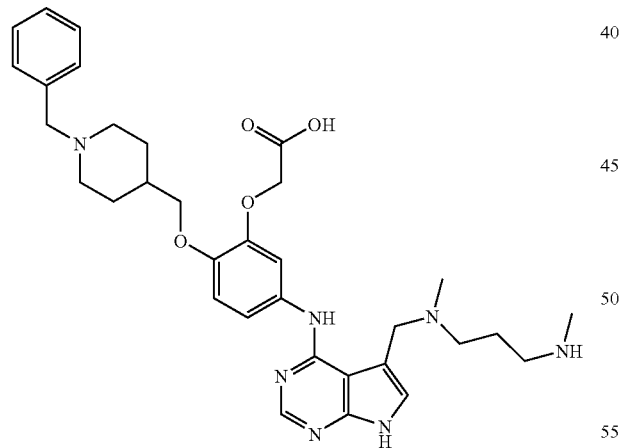

The crude intermediate 160 (max. 0.0025 mol) was added to a solution of 36% HCl solution (11 ml) in H₂O (22 ml). The reaction mixture was stirred at 60° C. for 4 hours. The reaction mixture was concentrated under reduced pressure. A mixture of LiOH.H₂O (0.0125 mol) in THF (22 ml) and 5 ml of H₂O were added and the reaction mixture was heated at 50° C. for 10 hours. An extra 5 equivalent of LiOH.H₂O (0.0125 mol), dissolved in 5 ml of H₂O was added and the heating was continued for an additional one hour. The reaction mixture was concentrated under reduced pressure. The concentrate was purified by HPLC (0.25% ammonium bicarbonate in H₂O/CH₃CN starting with 100/0 for 5 min, then from 100/0 to 70/30 over 25 min, then 0/100 for 10 min, and 100/0 for 10 min; Shandon 8 μm, Hyperprep C18 HS DBS 50 mm by 16.5 cm). The desired fractions were concentrated under reduced pressure to give a brown powder, yielding 0.2 g (10.5%) of intermediate 161.

Example A46 a) Preparation of Intermediate 162

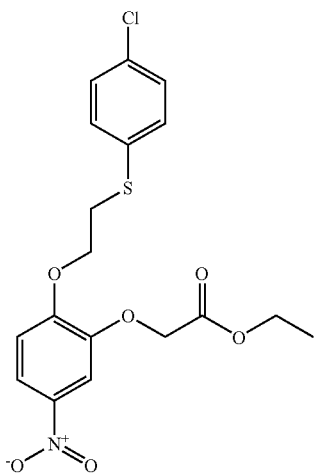

A solution of (2-hydroxy-5-nitrophenoxy)acetic acid ethyl ester (0.004146 mol), Ph₃P (0.008292 mol) and 2-[(4-chlorophenyl)thio]ethanol (0.006219 mol) in anhydrous THF (30 ml) was stirred under N₂ flow at r.t. A solution of DIAD (0.008292 mol) in anhydrous THF (10 ml) was added dropwise. The resultant reaction mixture was stirred for 6 hours at r.t. The solvent was evaporated under reduced pressure. The residue was dissolved in DCM. The organic solution was washed with H₂O (×2). The organic layer was separated, dried (MgSO₄), filtered and the solvent was evaporated. The crude residue was stirred in diethyl ether and the precipitate was removed by filtration. The filtrate was concentrated under reduced pressure. The residue was purified by HPLC. The product fractions were collected and the solvent was evaporated, yielding 0.841 g (49.25%) of intermediate 162.

b) Preparation of Intermediate 163

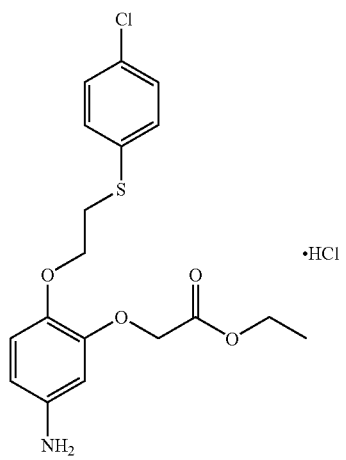

Pt/C 10% (0.500 g) was suspended in THF (50 ml), under N₂ flow. A 4% thiophene solution (0.5 ml) was added. Intermediate 162 (0.002042 mol) was added and the reaction mixture was stirred under H₂ atmosphere until 3 equivalents of H₂ were taken up. The catalyst was removed by filtration over dicalite. The filtrate was evaporated under reduced pressure. The residue was dissolved in DCM and treated with HCl gas for 5 minutes. The solvent was removed in vacuo, yielding 0.663 g (77.6%) of intermediate 163(.HCl)

c) Preparation of Intermediate 164

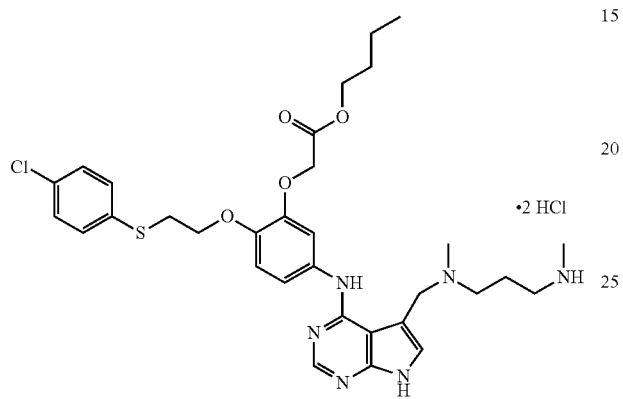

A solution of intermediate 163 (0.001133 mol), intermediate 32 (0.001359 mol) and HCl/Dioxane (4N) (0.5 ml) in 1-butanol (10 ml) was stirred and heated at 100° C. for 30 min. The reaction mixture was used as intermediate 164(0.2HCl) in the next step.

d) Preparation of Intermediate 165

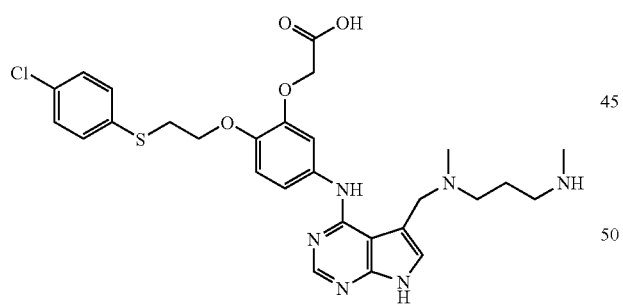

Crude intermediate 164 (0.001133 mol) was added to a solution of 36% HCl solution (5 ml) in H₂O (10 ml). The reaction mixture was stirred at 60° C. for 4 hours. The reaction mixture was concentrated under reduced pressure. A mixture of LiOH (0.005665 mol) and THF (10 ml) in 5 ml of H₂O was added and the reaction mixture was heated at 50° C. for 10 hours. An extra 5 equivalents of LiOH (0.005665 mol), dissolved in 5 ml of H₂O, was added and the heating was continued for an additional one hour. The reaction mixture was concentrated under reduced pressure and the residue was purified by HPLC (0.25% ammonium carbonate in H₂O/CH₃CN from 100/0 to 70/30 aver 60 min, then 0/100 for 20 min; Shandon 8 nm, Hyperprep C18 HS DBS 50 mm by 16.5 cm). The product fractions were collected and the solvent was evaporated under reduced pressure, yielding 0.240 g (32.6%) of intermediate 165.

Example A47 a) Preparation of Intermediate 166

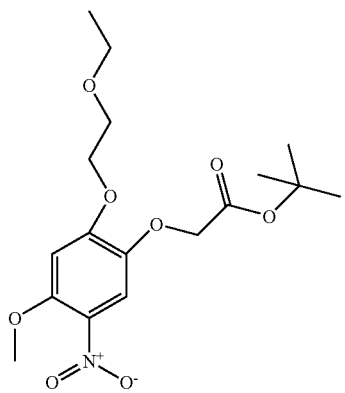

DMF (12 ml) was treated with NaH (0.0038 mol), under N₂-flow at r.t. A solution of 2-ethoxy-ethanol (0.0038 mol) in DMF (6 ml) was added dropwise. The resultant mixture was stirred for one hour. Then a solution of 5-methoxy-6-nitro-1,3-benzodioxole (0.00254 mol) in DMF (6 ml) was added dropwise and the reaction mixture was stirred for one hour. A solution of 2-bromoacetic acid 1,1-dimethylethyl ester (0.0038 mol) in DMF (6 ml) was added dropwise and the reaction mixture was stirred for 2 hours at r.t. The reaction was poured out into ice water and stirred for 15 minutes. The desired product was filtered off, washed with H₂O and dried in vacuo at 50° C., yielding 0.42 g (44.6%) of intermediate 166 b) Preparation of Intermediate 167

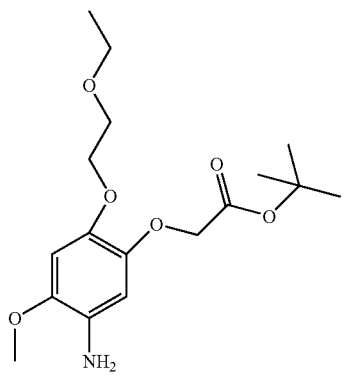

The catalyst Pd/C 10% (0.200 g) was suspended in THF (100 ml), under N₂ flow. A 4% thiophene solution (1 ml) was added. Intermediate 166 (0.00113 mol) was added and the reaction mixture was stirred at 25° C. under H₂ atmosphere until 3 equivalents of hydrogen were taken up. The catalyst was removed by filtration over dicalite. The solvent was removed under reduced pressure, yielding 0.39 g (53.53%) of crude residue was used as intermediate 167 in the next step.

c) Preparation of Intermediate 168

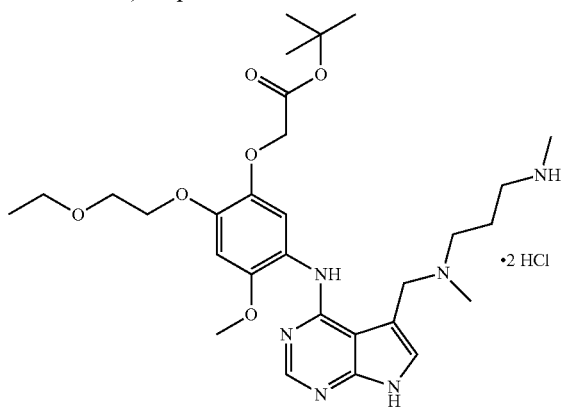

A mixture of intermediate 32 (0.00106 mol) and intermediate 167 (0.00106 mol) in HCl/Dioxane (4N) (1 ml) and n-Butanol (10 ml) was heated under microwave conditions for 2 hours at 100° C. The solution was concentrated under reduced pressure. The crude residual fraction was used as intermediate 168(0.2HCl) in the next step.

d) Preparation of Intermediate 169

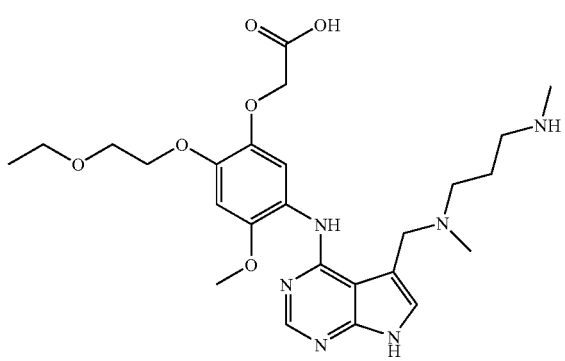

A mixture of intermediate 168 (0.000703 mol) in concentrated HCl (2 ml) and dioxane (20 ml) was heated to 85° C. for 4 hours. The solvent was removed under reduced pressure. The crude residue was purified by high-performance liquid chromatography over RP-18 (eluent:(0.25% $NH_4HCO_3$ in $H_2O$)/$CH_3CN$/v/v 100/0-75/25-0/100). The product fractions were collected and evaporated to dryness. The residue was dried in vacuo at 50° C., yielding 0.145 g (39.9%) of intermediate 169.

Example A48 a) Preparation of Intermediate 170

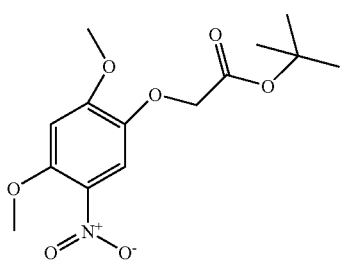

DMF (6 ml) was treated with NaH (0.0019 mol) under $N_2$-flow at r.t. Then, a solution of MeOH (0.0019 mol) in DMF (3 ml) was added dropwise. The resultant reaction mixture was stirred for one hour. Then, a solution of 5-methoxy-6-nitro-1,3-benzodioxole (0.00127 mol) in DMF (3 ml) was added dropwise and the reaction mixture was stirred for one hour. A solution of 2-bromoacetic acid 1,1-dimethylethyl ester (0.0019 mol) in DMF (3 ml) was added dropwise and the reaction mixture was stirred for 2 hours. The reaction was poured out into ice water and stirred for 15 minutes. The product was filtered off, washed with $H_2O$ and dried in vacuo at 50° C., yielding 0.22 g (55.4%) of intermediate 170.

b) Preparation of Intermediate 171

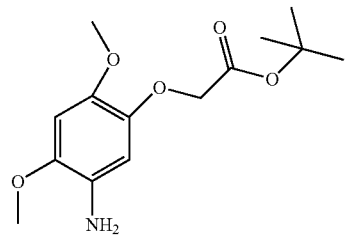

The catalyst Pd/C 10% (0.100 g) was suspended in THF (40 ml) under $N_2$ flow. A 4% thiophene solution (0.1 ml) was added. Intermediate 170 (0.000702 mol) was added and the reaction mixture was hydrogenated at a temperature of 25° C. under $H_2$ atmosphere until 3 equivalents of hydrogen were taken up. The catalyst was removed by filtration over dicalite. The filtrate was concentrated under reduced pressure, yielding 0.2 g (54.3%) of residue was used as intermediate 171 in the next step.

c) Preparation of Intermediate 172

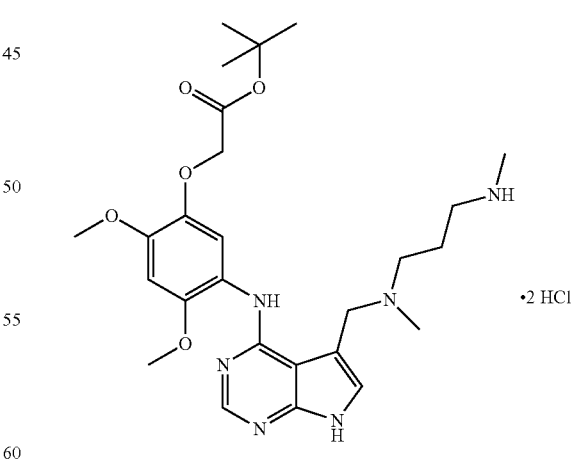

A mixture of intermediate 32 (0.000706 mol) and intermediate 171 (0.000706 mol) in HCl/Dioxane (4N) (1 ml) and n-Butanol (10 ml) was heated under microwave conditions for 2 hours at 100° C. The solution was concentrated under reduced pressure, yielding 0.362 g (30.9%) of crude residual fraction, used as intermediate 172 (2HCl) in the next step.

d) Preparation of Intermediate 173

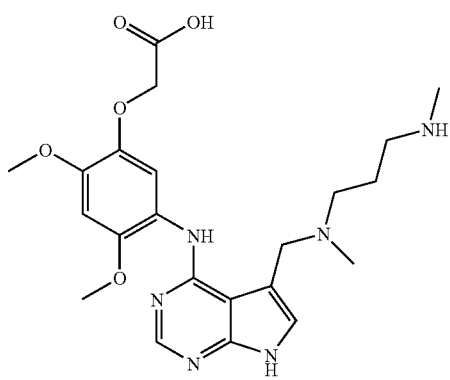

A solution of intermediate 172 (0.000703 mol) in concentrated HCl (1 ml) and dioxane (10 ml) was heated to 95° C. and stirred for 90 minutes. The solvent was removed under reduced pressure. The crude residue was purified by high-performance liquid chromatography over RP-18 (eluent: (0.50% $NH_4HCO_3$ in $H_2O$)/$CH_3CN$/v/v 80/20-20/80-0/100). The product fractions were collected and evaporated to dryness. The residue was dried in vacuo at 50° C., yielding 0.078 g (24.2%) of intermediate 173.

Example A49 a) Preparation of Intermediate 174

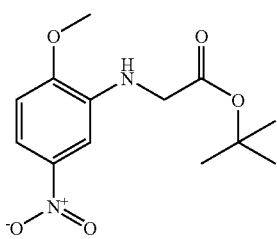

A solution of 2-methoxy-5-nitrobenzenamine (0.0119 mol) and DIPEA (0.0238 mol) in DMF (65 ml) was stirred at r.t. A solution of 2-bromoacetic acid 1,1-dimethylethyl ester (0.0238 mol) in DMF (10 ml) was added dropwise. The reaction mixture was heated to 85° C. for 18 hours. The reaction mixture was poured out into ice water. The product was extracted with EtOAc. The separated organic layer was dried ($MgSO_4$), filtered and the solvent evaporated, yielding 2.1 g (45.03%) of intermediate 174.

b) Preparation of Intermediate 175

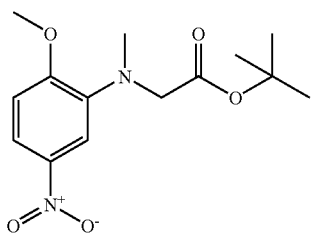

A solution of intermediate 174 (0.00354 mol) and $K_2CO_3$ (0.00531 mol) in $CH_3CN$ (60 ml) was stirred at ambient temperature for 20 minutes. $CH_3I$ (2 equiv) was added. The reaction mixture was heated to 80° C. and stirred for 18 hours. An extra amount of $CH_3I$ (2 equiv) was added and the reaction mixture was heated for an additional 18 hours. Another 2 equivalents of $CH_3I$ were added and the reaction mixture was stirred for 18 hours at 80° C. The solvent was removed under reduced pressure. The residual fraction was dissolved in EtOAc and washed with $H_2O$ twice. The organic layer was dried ($MgSO_4$), filtered and evaporated to dryness, yielding 0.8 g (76.2%) of intermediate 175.

c) Preparation of Intermediate 176

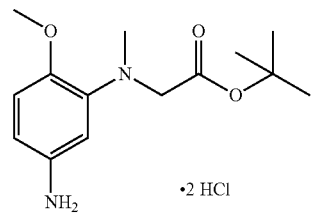

The catalyst Pd/C 10% (0.100 g) was suspended in THF (100 ml), under $N_2$ flow. a 4% Thiophene solution (1 ml) was added, then intermediate 175 (0.0027 mol) was added and the reaction mixture was stirred at a 25° C. under $H_2$ atmosphere until 3 equivalents of hydrogen were taken up. The catalyst was removed by filtration over dicalite. The solvent was removed under reduced pressure. The residue was dissolved in DCM and treated with HCl gas for 5 min. The solvent was removed under reduced pressure, yielding 0.91 g (44.7%) of intermediate 176 (0.2HCl) used as such in the next step.

d) Preparation of Intermediate 177

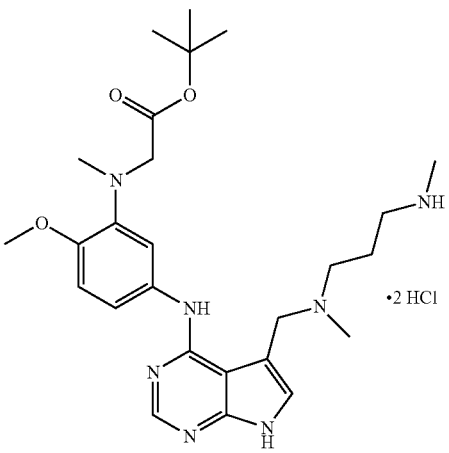

A mixture of intermediate 176 (0.00265 mol) and intermediate 32 (0.00265 mol) in HCl/Dioxane (4N) (2 ml) and n-butanol (50 ml) was heated to 100° C. for one hour under microwave conditions. The solvent was removed under reduced pressure, yielding 1.3 g (54.16%) of crude intermediate 177(0.2HCl) used as such in the next step.

e) Preparation of Intermediate 178

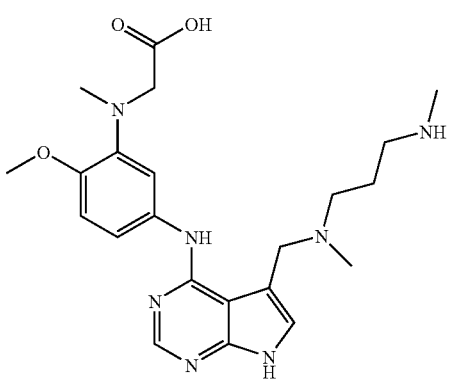

A solution of intermediate 177 (0.00201 mol), Dioxane (50 ml), concentrated HCl (2 ml) and H$_2$O (5 ml) was heated to 85° C. for 4 hours. The solvent was removed under reduced pressure. The crude residue was purified by high-performance liquid chromatography over RP-18 (eluent:(0.25% NH$_4$HCO$_3$ in H$_2$O)/CH$_3$CN/CH$_3$OH/v/v 75/25/0-0/100/0-0/0/100). The desired fractions were collected and evaporated to dryness. The residue was dried in vacuo at 50° C., yielding 0.020 g (2.26%) of intermediate 178.

Example A50 a) Preparation of Intermediate 179

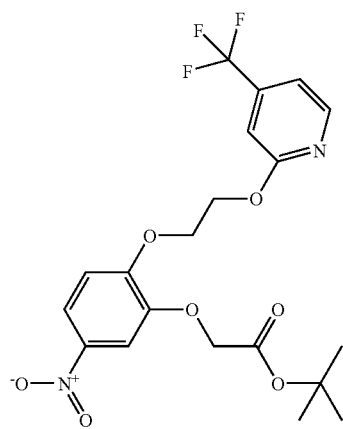

A solution of DMF (25 ml) was treated with NaH (0.0018 mol), under N$_2$-flow at r.t. A solution of 2-[[4-(trifluoromethyl)-2-pyridinyl]oxy]ethanol (0.0018 mol) in DMF (5 ml) was added dropwise. After addition, the mixture was stirred for one hour. Then a solution of 5-nitro-1,3-benzodioxole (0.0012 mol) in DMF (5 ml) was added dropwise and the resultant reaction mixture was stirred for 4 hours at r.t. A solution of 2-bromoacetic acid 1,1-dimethylethyl ester (0.0018 mol) in DMF (5 ml) was added dropwise and the entire mixture was stirred for 18 hours. The reaction mixture was poured out into ice water. The product was extracted with EtOAc (3 times) and the organic layer was dried (MgSO$_4$), filtered and evaporated to dryness. The crude residue was purified by high-performance liquid chromatography over RP-18 (eluent:(0.25% NH$_4$HCO$_3$ in H$_2$O)/CH$_3$CN//v/v 90/10-10/90-0/100). The product fractions were collected and evaporated to dryness yielding 0.26 g (47.4%) used as intermediate 179 in the next step.

b) Preparation of Intermediate 180

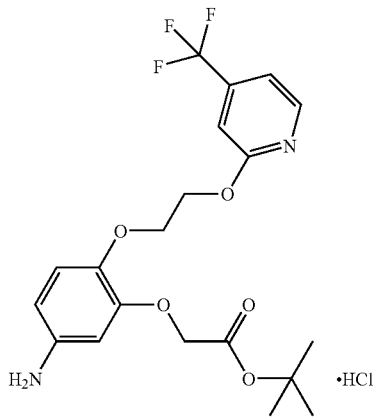

Catalyst Pd/C 10% (0.100 g) was suspended in THF (100 ml) under N$_2$ flow. A 4% thiophene solution (1 ml) was added. Intermediate 179 (0.000567 mol) was added. The reaction mixture was stirred at a temperature of 25° C. under H$_2$ atmosphere until 3 equivalents of hydrogen were taken up. The catalyst was removed by filtration over dicalite. The filtrate was evaporated under reduced pressure. The residual fraction was dissolved in DCM and treated with HCl gas for 2 min. The reaction mixture was concentrated and the residue (0.3 g; 61.4%) was used as intermediate 180 in the next step.

c) Preparation of Intermediate 181

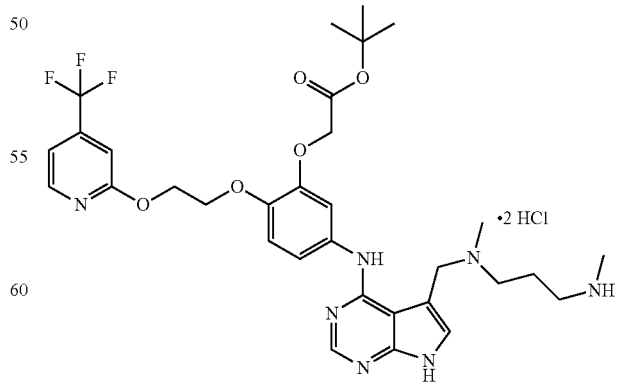

A solution of intermediate 180 (0.000645 mol), intermediate 32 (0.000774 mol) and HCl/Dioxane (4N) (0.3 ml) in 1-butanol (6 ml) was heated at 100° C. for 30 min. The obtained mixture was used as intermediate 181(0.2HCl) in the next step d) Preparation of Intermediate 182

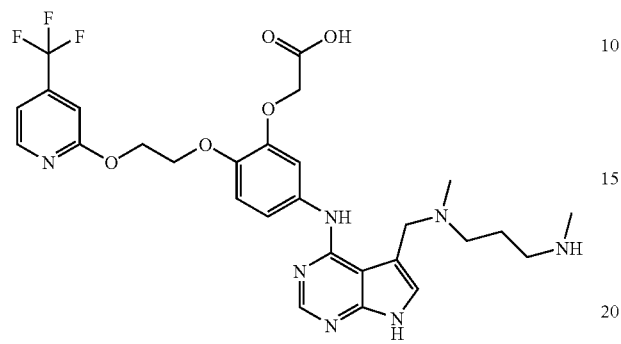

Intermediate 181 (max. 0.000645 mol) was added to a solution of 36% HCl (3 ml) in H₂O (6 ml). The reaction mixture was stirred at 60° C. for 4 hours. The reaction mixture was concentrated under reduced pressure. A mixture of LiOH (0.003225 mol) and THF (6 ml) in 5 ml of H₂O was added and the reaction mixture was heated at 50° C. for 2 hours. The reaction mixture was concentrated under reduced pressure and purified by HPLC (0.5% ammonium carbonate in H₂O/ MeOH/CH₃CN from 75/25/0 to 0/50/50 over 44 min, then from 0/50/50 to 0/0/100 over 13 min; Shandon 8 μm, Hyperprep C18 HS DBS 50 mm by 16.5 cm) The desired fractions were collected and concentrated under reduced pressure, yielding 0.025 g (5.20%) of intermediate 182.

Example A51 a) Preparation of Intermediate 183

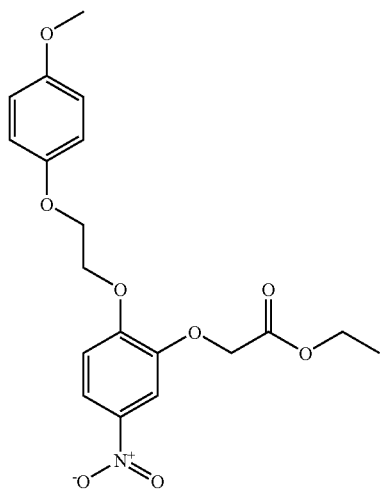

A solution of 4-methoxyphenol (0.01494 mol) and K₂CO₃ (0.01494 mol) in anhydrous DMF (80 ml) was heated at 60° C. for 30 minutes (strong purple pigmentation appeared). Intermediate 115 (0.01149 mol) was added and the reaction mixture was heated at 60° C. for 22 hours. The mixture was poured out into ice water. The product was extracted with toluene (3×). The organic fraction was dried (MgSO₄), filtered and evaporated to dryness. The oil was purified by HPLC (0.5% ammonium carbonate in H₂O/CH₃CN from 80/20 to 0/100 over 60 min, then 0/100 for 10 min; Shandon 8 μm, Hyperprep C18 HS DBS 50 mm by 16.5 cm). The product fractions were concentrated under reduced pressure to give a yellow oil, yielding 0.380 g (8.45%) of intermediate 183.

b) Preparation of Intermediate 184

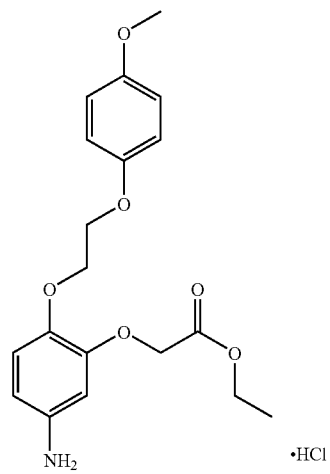

Pd/C 10% (0.100 g) was suspended in THF (50 ml) under N₂ flow. A 4% thiophene solution (0.1 ml) was added and then intermediate 183 (0.000971 mol) was added. The reaction mixture was stirred under H₂ atmosphere until 3 equivalents of H₂ were taken up. The catalyst was removed by filtration over dicalite. The solution was concentrated under reduced pressure. The residue was dissolved in DCM and treated with HCl gas for 5 minutes. The solvent was removed in vacuo to give 0.5025 g (93.66%) of a solid used as intermediate 184 (.HCl) in the next step.

c) Preparation of Intermediate 185

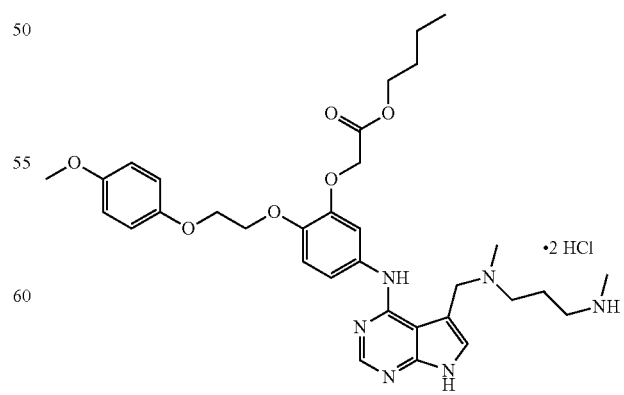

A solution of intermediate 184 (0.001262 mol), intermediate 32 (0.001514 mol) and HCl/Dioxane (4N) (0.5 ml) in 1-Butanol (10 ml) was heated at 100° C. for 30 minutes, yielding intermediate 185(0.2HCl) used as such in the next step.

d) Preparation of Intermediate 186

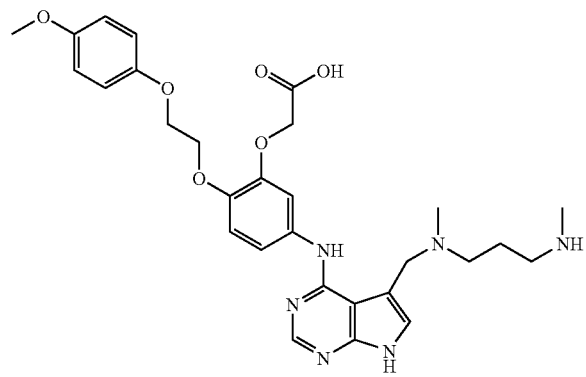

Crude intermediate 185 (max. 0.001262 mol) was added to a solution of 36% HCl solution (6 ml) in H$_2$O (12 ml). The reaction mixture was stirred at 60° C. for 4 hours. The reaction mixture was concentrated under reduced pressure. A mixture of LiOH (0.00631 mol) and THF (12 ml) in 5 ml of H$_2$O was added and the reaction mixture was heated at 50° C. for 10 hours. An extra 5 equivalent of LiOH (0.00631 mol), dissolved in 5 ml of H$_2$O, was added and the heating was continued for an additional one hour. The reaction mixture was concentrated under reduced pressure and purified by HPLC (0.5% ammonium carbonate in H$_2$O/MeOH/CH$_3$CN from 75/25/0 to 0/0/100 over 57 min, then 0/0/100 for 4 min; Shandon 8 μm, Hyperprep C18 HS DBS 50 mm by 16.5 cm). The product fractions were collected and concentrated under reduced pressure, yielding 0.040 g (4.9%) of intermediate 186.

Example A52 a) Preparation of Intermediate 187

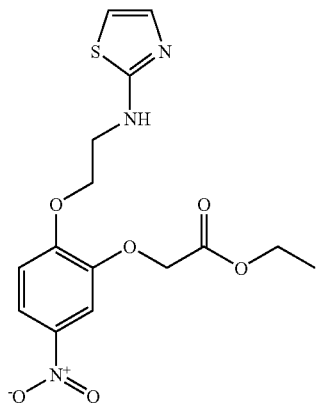

A solution of (2-hydroxy-5-nitrophenoxy)acetic acid ethyl ester (0.009246 mol), (Ph)$_3$P (0.018493 mol) and 2-(2-thiazolylamino)ethanol (0.01387 mol) in anhydrous THF (80 ml) was stirred under N$_2$ flow at r.t. while a solution of DIAD (0.018493 mol) in anhydrous THF (10 ml) was added dropwise. After addition the reaction mixture was stirred for 6 hours.

The reaction mixture was concentrated under reduced pressure. The residue was dissolved in CH$_2$Cl$_2$ and washed with H$_2$O (×2). The organic layer was dried (MgSO$_4$), filtered and evaporated to dryness. The residue was purified by HPLC (eluent: CH$_2$Cl$_2$/ethanol starting with 100/0 for 15 min, then from 100/0 to 95/5 over 15 min, then 95/5 for 5 min, and from 90/10 to 0/100 over 15 min; Shandon 25-40 μm, silica gel 60, 50 mm by 20 cm). The product fractions were concentrated under reduced pressure, yielding 3.2 g (92%) of intermediate 187.

b) Preparation of Intermediate 188

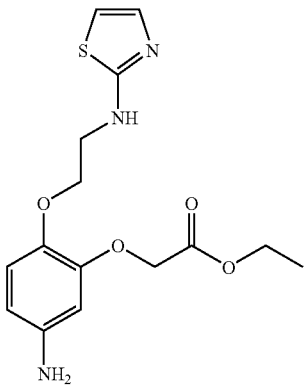

The catalyst Pd/C 10% (0.300 g) was suspended in THF (100 ml), under N$_2$ flow. A 4% thiophene solution (1 ml) was added. Intermediate 187 (0.002722 mol) was added. The reaction mixture was stirred at 25° C. under H$_2$ atmosphere until 3 equivalents of hydrogen were taken up. The catalyst was removed by filtration over dicalite. The solvent was removed under pressure, yielding 1.44 g (112.9%) crude residue, used as intermediate 188 in the next step.

c) Preparation of Intermediate 189

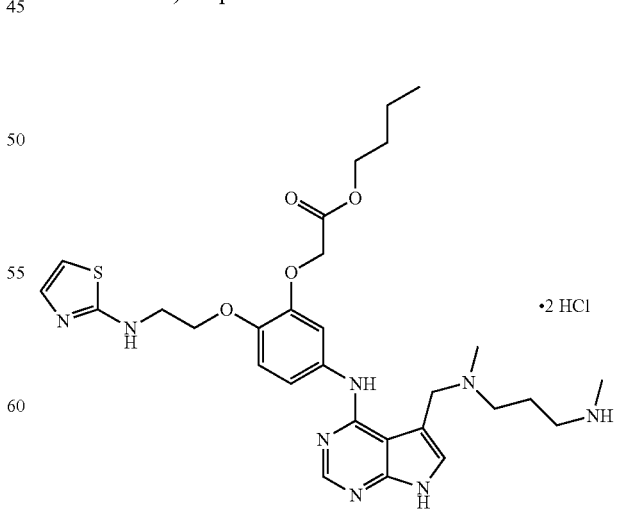

A solution of intermediate 188 (0.002265 mol), intermediate 32 (0.002718 mol) and HCl/Dioxane (4N) (1 ml) in 1-butanol (20 ml) was heated at 100° C. for 30 min. The resulting mixture was used as intermediate 189(0.2HCl) in the next step.

d) Preparation of Intermediate 190

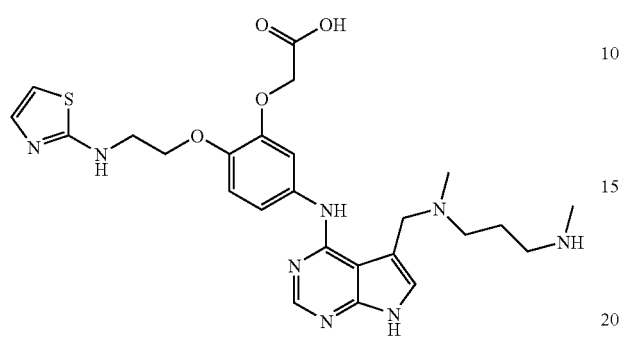

Intermediate 189 (max. 0.002265 mol) was added to a solution of 36% HCl (10 ml) in H₂O (20 ml). The reaction mixture was stirred at 60° C. for 4 hours. The reaction mixture was concentrated under reduced pressure. A mixture of LiOH (0.011325 mol) and THF (20 ml) in 5 ml of H₂O was added and the reaction mixture was heated at 50° C. for 4 hours. The reaction mixture was concentrated under reduced pressure and the concentrate was purified by HPLC (0.25% ammonium bicarbonate in H₂O/CH₃CN from 100/0 to 50/50 over 40 min, then 0/100 for 10 min and 100/0 for 10 min; Shandon 8 μm, Hyperprep C18 HS DBS 50 mm by 16.5 cm). The product fractions were collected and concentrated under reduced pressure, yielding 0.120 g (9.60%) of intermediate 190.

Example A53 a) Preparation of Intermediate 191

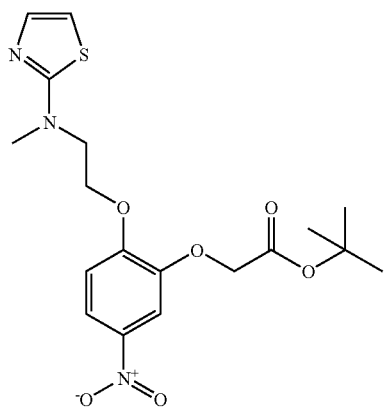

A solution of DMF (42 ml) was treated with NaH (0.0158 mol) under N₂-flow at r.t. A solution of 2-(methyl-2-thiazolylamino)ethanol (0.0158 mol) in DMF (12 ml) was added dropwise and then the reaction mixture was stirred for one hour. A solution of 5-nitro-1,3-benzodioxole (0.0105 mol) in DMF (12 ml) was added dropwise and stirring was continued for one hour. A solution of 2-bromoacetic acid 1,1-dimethylethyl ester (0.0158 mol) in DMF (12 ml) was added dropwise and the mixture was stirred for one hour. The reaction mixture was poured out into ice water. The product was extracted with EtOAc (twice) and the organic layer was dried, filtered and evaporated to dryness. The residue was purified by HPLC (0.5% ammonium bicarbonate in H₂O/MeOH/CH₃CN from 85/15/0 to 46/25/29 over 24 min, then 0/50/50 for 4 min; Shandon 8 μm, Hyperprep C18 BDS 100 Å, 50 mm by 20 cm). The product fractions were collected and evaporated under reduced pressure, yielding 3 g (69.55%) of intermediate 191.

b) Preparation of Intermediate 192

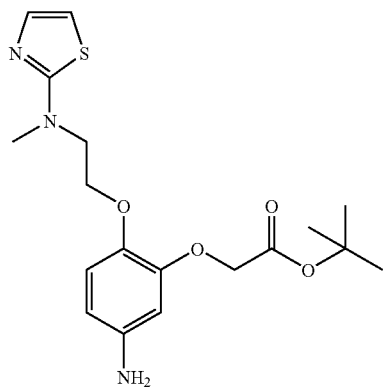

Catalyst Pd/C 10% (0.300 g) was suspended in THF (100 ml), under N₂ flow. A 4% thiophene solution (1 ml) was added, then intermediate 191 (0.00244 mol) was added. The reaction mixture was stirred at a temperature of 25° C. under H₂ atmosphere until 3 equivalent of hydrogen were taken up. The catalyst was removed by filtration over dicalite. The solvent was removed under reduced pressure, yielding 1.09 g (70.6% (60% P) of intermediate 192.

c) Preparation of Intermediate 193

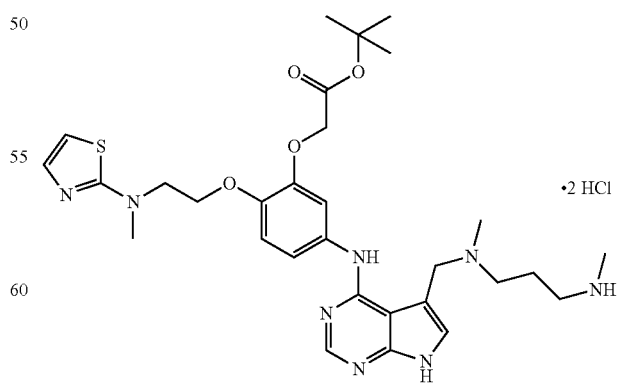

A solution of intermediate 192 (0.002265 mol), intermediate 32 (0.002718 mol) and HCl/Dioxane (4N) (1 ml) in 1-butanol (20 ml) was heated at 100° C. for 30 min. The mixture was used as intermediate 193(0.2HCl) in the next step d) Preparation of Intermediate 194

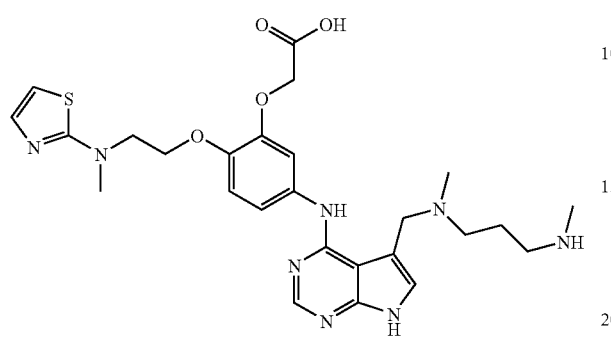

Intermediate 193 (2.265 mmol) was added to a solution of 36% HCl (10 ml) in H$_2$O (20 ml). The reaction mixture was stirred at 60° C. for 4 hours. The reaction mixture was concentrated under reduced pressure. A mixture of LiOH (0.011325 mol) and THF (20 ml) in 5 ml of H$_2$O was added and the reaction mixture was heated at 50° C. for 2 hours. The reaction mixture was concentrated under reduced pressure and purified by HPLC (0.25% ammonium bicarbonate in H$_2$O/CH$_3$CN from 100/0 to 50/50 over 40 min, then 0/100 for 10 min and 100/0 for 10 min; Shandon 8 μm, Hyperprep C18 HS DBS 50 mm by 16.5 cm). The product fractions were collected and concentrated under reduced pressure, yielding 0.440 g (25.9%) of intermediate 194.

Example A54 a) Preparation of Intermediate 195

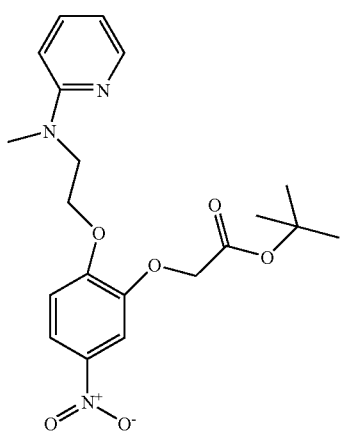

A solution of DMF (35 ml) was treated with NaH (0.00898 mol), under N$_2$-flow, at r.t. A solution of 2-(methyl-2-pyridinylamino)ethanol (0.00898 mol) in DMF (15 ml) was added dropwise. The reaction mixture was stirred for one hour. Then a solution of 5-nitro-1,3-benzodioxole (0.00598 mol) in DMF (15 ml) was added dropwise and stirring was continued for 4 hours. A solution of 2-bromoacetic acid 1,1-dimethylethyl ester (0.00898 mol) in DMF (15 ml) was added dropwise and the entire mixture was stirred for 18 hours. The reaction was completed and the mixture was poured out into ice water. The product was extracted with EtOAc (3 times) and the organic layer was dried (MgSO$_4$), filtered and evaporated to dryness. The crude residue (3.1 g; 74.5%) was used as intermediate 195 in the next step.

b) Preparation of Intermediate 196

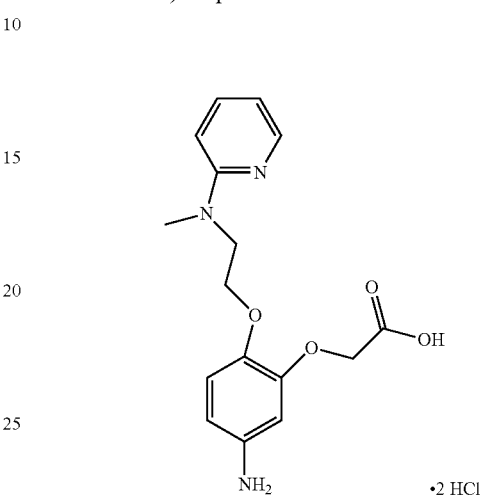

Catalyst Pd/C 10% (0.5 g) was suspended in THF (100 ml), under N$_2$ flow. A 4% thiophene solution (1 ml) was added. Intermediate 195 (0.00595 mol) was added. The reaction mixture was stirred at 25° C. under H$_2$ atmosphere until 3 equivalents of hydrogen were taken up. The catalyst was removed by filtration over dicalite. The solvent was removed under reduced pressure. The residue was dissolved in CH$_2$Cl$_2$ and treated with HCl gas for 5 min. The solvent was removed under reduced pressure. The crude dark brown solid (2.3 g; 79.3%) was used as intermediate 196(0.2HCl) in the next step.

c) Preparation of Intermediate 197

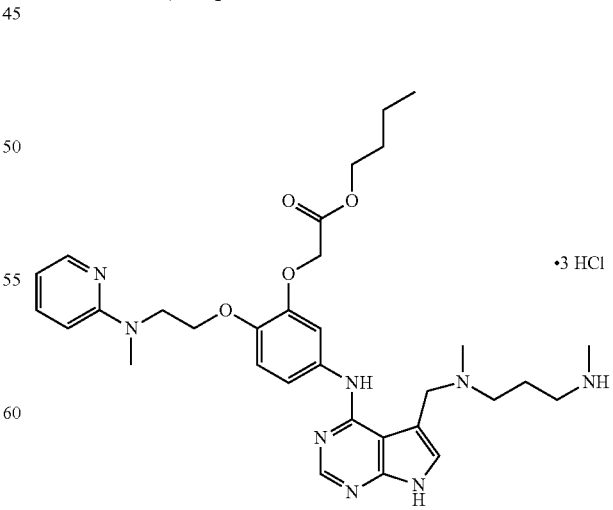

A solution of intermediate 196 (0.001133 mol), intermediate 32 (0.001359 mol) and HCl/Dioxane (4N) (0.5 ml) in d) Preparation of Intermediate 198

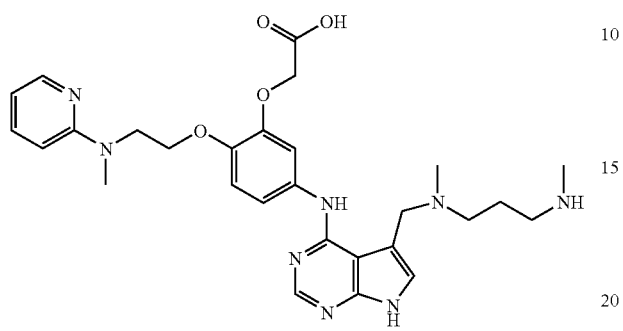

Intermediate 197 (0.001133 mol) was added to a solution of 36% HCl (5 ml) in H$_2$O (10 ml). The reaction mixture was stirred at 60° C. for 4 hours. The reaction mixture was concentrated under reduced pressure. A mixture of LiOH (0.005665 mol) and THF (10 ml) in 5 ml of H$_2$O was added and the reaction mixture was heated at 50° C. for 10 hours. An extra 5 equivalent of LiOH (0.005665 mol), dissolved in 5 ml of H$_2$O, was added and the heating was continued for an additional one hour. The reaction mixture was concentrated under reduced pressure and the residue was purified by HPLC (0.25% ammonium bicarbonate in H$_2$O/CH$_3$CN from 100/0 to 60/40 over 60 min, then 0/100 for 10 min; Shandon 8 µm, Hyperprep C18 HS DBS 50 mm by 16.5 cm). The product fractions were collected and concentrated under reduced pressure, yielding 0.200 g (84%) of intermediate 198.

Example A55 a) Preparation of Intermediate 199

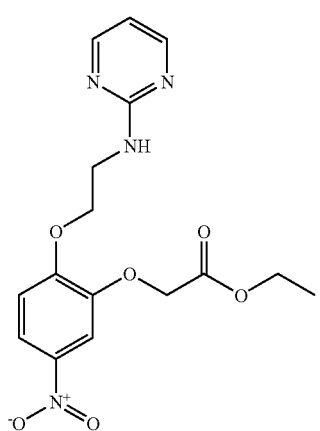

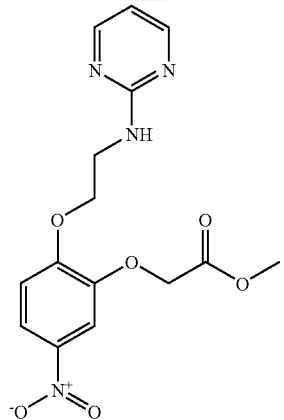

A solution of (2-hydroxy-5-nitrophenoxy)acetic acid ethyl ester (0.009582 mol), (Ph)$_3$P (0.019163 mol) and 2-(2-pyrimidinylamino)ethanol (0.014372 mol) in anhydrous THF (83 ml) was stirred under N$_2$ flow at r.t., while a solution of DIAD (0.019163 mol) in anhydrous THF (10 ml) was added dropwise. After addition, the reaction mixture was stirred for 24 hours. An additional 0.5 eq. of (Ph)$_3$P and DIAD and 0.38 eq. of 2-(2-pyrimidinylamino)ethanol was added and the reaction mixture was stirred under N$_2$ flow for 24 hours. The reaction mixture was concentrated under reduced pressure, and the residue was dissolved in DIPE. The precipitate was filtered off. The filtrate was concentrated under reduced pressure and the residue was purified by HPLC (0.5% ammonium carbonate in H$_2$O/MeOH from 70/30 to 30/70 over 24 min; then 0/100 for 8 min, Shandon 8 µm, Hyperprep C18 HS DBS 50 mm by 21 cm). The product fractions were collected and reduced under reduced pressure, yielding 1 g of intermediate 199.(mixture of methyl and ethyl ester)

b) Preparation of Intermediate 200

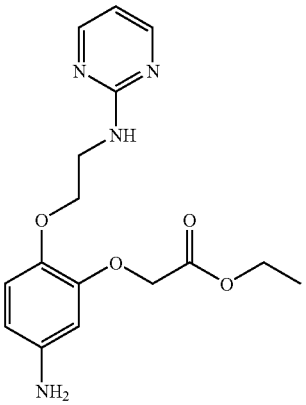

-continued

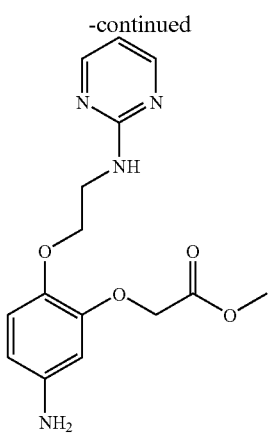

Catalyst Pd/C 10% (0.100 g) was suspended in THF (100 ml) under $N_2$ atmosphere. A 4% Thiophene solution (1 ml) was added. Intermediate 199 was added and the reaction mixture was stirred at a temperature of 25° C. under $H_2$ atmosphere until 3 equivalents of hydrogen were taken up. The catalyst was removed by filtration over dicalite. The solvent was removed under reduced pressure, yielding 0.169 g of intermediate 200.

c) Preparation of Intermediate 201

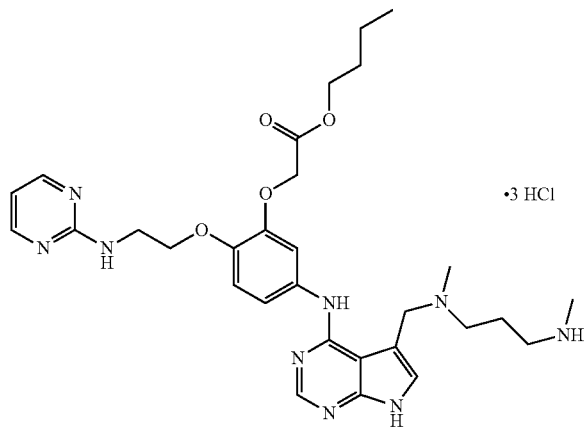

A mixture of intermediate 32 (0.00061 mol) and HCl/Dioxane (4N) (0.000265 mol) in Butanol (4.5 ml) was added to intermediate 200 (0.254 mmol) and the reaction mixture was heated at 100° C. for 30 min. The precipitate was filtered off, yielding intermediate 201(0.3HCl).

d) Preparation of Intermediate 202

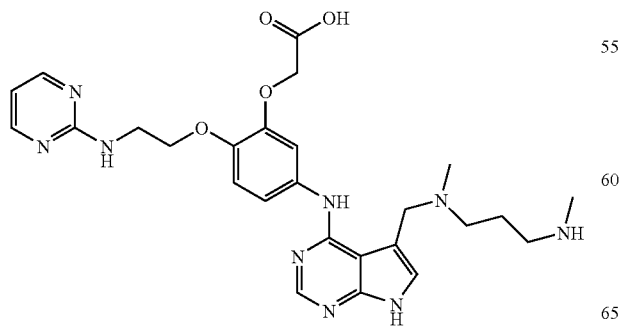

Crude intermediate 201 (0.000338 mol) was added to a solution of 36% HCl solution (1.4 ml) in $H_2O$ (2.8 ml). The reaction mixture was stirred at 60° C. for one hour. The reaction mixture was concentrated under reduced pressure. A mixture of LiOH (0.00169 mol) and THF (1.4 ml) in 0.5 ml of $H_2O$ was added and the reaction mixture was heated at 50° C. for one hour. The reaction mixture was concentrated under reduced pressure and the residue was purified by HPLC (0.2% ammonium bicarbonate in $H_2O/CH_3CN$ starting with 100/0 for 10 min, then from 100/0 to 0/100 over 60 min, then 0/100 for 10 min; Shandon 8 μm, Hyperprep C18 BDS 100 Å 50 mm by 21 cm). The product fractions were collected and concentrated under vacuum, yielding 0.030 g (15.6%) of intermediate 202.

Example A56 a) Preparation of Intermediate 203

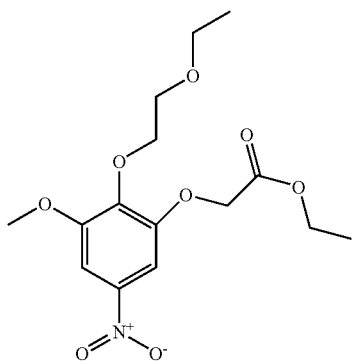

60% NaH in mineral oil (0.03804 mol) was suspended in DMF (60 ml). The suspension was stirred for 30 min. A solution of 2-ethoxy-ethanol (0.03804 mol) in DMF (40 ml) was added dropwise over a 10-min period. The mixture was stirred for 15 min. 4-methoxy-6-nitro-1,3-benzodioxole (0.02536 mol) was added portionwise. The reaction mixture was stirred for 16 hours at r.t. 2-bromoacetic acid ethyl ester (0.03804 mol) was added and the resulting reaction solution was stirred for an additional 4 hours. The solvent was evaporated. The residue was partitioned between brine and EtOAc (3×100 ml). The organic layers were dried ($MgSO_4$), filtered and concentrated to dryness, yielding intermediate 203 used in the next reaction step without further purification.

b) Preparation of Intermediate 204

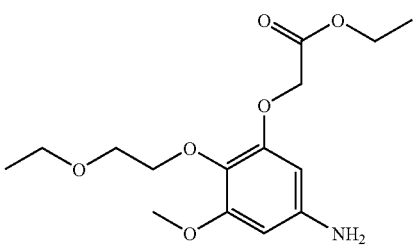

Intermediate 203 (0.02536 mol) was dissolved in EtOH (100 ml) and this solution was hydrogenated under atmospheric pressure at r.t. with Pd/C 10% (1.59 g) as a catalyst After uptake of H$_2$ (3 equiv), the catalyst was filtered off over a pad of Celite and the filtrate was evaporated. A brown oil was obtained which was partitioned between an aqueous NaHCO$_3$ solution and EtOAc (3×100 ml). The organic layers were combined, dried (MgSO$_4$), filtered and concentrated to dryness. The residue was purified by flash chromatography using hexane/EtOAc mixtures as eluents, yielding 72% of intermediate 204.

c) Preparation of Intermediate 205

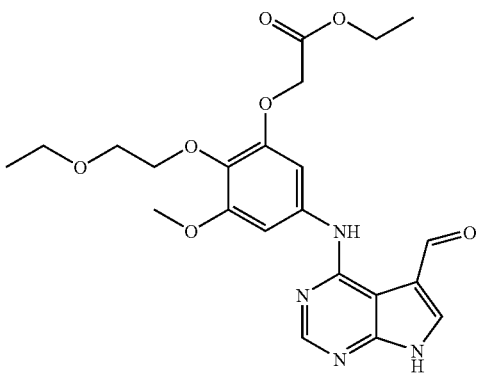

A 37% HCl solution (0.230 ml) was added to a solution of intermediate 1 (0.01116 mol) and intermediate 204 (0.02233 mol) in CH$_3$CN (50 ml). The reaction mixture was stirred and refluxed for 5 hours, then heated at 45° C. overnight. The solvent was evaporated and the residue was partitioned between an aqueous Na$_2$CO$_3$ solution and EtOAc and extracted. The organic layers were combined, dried (MgSO$_4$), filtered and the solvent was evaporated. The residue was purified by flash chromatography (eluent:n-Hexane/EtOAc 1:1). The product fractions were collected and the solvent was evaporated, yielding 3.0 g (60%) of intermediate 205.

d) Preparation of Intermediate 206

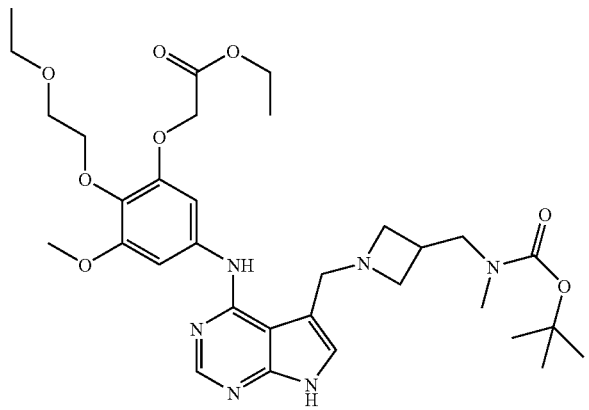

A mixture of intermediate 205 (0.00218 mol) and intermediate 98 (0.00262 mol) in THF (q.s.) was stirred for one hour at r.t. NaBH(OAc)$_3$ (0.00654 mol) was added. The resultant reaction mixture was stirred at r.t. for 16 hours. The mixture was concentrated, and the concentrate was partitioned between an aqueous NaHCO$_3$ solution and EtOAc, and extracted. The organic layers were combined, dried (MgSO$_4$), filtered and the solvent was evaporated to dryness. Intermediate 206 was used in the next reaction step without further purification.

e) Preparation of Intermediate 207

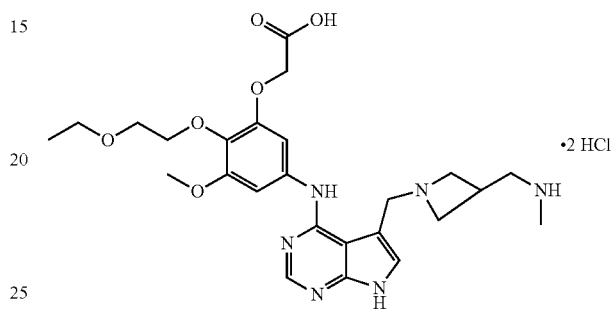

Intermediate 206 (0.00218 mol) was dissolved in CH$_3$CN (30 ml). 37% HCl solution (3 ml) and H$_2$O (9 ml) were added. The reaction mixture was stirred at 60° C. for 2 hours. The crude reaction mixture was concentrated to dryness (under oil pump vacuum). The crude residue was used as intermediate 207(0.2HCl) in the next reaction step.

Example A57 a) Preparation of Intermediate 208

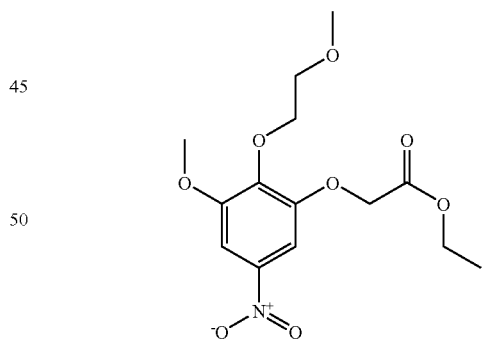

60% NaH in mineral oil (0.03804 mol) was suspended in DMF (60 ml). The suspension was stirred for 30 min. A solution of 2-methoxy-ethanol (0.03804 mol) in DMF (40 ml) was added dropwise over a 10-min period. The mixture was stirred for 15 min. 4-methoxy-6-nitro-1,3-benzodioxole (0.02536 mol) was added portionwise. The resultant reaction mixture was stirred for 16 hours at r.t. 2-bromoacetic acid ethyl ester (0.03804 mol) was added and the resulting reaction solution was stirred for an additional 4 hours. The solvent was evaporated. The residue was partitioned between brine and EtOAc (3×100 mL). The organic layers were combined, dried (MgSO₄), filtered and the solvent was evaporated, yielding crude intermediate 208 used as such in next reaction step.

b) Preparation of Intermediate 209

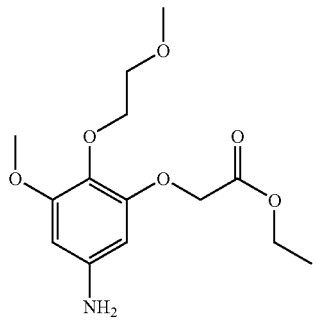

A solution of intermediate 208 (0.02536 mol) in EtOH (100 ml) was hydrogenated under atmospheric H₂ pressure at r.t. with Pd/C 10% (1.67 g) as a catalyst. After uptake of H₂ (3 equiv), the catalyst was filtered off over a pad of Celite and the filtrate was evaporated. A brown oil was obtained which was partitioned between an aqueous NaHCO₃ solution and EtOAc (3×100 ml). The organic layers were combined, dried (MgSO₄), filtered and concentrated to dryness. The residue was purified by flash column chromatography (eluent: hexane/EtOAc mixtures). The product fractions were collected and the solvent was evaporated, yielding 81% of intermediate 209.

c) Preparation of Intermediate 210

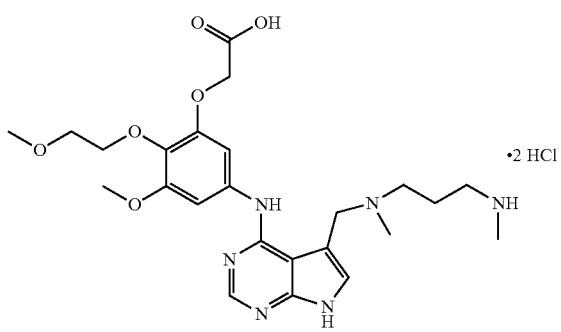

To a solution of intermediate 32 (0.0037 mol) and intermediate 209 (1.2 equiv; 0.0045 mol) in CH₃CN (45 ml), HCl/Dioxane (4N) (0.00555 mol) was added and the reaction mixture was stirred and for 5 hours at 80° C. Then a 12% HCl solution (45 ml) was added. The mixture was heated for 2 hours at 60° C. The mixture was concentrated to dryness and the residue was dried under high vacuum, yielding intermediate 210(0.2HCl).

B. Preparation of the Compounds

Example B1

Preparation of Compound 1

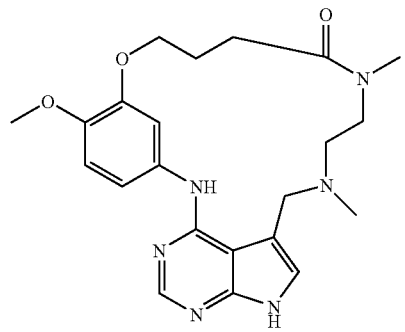

Intermediate 8 (0.00025 mol) was dissolved in DMF (10 ml). This solution was added dropwise to a mixture of HBTU (2.2 eq., 0.00055 mol) and DIPEA (30 eq., 0.0075 mol) in DMF, using a Watson-Marlow peristaltic pump (0.50 rpm). The reaction mixture was stirred for one hour at r.t. and was quenched by addition of NH₃/MeOH (1 ml). The solvent was evaporated. The residue was washed with a saturated aq. Na₂CO₃ solution and was then purified by flash column chromatography over silica gel (eluent:DCM/MeOH mixture). The products were precipitated in a mixture of EtOAc/Et₂O, filtered off and dried. Yield: 0.016 g of compound 1.

Example B2

Preparation of Compound 2

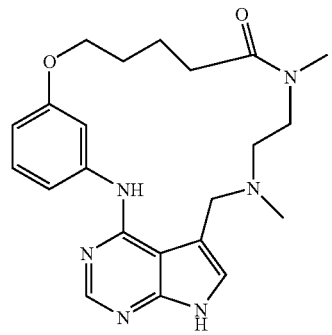

Intermediate 10 (0.00025 mol) was dissolved in DMF (10 ml). This solution was added dropwise to a mixture of HBTU (2.2 eq., 0.00055 mol) and DIPEA (30 eq., 0.0075 mol) in DMF, using a Watson-Marlow peristaltic pump (0.50 rpm). The reaction mixture was stirred for one hour at r.t. and was then quenched by addition of NH₃/MeOH (1 ml). The solvent was evaporated. The residue was washed with a saturated aq. Na₂CO₃ solution and was then purified by flash column chromatography over silica gel (eluent: DCM/MeOH mixture).

The products were precipitated in a mixture of EtOAc/Et₂O, filtered off and dried. Yield: 0.015 g of compound 2.

Example B3

Preparation of Compound 3

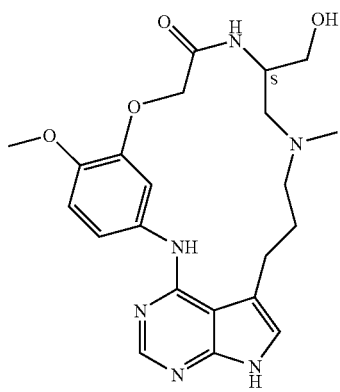

A mixture of intermediate 17 (0.00076 mol) in MeOH (30 ml) and NaOH (15 ml; 1 N) was stirred for 16 hours at r.t. More NaOH (15 ml; 1 N) was added and the reaction mixture was stirred for 16 hours at r.t. The resulting precipitate was filtered off, washed with CH₃CN and was then dried. Yield: 0.236 g of compound 3 (70.6%; S-enantiomer).

Example B4

Preparation of Compound 4

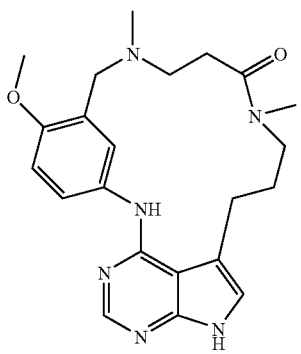

A mixture of intermediate 24 (0.00019 mol) in MeOH (30 ml) and NaOH (15 ml; 1 M) was stirred for 2 hours at r.t. This mixture was extracted with DCM. The separated organic layer was dried, filtered and the solvent evaporated. The residue was purified over silica gel on a glass filter (eluent: DCM/(MeOH/NH₃) 90/10). The product fractions were collected and the solvent was evaporated. Yield: 0.105 g of compound 4.

Example B5

Preparation of Compound 5

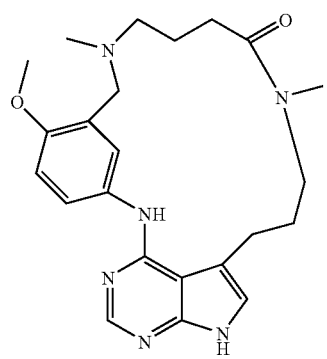

A mixture of intermediate 27 (0.00007 mol) in MeOH (10 ml) and NaOH (3 ml; 1 M) was stirred for 1 hour at r.t. This mixture was poured out into H₂O. The mixture was extracted with DCM. The separated organic layer was dried, filtered and the solvent evaporated. The residue (0.033 g) was purified by HPLC. The product fractions were collected and the solvent was evaporated. Yield: 0.016 g of compound 5 (15.8%).

Example B6

Preparation of Compound 6

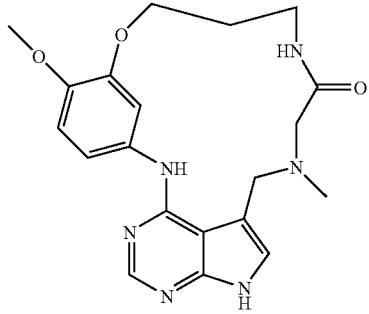

Reaction under N₂ atmosphere. A mixture of PyBOP (0.00085 mol) and Et₃N (0.0017 mol) in DMF (25 ml) was stirred at r.t. under N₂ flow. A solution of intermediate 31 (0.00017 mol) in DMF (25 ml) was added dropwise and the resultant reaction mixture was stirred for one hour at r.t. The mixture was treated with H₂O (decomposition). The solvent was evaporated. The residue was purified by HPLC. The product fractions were collected and the solvent was evaporated. Yield: 0.026 g of compound 6 (38.6%).

Example B7

Preparation of Compound 7

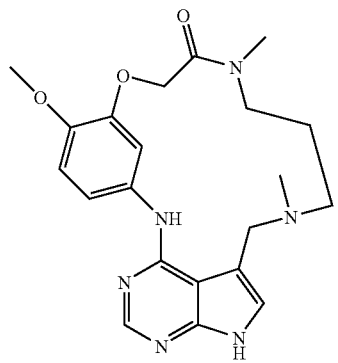

A mixture of PyBOP (0.0005 mol) and Et₃N (0.0010 mol) in DMF (20 ml) was stirred at r.t. under N₂ atmosphere. A solution of intermediate 34 (0.0001 mol) in DMF (20 ml) was added dropwise. The resultant reaction mixture was stirred for 1 hour at r.t. H₂O was added (decomposition). The solvent was evaporated. The residue was purified by HPLC. The product fractions were collected and the solvent was evaporated. Yield: 0.022 g of compound 7 (53.7%).

Example B8

Preparation of Compound 8

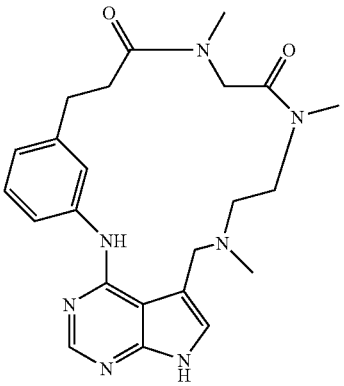

Reaction under N₂ atmosphere. A mixture of PyBOP (0.00045 mol) and Et₃N (0.0009 mol) in DMF (20 ml; dry) was stirred under N₂ flow. A solution of intermediate 38 (0.00009 mol) in DMF (20 ml; dry) was added dropwise. The reaction mixture was stirred for 1 hour at r.t. H₂O was added (decomposition). The solvent was evaporated. The residue was purified by HPLC. The product fractions were collected and the solvent was evaporated. Yield: 0.032 g of compound 8.

Example B9

Preparation of Compound 9

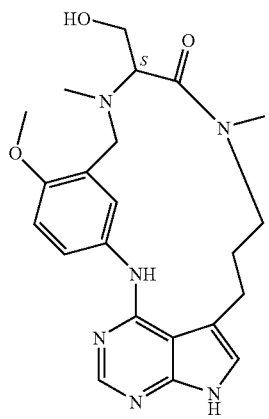

A mixture of intermediate 42 (max. 0.000317 mol) in MeOH (25 ml) and NaOH (25 ml; 1 N) was stirred for 2 hours at r.t. This mixture was extracted with DCM. The separated organic layer was dried, filtered and the solvent evaporated. The residue was purified by reversed-phase HPLC (Shandon Hyperprep® C18 BDS (Base Deactivated Silica) 8 μm, 250 g, I.D. 5 cm). The mentioned mobile phases were used to apply a gradient (phase A: 0.25% NH₄HCO₃ solution in H₂O; phase B: CH₃OH (optional); phase C: CH₃CN). The product fractions were collected and the solvent was evaporated. Yield: 0.120 g of compound 9 (S-enantiomer). Yield over 5 reaction steps: 28.3%.

Example B10

Preparation of Compound 10

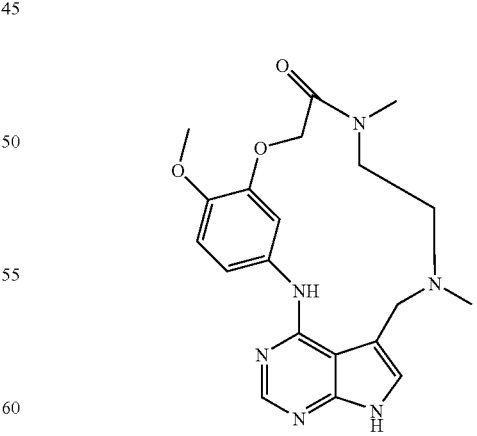

A mixture of PyBOP (4.28 g, 0.0082 mol), Et₃N (0.82 g, 0.0082 mol) and DMF (100 ml) was stirred at r.t. under N₂ flow. Intermediate 44 (0.680 g, 0.0017 mol) in DMF (100 ml) was added dropwise to the mixture and stirring was continued for 1 hour. The reaction mixture was cooled on a cold waterbath and H₂O (20 ml) was added dropwise to the reaction mixture. The mixture was continued stirring for 1 hour. Then the solvent was evaporated to dryness and the residue was purified by HPLC method C. The pure fractions were evaporated to dryness and evaporated with MeOH at 60° C. The residue was stirred in DIPE, filtered off and dried. Yield: 0.275 g of compound 10 (42%).

Example B11

Preparation of Compound 11

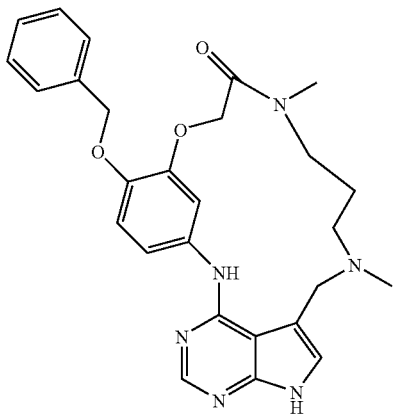

A mixture of PyBOP (0.26 g, 0.0005 mol) and Et₃N (0.050 g, 0.0005 mol) in DMF (20 ml) was stirred at r.t. under N₂ flow. A solution of intermediate 48 (0.045 g, 0.0001 mol) in DMF (20 ml) was added dropwise to the mixture. Stirring was continued for 1 hour. Then, the reaction mixture was cooled on a cold waterbath, and H₂O (20 ml) was added dropwise. Stirring was continued for 1 hour. The reaction mixture was evaporated to dryness and the residue was purified by HPLC method A. The pure fractions were evaporated to dryness. The residue was taken up into H₂O and was extracted with DCM. The organic layer was separated, dried, filtered and the solvent was evaporated. The residue was stirred in DIPE, filtered off and dried. Yield: 0.026 g of compound 11 (59.4%).

Example B12

Preparation of Compound 12

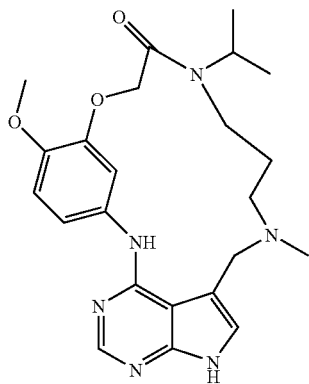

A mixture of PyBOP (4.20 g, 0.0080 mol), Et₃N (0.8 g, 0.0080 mol) and DMF (100 ml) was stirred at r.t. under N₂ flow. Intermediate 54 (0.696 g, 0.0016 mol) in DMF (100 ml) was added dropwise. Stirring was continued for 1 hour. The reaction mixture was cooled on a cold waterbath and H₂O (20 ml) was added dropwise. Stirring was continued for 1 hour. Then the solvent was evaporated to dryness and the residue was purified by HPLC method A. The pure fractions were evaporated to dryness and evaporated with MeOH at 60° C. The residue was stirred in DIPE, filtered off and dried. Yield: 0.338 g of compound 12 (48.2%).

Example B13

Preparation of Compound 13

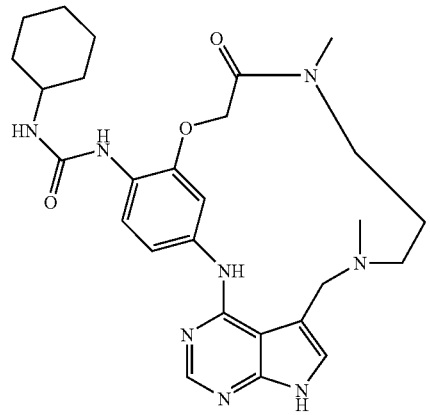

A mixture of PyBOP (1.836 g, 0.0035 mol) and Et₃N (0.353 g, 0.0035 mol) in DMF (50 ml) was stirred at r.t. under N₂ flow. A solution of intermediate 59 (0.380 g, 0.0007 mol) in DMF (50 ml) was added dropwise. Stirring was continued for 1 hour. The reaction mixture was cooled on a cold waterbath and H₂O (20 ml) was added dropwise. Stirring was continued for 1 hour. The reaction mixture was evaporated to dryness and purified by HPLC method B. The pure fractions were collected, evaporated to dryness, stirred in dipe, filtered off and dried. Yield: 0.048 g of compound 13.

Example B14

Preparation of Compound 14

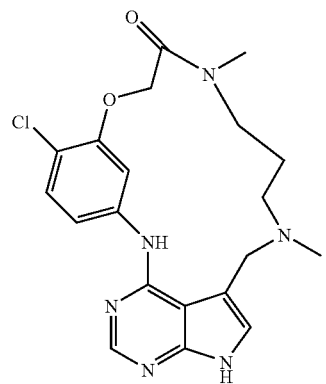

A mixture of PyBOP (2.080 g, 0.0040 mol), Et₃N (0.400 g, 0.0040 mol) and DMF (50 ml) was stirred at r.t. under N₂ flow. Intermediate 62 (0.340 g, 0.0008 mol) in DMF (50 ml) was added dropwise. The reaction mixture was cooled on a cold waterbath and H₂O (20 ml) was added dropwise. Stirring was continued for 1 hour. The reaction mixture was evaporated to dryness and purified by HPLC. The pure fractions were evaporated to dryness. Yield: 0.184 g of compound 14 (56%).

Example B15

Preparation of Compound 15

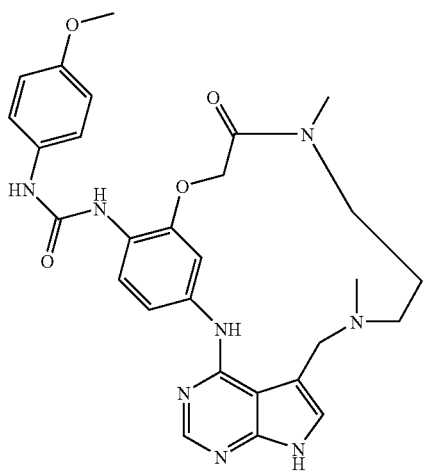

A mixture of PyBOP (1.300 g, 0.0025 mol), Et₃N (0.253 g, 0.0025 mol) and DMF (50 ml) was stirred at r.t. under N₂ flow. Then intermediate 66 (0.270 g, 0.0005 mol) in DMF (50 ml) was added dropwise. Stirring was continued for 1 hour. The reaction mixture was cooled on a cold waterbath and H₂O (20 ml) was added dropwise. Stirring was continued for 1 hour. The reaction mixture was evaporated to dryness and purified by HPLC method C. The pure fractions were collected and evaporated to dryness. The residue was stirred in dipe, filtered off and dried. Yield: 0.073 g of compound 15.

Example B16

Preparation of Compound 30

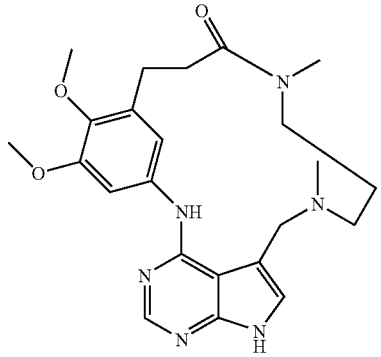

A mixture of intermediate 72 (0.0011 mol) in DMF (75 ml) was added dropwise to a mixture of PyBOP (0.0055 mol) and Et₃N (0.011 mol) in DMF (75 ml). The reaction mixture was stirred at r.t. under N₂ atmosphere until the reaction was finished. The solvent was evaporated. The residue (0.037 g) was stirred in DIPE, filtered off and dried. Yield: 0.015 g of compound 30.

Example B17

Preparation of Compound 63

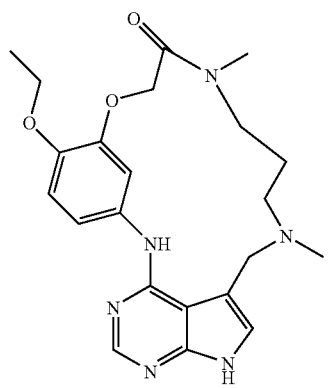

A mixture of PyBOP (1.450 g, 0.0028 mol) and Et₃N (0.28 g, 0.0028 mol) in DMF (30 ml) was stirred at r.t. under N₂ flow. Intermediate 76 (0.280 g, 0.0006 mol) in DMF (30 ml) was added dropwise. The resultant reaction mixture was stirred for one hour. The reaction mixture was cooled on a cold water-bath. H₂O (20 ml) was added dropwise and stirring was continued for 1 hour. The solvent was evaporated. The residue was purified by HPLC (HPLC method A). The product fractions were collected and the solvent was evaporated. Yield: 0.040 g of compound 63 (17%).

Example B18

Preparation of Compound 73

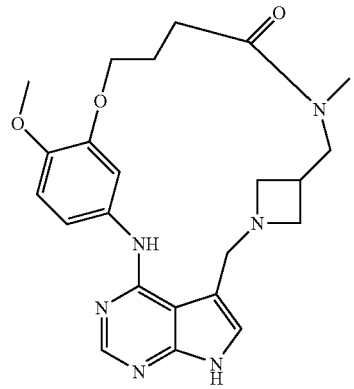

A mixture of PyBOP (1.040 g, 0.002 mol) and Et₃N (0.2 g, 0.002 mol) in DMF (25 ml) was stirred at r.t. under N₂ flow. A solution of intermediate 103 (0.180 g, 0.00040 mol) in DMF (25 ml) was added dropwise and the mixture was stirred for 1 hour. Then the reaction mixture was cooled on a cold waterbath, H₂O (20 ml) was added dropwise and the mixture was stirred for 1 hour. Subsequently, the solvent was evaporated to dryness and the residue was purified by reversed-phase HPLC (Shandon Hyperprep® C18 BDS (Base Deactivated Silica) 8 μm, 250 g, I.D. 5 cm). A gradient with 3 mobile phases was applied. Phase A: a 0.25% NH₄HCO₃ solution in H₂O; phase B: CH₃OH; phase C: CH₃CN). The desired fractions were collected and the solvent was evaporated. The residue was stirred in DIPE, filtered off and dried. Yield: 0.070 g of compound 73.

Example B19

Preparation of Compound 69

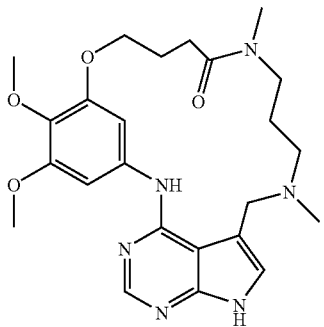

Intermediate 79 (0.0019 mol) in DMF (10 ml) was added over about 2 hours to a solution of HBTU (0.0042 mol) and DIPEA (0.0571 mol) in DMF (350 ml), using a Watson Marlow pump (0.75 rpm). After the addition was completed, the reaction mixture was stirred for 30 minutes. Then, 2 ml of ammonia (7 N solution in MeOH) was added and the mixture was stirred for 30 additional minutes. The solvent was evaporated and the crude was dissolved in DCM, washed with a 1 M Na₂CO₃ solution, dried (MgSO₄), filtered and concentrated to dryness. The product was purified by flash column chromatography on silica gel, using as eluent a mixture of DCM/MeOH (+1% NH₃/MeOH) (ratios: 100/0-70/1-60/1-50/1). The product fractions were collected and the solvent was evaporated. The residue was dried (vacuum, r.t.) yielding a white solid. Yield: 0.015 g of compound 69.

Example B20

Preparation of Compound 84

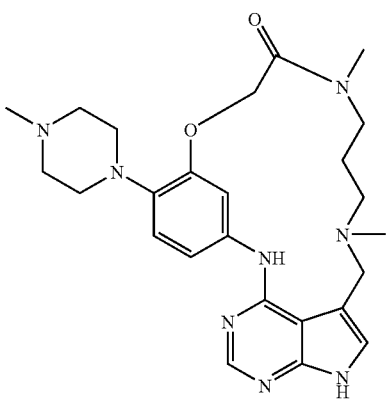

A solution of intermediate 143 (crude; approx. 0.0009 mol) in DMF (10 ml) was added over a 3 hour period to a solution of HBTU (0.73 g, 0.0019 mol) and DIPEA (4.4 ml, 0.0262 mol) in DMF (155 ml), using a Watson Marlow pump (0.75 rpm). After the addition was completed, the reaction mixture was stirred for 30 minutes. Then, 1 ml of NH₃ (7 N solution in MeOH) was added and the mixture was stirred for 30 minutes. The solvent was evaporated and the crude was dissolved in DCM. The organic solution was washed with an aq. 1 M Na₂CO₃ solution, dried (MgSO₄), filtered and concentrated to dryness. The residue was purified by flash column chromatography over silica gel (eluent: a mixture of DCM/MeOH (ratios: 100/0-70/1-60/1-50/1-40/1-30/1). The product fractions were collected and the solvent was evaporated. The residue was dried (vacuum, r.t.) yielding a white solid. Yield: 0.106 g of compound 84.

Example B21
Preparation of Compound 70

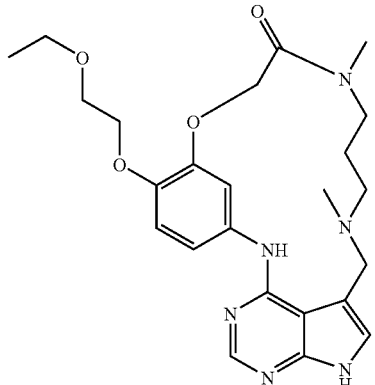

A mixture of PyBOP (2.73 g, 0.00524 mol), Et₃N (0.53 g, 0.00524 mol) and DMF (50 ml) was stirred at r.t. under N₂ flow. A mixture of intermediate 84 (0.51 g, 0.00105 mol) in DMF (80 ml) was added dropwise over 2 hours. The reaction mixture was stirred for 1 hour and was then cooled on a cold waterbath. H₂O (20 ml) was added dropwise and the mixture was stirred again for 1 hour. Then the solvent was evaporated and the residue (4.3 g) was purified by HPLC (a gradient with NH₄OAc buffer/CH₃CN and MeOH was applied). After workup, 0.75 g of residue was obtained. H₂O and K₂CO₃ were added to the residue and the product was extracted with DCM. The solvent of the organic layer was evaporated to yield 0.31 g of compound 70 (63%).

Example B22
Preparation of Compound 83

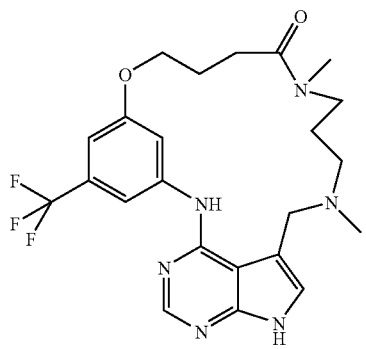

Intermediate 138 (crude, max. 0.0019 mol) in DMF (10 ml) was added over about 2 hours to a solution of HBTU (1.58 g, 0.0042 mol) and DIPEA (9.7 ml, 0.0571 mol) in DMF (350 ml), using a Watson Marlow pump (0.75 rpm). After the addition was completed, the reaction mixture was stirred for 30 minutes. Then, 2 ml of NH₃ (7 N solution in MeOH) was added and the mixture was stirred for 30 minutes. The solvent was evaporated and the crude was dissolved in DCM. The organic solution was washed with an aq. 1 M Na$_2$CO$_3$ solution, dried (MgSO$_4$), filtered and concentrated to dryness. The residue was purified by flash column chromatography on silica gel (eluent:DCM/MeOH (+1% NH$_3$/CH$_3$OH) (ratios: 100/0-70/1-60/1-50/1-40/1-30/1). The product fractions were collected and the solvent was evaporated. The products were dried (vacuum, r.t.), yielding 0.054 g of compound 83 (6%) as a white solid.

Example B23

Preparation of Compound 85

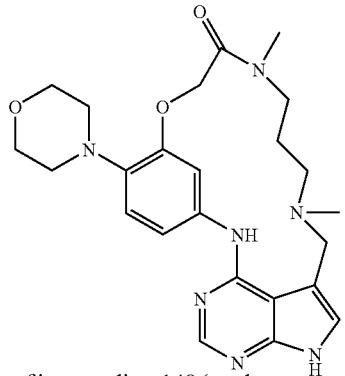

A solution of intermediate 148 (crude; approx. 0.0009 mol) in DMF (10 ml) was added over a 3-hour period to a solution of HBTU (0.73 g, 0.0019 mol) and DIPEA (4.4 ml, 0.0262 mol) in DMF (155 ml), using a Watson Marlow pump (0.75 rpm). After the addition was completed, the reaction mixture was stirred for 30 minutes. Then, 1 ml of NH$_3$ (7 N solution in MeOH) was added and the mixture was stirred for 30 minutes. The solvent was evaporated and the residue was dissolved in DCM. The organic solution was washed with an aq. 1 M Na$_2$CO$_3$ solution, dried (MgSO$_4$), filtered and concentrated to dryness. The residue was purified by flash column chromatography over silica gel (eluent: a mixture of DCM/MeOH (ratio: 100/0-70/1-60/1-50/1-40/1-30/1). The product fractions were collected and the solvent was evaporated. The product was dried (vacuum, r.t.) yielding 0.089 g of compound 85 as a white solid.

Example B24

Preparation of Compound 71

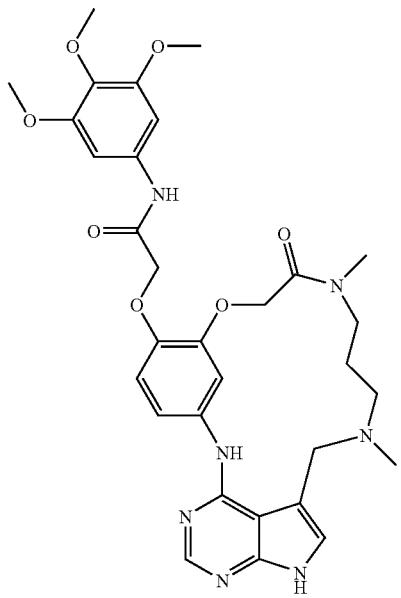

A mixture of PyBOP (1.22 g, 0.00235 mol), Et$_3$N (0.24 g, 0.00235 mol) and DMF (30 ml) was stirred under N$_2$ flow at r.t. A mixture of intermediate 88 (0.30 g, 0.00047 mol) in DMF (40 ml) was added dropwise over 2 hours. The reaction mixture was stirred for 1 hour. Subsequently, the mixture was cooled on a cold waterbath, H$_2$O (20 ml) was added dropwise and the mixture was stirred for another hour. Then the solvent was evaporated and the residue was purified by reversed-phase HPLC (Shandon Hyperprep® C18 BDS (Base Deactivated Silica) 8 µm, 250 g, I.D. 5 cm). A gradient with 3 mobile phases was applied. Phase A: a 0.25% NH$_4$HCO$_3$ solution in water; phase B: CH$_3$OH; phase C: CH$_3$CN). The desired fractions were collected and the solvent was evaporated. Yield: 0.115 g of compound 71 (39.5%).

Example B25

Preparation of Compound 72

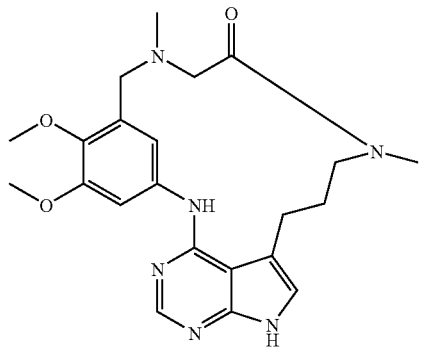

A mixture of intermediate 96 (0.0024 mol) in NaOH (58 ml; 1 M solution) and MeOH (100 ml) was stirred for 2 hours at r.t. The reaction mixture was extracted with DCM. The aq. layer was extracted with more DCM. The organic extracts were washed with a saturated aq. K$_2$CO$_3$ solution, dried, filtered and the filtrate was concentrated to dryness. The residue was purified by column chromatography over silica gel eluting with DCM/MeOH. The product fractions were collected and the solvent was evaporated. The residue was purified by reversed-phase column chromatography. The product fractions were collected and the solvent was evaporated. The residue was recrystallized from CH$_3$CN, filtered off and dried. Yield: 0.099 g of compound 72 (10%).

Example B26

Preparation of Compound 74

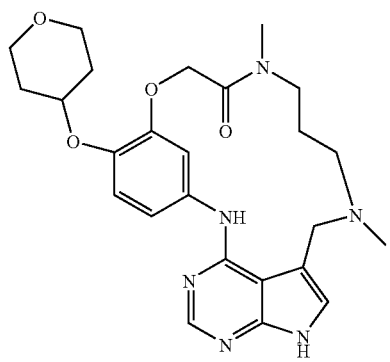

A solution of intermediate 107 (0.26 g, 0.00052 mol) in DMF (40 ml) was added at r.t. under $N_2$ flow to a stirred mixture of PyBOP (1.3 g, 0.0025 mol) and $Et_3N$ (0.34 ml, 0.0025 mol) in DMF (40 ml). The reaction mixture was stirred for 1 hour and $H_2O$ (15 ml) was added. The mixture was stirred for 1 hour. Subsequently, the solvent was evaporated and the residue was purified by HPLC (RP-18; eluent: (0.25% $NH_4HCO_3$ in $H_2O$)/$CH_3CN$ v/v 100/0-0/100). The desired fractions were collected and the solvent was evaporated. Yield: 0.17 g of compound 74.

Example B27

Preparation of Compound 75

A solution of intermediate 110 (0.750 g, 0.0016 mol) in DMF (117 ml) was added dropwise at r.t. under $N_2$ flow to a stirred mixture of PyBOP (4.11 g, 0.0079 mol) and $Et_3N$ (1.10 ml, 0.0079 mol) in DMF (117 ml). The mixture was stirred for 1 hour and then $H_2O$ (15 ml) was added and stirring was continued for 1 hour. Then the mixture was evaporated and the residue was purified by HPLC (Shandon Hyperprep® C18 HS BDS; 8 µm, 50 mm by 16.5 cm). A gradient with 2 mobile phases was applied: (0.25% $NH_4HCO_3$ in $H_2O$)/$CH_3CN$ from 100/0 to 80/20 in 10 minutes; then 0/100 for 8 minutes and finally 100/0 for 12 minutes. After workup, the powder was dissolved in MeOH and concentrated under reduced pressure. The solid was dried (vacuum, 50° C.). Yield: 0.230 g of compound 75 (31% yield).

Example B28

Preparation of Compound 76

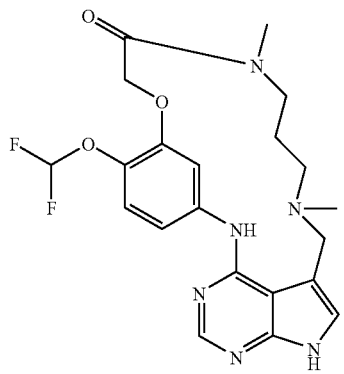

A solution of intermediate 114 (crude; max. 0.00226 mol) in DMF (115 ml) was added very slowly (over 1 one hour using a Marlow peristaltic pump) to a solution of HBTU (1.896 g, 0.005 mol) and DIPEA (0.0565 mol) in DMF (55 ml). The reaction mixture was stirred for an additional hour and was then quenched with 4 ml of 7 N $NH_3$ in MeOH. The reaction mixture was concentrated to dryness and the residue was partitioned between DCM and a saturated aq. $K_2CO_3$ solution. The aq. layer was extracted with more DCM. The organic extracts were washed with a saturated aq. $K_2CO_3$ solution, dried, filtered and the filtrate was concentrated to dryness. The residue was purified by column chromatography (eluent: DCM/MeOH gradient). The product fractions were collected and the solvent was evaporated. The residue was recrystallized from $CH_3CN$, filtered off and dried. Yield: 0.043 g of compound 76 (4% yield).

Example B29

Preparation of Compound 77

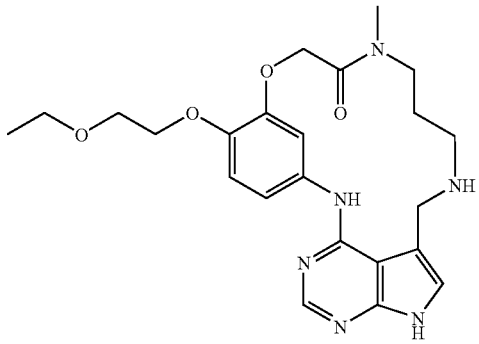

A solution of intermediate 119 (crude; 0.1 g, max. 0.00018 mol) in DMF (25 ml) was added dropwise at r.t. under $N_2$ flow to a stirred mixture of PyBOP (0.468 g, 0.0009 mol) and $Et_3N$ (0.126 ml, 0.0009 mol) in DMF (25 ml). The mixture was stirred for 1 hour and then $H_2O$ (20 ml) was added and stirring was continued for 1 hour. The solvent was evaporated and the residue was purified by HPLC (RP-18; eluent: (0.25% $NH_4HCO_3$ in $H_2O$)/$CH_3CN$ v/v 100/0-0/100). The desired fractions were collected and the solvent was evaporated. Yield: 0.004 g of compound 77.

Example B30

Preparation of Compound 78

A solution of intermediate 123 (0.287 g, 0.000496 mol) in DMF (35 ml) was dropwise added at r.t. under N₂ flow to a stirred mixture of PyBOP (1.29 g, 0.00248 mol) and Et₃N (0.35 ml) in DMF (70 ml). The mixture was stirred for 1 hour and then H₂O (4.6 ml) was added and stirring was continued for 1 hour. The solvent was evaporated. The residue was purified by HPLC method B. The desired fractions were collected and the solvent was evaporated. The solid was dried (vacuum, 50° C.). Yield: 0.1828 g of compound 78 (65.7%).

Example B31

Preparation of Compound 79

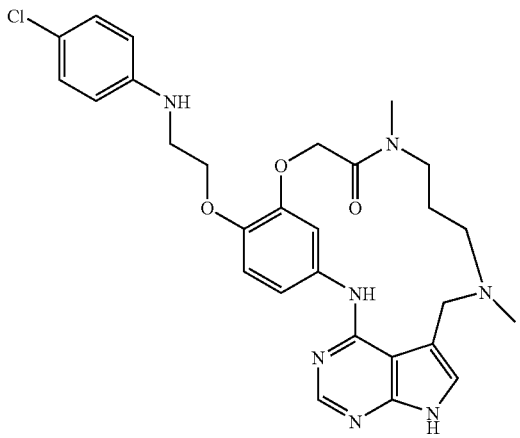

A solution of intermediate 126 (0.1 g, 0.000176 mol) in DMF (13 ml) was dropwise added at r.t. under N₂ flow to a stirred mixture of PyBOP (0.458 g, 0.00088 mol) and Et₃N (0.13 ml) in DMF (13 ml). The mixture was stirred for 1 hour and then H₂O (1.6 ml) was added and stirring was continued for 1 hour. The solvent was evaporated. The residue was purified by HPLC method C. The desired fractions were collected and the solvent was evaporated. The solid was dried (vacuum, 50° C.). Yield: 0.0657 g of compound 79 (67.8%).

Example B32

Preparation of Compound 80

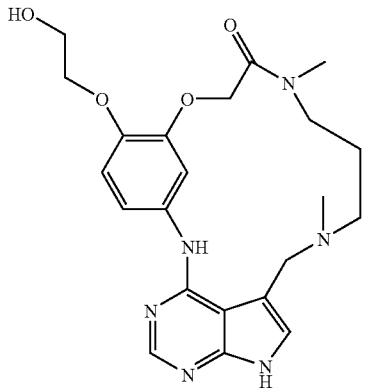

A solution of intermediate 130 (0.160 g, 0.000349 mol) in DMF (25 ml) was added dropwise at r.t. under N₂ flow to a stirred mixture of PyBOP (0.907 g, 0.001745 mol) and Et₃N (0.174 g) in DMF (25 ml). The mixture was stirred for 1 hour and then H₂O was added. The solvent was evaporated and the residue was purified by HPLC method B. After workup, the residue was stirred in DIPE. The precipitate was filtered off and dried. Yield: 0.055 g of compound 80 (35.7%).

Example B33

Preparation of Compound 81

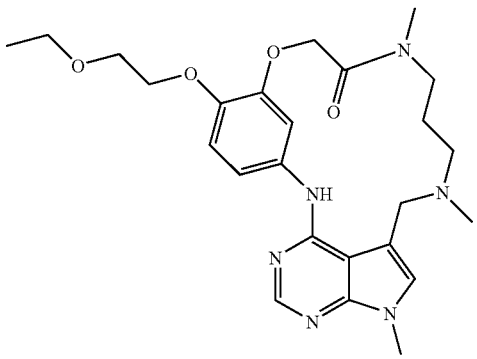

A mixture of compound 70 (0.1 g, 0.000213 mol) and Cs₂CO₃ (0.069537 g, 0.000213 mol) in DMF (10 ml) was stirred at r.t. for 15 minutes. CH₃I (0.013286 ml, 0.000213 mol) was added and the reaction mixture was stirred for 18 hours. Then the solvent was evaporated. The residue was purified by HPLC (RP-18; eluent: (0.25% NH₄HCO₃ in H₂O)/CH₃CN v/v 100/0-0/100). The desired fractions were collected and the solvent was evaporated and co-evaporated with toluene. The residue was dried (vacuum, 50° C.). Yield: 0.042 g of compound 81 (40.7%).

Example B34

Preparation of Compound 82

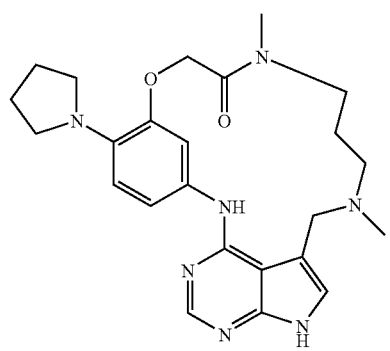

A solution of intermediate 134 (0.030 g, 0.0000642 mol) in DMF (30 ml) was added dropwise at r.t. under N₂ flow to a stirred mixture of PyBOP (0.1669 g, 0.000321 mol) and Et₃N (0.0447 ml, 0.000321 mol) in DMF (30 ml). The mixture was stirred for 1 hour and then H₂O (20 ml) was added. The mixture was stirred for 1 hour and then the solvent was evaporated. The residue was purified by HPLC method C.

The product fractions were collected and the solvent was evaporated. The residue was dried (vacuum, 50° C.). Yield: 0.008 g of compound 82 (27.7%).

Example B35

Preparation of Compound 147

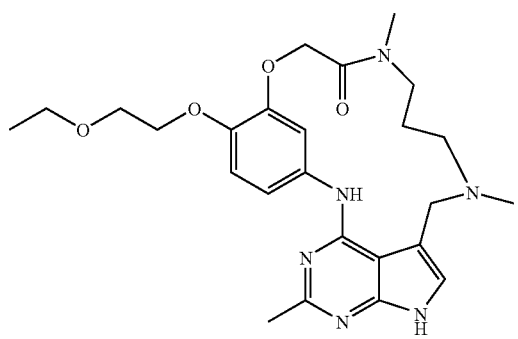

Reaction under N$_2$ atmosphere. A solution of intermediate 155 (0.00026 mol) in DMF (40 ml) was added dropwise to a mixture of PyBOP (0.000779 mol) and Et$_3$N (0.001298 mol) in DMF (40 ml), stirred at r.t. Stirring was continued for one hour. Then H$_2$O (10 ml) was added and the resultant mixture was stirred for one hour. The reaction mixture was concentrated under reduced pressure. The crude residue was purified by high-performance liquid chromatography over RP-18 (eluent:(0.25% NH4HCO3 in H2O)/CH3CN/CH3OH/v/v 100/0/0-70/30/0-0/50/50). The desired fractions were collected and evaporated to dryness. Then, the product was repurified over silica gel (eluent: DCM/DCM-CH$_3$OH 9/1//EtOH v/v 100/0/0-0/100/0-0/0/100). The product fractions were collected and evaporated to dryness. The residual fraction was dried in vacuo at 50° C., yielding 0.025 g (19.9%) of compound 147.

Example B36

Preparation of Compound 148

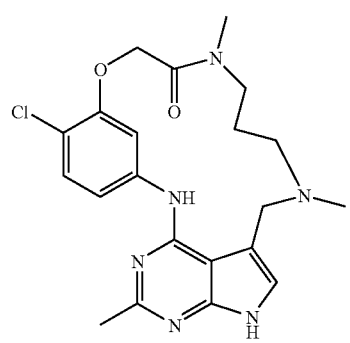

A solution of intermediate 157 (0.0000671 mol) in DMF (15 ml) was added dropwise to a mixture of PyBOP (0.000201 mol) and Et$_3$N (0.00036 mol) in DMF (15 ml), stirred at r.t. under N$_2$ flow. Stirring was continued for one hour. Then H$_2$O (5 ml) was added and the entire mixture was stirred for one hour. The reaction mixture was concentrated under reduced pressure. The crude residual fraction was purified by high-performance liquid chromatography over RP-18 (eluent:(0.25% NH$_4$HCO$_3$ in H$_2$O)/CH$_3$CN/v/v 100/0-50/50-0/100). The product fractions were collected and evaporated to dryness. The residue was dried in vacuo at 50° C., yielding 0.021 g (72.9%) of compound 148.

Example B37

Preparation of Compound 149

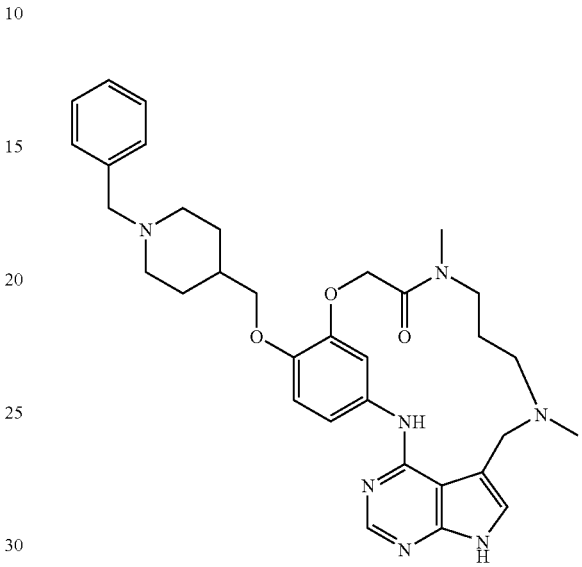

A solution of intermediate 161 (0.000332 mol) in DMF (25 ml) was added dropwise to a mixture of PyBOP (0.001662 mol) and Et$_3$N (0.25 ml) in DMF (25 ml), stirred at r.t. under N$_2$ flow. Stirring was continued for one hour, then 2 ml of H$_2$O was added and the reaction mixture was stirred for one hour. The solvent was evaporated under reduced pressure and the residue was purified by HPLC (0.25% ammonium bicarbonate in H$_2$O/CH$_3$CN from 100/0 to 70/30 over 60 minutes, then 0/100 for 10 minutes; Shandon 8 μm, Hyperprep C18 BDS 100 Å 50 mm by 16.5 cm).

The product fractions were collected and the solvent was evaporated under reduced pressure. The solid was dried under vacuum at 50° C., yielding 0.047 g (23.7%) of compound 149.

Example B38

Preparation of Compound 150

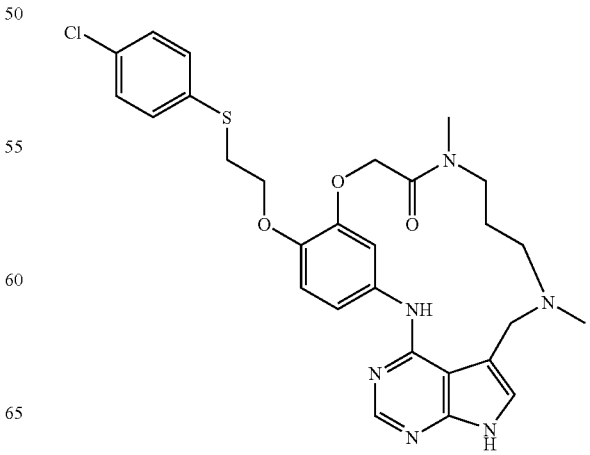

A solution of intermediate 165 (0.00041 mol) in DMF (30 ml) was added dropwise to a mixture of PyBOP (0.002051 mol) and Et₃N (0.3 ml) in DMF (30 ml), stirred at r.t. under N₂ flow. Stirring was continued for one hour, then 2 ml of H₂O was added and the resultant reaction mixture was stirred for one hour at r.t. The reaction mixture was concentrated under reduced pressure and the residue was purified by HPLC (0.25% ammonium bicarbonate in H₂O/CH₃CN from 100/0 to 50/50 over 40 minutes, then 0/100 for 10 minutes and 100/0 for 10 minutes; Shandon 8 µm, Hyperprep C18 BDS 100 Å 50 mm by 16.5 cm). The product fractions were collected and concentrated under reduced pressure. The solid was dried under vacuum at 50° C., yielding 0.110 g (46.8%) of compound 150.

Example B39

Preparation of Compound 151

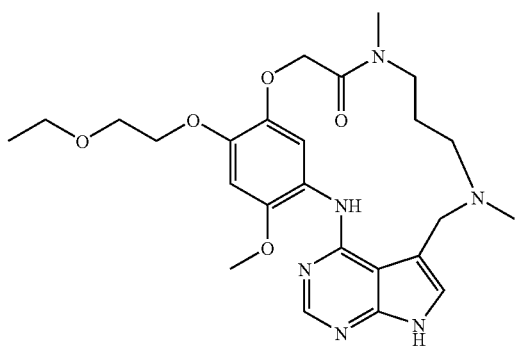

A solution of intermediate 169 (0.000281 mol) in DMF (50 ml) was added dropwise to a mixture of PyBOP (0.000982 mol) and Et₃N (0.001403 mol) in DMF (50 ml), stirred at r.t. under N₂-flow. Stirring was continued for one hour, then 5 ml H₂O was added and the entire mixture was stirred for one hour. The reaction mixture was concentrated under reduced pressure. The crude residual fraction was purified by high-performance liquid chromatography over RP-18 (eluent: (0.25% NH₄HCO₃ in H₂O)/CH₃CN/v/v 100/0-50/50-0/100). The product fractions were collected and evaporated to dryness. The residue was dried in vacuo at 50° C., yielding 0.035 g (25.0%) of compound 151.

Example B40

Preparation of Compound 152

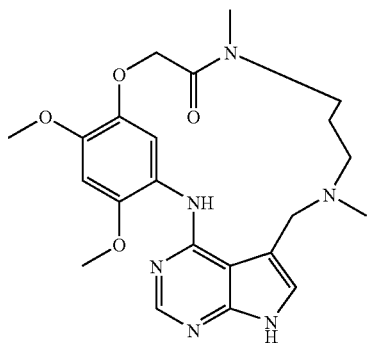

A solution of intermediate 173 (0.00017 mol) in DMF (20 ml) was added dropwise to a mixture of PyBOP (0.000851 mol) and Et₃N (0.000851 mol) in DMF (20 ml), stirred at r.t. under N2-flow. Stirring was continued for one hour, then 10 ml H₂O was added and the entire mixture was stirred for one hour. The reaction mixture was concentrated under reduced pressure. The crude residue was purified by high-performance liquid chromatography over RP-18 (eluent:(0.25% NH₄HCO₃ in H₂O)/CH₃OH/CH₃CN/v/v 75/25/0-0/50/50-0/100). The product fractions were collected and evaporated to dryness. The residue was dried in vacuo at 50° C., yielding 0.005 g (3.74%) of compound 152.

Example B41

Preparation of Compound 153

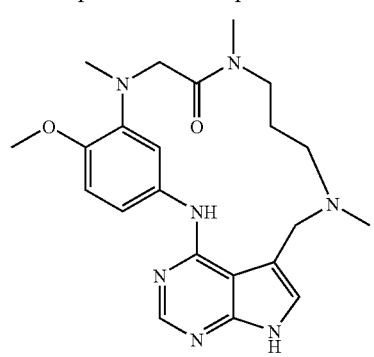

A solution of intermediate 178 (0.0000453 mol) in DMF (10 ml) was added dropwise to a mixture of PyBOP (0.000136 mol) and Et₃N (0.000226 mol) in DMF (10 ml), the reaction mixture was stirred at r.t. under N₂-flow. Stirring was continued for one hour, then 5 ml of H₂O was added and the mixture was stirred for one hour. The reaction mixture was concentrated under reduced pressure. The crude residue was purified by high-performance liquid chromatography over RP-18 (eluent:(0.25% NH₄HCO₃ in H₂O)/CH₃CN/CH₃OH/v/v 100/0/0-70/30/0-0/50/50). The product fractions were collected and evaporated to dryness. The residue was dried in vacuo at 50° C., yielding 0.005 g (26.1%) of compound 153.

Example B42

Preparation of Compound 154

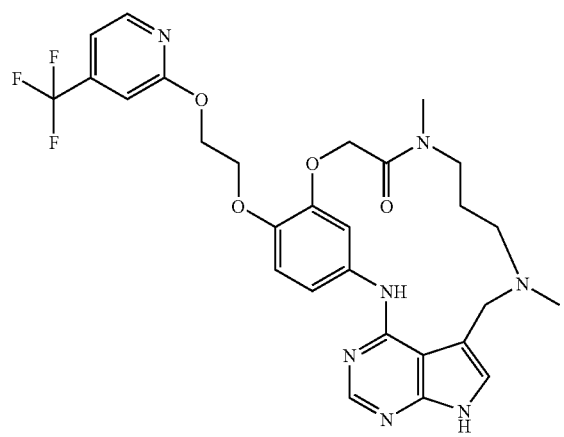

A solution of intermediate 182 (0.0000414 mol) in DMF (3 ml) was added dropwise to a mixture of PyBOP (0.000207 mol) and Et₃N (0.3 ml) in DMF (3 ml), stirred at r.t. under N₂ flow. Stirring was continued for one hour. Then 0.5 ml of H₂O was added and the mixture was stirred for one hour. The reaction mixture was concentrated under reduced pressure and the residue was purified by HPLC (0.2% ammonium bicarbonate in H₂O/CH₃CN from 80/20 to 0/100 over 60 min, then 0/100 for 10 min; Shandon 8 µm, Hyperprep C18 BDS 100 Å, 50 mm by 21 cm). The product fractions were collected and concentrated under reduced pressure. The solid was dried under vacuum at 50° C., yielding 0.0038 g (15.7%) of compound 154.

Example B43

Preparation of Compound 155

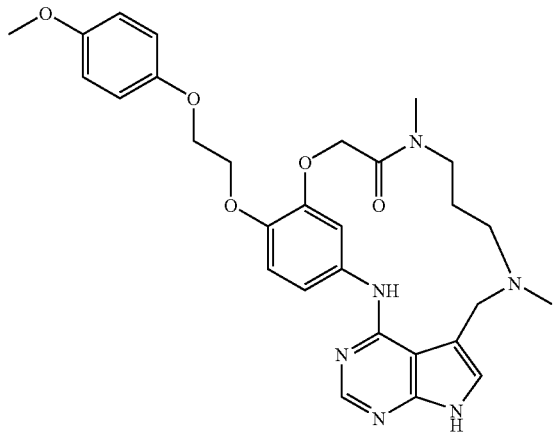

A solution of intermediate 186 (0.0000708 mol) in DMF (5 ml) was added dropwise to a mixture of PyBOP (0.000354 mol) and Et$_3$N (0.5 ml) in DMF (5 ml), stirred at r.t. under N$_2$ flow. Stirring was continued for one hour. H$_2$O (0.5 ml) was added and the mixture was stirred for one hour. The reaction mixture was concentrated under reduced pressure and the residue was purified by HPLC (0.25% ammonium bicarbonate in H$_2$O/CH$_3$CN from 100/0 to 0/100 over 40 min, then 0/100 for 10 min; Shandon 8 μm, Hyperprep C18 BDS 100 Å, 50 mm by 16.5 cm), then (0.25% ammonium bicarbonate in H$_2$O/CH$_3$CN from 80/20 to 30/70 over 50 min, then from 30/70 to 0/100 over 10 min and 0/100 for 8 min; Shandon 8 μm, Hyperprep C18 BDS 100 Å, 50 mm by 16.5 cm). The product fractions were collected and concentrated under reduced pressure. The solid was dried under vacuum at 50° C., yielding 0.0141 g (33.5%) of compound 155.

Example B44

Preparation of Compound 156

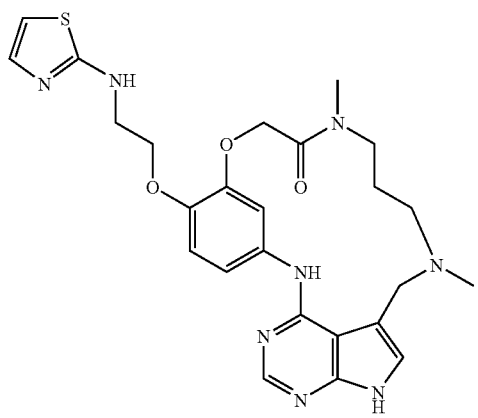

A solution of intermediate 190 (0.000222 mol) in DMF (15 ml) was added dropwise to a mixture of PyBOP (0.00111 mol) and Et$_3$N (1.5 ml) in DMF (15 ml), stirred at r.t. under N$_2$ flow. Stirring was continued for one hour, then 0.5 ml of H$_2$O was added and the entire mixture was stirred for one hour. The reaction mixture was concentrated under reduced pressure and the residue was purified by HPLC (0.25% ammonium bicarbonate in H$_2$O/CH$_3$CN from 100/0 to 50/50 over 40 min, then 0/100 for 10 min; Shandon 8 μm, Hyperprep C18 BDS 100 Å, 50 mm by 16.5 cm). The product fractions were collected and concentrated under reduced pressure. The solid was dried under vacuum at 50° C., yielding 0.0621 g (48.7%) of compound 156.

Example B45

Preparation of Compound 157

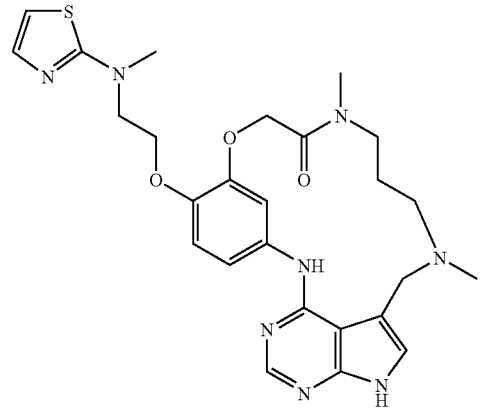

A solution of intermediate 194 (0.000793 mol) in DMF (50 ml) was added dropwise to a mixture of PyBOP (0.00397 mol) and Et$_3$N (5 ml) in DMF (50 ml), stirred at r.t. under N$_2$ flow. Stirring was continued for one hour. H$_2$O (0.5 ml) was added. The resultant reaction mixture was stirred for one hour. The reaction mixture was concentrated under reduced pressure and the residue was purified by HPLC (0.25% ammonium bicarbonate in H$_2$O/CH$_3$CN from 90/10 to 30/70 over 40 min, then 0/100 for 10 min; Shandon 8 μm, Hyperprep C18 BDS 100 Å, 50 mm by 16.5 cm). The product fractions were collected and concentrated under reduced pressure. The residue was further purified (eluent: DCM/MeOH/ethanol from 100/0/0 to 95/5/0 over 40 min, then 95/5/0 for 10 min; and 0/0/100 for 10 min, Shandon 5 μm, Kromasil silica gel 100 Å 50 mm by 20 cm). The product fractions were collected and concentrated under reduced pressure. The solid was dried under vacuum at 50° C., yielding 0.088 g (20.25%) of compound 157.

Example B46

Preparation of Compound 158

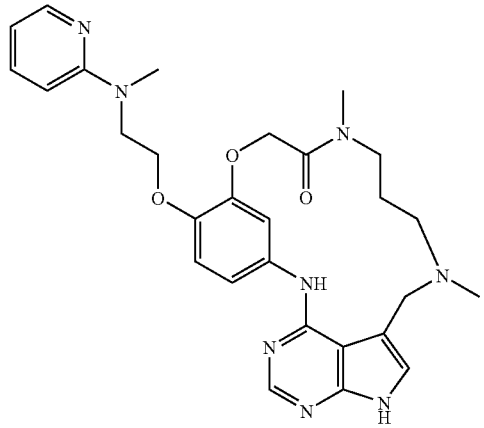

A solution of intermediate 198 (0.000365 mol) in DMF (27 ml) was added dropwise to a mixture of PyBOP (0.001823 mol) and Et₃N (2.7 ml) in DMF (27 ml) stirred at r.t. under N₂ flow. Stirring was continued for one hour, then 2 ml of H₂O was added and the entire mixture was stirred for one hour. The reaction mixture was concentrated under reduced pressure and the residue was purified by HPLC (0.2% ammonium bicarbonate in H₂O/CH₃CN from 80/20 to 0/100 over 60 min, then 0/100 for 10 min; Shandon 8 μm, Hyperprep C18 BDS 100 Å, 50 mm by 21 cm). The product fractions were collected and concentrated under reduced pressure. The solid was dried under vacuum at 50° C., yielding 0.129 g (66%) of compound 158.

Example B47

Preparation of Compound 159

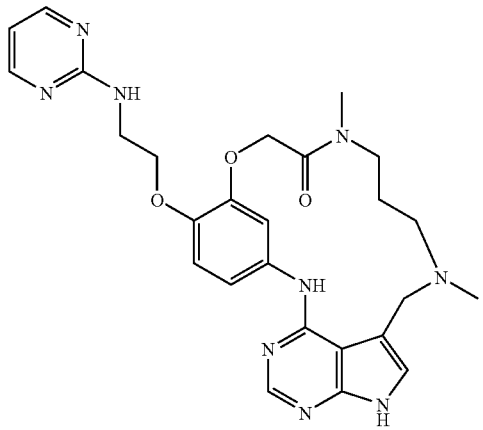

A solution of intermediate 202 (0.0000653 mol) in DMF (4 ml) was added dropwise to a mixture of PyBOP (0.000327 mol) and Et₃N (0.4 ml) in DMF (4 ml), stirred at r.t. under N₂ flow. Stirring was continued for one hour, then 1 ml of H₂O was added and the entire mixture was stirred for one hour. The reaction mixture was concentrated under reduced pressure and the residue was purified by HPLC (DCM/CH₃OH/EtOH from 100/0/0 to 90/10/0 40 min, then 90/10/0 for 10 min and 0/0/100 for 10 min; Shandon 5 μm, 200 g Kromasil silica gel 100 Å 50 mm by 20 cm). The product fractions were collected and concentrated under reduced pressure. The solid was dried under vacuum at 50° C., yielding 0.0188 g (51.7%) of compound 159.

Example B48

Preparation of Compound 160

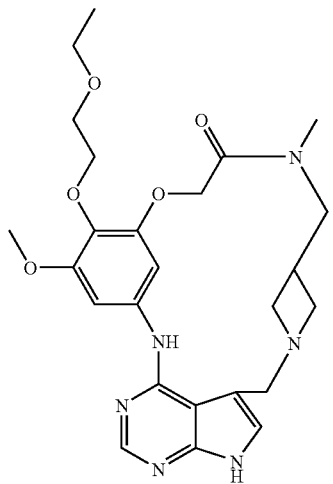

A solution of intermediate 207 (0.00218 mol) in DMF (109 ml) was added very slowly (over a 60-min period, using a Marlow peristaltic pump) to a solution of PyBOP (0.00479 mol) and DIPEA (0.0545 mol) in DMF (54 ml). After the addition was completed, the reaction mixture was stirred for an additional 1 hour before being quenched by adding 4 ml of 7 N ammonia in MeOH. The reaction mixture was concentrated to dryness and the residue was partitioned between EtOAc and a saturated aqueous sodium bicarbonate solution. The organic extracts were washed with brine, dried and concentrated to dryness. The residue was purified by column chromatography over silica gel (eluent: DCM-CH₃OH gradient). The pure fractions were combined and concentrated. The residue was recrystallized from CH₃CN, filtered off and dried, yielding 0.250 g (23%) of compound 160.

Example B49

Preparation of Compound 161

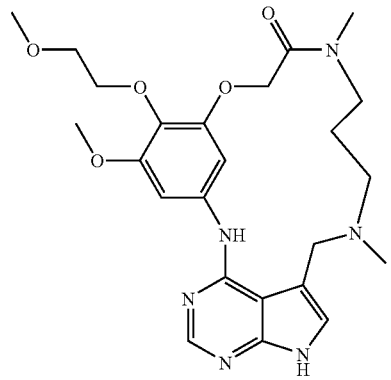

A solution of intermediate 210 (0.0037 mol) in DMF (190 ml) was added very slowly (over a 60 min period, using a Marlow peristaltic pump), to a solution of PyBOP (0.00814 mol) and DIPEA (0.0925 mol) in DMF (95 ml). After the addition was completed, the reaction mixture was stirred for an additional 1 hour before being quenched by adding 4 ml of 7 N ammonia in MeOH. The reaction mixture was concentrated to dryness. The residue was partitioned between EtOAc and a saturated aqueous sodium bicarbonate solution. The organic extracts were washed with brine, dried, filtered and the filtrate was concentrated to dryness. The residue was purified by column chromatography over silica gel (eluent: DCM-CH₃OH gradient). The product fractions were collected and the solvent was evaporated. The residue was recrystallized from CH₃CN, filtered off and dried, yielding 0.148 g (8.2%) of compound 161.

The compounds in Table 1 were prepared by analogy to one of the procedures described above, indicated by Ex. No. The exemplified procedures are indicated by a '*'. All the compounds are free bases.
TABLE 1
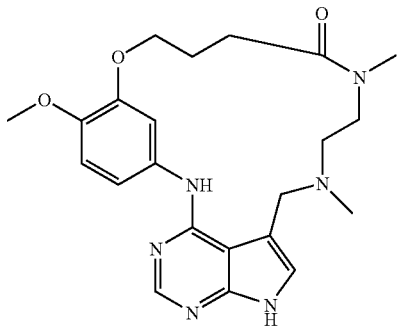
Co. No. 1; Ex. No. B1*
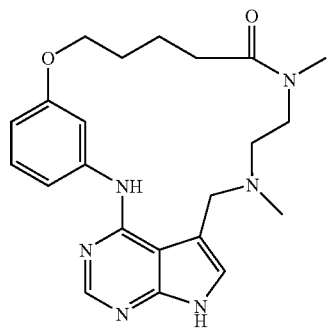
Co. No. 2; Ex. No. B2*
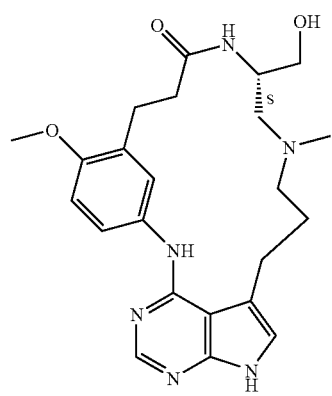
Co. No. 3 (S-enantiomer); Ex. No. B3*
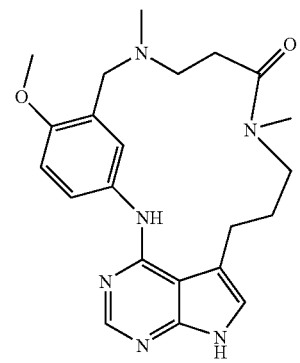
Co. No. 4; Ex. No. B4*
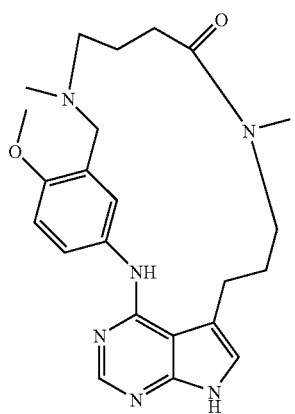
Co. No. 5; Ex. No. B5*
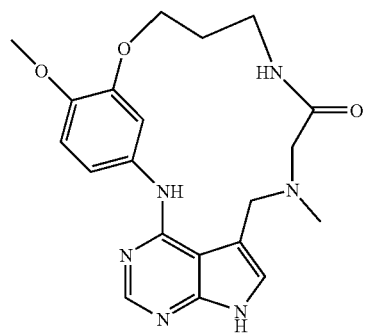
Co. No. 6; Ex. No. B6*

TABLE 1-continued
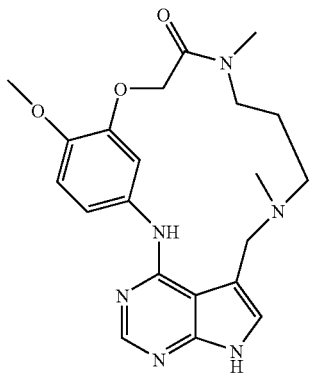
Co. No. 7; Ex. No. B7*
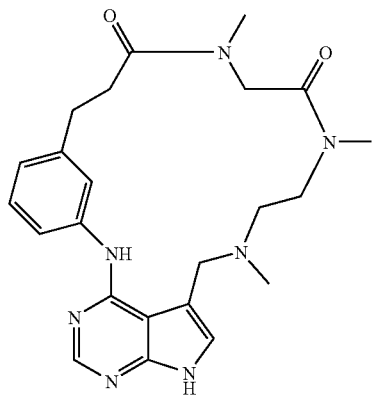
Co. No. 8; Ex. No. B8*
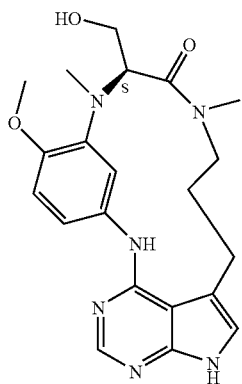
Co. No. 9 (S-enantiomer); Ex. No. B9*
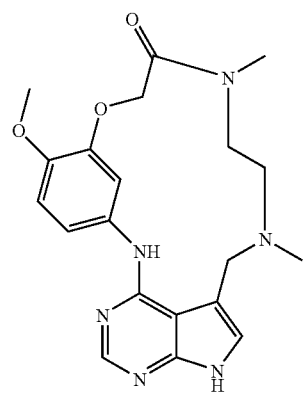
Co. No. 10, Ex. No. B10*
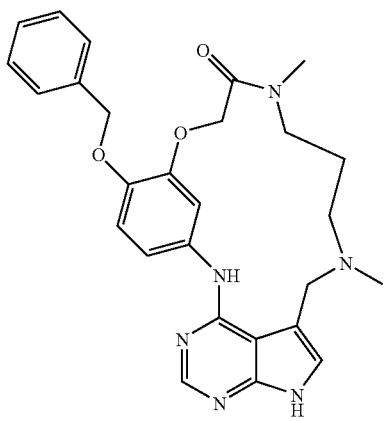
Co. No. 11; Ex. No. B11*
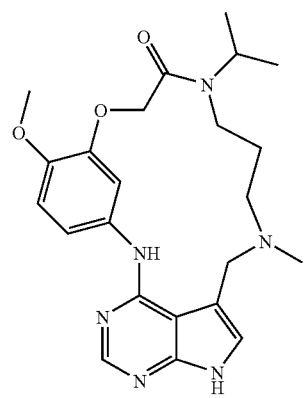
Co. No. 12; Ex. No. B12*

TABLE 1-continued
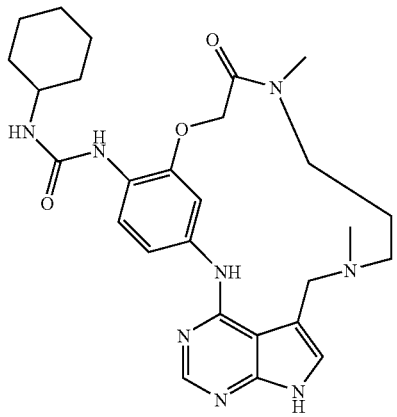
Co. No. 13; Ex. No. B13*
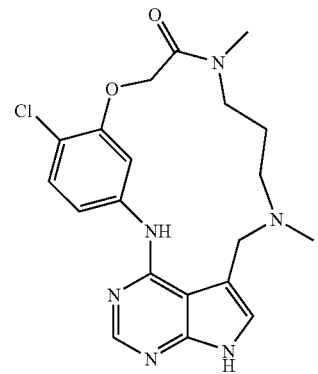
Co. No. 14; Ex. No. B14*
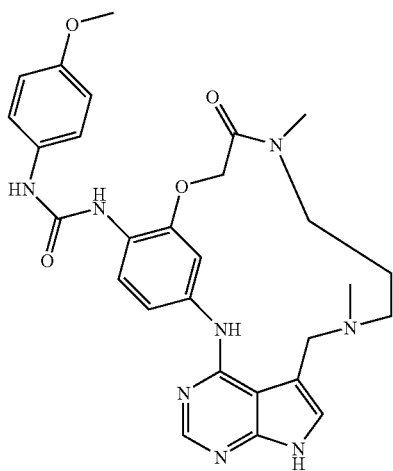
Co. No. 15; Ex. No. B15*
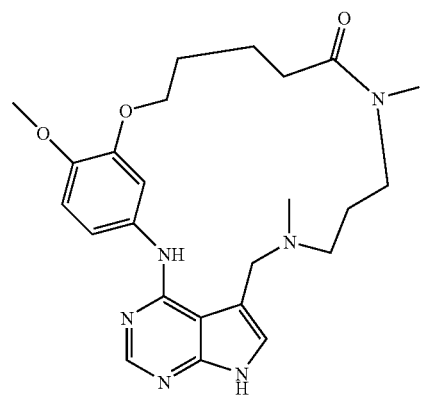
Co. No. 16; Ex. No. B7
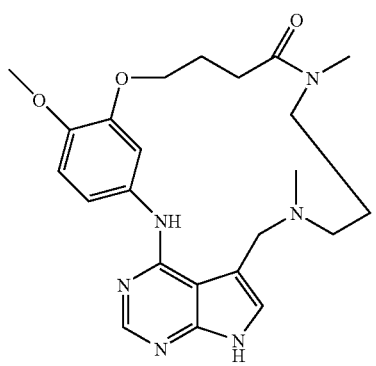
Co. No. 17; Ex. No. B7
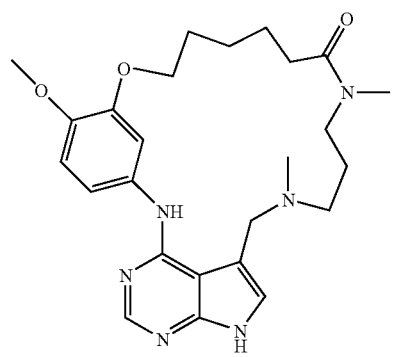
Co. No. 18; Ex. No. B7

TABLE 1-continued
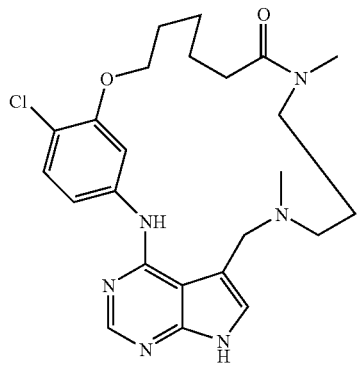
Co. No. 19; Ex. No. B7
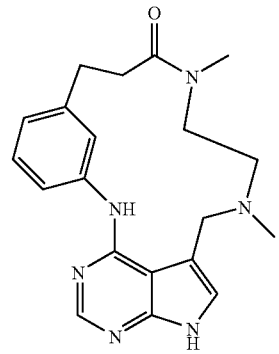
Co. No. 20; Ex. No. B16
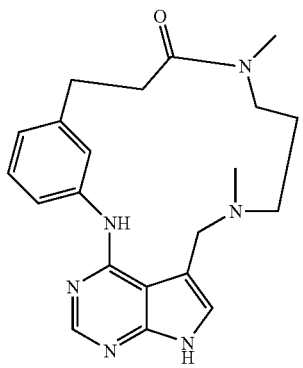
Co. No. 21; Ex. No. B16
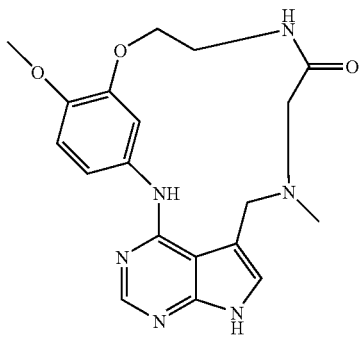
Co. No. 22; Ex. No. B6
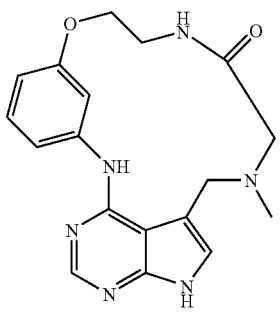
Co. No. 23; Ex. No. B6
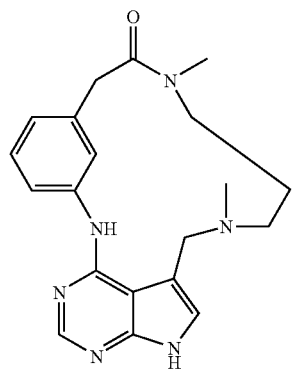
Co. No. 24; Ex. No. B16

TABLE 1-continued
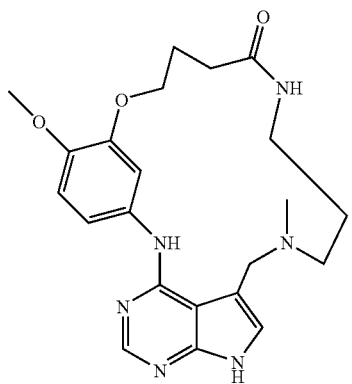
Co. No. 25; Ex. No. B7
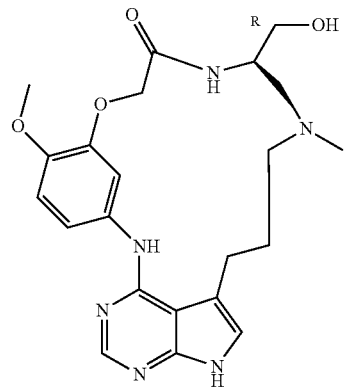
Co. No. 26 (R-enantiomer); Ex. No. B3
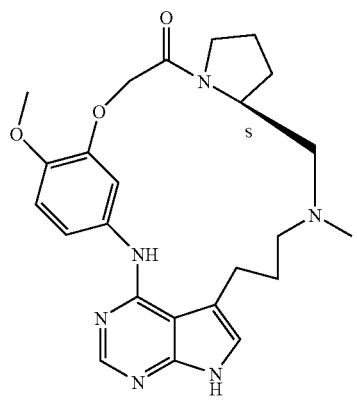
Co. No. 27 (S-enantiomer); Ex. No. B3
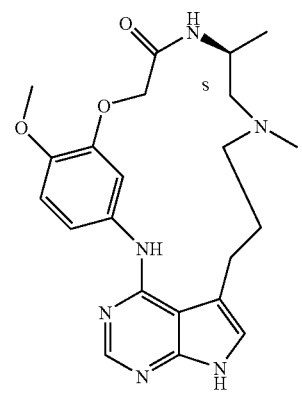
Co. No. 28 (S-enantiomer); Ex. No. B3
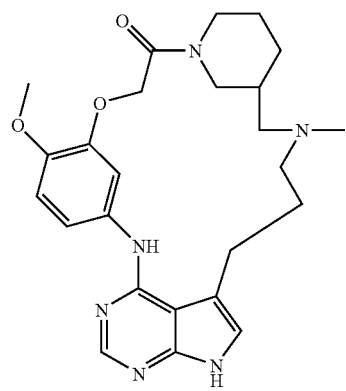
Co. No. 29; Ex. No. B3
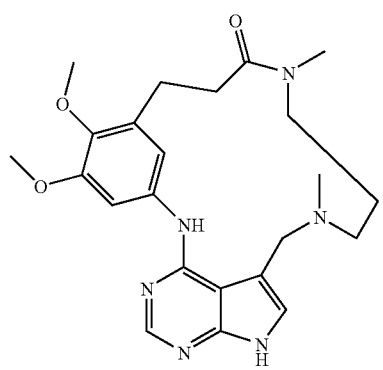
Co. No. 30; Ex. No. B16*

TABLE 1-continued
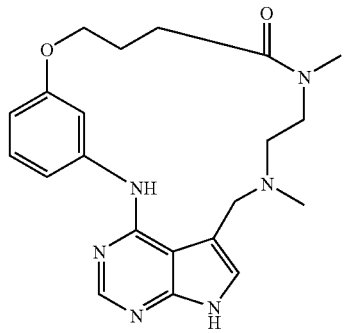
Co. No. 31; Ex. No. B1
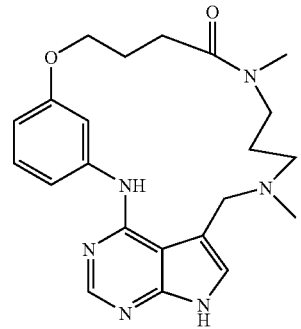
Co. No. 32; Ex. No. B7
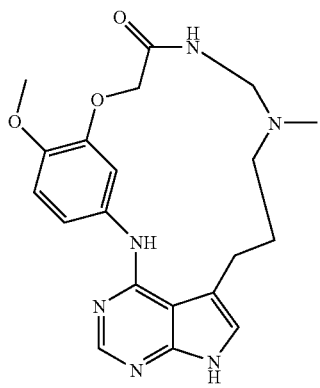
Co. No. 33; Ex. No. B3
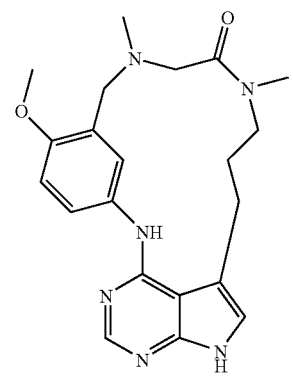
Co. No. 34; Ex. No. B4
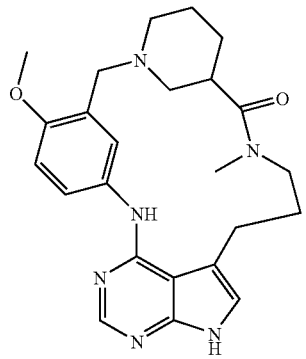
Co. No. 35; Ex. No. B4
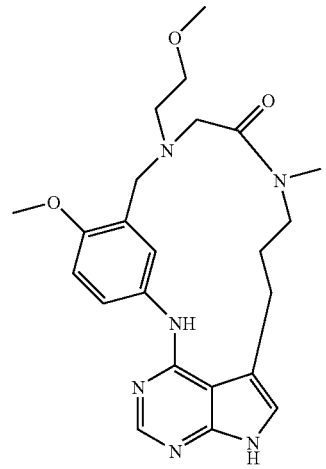
Co. No. 36; Ex. No. B4

TABLE 1-continued
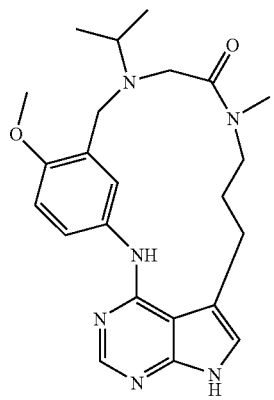
Co. No. 37; Ex. No. B4
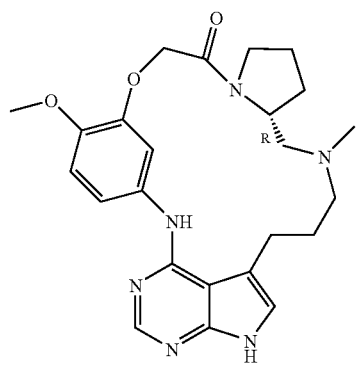
Co. No. 38 (R-enantiomer); Ex. No. B4
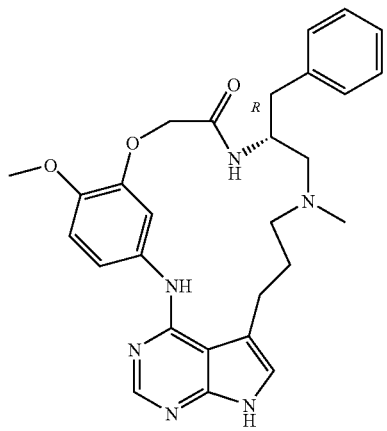
Co. No. 39 (R-enantiomer); Ex. No. B3
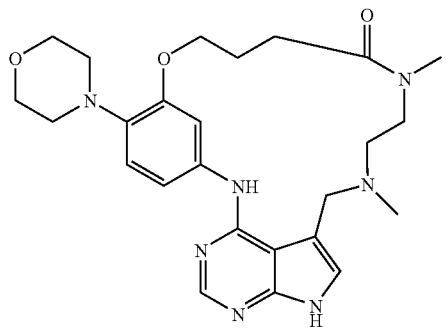
Co. No. 40; Ex. No. B23
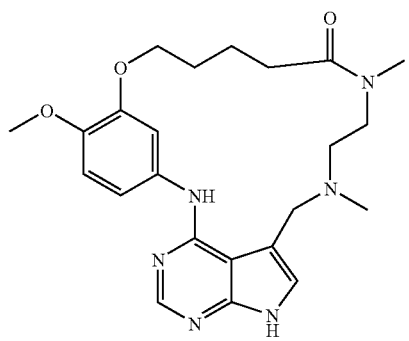
Co. No. 41; Ex. No. B1
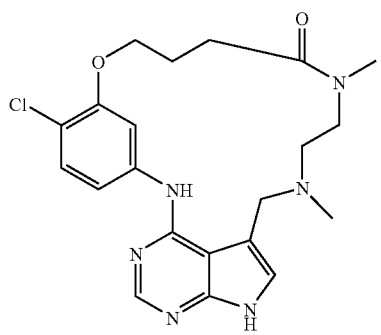
Co. No. 42; Ex. No. B1
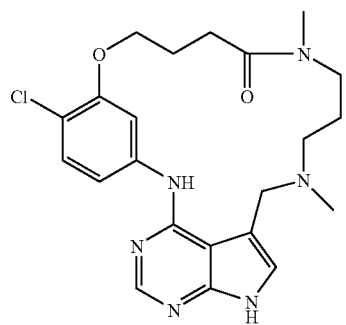
Co. No. 43; Ex. No. B7
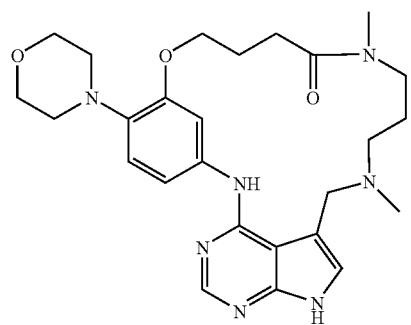
Co. No. 44; Ex. No. B23

TABLE 1-continued
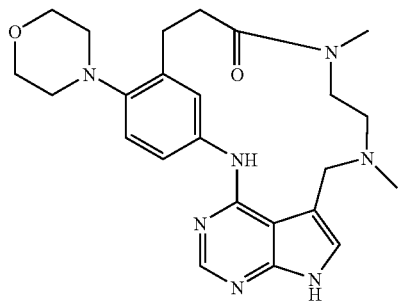
Co. No. 45; Ex. No. B23
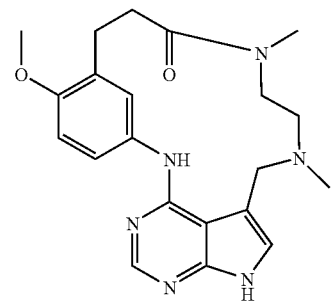
Co. No. 46; Ex. No. B16
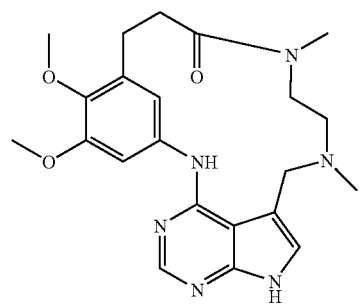
Co. No. 47; Ex. No. B16
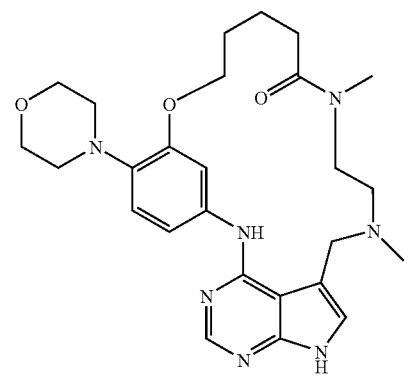
Co. No. 48; Ex. No. B23
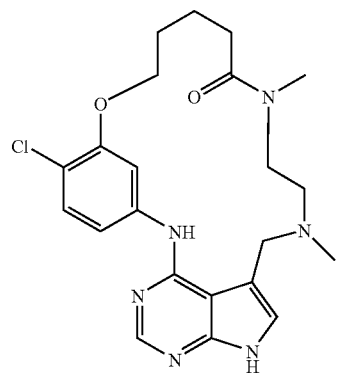
Co. No. 49; Ex. No. B1
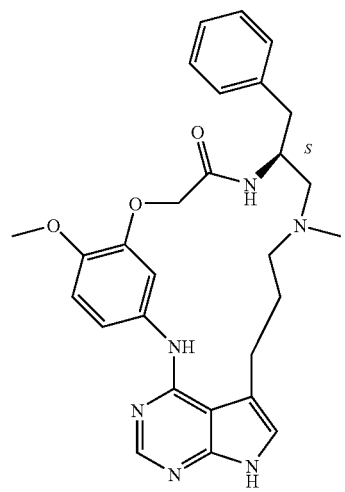
Co. No. 50 (S-enantiomer); Ex. No. B3

TABLE 1-continued
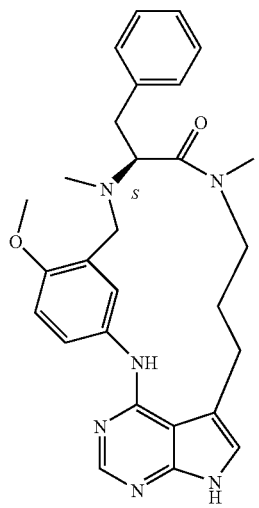
Co. No. 51 (S-enantiomer); Ex. No. B4
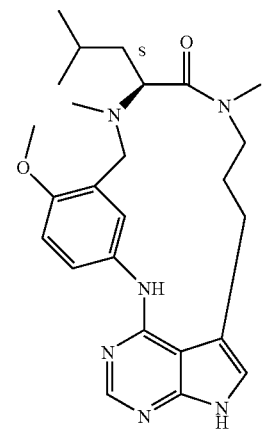
Co. No. 52 (S-enantiomer); Ex. No. B4
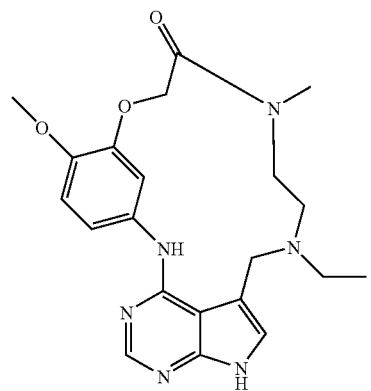
Co. No. 53; Ex. No. B7
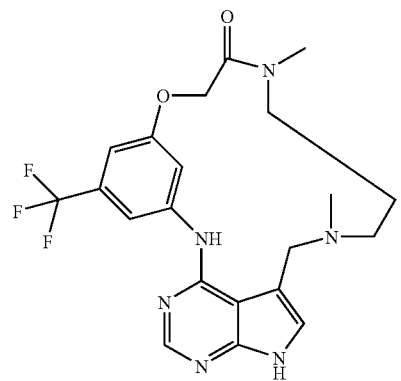
Co. No. 54; Ex. No. B7
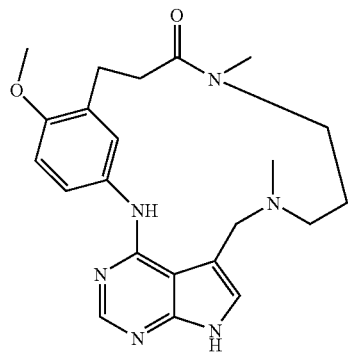
Co. No. 55; Ex. No. B16
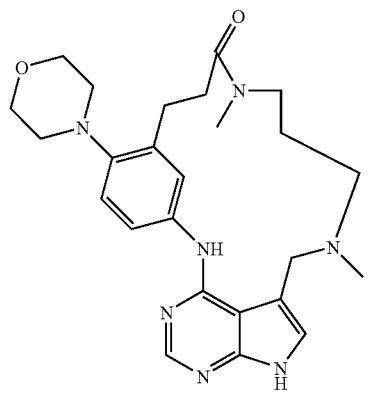
Co. No. 56; Ex. No. B23

TABLE 1-continued
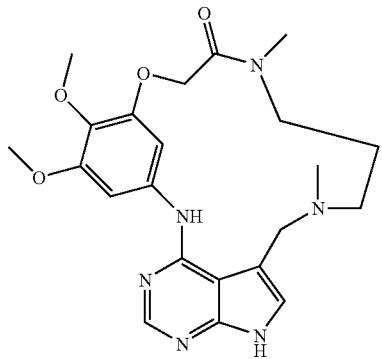
Co. No. 57; Ex. No. B19
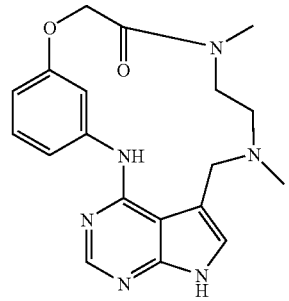
Co. No. 58; Ex. No. B1
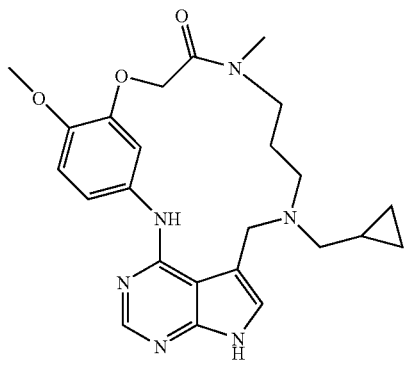
Co. No. 59; Ex. No. B7
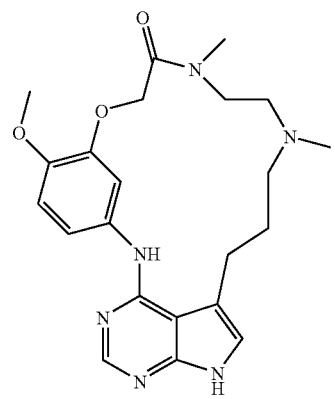
Co. No. 60; Ex. No. B3
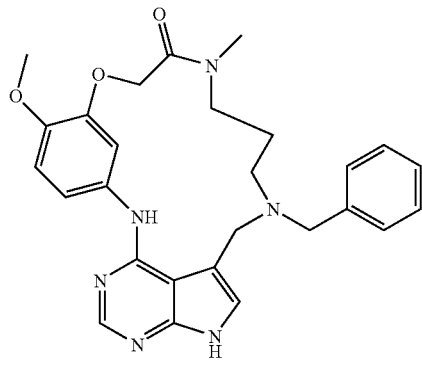
Co. No. 61; Ex. No. B7
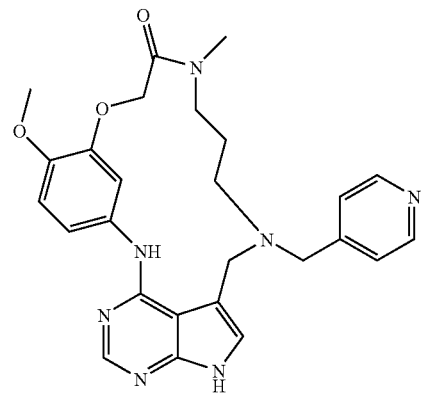
Co. No. 62; Ex. No. B7

TABLE 1-continued
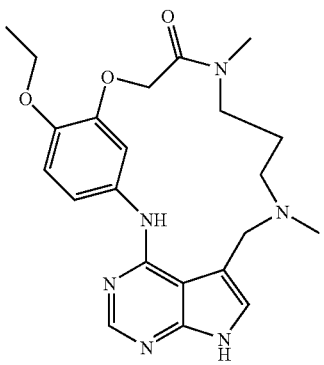
Co. No. 63; Ex. No. B17*
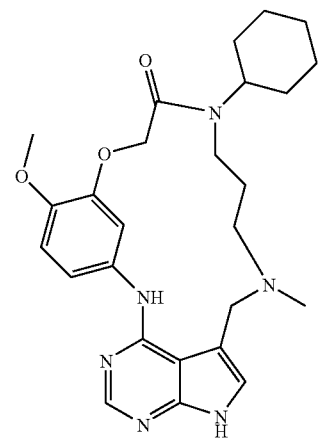
Co. No. 64; Ex. No. B12
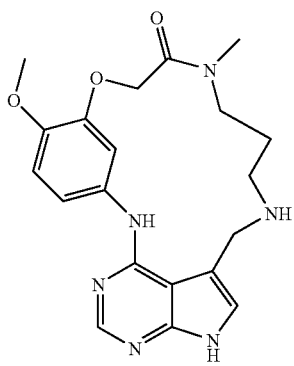
Co. No. 65; Ex. No. B7
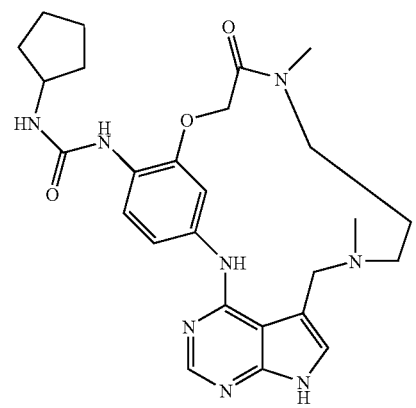
Co. No. 66; Ex. No. B13
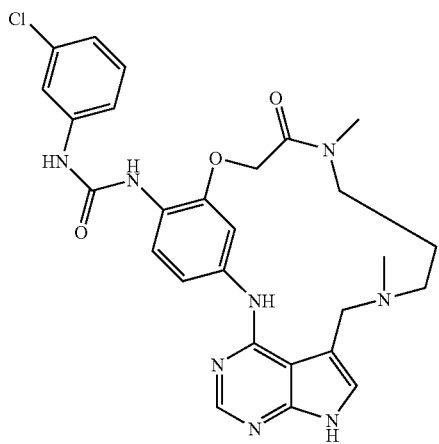
Co. No. 67; Ex. No. B13
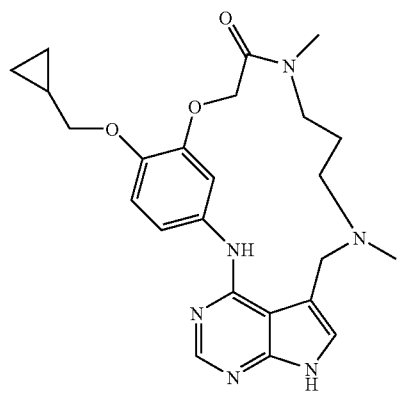
Co. No. 68; Ex. No. B7

TABLE 1-continued
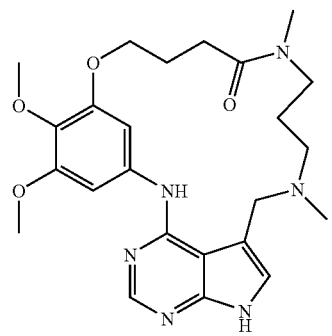
Co. No. 69; Ex. No. B19*
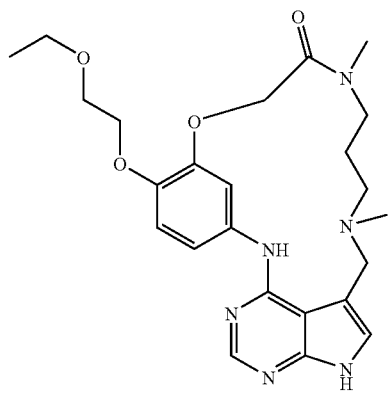
Co. No. 70; Ex. No. B21*
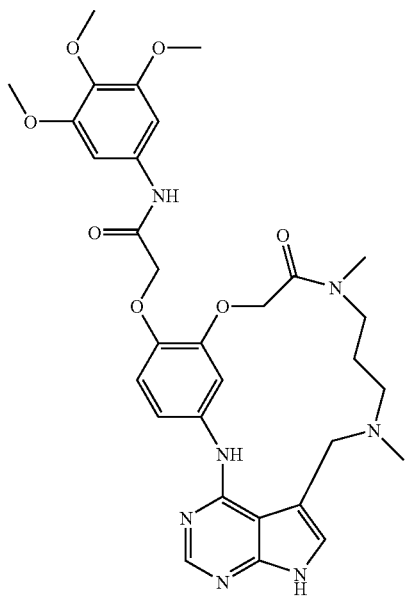
Co. No. 71; Ex. No. B24*
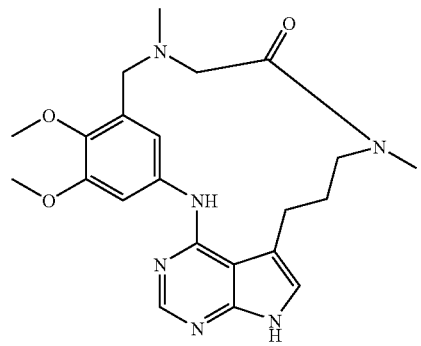
Co. No. 72; Ex. No. B25*
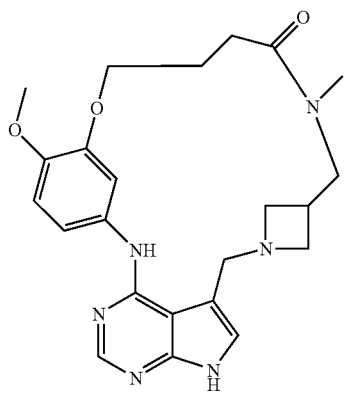
Co. No. 73; Ex. No. B18*
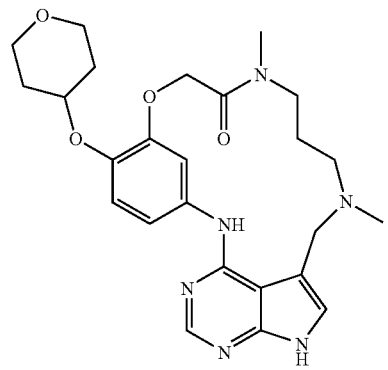
Co. No. 74; Ex. No. B26*

TABLE 1-continued
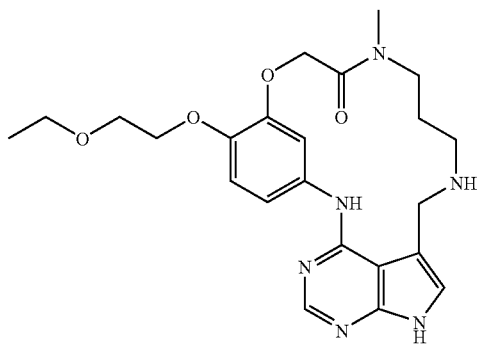
Co. No. 75; Ex. No. B27*
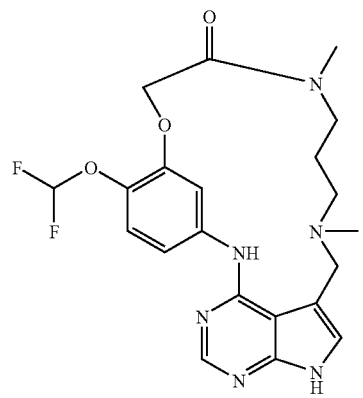
Co. No. 76; Ex. No. B28*
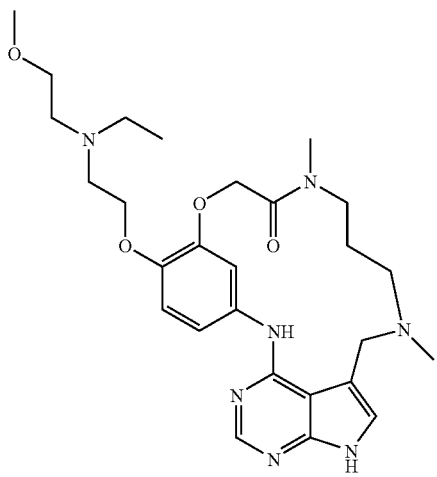
Co. No. 77; Ex. No. B29*
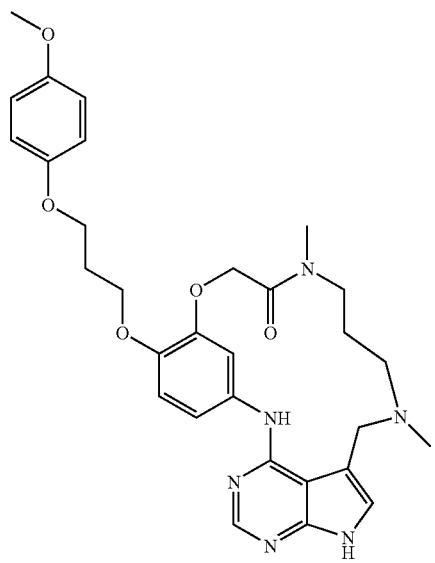
Co. No. 78; Ex. No. B30*
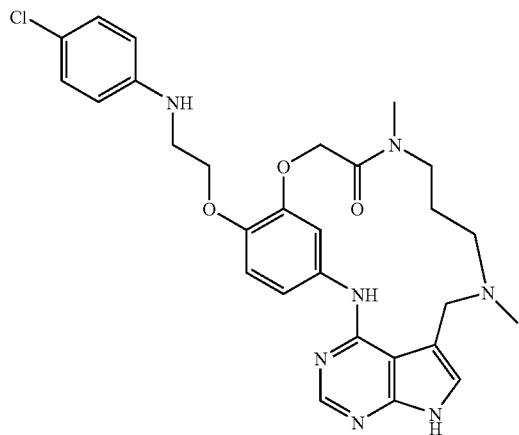
Co. No. 79; Ex. No. B31*
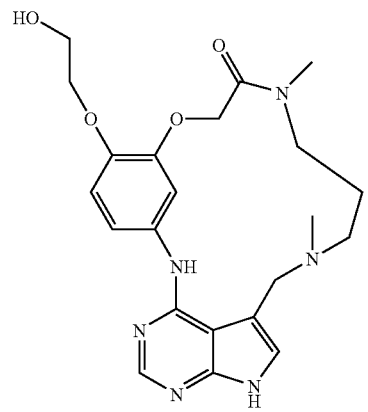
Co. No. 80; Ex. No. B32*

TABLE 1-continued
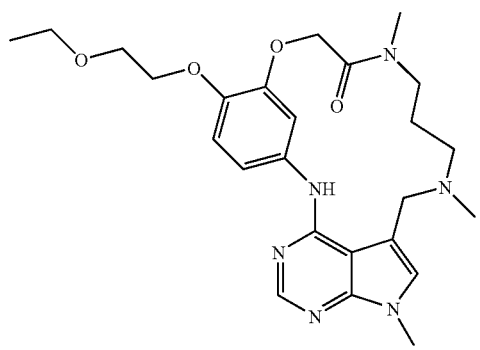
Co. No. 81; Ex. No. B33*
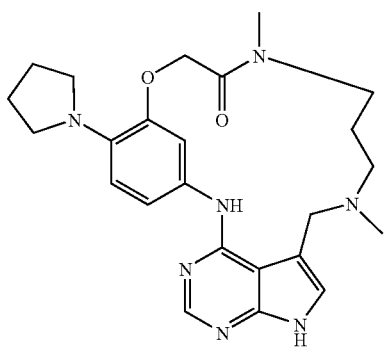
Co. No. 82; Ex. No. B34*
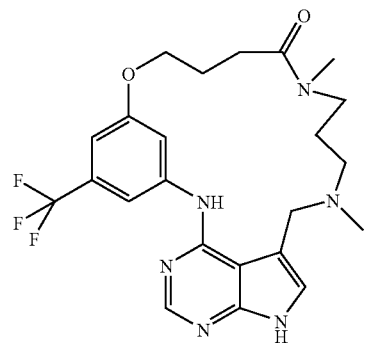
Co. No. 83; Ex. No. B22*
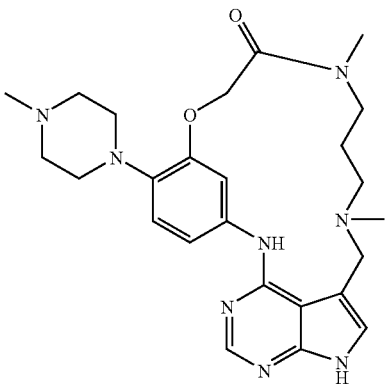
Co. No. 84; Ex. No. B20*
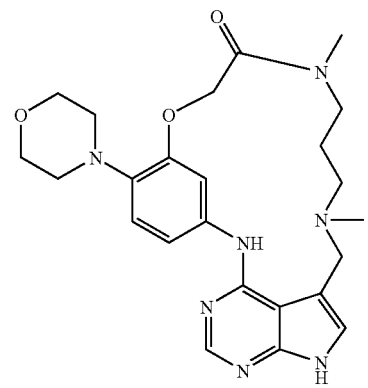
Co. No. 85; Ex. No. B23*
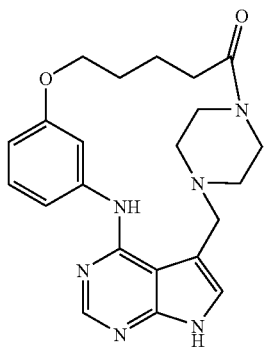
Co. No. 86 ; Ex. No. B2

TABLE 1-continued
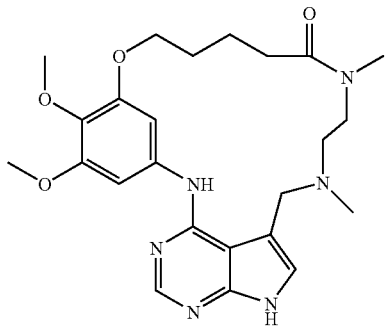
Co. No. 87; Ex. No. B19
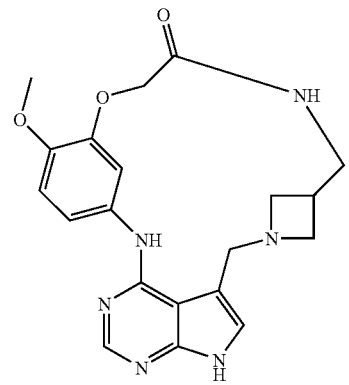
Co. No. 88; Ex. No. B18
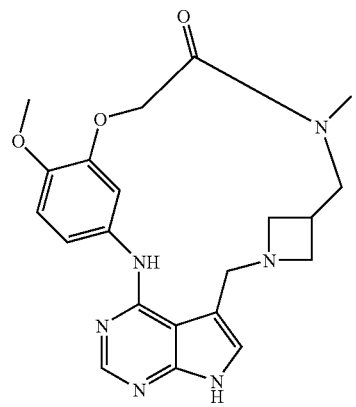
Co. No. 89; Ex. No. B18
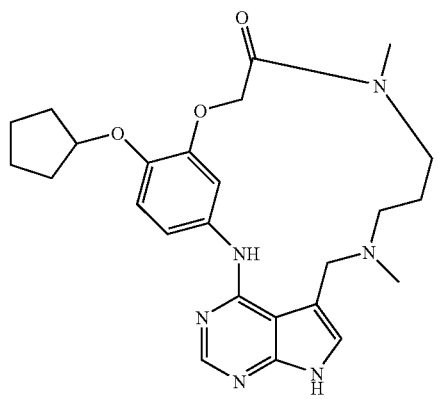
Co. No. 90; Ex. No. B26
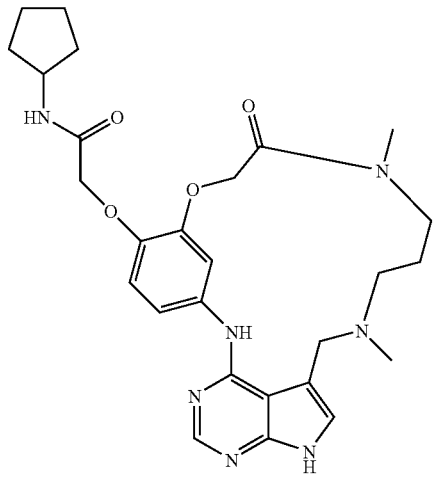
Co. No. 91; Ex. No. B24
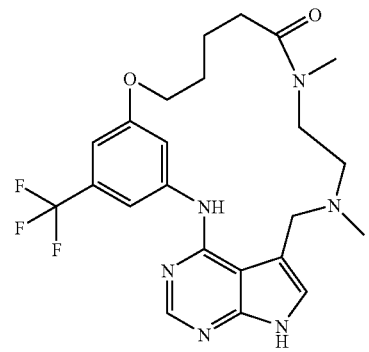
Co. No. 92; Ex. No. B22

TABLE 1-continued
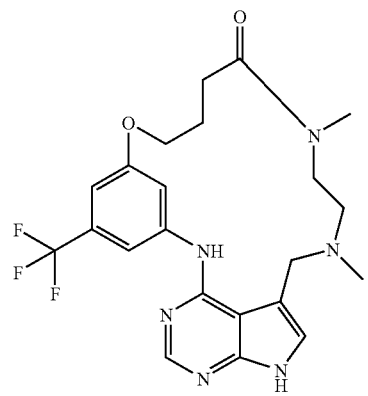
Co. No. 93; Ex. No. B22
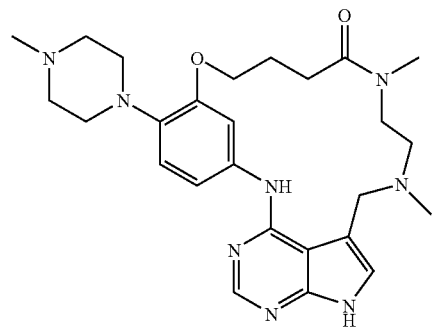
Co. No. 94; Ex. No. B20
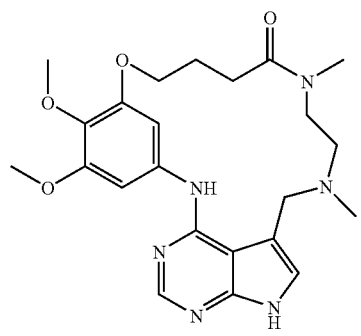
Co. No. 95; Ex. No. B19
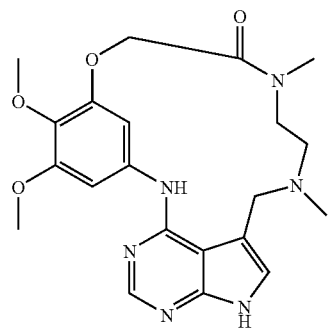
Co. No. 96; Ex. No. B19
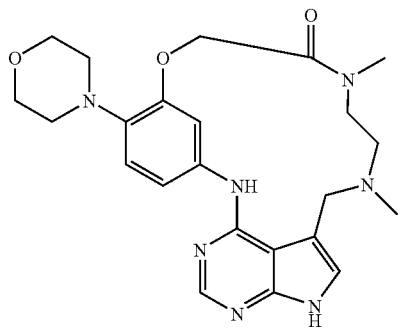
Co. No. 97; Ex. No. B23
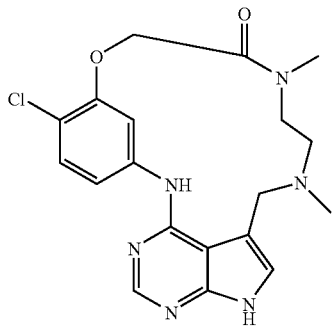
Co. No. 98; Ex. No. B14
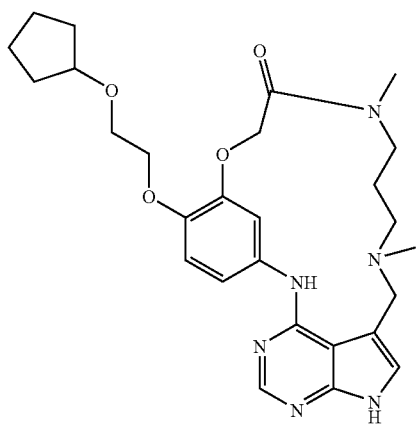
Co. No. 99; Ex. No. B21
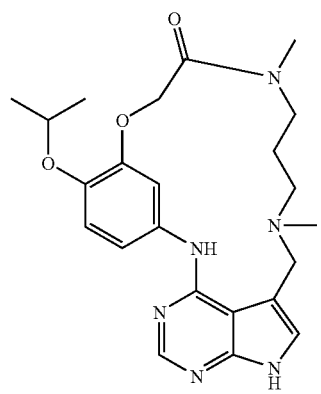
Co. No. 100; Ex. No. B21

TABLE 1-continued
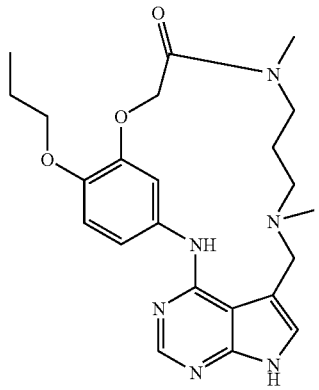
Co. No. 101; Ex. No. B21
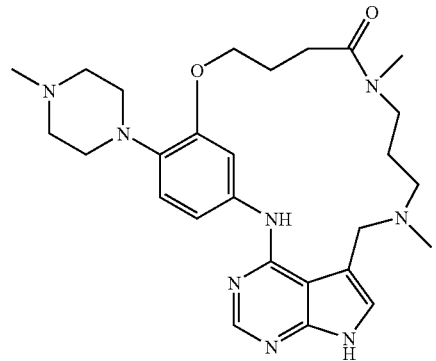
Co. No. 102; Ex. No. B20
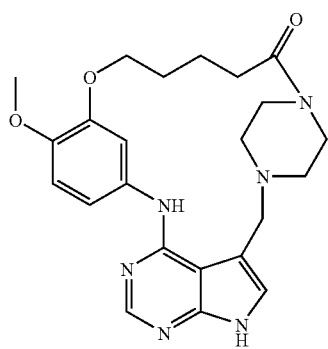
Co. No. 103; Ex. No. B2
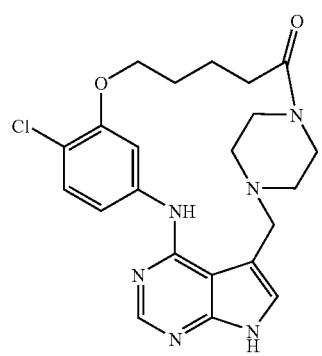
Co. No. 104; Ex. No. B14
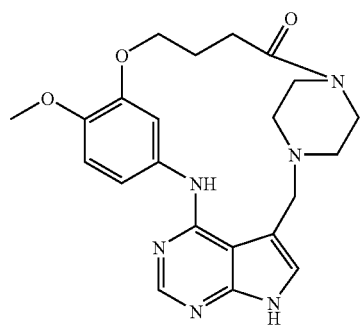
Co. No. 105; Ex. No. B2
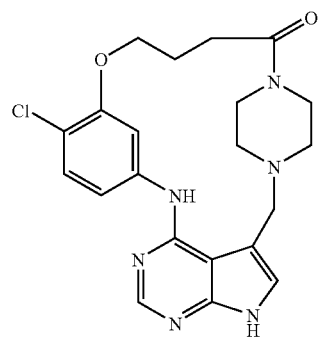
Co. No. 106; Ex. No. B14
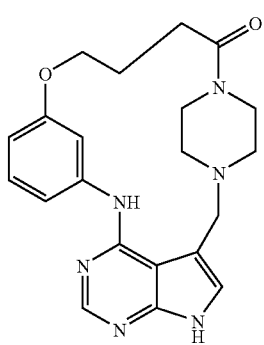
Co. No. 107; Ex. No. B1
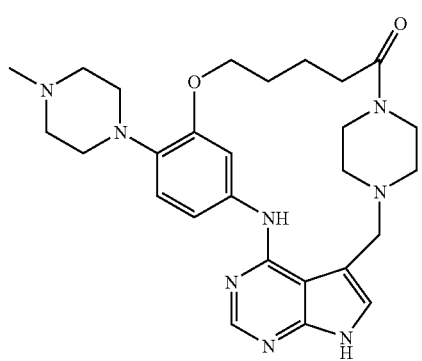
Co. No. 108; Ex. No. B20

TABLE 1-continued
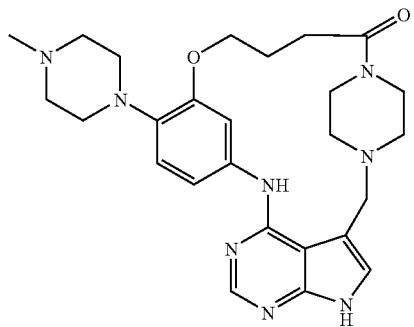
Co. No. 109; Ex. No. B20
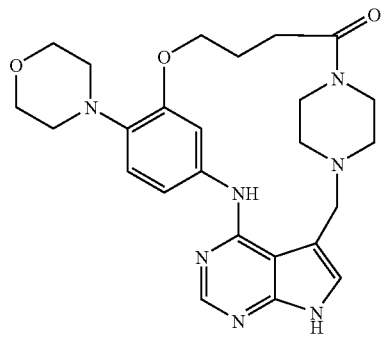
Co. No. 110; Ex. No. B23
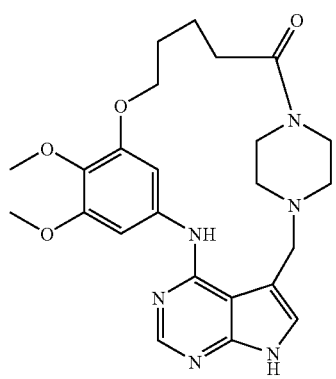
Co. No. 111; Ex. No. B19
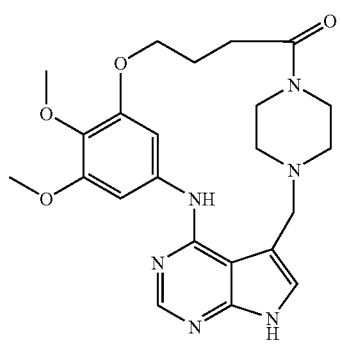
Co. No. 112; Ex. No. B19
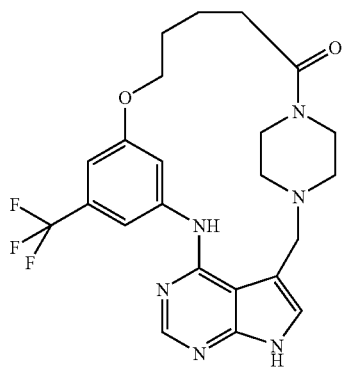
Co. No. 113; Ex. No. B22
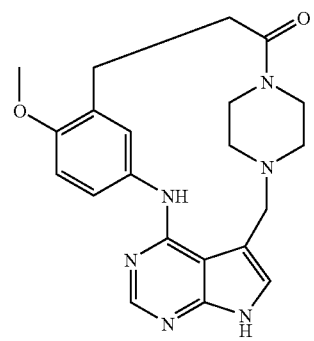
Co. No. 114; Ex. No. B16
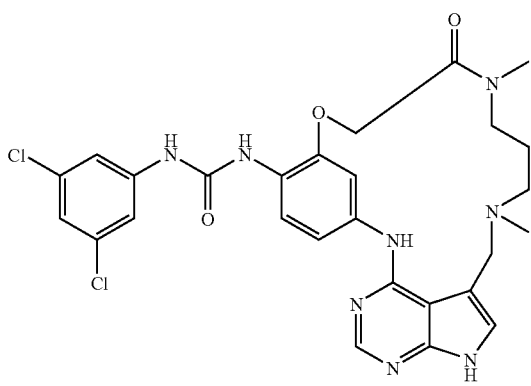
Co. No. 115; Ex. No. B15
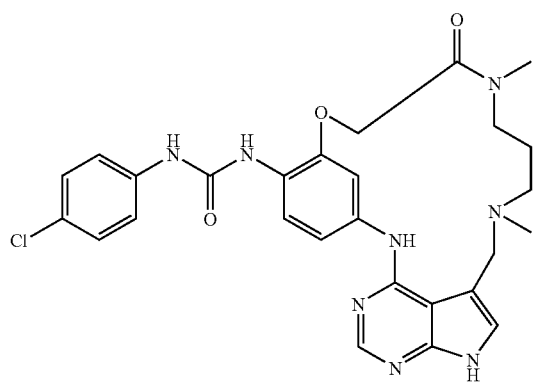
Co. No. 116; Ex. No. B15

TABLE 1-continued
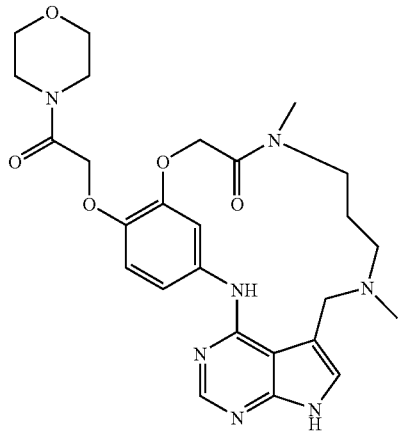
Co. No. 117; Ex. No. B24
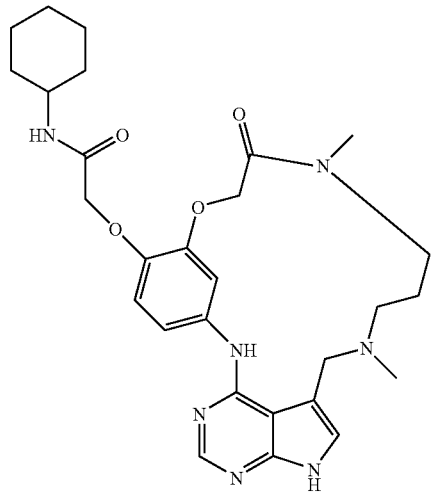
Co. No. 118; Ex. No. B24
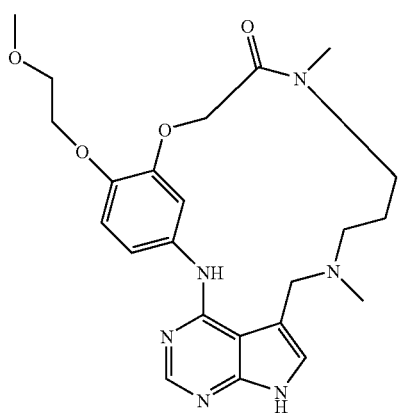
Co. No. 119; Ex. No. B21
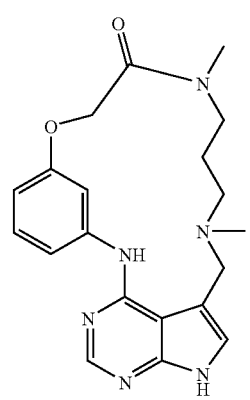
Co. No. 120; Ex. No. B7
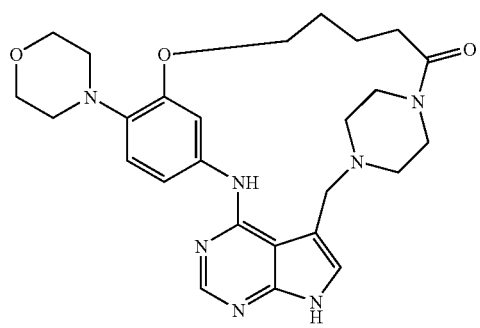
Co. No. 121; Ex. No. B23
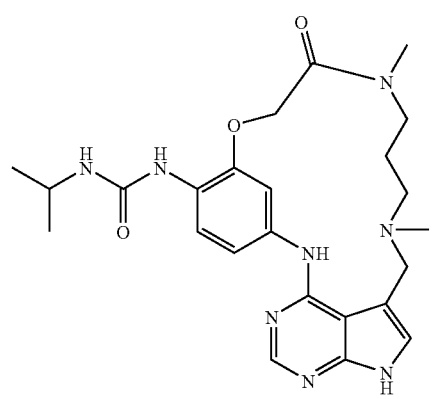
Co. No. 122; Ex. No. B15

TABLE 1-continued
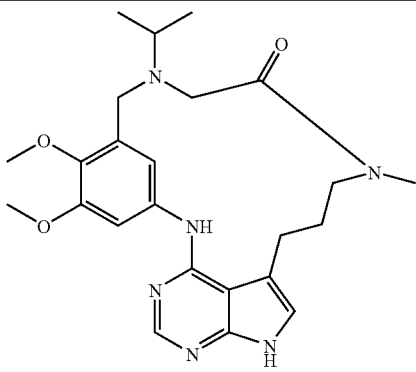
Co. No. 123; Ex. No. B25
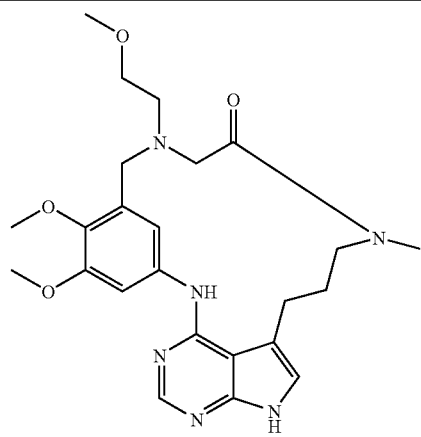
Co. No. 124; Ex. No. B25
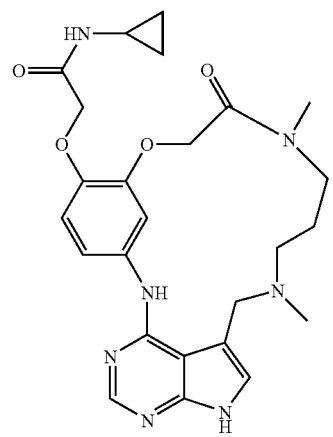
Co. No. 125; Ex. No. B24
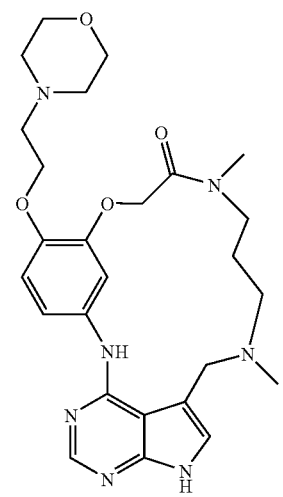
Co. No. 126; Ex. No. B21
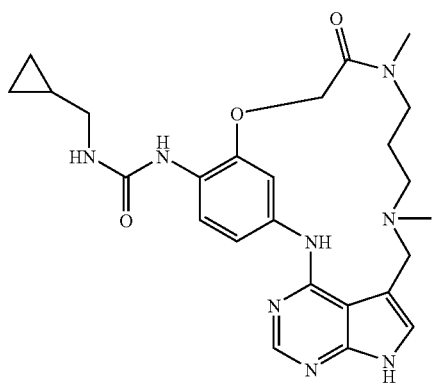
Co. No. 127; Ex. No. B15
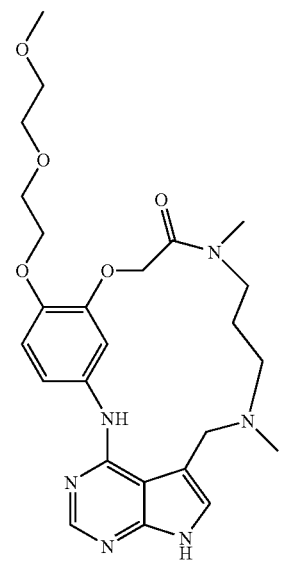
Co. No. 128; Ex. No. B21

TABLE 1-continued
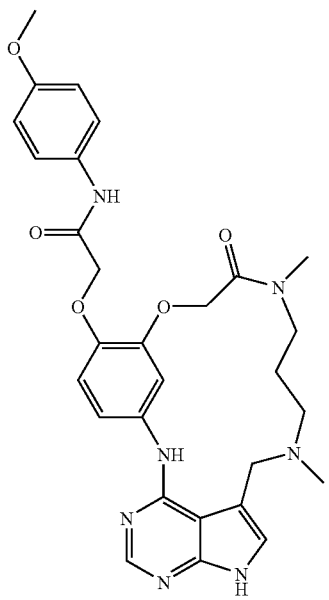
Co. No. 129; Ex. No. B24
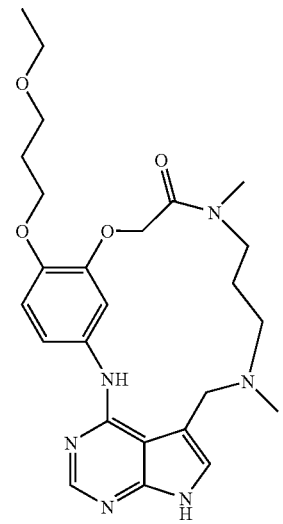
Co. No. 130; Ex. No. B21
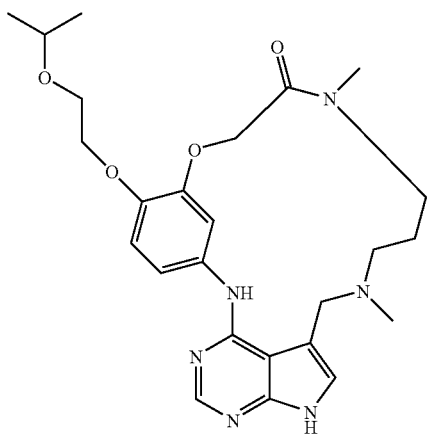
Co. No. 131; Ex. No. B21
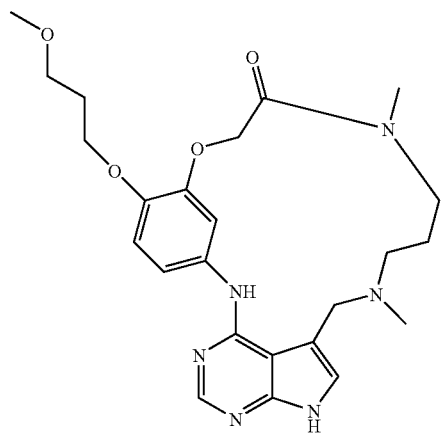
Co. No. 132; Ex. No. B21
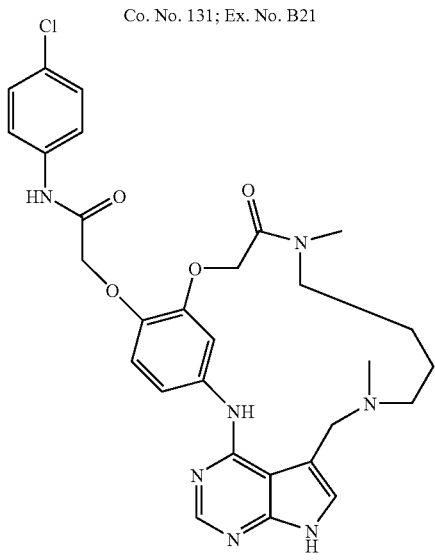
Co. No. 133; Ex. No. B24
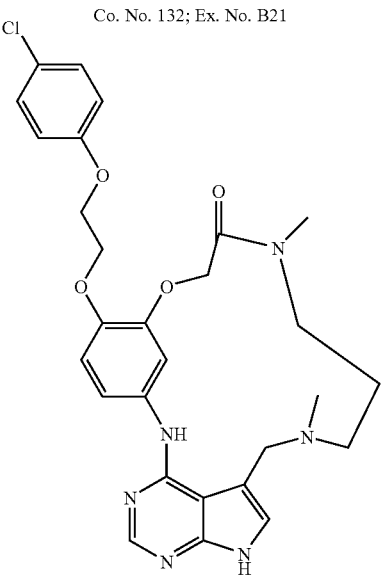
Co. No. 134; Ex. No. B30

TABLE 1-continued
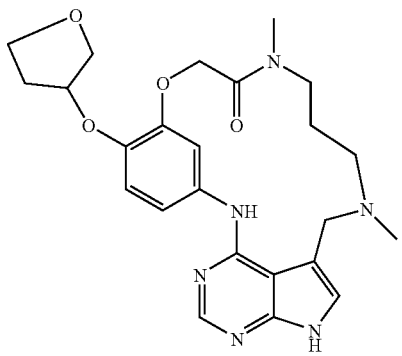
Co. No. 135; Ex. No. B26
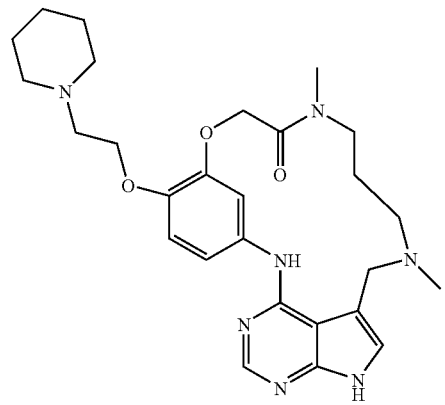
Co. No. 136; Ex. No. B26
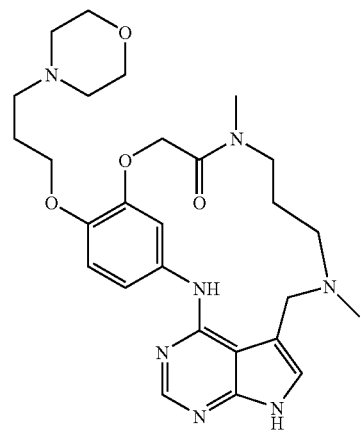
Co. No. 137; Ex. No. B29
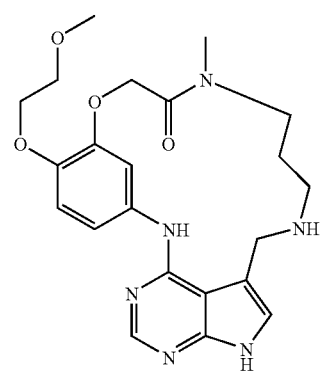
Co. No. 138; Ex. No. B27
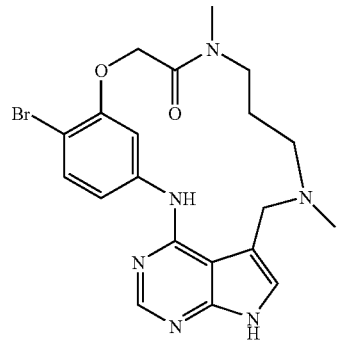
Co. No. 139; Ex. No. B14
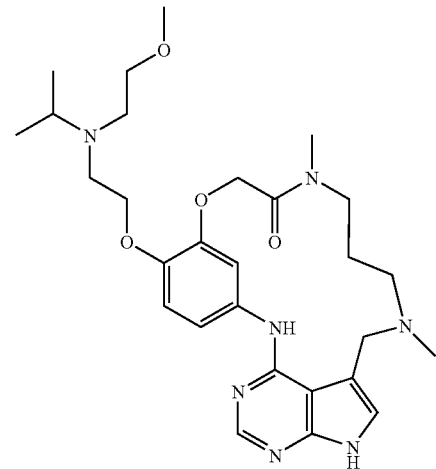
Co. No. 140; Ex. No. B29

TABLE 1-continued
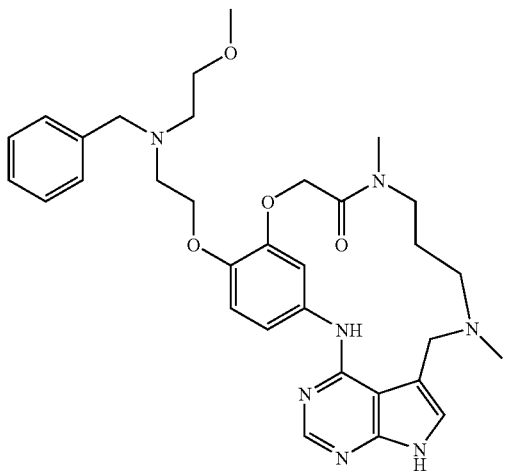
Co. No. 141; Ex. No. B29
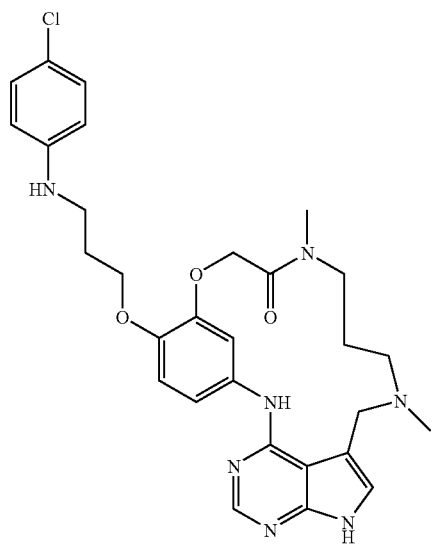
Co. No. 142; Ex. No. B31
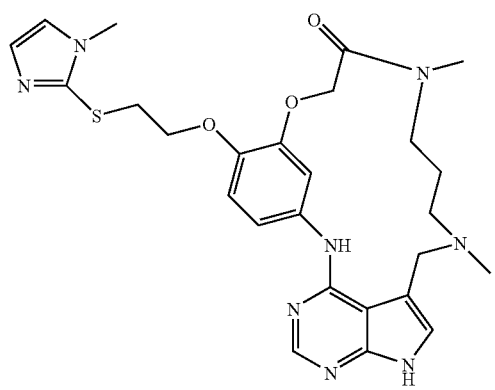
Co. No. 143; Ex. No. B26
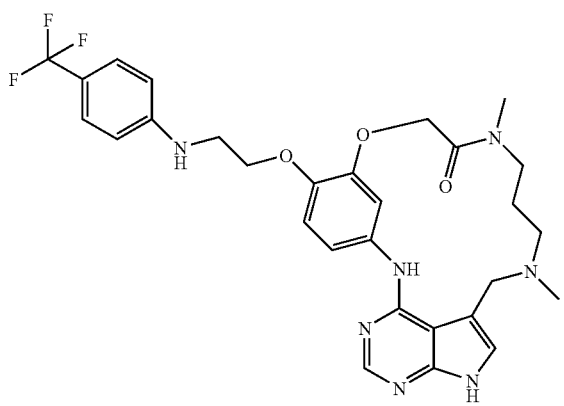
Co. No. 144; Ex. No. B31
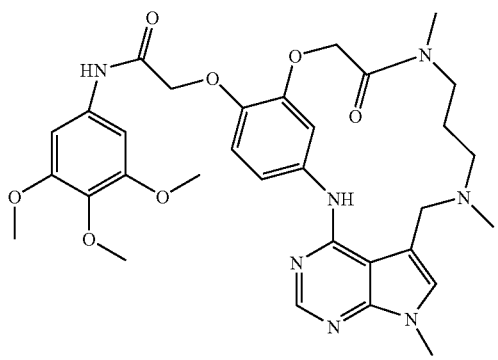
Co. No. 145; Ex. No. B33
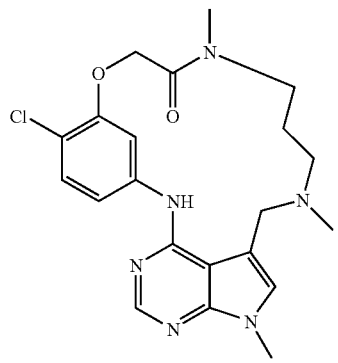
Co. No. 146; Ex. No. B33

TABLE 1-continued
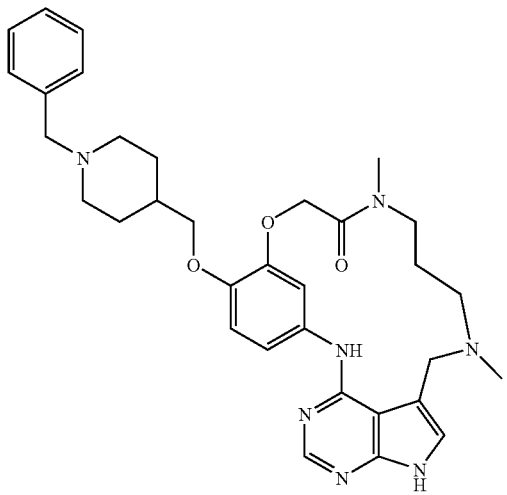
Co. No. 149; Ex. No. B37*
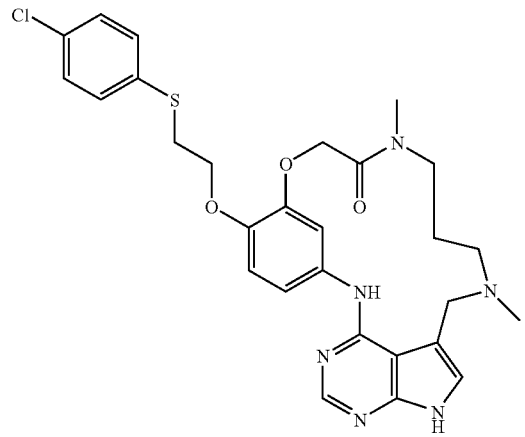
Co. No. 150; Ex. No. B38*
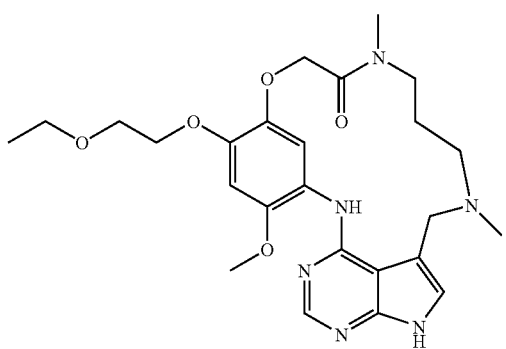
Co. No. 151; Ex. No. B39*
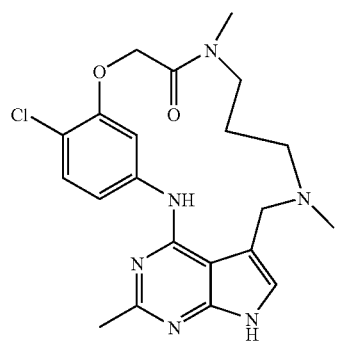
Co. No. 148; Ex. No. B36*
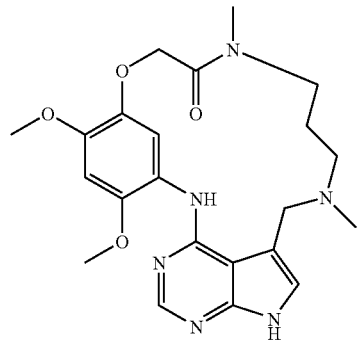
Co. No. 152; Ex. No. B40*
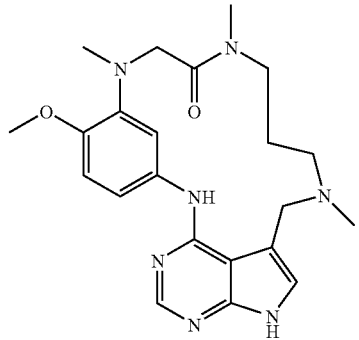
Co. No. 153; Ex. No. B41*

TABLE 1-continued
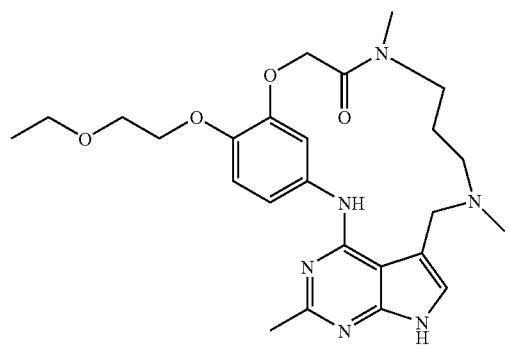
Co. No. 147; Ex. No. B35*
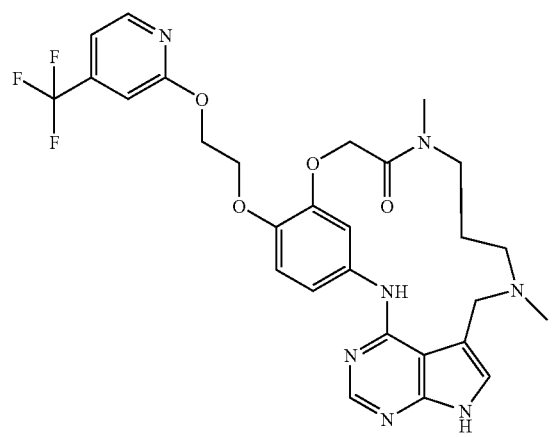
Co. No. 154; Ex. No. B42*
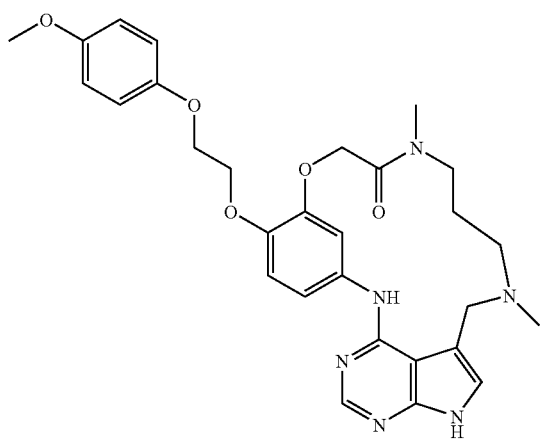
Co. No. 155; Ex. No. B43*
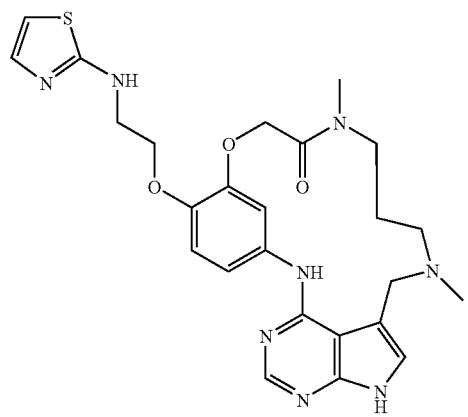
Co. No. 156; Ex. No. B44*
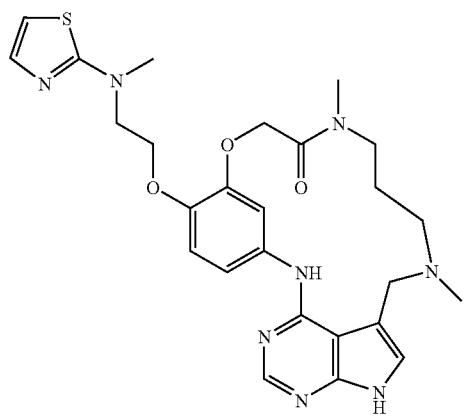
Co. No. 147; Ex. No. B45*
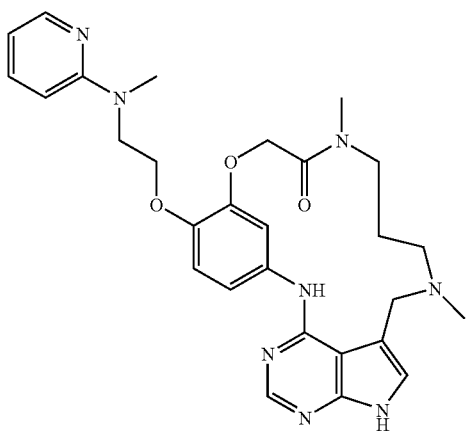
Co. No. 158; Ex. No. B46*

TABLE 1-continued
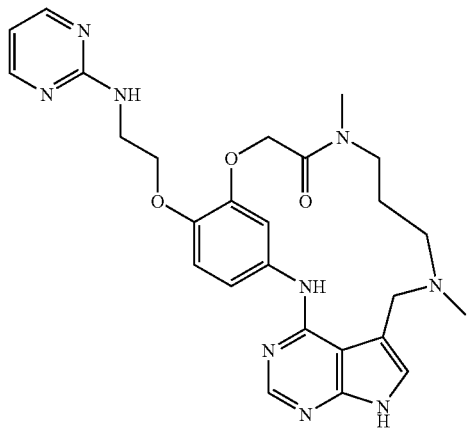
Co. No. 159; Ex. No. B47*
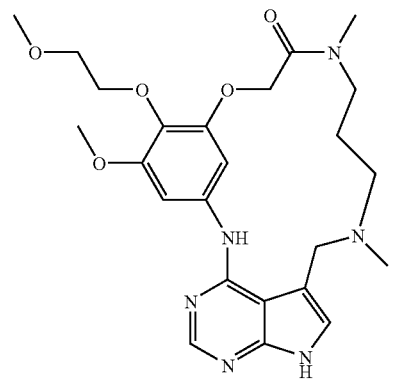
Co. No. 161; Ex. No. B49*
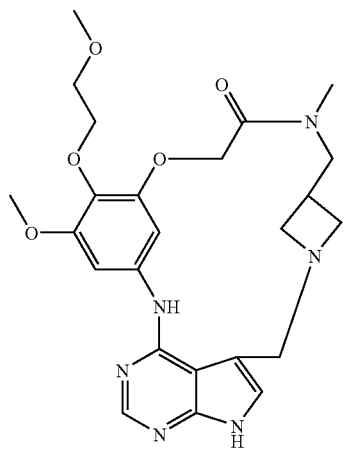
Co. No. 160; Ex. No. B48*
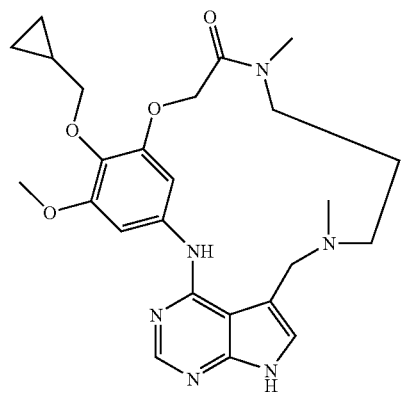
Co. No. 162; Ex. No. B49
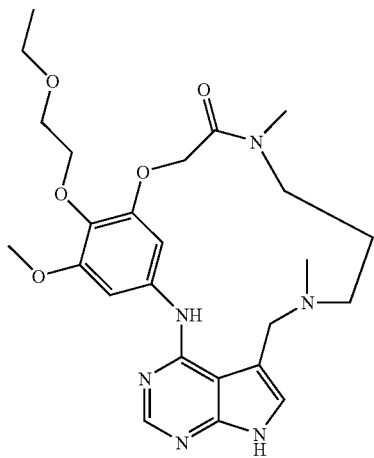
Co. No. 163; Ex. No. B49
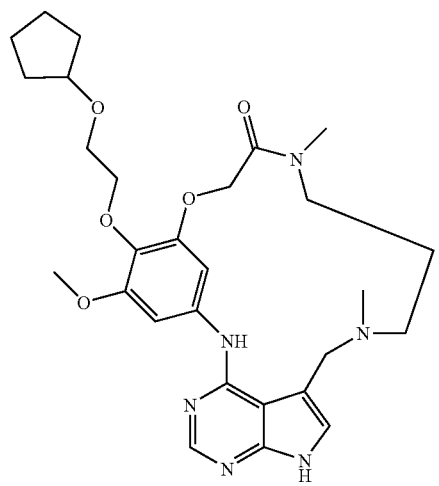
Co. No. 164; Ex. No. B49

TABLE 1-continued
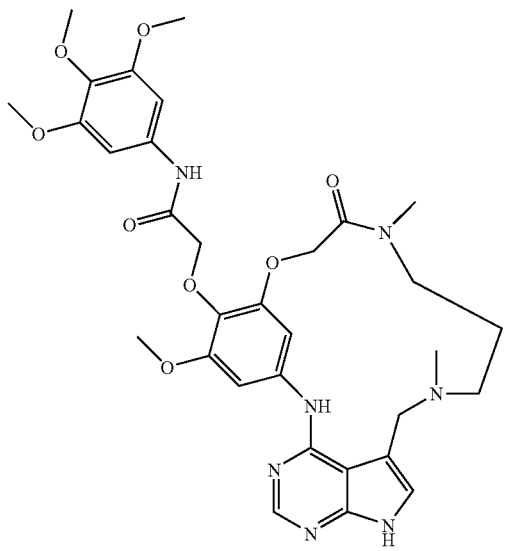
Co. No. 165; Ex. No. B49
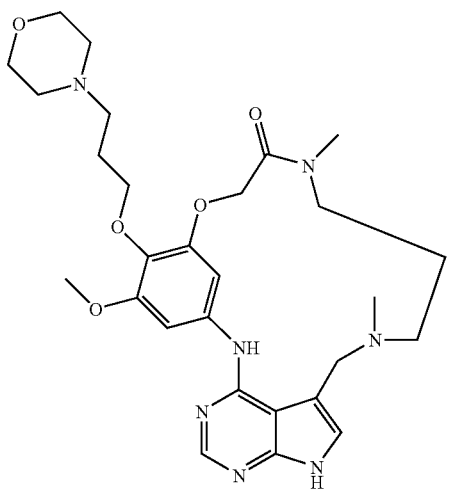
Co. No. 166; Ex. No. B49
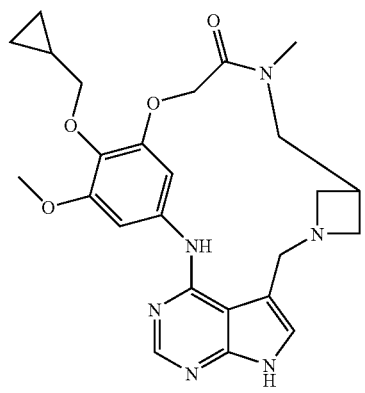
Co. No. 167; Ex. No. B48
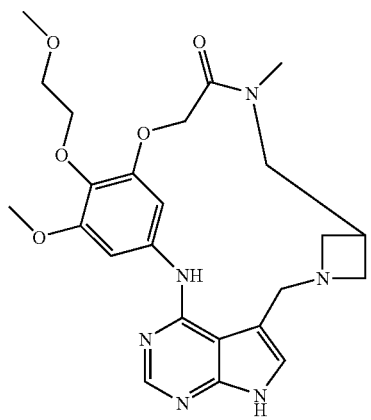
Co. No. 168; Ex. No. B48
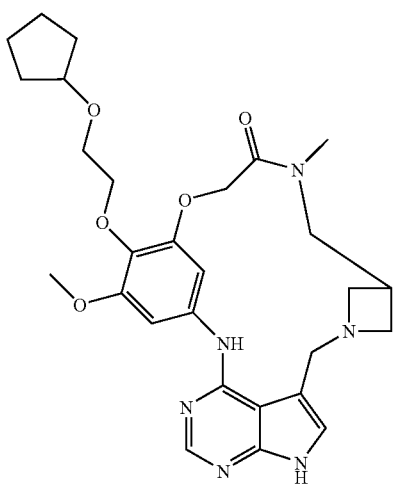
Co. No. 169 Ex. No. B48
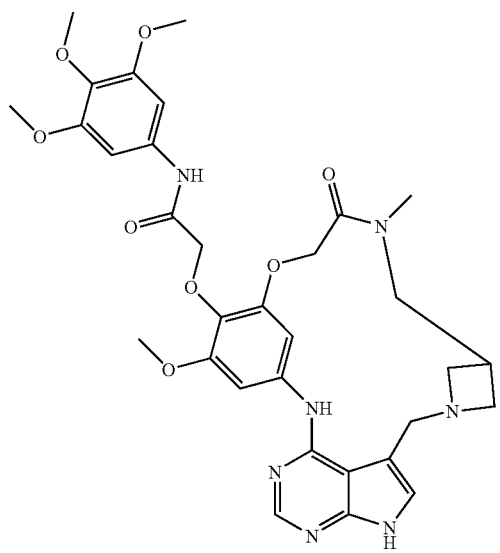
Co. No. 170 Ex. No. B48

TABLE 1-continued

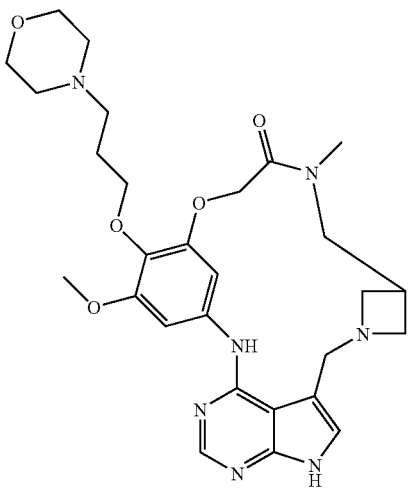

Co. No. 171 Ex. No. B48

Compound Identification

Melting Points

For a number of compounds, melting points (m.p.) were determined with a DSC823e (Mettler-Toledo). Melting points were measured with a temperature gradient of 30° C./minute. Maximum temperature was 400° C.

Values are peak values and are obtained with experimental uncertainties that are commonly associated with this analytical method.

TABLE 2a

Melting Points

| Co. No. | m.p. (° C.) | Co. No. | m.p. (° C.) | Co. No. | m.p. (° C.) |
|---|---|---|---|---|---|
| 7 | 267.9 | 59 | 260.8 | 73 | 265.3 |
| 53 | 252.3 | 60 | 284.5 | 74 | 270.9 |
| 54 | 287.3 | 10 | 249.3 | 75 | 237.4 |
| 55 | 281.2 | 64 | 273.1 | 78 | 222.2 |
| 57 | 270.2 | 70 | 237.8 | 79 | 269.3 |
| 81 | 221.0 | 136 | decomp | 147 | 251.0 |
| 89 | 272.5 | 137 | 256.3 | 156 | 238.4 |
| 91 | 250.6 | 141 | 211.2 | 155 | 250.4 |
| 119 | 243.4 | 142 | 243.4 | 149 | 241.0 |
| 133 | 250.2 | 144 | 270.8 | 150 | 252.6 |
| 134 | 252.3 | 145 | 284.1 | 160 | 258.4 |
| 135 | 257.8 | 157 | 232.2 | 161 | 201.4 |

'decomp' means decomposition

LCMS

For LCMS-characterization of the compounds of the present invention, the following methods were used.

General Procedure A

The HPLC measurement was performed using an Alliance HT 2790 (Waters) system comprising a quaternary pump with degasser, an autosampler, a column oven (set at 40° C. unless otherwise indicated), a diode-array detector (DAD) and a column as specified in the respective methods below. Flow from the column was split to a MS detector. The MS detector was configured with an electrospray ionization source. Mass spectra were acquired by scanning from 100 to 1000 in 1 second using a dwell time of 0.1 second. The capillary needle voltage was 3 kV and the source temperature was maintained at 140° C. (DSC). $N_2$ was used as the nebulizer gas. Data acquisition was performed with a Waters-Micromass MassLynx-Openlynx data system.

General Procedure B

The LC measurement was performed using an Acquity UPLC (Waters) (Ultra Performance Liquid Chromatography) system comprising a binary pump, a sample organizer, a column heater (set at 55° C.), a diode-array detector (DAD) and a column as specified in the respective methods below. Flow from the column was split to a MS detector. The MS detector was configured with an electrospray ionization source. Mass spectra were acquired by scanning from 100 to 1000 in 0.18 seconds using a dwell time of 0.02 seconds. The capillary needle voltage was 3.5 kV and the source temperature was maintained at 140° C. (DSC). $N_2$ was used as the nebulizer gas. Data acquisition was performed with a Waters-Micromass MassLynx-Openlynx data system.

General Procedure C

The HPLC measurement was performed using an Agilent 1100 series liquid chromatography system comprising a binary pump with degasser, an autosampler, a column oven, a UV detector and a column as specified in the respective methods below. Flow from the column was split to a MS spectrometer. The MS detector was configured with an electrospray ionization source. The capillary voltage was 3 kV, the quadrupole temperature was maintained at 100° C. and the desolvation temperature was 300° C. $N_2$ was used as the nebulizer gas. Data acquisition was performed with an Agilent Chemstation data system.

LCMS Method 1

In addition to general procedure B: Reversed phase UPLC (Ultra Performance Liquid Chromatography) was carried out on a bridged ethylsiloxane/silica (BEH) C18 column (1.7 μm, 2.1×50 mm) with a flow rate of 0.8 ml/min. Two mobile phases (mobile phase A: 0.1% formic acid in $H_2O$/MeOH 95/5; mobile phase B: MeOH) were used to run a gradient condition from 95% A and 5% B to 5% A and 95% B in 1.3 minutes and hold for 0.2 minutes. An injection volume of 0.5 μl was used. Cone voltage was 10 V for positive ionization mode and 20 V for negative ionization mode.

LCMS Method 2

In addition to general procedure A: Column heater was set at 60° C. Reversed phase HPLC was carried out on an Xterra MS C18 column (3.5 μm, 4.6×100 mm) with a flow rate of 1.6 ml/min. Three mobile phases (mobile phase A: 95% 25 mM ammoniumacetate+5% CH$_3$CN; mobile phase B: CH$_3$CN; mobile phase C: MeOH) were employed to run a gradient condition from 100% A to 50% B and 50% C in 6.5 minutes, to 100% B in 0.5 minute and hold these conditions for 1 minute and reequilibrate with 100% A for 1.5 minutes. An injection volume of 10 μl was used. Cone voltage was 10 V for positive ionization mode and 20 V for negative ionization mode.

LCMS Method 3

In addition to general procedure A: Reversed phase HPLC was carried out on an Xterra MS C18 column (3.5 μm, 4.6×100 mm) with a flow rate of 1.6 ml/min. Three mobile phases (mobile phase A: 95% 25 mM ammoniumacetate+5% CH$_3$CN; mobile phase B: CH$_3$CN; mobile phase C: MeOH) were employed to run a gradient condition from 100% A to 1% A, 49% B and 50% C in 6.5 minutes, to 1% A and 99% B in 1 minute and hold these conditions for 1 minute and reequilibrate with 100% A for 1.5 minutes. An injection volume of 10 μl was used. Cone voltage was 10 V for positive ionization mode and 20 V for negative ionization mode.

LCMS Method 4

In addition to general procedure A: Column heater was set at 45° C. Reversed phase HPLC was carried out on an Xterra MS C18 column (3.5 μm, 4.6×100 mm) with a flow rate of 1.6 ml/min. Three mobile phases (mobile phase A: 0.1% formic acid in H$_2$O/MeOH 95/5; mobile phase B: CH$_3$CN; mobile phase C: MeOH) were employed to run a gradient condition from 100% A to 1% A, 49% B and 50% C in 7 minutes and hold these conditions for 1 minute. An injection volume of 10 μl was used. Cone voltage was 10 V for positive ionization mode.

LCMS Method 5

In addition to general procedure A: Column heater was set at 45° C. Reversed phase HPLC was carried out on an Atlantis C18 column (3.5 μm, 4.6×100 mm) with a flow rate of 1.6 ml/min. Two mobile phases (mobile phase A: 70% MeOH+30% H$_2$O; mobile phase B: 0.1% formic acid in H$_2$O/MeOH 95/5) were employed to run a gradient condition from 100% B to 5% B+95% A in 9 minutes and hold these conditions for 3 minutes. An injection volume of 10 μl was used.

LCMS Method 6

In addition to general procedure C: Reversed phase HPLC was carried out on a YMC-Pack ODS-AQ C18 column (4.6×50 mm) with a flow rate of 2.6 ml/min. A gradient run was used from 95% water and 5% CH$_3$CN to 95% CH$_3$CN in 4.80 minutes and was hold for 1.20 minutes. Mass spectra were acquired by scanning from 100 to 1400. Injection volume was 10 μl Column temperature was 35° C.

LCMS Method 7

In addition to general procedure C: Reversed phase HPLC was carried out on a YMC-Pack ODS-AQ C18 column (4.6×50 mm) with a flow rate of 2.6 ml/min. A gradient run was used from 95% H$_2$O and 5% CH$_3$CN to 95% CH$_3$CN in 7.30 minutes and was hold for 1.20 minutes. Mass spectra were acquired by scanning from 100 to 1000. Injection volume was 10 μl Column temperature was 35° C.

LCMS Method 8

In addition to general procedure C: Reversed phase HPLC was carried out on a YMC-Pack ODS-AQ C18 column (4.6×50 mm) with a flow rate of 2.6 ml/min. A gradient run was used from 88% H$_2$O and 12% CH$_3$CN to 88% CH$_3$CN in 3.40 minutes and was hold for 1.20 minutes. Mass spectra were acquired by scanning from 110 to 1000. Injection volume was 10 μl Column temperature was 35° C.

LCMS Method 9

In addition to the general procedure A: Reversed phase HPLC was carried out on an Xterra MS C18 column (3.5 μm, 4.6×100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 1% A, 49% B and 50% C in 6.5 minutes, to 1% A and 99% B in 1 minute and hold these conditions for 1 minute and reequilibrate with 100% A for 1.5 minutes. An injection volume of 10 μl was used. Cone voltage was 10 V for positive ionization mode and 20 V for negative ionization mode.

LCMS Method 10

In addition to the general procedure A: Column heater was set at 60° C. Reversed phase HPLC was carried out on an Xterra MS C18 column (3.5 μm, 4.6×100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 50% B and 50% C in 6.5 minutes, to 100% B in 0.5 minute and hold these conditions for 1 minute and reequilibrate with 100% A for 1.5 minutes. An injection volume of 10 μl was used. Cone voltage was 10 V for positive ionization mode and 20 V for negative ionization mode.

TABLE 2b

LCMS data - Retention time ($R_t$ in minutes), (MH)$^+$ peak, LCMS method refers to the method used for LCMS.

| Co. No. | $R_t$ | (MH)$^+$ | LCMS Method | Co. No. | $R_t$ | (MH)$^+$ | LCMS Method |
|---|---|---|---|---|---|---|---|
| 16 | 0.72 | 453 | 1 | 22 | 0.57 | 383 | 1 |
| 17 | 0.64 | 439 | 1 | 23 | 0.60 | 353 | 1 |
| 18 | 0.76 | 467 | 1 | 24 | 0.52 | 365 | 1 |
| 19 | 0.96 | 471 | 1 | 25 | 0.55 | 425 | 1 |
| 20 | 0.59 | 365 | 1 | 5 | 0.56 | 423 | 1 |
| 7 | 0.50 | 411 | 1 | 26 | 2.98 | 441 | 2 |
| 21 | 0.60 | 379 | 1 | 27 | 0.41 | 451 | 1 |
| 8 | 0.57 | 436 | 1 | 28 | 0.43 | 425 | 1 |
| 6 | 0.68 | 397 | 1 | 29 | 0.37 | 465 | 1 |
| 30 | 0.65 | 439 | 1 | 57 | 0.56 | 441 | 1 |
| 31 | 0.80 | 395 | 1 | 58 | 0.55 | 367 | 1 |
| 32 | 0.69 | 409 | 1 | 59 | 0.63 | 451 | 1 |
| 33 | 0.43 | 411 | 1 | 60 | 0.37 | 425 | 1 |
| 34 | 2.63 | 395 | 2 | 61 | 0.93 | 487 | 1 |
| 4 | 0.48 | 409 | 1 | 15 | 0.81 | 545 | 1 |
| 35 | 0.53 | 435 | 1 | 62 | 0.67 | 488 | 1 |
| 36 | 0.55 | 439 | 1 | 63 | 0.62 | 425 | 1 |
| 37 | 0.52 | 423 | 1 | 11 | 5.06 | 487 | 2 |
| 38 | 0.40 | 451 | 1 | 10 | 0.52 | 397 | 1 |
| 39 | 4.78 | 501 | 2 | 64 | 0.82 | 479 | 1 |
| 3 | 0.41 | 441 | 1 | 12 | 0.62 | 439 | 1 |
| 1 | 0.70 | 425 | 1 | 65 | 0.46 | 397 | 1 |
| 40 | 0.88 | 480 | 8 | 66 | 0.78 | 507 | 1 |
| 41 | 0.76 | 439 | 8 | 67 | 0.97 | 549 | 1 |
| 2 | 0.77 | 409 | 1 | 14 | 0.70 | 415 | 1 |
| 42 | 1.02 | 429 | 1 | 13 | 0.87 | 521 | 1 |
| 43 | 0.85 | 443 | 1 | 68 | 0.74 | 451 | 1 |
| 44 | 0.85 | 494 | 8 | 69 | 1.30 | 469 | 6 |
| 45 | 0.71 | 450 | 1 | 70 | 4.48 | 469 | 3 |
| 46 | 0.61 | 395 | 1 | 71 | 4.76 | 620 | 3 |
| 47 | 0.65 | 425 | 1 | 72 | 0.93 | 425 | 6 |
| 48 | 0.68 | 494 | 1 | 73 | 4.41 | 437 | 3 |
| 49 | 0.92 | 443 | 1 | 74 | 4.35 | 481 | 3 |
| 50 | 4.70 | 501 | 2 | 75 | 4.20 | 455 | 3 |
| 51 | 0.70 | 485 | 1 | 76 | 1.46 | 447 | 6 |
| 52 | 0.61 | 451 | 1 | 78 | 5.27 | 561 | 2 |
| 9 | 0.40 | 425 | 1 | 79 | 5.42 | 550 | 2 |
| 53 | 0.53 | 425 | 1 | 80 | 3.49 | 441 | 2 |

TABLE 2b-continued

LCMS data - Retention time ($R_t$ in minutes), $(MH)^+$ peak, LCMS method refers to the method used for LCMS.

| Co. No. | $R_t$ | $(MH)^+$ | LCMS Method | Co. No. | $R_t$ | $(MH)^+$ | LCMS Method |
|---|---|---|---|---|---|---|---|
| 54 | 0.85 | 449 | 1 | 82 | 3.02 | 450 | 5 |
| 55 | 1.23. | 409 | 6 | 83 | 1.84 | 477 | 6 |
| 56 | 0.68 | 464 | 1 | 84 | 0.45 | 479 | 7 |
| 85 | 1.06 | 466 | 6 | 117 | 3.80 | 524 | 3 |
| 86 | 1.46 | 407 | 6 | 118 | 3.38 | 536 | 4 |
| 87 | 1.35 | 469 | 6 | 119 | 4.02 | 455 | 2 |
| 88 | 3.23 | 395 | 3 | 120 | 1.10 | 381 | 6 |
| 89 | 3.62 | 409 | 3 | 121 | 1.34 | 492 | 6 |
| 90 | 5.32 | 465 | 3 | 122 | 1.23 | 481 | 6 |
| 91 | 4.76 | 522 | 3 | 123 | 1.14 | 453 | 6 |
| 92 | 2.14 | 477 | 6 | 124 | 1.15 | 469 | 6 |
| 93 | 2.43 | 463 | 6 | 125 | 4.06 | 494 | 3 |
| 94 | 0.91 | 493 | 6 | 126 | 3.98 | 510 | 2 |
| 95 | 1.44 | 455 | 6 | 127 | 1.35 | 493 | 6 |
| 96 | 1.23 | 427 | 6 | 128 | 4.08 | 499 | 2 |
| 97 | 1.22 | 452 | 6 | 129 | 4.79 | 560 | 3 |
| 98 | 1.57 | 401 | 6 | 130 | 4.81 | 483 | 3 |
| 99 | 1.61 | 509 | 6 | 131 | 0.73 | 483 | 1 |
| 100 | 1.46 | 439 | 7 | 132 | 0.64 | 469 | 1 |
| 101 | 1.53 | 439 | 7 | 133 | 5.12 | 564 | 2 |
| 102 | 0.79 | 507 | 6 | 134 | 5.47 | 551 | 2 |
| 103 | 1.19 | 437 | 6 | 135 | 4.14 | 467 | 3 |
| 104 | 1.69 | 441 | 6 | 136 | 3.64 | 508 | 3 |
| 105 | 1.31 | 423 | 6 | 137 | 4.07 | 524 | 3 |
| 106 | 1.96 | 427 | 6 | 138 | 3.63 | 441 | 2 |
| 107 | 1.48 | 393 | 6 | 139 | 0.76 | 459 | 1 |
| 108 | 0.92 | 505 | 6 | 140 | 4.06 | 540 | 2 |
| 109 | 0.98 | 491 | 6 | 141 | 5.44 | 588 | 2 |
| 110 | 1.51 | 478 | 6 | 142 | 5.60 | 564 | 2 |
| 111 | 1.41 | 467 | 6 | 143 | 4.50 | 537 | 3 |
| 112 | 1.54 | 453 | 6 | 144 | 5.57 | 584 | 2 |
| 113 | 2.28 | 475 | 6 | 145 | 5.19 | 634 | 3 |
| 114 | 1.75 | 393 | 6 | 146 | 5.24 | 429 | 3 |
| 115 | 2.29 | 583 | 6 | 159 | 4.43 | 518 | 9 |
| 116 | 2.01 | 549 | 6 | 158 | 5.23 | 531 | 9 |
| 156 | 4.67 | 523 | 9 | 157 | 5.02 | 537 | 9 |
| 155 | 5.41 | 547 | 9 | 150 | 6.24 | 567 | 9 |
| 147 | 4.66 | 483 | 10 | 149 | 5.07 | 584 | 9 |
| 153 | 4.28 | 424 | 10 | 154 | 6.52 | 586 | 5 |
| 152 | 3.87 | 441 | 10 | 160 | 0.70 | 497 | 1 |
| 148 | 4.87 | 429 | 10 | 161 | 0.63 | 485 | 1 |
| 151 | 3.67 | 499 | 10 | | | | |

C. Pharmacological Example

C1. Kinase Profiling

The in vitro inhibition of a panel of kinases was assessed using either the scintillation proximity assay (SPA) as described by Cook, N. D. et al., Advances in Experimental Medicine and Biology (1991), 36; p. 525-528.

In the SPA technology the activity of the kinase of interest is measured using an appropriate biotinylated substrate that is incubated with the aforementioned kinase protein in the presence of ($^{33}$P) radiolabeled ATP. ($^{33}$P) Phosphorylation of the substrate is subsequently measured through binding of the phosphorylated substrate to streptavidine coated beads that are based on the scintillant poly(vinyl toluene) (PVT-Beads). The scintillation intensity is detected by imaging on Leadseeker.

Detailed Description

All kinases are pre-diluted to a 10× working concentration prior to addition into the assay. The composition of the dilution buffer for each kinase is detailed below.

C1.1 PLK-4 Human

In a final reaction volume of 30 µl, PLK4 (h) (19 µg/ml) is incubated with 50 mM Hepes pH 8.0, 10 mM $MgCl_2$, 50 mM NaCl, 1 mM NaF, 1 mM DTT, 10 µM of peptide Biotin-RPRGQRDSSYYWE-OH, 1 µM ATP and 2 nM [γ-$^{33}$P-ATP] (6.0 µCi/ml). After incubation of 60 minutes at r.t., the reaction is stopped by addition of 40 µL of stop solution containing 8.7 mM EDTA, BSA 0.17%, 0.17% Triton X-100, 1.7 mg/ml SPA beads (GE-healthcare). The plate is centrifuged and read for Scintillation imaging on Leadseeker.

Table 3 provides the pIC50 values of the compounds according to the invention, obtained using the above mentioned kinase assay.

| Co. No. | PLK4 pIC50 | Co. No. | PLK4 pIC50 | Co. No. | PLK4 pIC50 |
|---|---|---|---|---|---|
| 16 | 6.9 | 9 | <5 | 104 | 5.7 |
| 17 | 6.6 | 53 | 6.9 | 105 | 6 |
| 18 | 6.4 | 54 | 6.6 | 106 | 5.2 |
| 19 | 6.5 | 55 | 6.1 | 107 | 5.2 |
| 20 | 6.2 | 56 | 5.3 | 108 | 5.1 |
| 7 | 7.4 | 57 | 5.4 | 109 | <5 |
| 21 | 6.3 | 58 | 7.3 | 110 | 5.1 |
| 8 | <5 | 59 | 6.8 | 111 | <5 |
| 6 | 6.3 | 60 | 6 | 112 | <5 |
| 22 | 5.9 | 61 | 7 | 113 | <5 |
| 23 | 5.8 | 15 | 7.6 | 114 | n.d. |
| 24 | 6.4 | 62 | 6.2 | 115 | 6.8 |
| 25 | 6.2 | 63 | 7.1 | 116 | 7.5 |
| 5 | <5 | 11 | 7.3 | 117 | 7.3 |
| 26 | n.d. | 10 | 6.9 | 118 | 7.6 |
| 27 | 5.2 | 64 | 6.6 | 119 | 7.6 |
| 28 | <5 | 12 | 7.1 | 120 | 7.5 |
| 29 | <5 | 65 | 7.1 | 121 | 5.2 |
| 30 | <5 | 66 | 7.4 | 122 | 6.7 |
| 31 | 6.1 | 67 | 7.2 | 85 | 6.8 |
| 32 | 6.3 | 14 | 7.3 | 84 | 6.7 |
| 33 | 5.3 | 13 | 7.6 | 72 | <5 |
| 34 | <5 | 68 | 7.4 | 123 | <5 |
| 4 | <5 | 86 | <5 | 124 | <5 |
| 35 | <5 | 87 | <5 | 125 | 7.6 |
| 36 | <5 | 88 | 6.3 | 74 | 6.7 |
| 37 | <5 | 89 | 6.6 | 135 | 6.8 |
| 38 | <5 | 73 | 6.7 | 126 | 6.3 |
| 39 | <5 | 90 | 7.5 | 136 | 6.6 |
| 3 | 5.8 | 91 | 7.6 | 127 | 7.3 |
| 1 | 6.9 | 92 | <5 | 137 | 6.4 |
| 40 | 5.9 | 93 | 5.2 | 128 | 7.6 |
| 41 | 5.6 | 94 | 5.3 | 138 | 7.6 |
| 2 | 5.5 | 95 | <5 | 129 | 7.3 |
| 42 | 6.1 | 96 | 5.3 | 130 | 7.4 |
| 43 | 6.3 | 97 | 6.1 | 71 | 7.1 |
| 44 | 5.8 | 69 | 5.7 | 76 | 7.4 |
| 45 | 5.5 | 98 | 7 | 139 | 7.2 |
| 46 | 6 | 99 | 7.6 | 131 | 7.3 |
| 47 | 5.2 | 70 | 7.6 | 132 | 7.1 |
| 48 | <5 | 100 | 7.3 | 77 | 7.2 |
| 49 | 5.5 | 101 | 7.4 | 140 | 6.8 |
| 50 | n.d. | 83 | 5.3 | 78 | 7.3 |
| 51 | <5 | 102 | 5.4 | 79 | 7 |
| 52 | <5 | 103 | 6.2 | 141 | 7.4 |
| 80 | 7.2 | 142 | 7.1 | 81 | 7.1 |
| 133 | 7.2 | 82 | 7.1 | 145 | 5.3 |
| 134 | 7.1 | 143 | 7.2 | 146 | 6.2 |
| 75 | 7.4 | 144 | n.d. | | | n.d.: not determined

C.2. Cellular Proliferation Assay

Cellular proliferation of these compounds was tested on a panel of different cell lines in the presence of 10% FCS serum (37° C. and 5% (v/v) $CO_2$). In a first step these cells were seeded and incubated for 24 hours in the absence of compound. In the second step the cells were incubated for 72 hours with the compounds to be tested for 72 hours. The viable cell number was finally assessed in a standard Alamar blue cell viability assay.

Detailed Description

The viable cell number was assessed by incubation for either 4 h (HCT-116, H1299) 6 h (U87-MG) or 24 h (A2780, PC3, MDA-MB-231) with Alamar blue (Resazurin 9 μg/ml, K-Ferrocyanide 90 μM, K-Ferricyanide 90 μM) and the converted fluorescent product was quantified on a fluorescent plate readed (544 nm/590 nm). Effect of the compounds is calculated as of on control cells.

pIC50 values obtained for compounds tested are presented in Table 4.

| Compound No. | PC-3 | A2780 | H1299 | HCT-116 | MDA/MB231 | U87MG |
|---|---|---|---|---|---|---|
| 16 | <5 | <5 | <5 | <5 | <5 | <5 |
| 17 | <5 | <5 | <5 | <5 | <5 | <5 |
| 18 | <5 | <5 | <5 | <5 | <5 | <5 |
| 19 | <5 | <5 | <5 | <5 | <5 | <5 |
| 20 | <5 | <5 | 5.0 | 5.1 | <5 | <5 |
| 7 | 5.7 | 6.2 | 6.0 | 6.3 | 5.8 | 5.9 |
| 21 | 5.4 | 5.7 | 5.7 | 5.8 | 5.3 | 5.7 |
| 8 | <5 | <5 | <5 | <5 | <5 | <5 |
| 6 | 5.4 | 5.8 | 5.8 | 5.9 | 5.3 | 5.8 |
| 22 | 5.2 | 5.7 | 5.5 | 5.7 | 5.0 | 5.6 |
| 23 | 5.5 | 6.0 | 6.0 | 5.9 | 5.3 | 5.8 |
| 24 | 5.0 | 5.3 | <5 | 5.4 | <5 | 5.0 |
| 25 | n.d. | n.d. | n.d. | n.d. | n.d. | n.d. |
| 5 | <5 | <5 | <5 | <5 | <5 | <5 |
| 26 | n.d. | n.d. | n.d. | n.d. | n.d. | n.d. |
| 27 | <5 | <5 | <5 | <5 | <5 | <5 |
| 28 | <5 | <5 | <5 | <5 | <5 | <5 |
| 29 | <5 | <5 | <5 | <5 | <5 | <5 |
| 30 | <5 | <5 | <5 | <5 | <5 | <5 |
| 31 | <5 | 5.4 | <5 | 5.2 | <5 | <5 |
| 32 | n.d. | n.d. | n.d. | n.d. | n.d. | n.d. |
| 33 | <5 | <5 | <5 | <5 | <5 | <5 |
| 34 | <5 | <5 | <5 | <5 | <5 | <5 |
| 4 | <5 | <5 | <5 | <5 | <5 | <5 |
| 35 | <5 | <5 | <5 | <5 | <5 | <5 |
| 36 | <5 | <5 | <5 | <5 | <5 | <5 |
| 37 | <5 | <5 | <5 | <5 | <5 | <5 |
| 38 | <5 | <5 | <5 | <5 | <5 | <5 |
| 39 | n.d. | n.d. | n.d. | n.d. | n.d. | n.d. |
| 3 | <5 | <5 | <5 | <5 | <5 | <5 |
| 1 | <5 | <5 | <5 | <5 | <5 | <5 |
| 40 | <5 | <5 | <5 | <5 | <5 | <5 |
| 41 | <5 | <5 | <5 | <5 | <5 | <5 |
| 2 | <5 | <5 | <5 | <5 | <5 | <5 |
| 42 | <5 | <5 | <5 | <5 | <5 | <5 |
| 43 | n.d. | n.d. | n.d. | n.d. | n.d. | n.d. |
| 44 | <5 | <5 | <5 | <5 | <5 | <5 |
| 45 | <5 | <5 | <5 | <5 | <5 | <5 |
| 46 | <5 | <5 | <5 | <5 | <5 | <5 |
| 47 | <5 | <5 | <5 | <5 | <5 | <5 |
| 48 | <5 | <5 | <5 | <5 | <5.5 | <5 |
| 49 | <5 | <5 | <5 | <5 | <5 | <5 |
| 50 | n.d. | n.d. | n.d. | n.d. | n.d. | n.d. |
| 51 | n.d. | n.d. | n.d. | n.d. | n.d. | n.d. |
| 52 | n.d. | n.d. | n.d. | n.d. | n.d. | n.d. |
| 9 | n.d. | n.d. | n.d. | n.d. | n.d. | n.d. |
| 53 | <5 | <5 | <5 | 5.1 | <5 | <5 |
| 54 | <5 | <5 | <5 | <5 | <5 | <5 |
| 55 | n.d. | n.d. | n.d. | n.d. | n.d. | n.d. |
| 56 | <5 | <5 | <5 | <5 | <5 | <5 |
| 57 | <5 | <5 | <5 | <5 | <5 | <5 |
| 58 | 5.1 | 5.5 | 5.3 | 5.6 | 5.0 | 5.2 |
| 59 | <5 | <5 | <5 | <5 | <5 | <5 |
| 60 | <5 | <5 | <5 | <5 | <5 | <5 |
| 61 | <5 | <5 | <5 | <5 | <5 | <5 |
| 15 | <5 | 6.1 | <5 | 6.1 | <5 | 5.7 |
| 62 | <5 | <5 | <5 | <5 | <5 | <5 |
| 63 | 5.6 | 6.3 | 5.7 | 6.2 | 5.5 | 5.7 |
| 11 | n.d. | n.d. | n.d. | n.d. | n.d. | n.d. |
| 10 | <5 | <5 | <5 | <5 | <5 | <5 |
| 64 | <5 | <5 | <5 | <5 | <5 | <5 |
| 12 | <5 | 5.3 | <5 | 5.1 | <5 | 5.2 |
| 65 | <5 | <5 | <5 | <5 | <5 | <5 |
| 66 | 5.1 | <5 | <5 | 5.3 | <5 | 5.8 |
| 67 | <5 | 5.6 | 5.6 | 6.1 | <5 | <5 |
| 14 | <5 | 5.4 | <5 | 6.2 | <5 | 6.1 |
| 13 | <5 | 6.0 | 5.4 | 5.7 | <5 | 5.4 |
| 68 | 5.5 | 6.2 | 5.8 | 6.2 | 5.7 | 5.8 |
| 86 | <5 | <5 | <5 | <5 | <5 | <5 |
| 87 | <5 | <5 | <5 | <5 | <5 | <5 |
| 88 | <5 | <5 | <5 | 5.3 | <5 | 5.0 |
| 89 | <5 | <5 | <5 | <5 | <5 | n.d. |
| 73 | <5 | <5 | <5 | <5 | <5 | n.d. |
| 90 | n.d. | n.d. | n.d. | n.d. | n.d. | n.d. |
| 91 | <5 | 6.1 | 5.5 | 5.8 | <5 | n.d. |
| 92 | <5 | <5 | 5.2 | <5 | <5 | n.d. |
| 93 | <5 | <5 | 5.9 | <5 | <5 | n.d. |
| 94 | 5.0 | <5 | <5 | <5 | <5 | n.d. |
| 95 | <5 | <5 | <5 | <5 | <5 | n.d. |
| 96 | <5 | <5 | <5 | <5 | <5 | n.d. |
| 97 | <5 | <5 | <5 | <5 | <5 | n.d. |
| 69 | <5 | <5 | <5 | <5 | <5 | n.d. |
| 98 | <5 | <5 | <5 | 5.3 | <5 | 5.2 |
| 99 | 5.2 | n.d. | 7.4 | 7.2 | <5 | n.d. |
| 70 | 5.4 | 7.1 | 6.3 | 7.0 | 5.6 | 5.8 |
| 100 | 5.7 | 5.8 | 6.2 | 5.8 | 5.2 | n.d. |
| 101 | 5.7 | 5.8 | 6.1 | 5.8 | 5.1 | n.d. |
| 83 | <5 | <5 | 5.4 | <5 | <5 | n.d. |
| 102 | 5.3 | 5.2 | 5.6 | 5.2 | <5 | n.d. |
| 103 | <5 | <5 | <5 | <5 | <5 | <5 |
| 104 | <5 | <5 | <5 | <5 | <5 | <5 |
| 105 | <5 | <5 | <5 | <5 | <5 | <5 |
| 106 | <5 | <5 | <5 | <5 | <5 | <5 |
| 107 | <5 | <5 | <5 | <5 | <5 | <5 |
| 108 | <5 | <5 | <5 | <5 | <5 | n.d. |
| 109 | <5 | <5 | <5 | <5 | <5 | n.d. |
| 110 | n.d. | n.d. | n.d. | n.d. | n.d. | n.d. |
| 111 | <5 | <5 | <5 | <5 | <5 | <5 |
| 112 | <5 | <5 | <5 | <5 | <5 | <5 |
| 113 | <5 | <5 | <5 | <5 | <5 | <5 |
| 114 | n.d. | n.d. | n.d. | n.d. | n.d. | n.d. |
| 115 | <5 | 6.0 | 5.8 | 6.1 | <5 | n.d. |
| 116 | 5.2 | 7.1 | 6.2 | 6.7 | 5.3 | 5.4 |
| 117 | <5 | 5.4 | <5 | <5 | <5 | n.d. |
| 118 | 5.2 | 6.4 | 5.8 | 6.2 | 5.2 | 5.5 |
| 119 | 5.6 | 6.5 | 6.0 | 6.5 | 5.7 | 5.8 |
| 120 | 6.0 | 6.3 | 6.0 | 6.4 | 6.0 | 6.1 |
| 121 | <5 | <5 | <5 | <5 | <5 | <5 |
| 122 | <5 | 5.4 | 5.1 | 5.2 | <5 | <5 |
| 85 | 5.3 | 5.8 | 5.7 | 5.7 | 5.1 | 5.7 |
| 84 | 5.6 | 6.3 | 5.5 | 6.0 | 5.4 | 5.9 |
| 72 | <5 | <5 | <5 | <5 | <5 | <5 |
| 123 | <5 | <5 | <5 | <5 | <5 | <5 |
| 124 | <5 | <5 | <5 | <5 | <5 | <5 |
| 125 | <5 | 5.9 | 5.2 | 5.3 | <5 | <5 |
| 74 | n.d. | n.d. | n.d. | n.d. | n.d. | n.d. |
| 135 | n.d. | n.d. | n.d. | n.d. | n.d. | n.d. |
| 126 | 5.1 | 5.7 | 5.1 | 5.4 | 5.0 | 5.2 |
| 136 | 5.6 | 6.0 | 5.3 | 5.6 | 5.5 | 5.8 |
| 127 | <5 | 5.3 | <5 | <5 | <5 | <5 |
| 137 | 5.5 | 6.1 | 5.4 | 5.9 | 5.5 | 5.8 |
| 128 | 5.2 | 6.4 | 6.0 | 6.3 | 5.3 | 5.6 |
| 138 | <5 | 6.2 | 5.3 | 6.0 | <5 | <5 |
| 129 | 6.0 | 7.2 | 6.7 | 7.1 | 5.9 | 6.1 |
| 130 | 5.3 | 6.3 | 5.8 | 6.2 | 5.5 | 5.7 |
| 71 | 5.2 | 6.0 | 5.4 | 5.7 | 5.3 | 5.6 |
| 76 | 5.7 | 6.1 | 5.9 | 5.7 | <5 | 5.6 |
| 139 | 6.0 | 6.2 | 6.1 | 6.3 | 5.8 | 6.0 |
| 131 | 5.1 | 7.3 | 7.0 | 7.2 | 5.5 | 5.7 |
| 132 | 5.4 | 5.9 | 5.4 | 5.8 | 5.4 | 5.7 |
| 77 | 5.5 | 5.6 | 5.1 | 5.5 | 5.3 | 5.5 |
| 140 | 5.8 | 6.0 | 5.5 | 6.0 | 5.8 | 6.0 |
| 78 | 5.3 | 5.9 | 5.6 | 5.9 | 5.2 | 5.4 |
| 79 | 5.4 | 6.7 | 6.1 | 6.6 | 5.3 | 5.5 |
| 141 | 5.5 | 6.7 | 5.9 | 6.4 | 5.4 | 5.6 |
| 80 | <5 | 5.2 | <5 | <5 | <5 | <5 |
| 133 | 5.6 | 7.2 | 6.7 | 7.1 | 5.5 | 5.6 |
| 134 | 5.2 | 7.4 | 6.4 | 6.9 | 5.3 | 5.5 |
| 75 | <5 | 6.2 | <5 | 6.1 | <5 | <5 |

-continued

| Compound No. | PC-3 | A2780 | H1299 | HCT-116 | MDA/MB231 | U87MG |
|---|---|---|---|---|---|---|
| 142 | 5.0 | 6.4 | 5.7 | 6.2 | <5 | 5.5 |
| 82 | 5.5 | 5.7 | 5.7 | 5.9 | 5.1 | 5.8 |
| 143 | 5.3 | 5.9 | 5.2 | 5.8 | 5.3 | 5.5 |
| 144 | n.d. | n.d. | n.d. | n.d. | n.d. | n.d. |
| 81 | <5 | 6.7 | 6.2 | 6.6 | 5.7 | 6.3 |
| 145 | <5 | <5 | <5 | <5 | <5 | <5 |
| 146 | <5 | <5 | <5 | <5 | <5 | <5 |
| 149 | 6.0 | 6.5 | 5 | 6.4 | 6.0 | 6.3 |
| 150 | 5.3 | 7.2 | 5 | 7.2 | 5.6 | n.d. |
| 151 | <5 | <5 | <5 | <5 | <5 | <5 |
| 148 | 5.3 | 5.8 | 5.4 | 5.3 | 5 | 5.5 |
| 153 | 5.2 | 5.7 | 5.4 | 5.8 | 5.1 | 5.5 |
| 147 | <5 | 5.6 | <5 | <5 | <5 | <5 |
| 154 | 5.3 | 6.6 | 6.2 | 6.5 | 5.3 | 6.00 |
| 155 | 5.6 | 7.5 | 6.9 | 7.2 | 5.6 | 6.6 |
| 156 | 5.5 | 6.3 | 5.7 | 6.2 | 5.5 | 5.9 |
| 157 | 5.5 | 6.3 | 5.9 | 6.3 | 5.5 | 6.0 |
| 157 | 5.6 | 6.4 | 6.00 | 6.3 | 5.6 | 6.00 |
| 159 | 5.1 | 5.8 | 5.2 | 5.7 | <5 | 5.5 | n.d.: not determined

The invention claimed is:

1. A compound of formula:

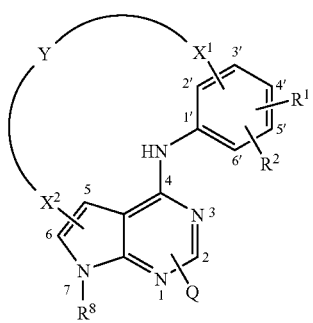

(I)

or the N-oxide, or a pharmaceutically acceptable addition salt, or a quaternary amine or a stereochemically isomeric form thereof, wherein Y represents —$C_{1-6}$alkyl-$NR^3$—CO—$C_{1-6}$alkyl-; —$C_{1-6}$alkyl-CO-$Het^1$-$C_{1-6}$alkyl-; —$C_{1-6}$alkyl-$Het^2$-CO—$NR^4$—$C_{1-6}$alkyl-; or —$C_{1-6}$alkyl-$NR^3$—CO—$C_{1-6}$alkyl-$NR^4$—CO—$C_{1-6}$alkyl-; wherein each —$C_{1-6}$alkyl-in any of —$C_{1-6}$alkyl-$NR^3$—CO—$C_{1-6}$alkyl-; —$C_{1-6}$alkyl-CO-$Het^1$-$C_{1-6}$alkyl-; —$C_{1-6}$alkyl-$Het^2$-CO—$NR^4$—$C_{1-6}$alkyl-; or —$C_{1-6}$alkyl-$NR^3$—CO—$C_{1-6}$alkyl-$NR^4$—CO—$C_{1-6}$alkyl-is optionally and independently substituted with a substituent selected from hydroxy, phenyl or $Het^3$;

$X^1$ represents a direct bond, —O—; —$NR^5$— or —$C_{1-4}$-alkyl-$NR^6$— where the —$C_{1-4}$-alkyl-moiety is directly attached to the phenyl ring;

$X^2$ represents a direct bond or —$C_{1-4}$-alkyl-$NR^7$— where the —$C_{1-4}$-alkyl-moiety is directly attached to the pyrrolopyrimidine ring system;

Q represents hydrogen, halogen, $C_{1-6}$alkyl, $C_{3-6}$cycloalkyl, $Het^5$, —$NR^9R^{10}$, $C_{1-4}$alkyl-O—, $C_{3-6}$cycloalkyl-O—, $Het^6$-O—, $Ar^1$—O—, $C_{1-4}$alkyl-S(O)$_{1-2}$—, $C_{3-6}$cycloalkyl-S(O)$_{1-2}$—, $Het^7$-S(O)$_{1-2}$—, $Ar^2$—S(O)$_{1-2}$, $C_{1-4}$alkyl-S— or $C_{3-6}$cycloalkyl-S—;

$R^1$ and $R^2$ each independently represent hydrogen; halo; hydroxy; $C_{1-6}$alkyl; $C_{3-6}$cycloalkyl; $C_{1-4}$-alkyl-O—; $C_{3-6}$cycloalkyl-O—; $Het^4$; cyano; $C_{1-6}$alkyl substituted with one or where possible two, three or more substituents selected from halo, hydroxy or $C_{1-4}$-alkyl-O—; $C_{1-4}$-alkyl-O— substituted with one or where possible two, three or more substituents selected from halo, hydroxy, $C_{1-4}$-alkyl-O—, $C_{1-4}$-alkyl-O—$C_{1-4}$-alkyl-O—, phenyl, $C_{3-6}$cycloalkyl, $C_{3-6}$cycloalkyl-O—, $C_{3-6}$cycloalkyl-NH—CO—, $Het^8$-O—, $Het^9$-CO—, $Ar^3$—O—, $Ar^4$—NH—CO—Het-S—, $Ar^6$—S—, $HetAr^1$—S—, thiazolyl-$NR^{11}$—, pyridinyl-$NR^{12}$—, pyrazinyl-NH—, $C_{1-4}$-alkyl-O—$C_{1-4}$-alkyl-$NR^{13}$—, $Ar^7$—NH—, $HetAr^2$—NH—; $C_{3-6}$cycloalkyl-O— substituted with one or where possible two, three or more substituents selected from halo, hydroxy or $C_{1-4}$-alkyl-O—; pyranyl-O—; tetrahydrofuran-O—; $Ar^8$—NH—CO—NH—; $C_{1-6}$alkyl-NH—CO—NH—; $C_{3-6}$cycloalkyl-NH—CO—NH—; $C_{3-6}$cycloalkyl-$C_{1-4}$-alkyl-NH—CO—$NR^{14}$—, $C_{1-4}$-alkyl-O—$NR^{15}$—, $Ar^5$—NH—;

$R^3$ and $R^4$ each independently represent hydrogen, $C_{1-4}$-alkyl, $C_{1-4}$-alkyl substituted with $C_{1-4}$-alkyl-O—, morpholinyl or piperazinyl; or $C_{3-6}$cycloalkyl;

$R^5$, $R^6$ and $R^7$ each independently represent hydrogen, $C_{1-4}$-alkyl, $C_{3-6}$cycloalkyl or $C_{1-4}$-alkyl substituted with $C_{1-4}$-alkyl-O—, $C_{3-6}$cycloalkyl, phenyl or pyridyl;

$R^8$ represents hydrogen, $C_{1-6}$alkyl or $C_{3-6}$cycloalkyl;

$R^9$, $R^{10}$, $R^{11}$, $R^{12}$ and $R^{13}$ each independently represent hydrogen, $C_{1-6}$alkyl, $C_{3-6}$cycloalkyl;

$R^{14}$ and $R^{15}$ each independently represent hydrogen, $C_{1-4}$-alkyl, $C_{3-6}$cycloalkyl or benzyl;

$Ar^1$, $Ar^2$, $Ar^3$, $Ar^4$, $Ar^5$, $Ar^6$, $Ar^7$ and $Ar^8$ each independently represent phenyl optionally substituted with one or where possible two or more substituents selected from halo, cyano, amino, $C_{1-4}$-alkyl, $C_{1-4}$-alkyl-O—, halo-$C_{1-4}$-alkyl, polyhalo-$C_{1-4}$-alkyl, $C_{3-6}$cycloalkyl, hydroxy-$C_{1-4}$-alkyl, $C_{1-4}$-alkyloxy$C_{1-4}$-alkyl or polyhydroxy-$C_{1-4}$-alkyl;

$Het^1$ and $Het^2$ each independently represent piperidinyl, piperazinyl, pyrrolidinyl or azetidinyl;

$Het^3$, $Het^4$, $Het^5$, $Het^6$, $Het^7$, $Het^8$ and $Het^9$ each independently represent morpholinyl, pyrrolidinyl, piperazinyl or piperidinyl wherein said $Het^3$, $Het^4$, $Het^5$, $Het^6$, $Het^7$, $Het^8$ and $Het^9$ is independently and optionally substituted with one or where possible two or more substituents selected from halo, cyano, amino, $C_{1-4}$-alkyl, halo-$C_{1-4}$-alkyl, polyhalo-$C_{1-4}$-alkyl, $C_{3-6}$cycloalkyl, phenyl, hydroxy-$C_{1-4}$-alkyl, $C_{1-4}$alkyloxy$C_{1-4}$alkyl or polyhydroxy-$C_{1-4}$-alkyl; and $HetAr^1$ and $HetAr^2$, each independently represent an aryl or heteroaryl ring system selected from the group consisting of phenyl, naphthyl, quinolinyl, benzoxazolyl, pyridyl, pyrazinyl, furanyl, thienyl, pyrimidinyl, isoxazolyl, isothiazolyl, oxazolyl, thiazolyl, pyrrolyl, pyrazolyl, indolyl, pyridazinyl, benzimidazolyl, benzothienyl and benzothiazolyl.

2. A compound of formula:

(I)

or the N-oxide, or a pharmaceutically acceptable addition salt, or a quaternary amine or a stereochemically isomeric form thereof, wherein Y represents —$C_{1-6}$alkyl-$NR^3$—CO—$C_{1-6}$alkyl-; —$C_{1-6}$alkyl-CO-$Het^1$-$C_{1-6}$alkyl-;   —$C_{1-6}$alkyl-$Het^2$-CO—$NR^4$—$C_{1-6}$alkyl-; or —$C_{1-6}$alkyl-$NR^3$—CO—$C_{1-6}$alkyl-$NR^4$—CO—$C_{1-6}$alkyl-; wherein each —$C_{1-6}$alkyl-in any of —$C_{1-6}$alkyl-$NR^3$—CO—$C_{1-6}$alkyl-; —$C_{1-6}$alkyl-CO-$Het^1$-$C_{1-6}$alkyl-;   —$C_{1-6}$alkyl-$Het^2$-CO—$NR^4$—$C_{1-6}$alkyl-; or —$C_{1-6}$alkyl-$NR^3$—CO—$C_{1-6}$alkyl-$NR^4$—CO—$C_{1-6}$alkyl-is optionally and independently substituted with a substituent selected from hydroxy, phenyl or $Het^3$;

$X^1$ represents a direct bond, —O—; —$NR^5$— or —$C_{1-4}$-alkyl-$NR^6$— where the —$C_{1-4}$-alkyl-moiety is directly attached to the phenyl ring;

$X^2$ represents a direct bond or —$C_{1-4}$-alkyl-$NR^7$— where the —$C_{1-4}$-alkyl-moiety is directly attached to the pyrrolopyrimidine ring system;

Q represents hydrogen, halogen, $C_{1-6}$alkyl, $C_{3-6}$cycloalkyl, $Het^5$, —$NR^9R^{10}$, $C_{1-4}$-alkyl-O—, $C_{3-6}$cycloalkyl-O—, $Het^6$-O—, $Ar^1$—O, $C_{1-4}$-alkyl-S(O)$_{1-2}$—, $C_{3-6}$cycloalkyl-S(O)$_{1-2}$—, $Het^7$-S(O)$_{1-2}$—, $Ar^2$—S(O)$_{1-2}$, $C_{1-4}$-alkyl-S— or $C_{3-6}$cycloalkyl-S—;

$R^1$ and $R^2$ each independently represent hydrogen; halo; $C_{1-6}$alkyl; $C_{3-6}$cycloalkyl; $C_{1-4}$-alkyl-O—; $C_{3-6}$cycloalkyl-O—; $Het^4$; cyano; $C_{1-6}$alkyl substituted with one or where possible two, three or more substituents selected from halo, hydroxy or $C_{1-4}$alkyl-O—; $C_{1-4}$-alkyl-O— substituted with one or where possible two, three or more substituents selected from halo, hydroxy, $C_{1-4}$-alkyl-O—, phenyl or $C_{3-6}$cycloalkyl; $C_{3-6}$cycloalkyl-O— substituted with one or where possible two, three or more substituents selected from halo, hydroxy or $C_{1-4}$-alkyl-O—; —NH—CO—NH—$Ar^1$; —NH—CO—NH—$C_{1-6}$alkyl; or —NH—CO—NH—$C_{3-6}$cycloalkyl;

$R^3$ and $R^4$ each independently represent hydrogen, $C_{1-4}$-alkyl, $C_{1-4}$-alkyl substituted with $C_{1-4}$-alkyl-O—, morpholinyl or piperazinyl; or $C_{3-6}$cycloalkyl;

$R^5$, $R^6$ and $R^7$ each independently represent hydrogen, $C_{1-4}$-alkyl, $C_{3-6}$cycloalkyl or $C_{1-4}$alkyl substituted with $C_{1-4}$-alkyl-O—, $C_{3-6}$cycloalkyl, phenyl or pyridyl;

$R^8$ represents hydrogen, $C_{1-6}$alkyl or $C_{3-6}$cycloalkyl;

$R^9$ and $R^{10}$ each independently represent hydrogen, $C_{1-6}$alkyl, $C_{3-6}$cycloalkyl;

$Ar^1$ and $Ar^2$ each independently represent phenyl optionally substituted with one or where possible two or more substituents selected from halo, cyano, amino, $C_{1-4}$-alkyl, $C_{1-4}$-alkyl-O—, halo-$C_{1-4}$-alkyl, polyhalo-$C_{1-4}$-alkyl, $C_{3-6}$cycloalkyl, hydroxy-$C_{1-4}$-alkyl, $C_{1-4}$-alkyloxy$C_{1-4}$-alkyl or polyhydroxy-$C_{1-4}$-alkyl;

$Het^1$ and $Het^2$ each independently represent piperidinyl, piperazinyl, pyrrolidinyl or azetidinyl;

$Het^3$ represents morpholinyl, pyrrolidinyl, piperazinyl or piperidinyl wherein said $Het^3$ is optionally substituted with one or where possible two or more substituents selected from halo, cyano, amino, $C_{1-4}$-alkyl, halo-$C_{1-4}$ - alkyl, polyhalo-$C_{1-4}$-alkyl, $C_{3-6}$cycloalkyl, hydroxy-$C_{1-4}$-alkyl, $C_{1-4}$-alkyloxy$C_{1-4}$-alkyl or polyhydroxy-$C_{1-4}$- alkyl;

$Het^4$ represents morpholinyl, pyrrolidinyl, piperazinyl or piperidinyl wherein said $Het^4$ is optionally substituted with one or where possible two or more substituents selected from halo, cyano, amino, $C_{1-4}$-alkyl, halo-$C_{1-4}$-alkyl, polyhalo-$C_{1-4}$-alkyl, $C_{3-6}$cycloalkyl, hydroxy-$C_{1-4}$-alkyl, $C_{1-4}$-alkyloxy$C_{1-4}$-alkyl or polyhydroxy-$C_{1-4}$- alkyl; and $Het^5$, $Het^6$ and $Het^7$ each independently represents morpholinyl, pyrrolidinyl, piperazinyl or piperidinyl wherein each said $Het^5$, $Het^6$ and $Het^7$ is independently and optionally substituted with one or where possible two or more substituents selected from halo, cyano, amino, $C_{1-4}$-alkyl, halo-$C_{1-4}$-alkyl, polyhalo-$C_{1-4}$-alkyl, $C_{3-6}$cycloalkyl, hydroxy-$C_{1-4}$-alkyl, $C_{1-4}$-alkyloxy$C_{1-4}$-alkyl or polyhydroxy-$C_{1-4}$-alkyl.

3. A compound as claimed in claim 1 in which:

Y represents —$C_{1-6}$alkyl-$NR^3$—CO—$C_{1-6}$alkyl-; —$C_{1-6}$alkyl-CO-$Het^1$-$C_{1-6}$alkyl-;   —$C_{1-6}$alkyl-$Het^2$-CO—$NR^4$—$C_{1-6}$alkyl-; or —$C_{1-6}$alkyl-$NR^3$—CO—$C_{1-6}$alkyl-$NR^4$—CO—$C_{1-6}$alkyl-; wherein each —$C_{1-6}$alkyl-in any of —$C_{1-6}$alkyl-$NR^3$—CO—$C_{1-6}$alkyl-; —$C_{1-6}$alkyl-CO-$Het^1$-$C_{1-6}$alkyl-;   —$C_{1-6}$alkyl-$Het^2$-CO—$NR^4$—$C_{1-6}$alkyl-; or —$C_{1-6}$alkyl-$NR^3$—CO—$C_{1-6}$alkyl-$NR^4$—CO—$C_{1-6}$alkyl-is optionally and independently substituted with a substituent selected from hydroxy or phenyl;

$X^1$ represents a direct bond, —O—; or —$C_{1-4}$-alkyl-$NR^6$— where the —$C_{1-4}$-alkyl-moiety is directly attached to the phenyl ring;

$X^2$ represents a direct bond or —$C_{1-4}$-alkyl-$NR^7$— where the —$C_{1-4}$-alkyl-moiety is directly attached to the pyrrolopyrimidine ring system;

Q represents hydrogen;

$R^1$ and $R^2$ each independently represent hydrogen; halo; $C_{1-4}$alkyl-O—; $Het^4$; $C_{1-6}$alkyl substituted with one or where possible two, three halo; $C_{1-4}$-alkyl-O— substituted with one or where possible two, three or more substituents selected from, phenyl or $C_{3-6}$cycloalkyl; —NH—CO—NH—$Ar^1$; or —NH—CO—NH—$C_{3-6}$cycloalkyl;

$R^3$ and $R^4$ each independently represent hydrogen, $C_{1-4}$-alkyl; or $C_{3-6}$cycloalkyl;

$R^5$, $R^6$ and $R^7$ each independently represent hydrogen, $C_{1-4}$-alkyl or $C_{1-4}$-alkyl substituted with $C_{1-4}$-alkyl-O—, $C_{3-6}$cycloalkyl, phenyl or pyridyl;

$R^8$ represents hydrogen;

$Ar^1$ represents phenyl optionally substituted with one or where possible two or more substituents selected from halo or $C_{1-4}$-alkyl-O—;

$Het^1$ and $Het^2$ each independently represent piperidinyl or pyrrolidinyl; and $Het^4$ represents morpholinyl, wherein said $Het^4$ is optionally substituted with one or where possible two or more substituents selected from halo, cyano, amino, $C_{1-4}$- alkyl, halo-$C_{1-4}$-alkyl, polyhalo-$C_{1-4}$-alkyl, $C_{3-6}$cycloalkyl, hydroxy-$C_{1-4}$-alkyl, $C_{1-4}$-alkyloxy$C_{1-4}$-alkyl or polyhydroxy-$C_{1-4}$-alkyl.

4. A compound as claimed in claim 1 in which:
Y represents —$C_{1-6}$alkyl-NR$^3$—CO—$C_{1-6}$alkyl; wherein each —$C_{1-6}$alkyl-in —$C_{1-6}$alkyl-NR$^3$—CO—$C_{1-6}$alkyl-is optionally and independently substituted with a substituent selected from hydroxy or phenyl;
$X^1$ represents —O—;
$X^2$ represents —$C_{1-4}$-alkyl-NR$^7$— where the —$C_{1-4}$-alkyl-moiety is directly attached to the pyrrolopyrimidine ring system;
Q represents hydrogen;
$R^1$ and $R^2$ each independently represent hydrogen or halo; $C_{1-4}$-alkyl-O—; $C_{1-6}$alkyl substituted with one or where possible two or three halo; $C_{1-4}$-alkyl-O— substituted with phenyl; —NH—CO—NH—Ar$^1$; or —NH—CO—NH—$C_{3-6}$cycloalkyl;
$R^3$ represents hydrogen, $C_{1-4}$-alkyl; or $C_{3-6}$cycloalkyl;
$R^7$ represents hydrogen, $C_{1-4}$-alkyl or $C_{1-4}$-alkyl substituted with $C_{3-6}$cycloalkyl or phenyl;
$R^8$ represents hydrogen; and
Ar$^1$ represents phenyl optionally substituted with one or more $C_{1-4}$-alkyl-O—.

5. A compound as claimed in claim 1 in which:
Y represents —$C_{1-6}$alkyl-NR$^3$—CO—$C_{1-6}$alkyl-; wherein each —$C_{1-6}$alkyl-in —$C_{1-6}$alkyl-NR$^3$—CO—$C_{1-6}$alkyl-is optionally and independently substituted with a substituent selected from hydroxy or phenyl;
$X^1$ represents —O—;
$X^2$ represents —$C_{1-4}$-alkyl-NR$^7$— where the —$C_{1-4}$-alkyl-moiety is directly attached to the pyrrolopyrimidine ring system;
Q represents hydrogen;
$R^1$ and $R^2$ each independently represent hydrogen; halo; or $C_{1-4}$-alkyl-O—;
$R^3$ represents hydrogen, $C_{1-4}$-alkyl; or $C_{3-6}$cycloalkyl;
$R^7$ represents hydrogen, $C_{1-4}$-alkyl or $C_{1-4}$-alkyl substituted with $C_{3-6}$cycloalkyl or phenyl; and
$R^8$ represents hydrogen.

6. A compound as claimed in claim 1 in which:
Y represents —$C_{1-6}$alkyl-NR$^3$—CO—$C_{1-6}$alkyl-; wherein each —$C_{1-6}$alkyl-in —$C_{1-6}$alkyl-NR$^3$—CO—$C_{1-6}$alkyl-is unsubstituted;
$X^1$ represents —O—;
$X^2$ represents —$C_{1-4}$-alkyl-NR$^7$—;
Q represents hydrogen;
$R^1$ and $R^2$ each independently represent hydrogen; halo; or $C_{1-4}$-alkyl-O—;
$R^3$ represents $C_{1-4}$alkyl;
$R^7$ represents $C_{1-4}$alkyl; and
$R^8$ represents hydrogen.

7. A compound as claimed in claim 1 selected from:
octahydro-10-methoxy-15,19-dimethyl-3H-11,7-metheno-12-oxa-2,3,5,6,15,18-hexaazacycloheptadec[1,2,3-cd]inden-14(13H)-one, 2,15,16,17,18,19-hexahydro-15,18-dimethyl-7,11-metheno-11H-12-oxa-2,3,5,6,15,19-hexaazacyclooctadec[1,2,3-cd]inden-14(13H)-one, 2,3,15,16,17,18,19,20-octahydro-10-methoxy-15-methyl-19-(phenylmethyl)-
N-(2,3,13,14,15,16,17,18,19,20-decahydro-15,19-dimethyl-14-oxo-11,7-metheno-7H-12-oxa-2,3,5,6,15,19-hexaazacyclooctadec[1,2,3-cd]inden-10-yl)-N'-(4-methoxyphenyl)-urea, 10-ethoxy-2,3,15,16,17,18,19,20-octahydro-15,19-dimethyl-7,11-metheno-11H-12-oxa-2,3,5,6,15,19-hexaazacyclooctadec[1,2,3-cd]inden-14(13H)-one,
2,3,15,16,17,18,19,20-octahydro-15,19-dimethyl-10-(phenylmethoxy)-7,11-metheno-11H-12-oxa-2,3,5,6,15,19-hexaazacyclooctadec[1,2,3-cd]inden-14(13H)-one,
2,3,15,16,17,18,19,20-octahydro-10-methoxy-19-methyl-15-(1-methylethyl)-7,11-metheno-11H-12-oxa-2,3,5,6,15,19-hexaazacyclooctadec[1,2,3-cd]inden-14(13H)-one,
2,3,15,16,17,18,19,20-octahydro-10-methoxy-15-methyl-7,11-metheno-11H-12-oxa-2,3,5,6,15,19-hexaazacyclooctadec[1,2,3-cd]inden-14(13H)-one,
N-cyclopentyl-N'-(2,3,13,14,15,16,17,18,19,20-decahydro-15,19-dimethyl-14-oxo-11,7-metheno-7H-12-oxa-2,3,5,6,15,19-hexaazacyclooctadec[1,2,3-cd]inden-10-yl)-urea,
N-(3-chlorophenyl)-N'-(2,3,13,14,15,16,17,18,19,20-decahydro-15,19-dimethyl-14-oxo-11,7-metheno-7H-12-oxa-2,3,5,6,15,19-hexaazacyclooctadec[1,2,3-cd]inden-10-yl)-urea,
10-chloro-2,3,15,16,17,18,19,20-octahydro-15,19-dimethyl-7,11-metheno-11H-12-oxa-2,3,5,6,15,19-hexaazacyclooctadec[1,2,3-cd]inden-14(13H)-one,
N-cyclohexyl-N'-(2,3,13,14,15,16,17,18,19,20-decahydro-15,19-dimethyl-14-oxo-11,7-metheno-7H-12-oxa-2,3,5,6,15,19-hexaazacyclooctadec[1,2,3-cd]inden-10-yl)-urea,
10-(cyclopropylmethoxy)-2,3,15,16,17,18,19,20-octahydro-15,19-dimethyl-7,11-metheno-11H-12-oxa-2,3,5,6,15,19-hexaazacyclooctadec[1,2,3-cd]inden-14(13H)-one,
10-(cyclopentyloxy)-2,3,15,16,17,18,19,20-octahydro-15,19-dimethyl-7,11-metheno-11H-12-oxa-2,3,5,6,15,19-hexaazacyclooctadec[1,2,3-cd]inden-14(13H)-one,
N-cyclopentyl-2-[(2,3,13,14,15,16,17,18,19,20-decahydro-15,19-dimethyl-14-oxo-7,11-metheno-11H-12-oxa-2,3,5,6,15,19-hexaazacyclooctadec[1,2,3-cd]inden-10-yl)oxy]-acetamide,
10-[2-(cyclopentyloxy)ethoxy]-2,3,15,16,17,18,19,20-octahydro-15,19-dimethyl-11,7-metheno-7H-12-oxa-2,3,5,6,15,19-hexaazacyclooctadec[1,2,3-cd]inden-14(13H)-one,
10-(2-ethoxyethoxy)-2,3,15,16,17,18,19,20-octahydro-15,19-dimethyl-11,7-metheno-7H-12-oxa-2,3,5,6,15,19-hexaazacyclooctadec[1,2,3-cd]inden-14(13H)-one,
2,3,15,16,17,18,19,20-octahydro-15,19-dimethyl-10-(1-methylethoxy)-11,7-metheno-7H-12-oxa-2,3,5,6,15,19-hexaazacyclooctadec[1,2,3-cd]inden-14(13H)-one,
2,3,15,16,17,18,19,20-octahydro-15,19-dimethyl-10-propoxy-11,7-metheno-7H-12-oxa-2,3,5,6,15,19-hexaazacyclooctadec[1,2,3-cd]inden-14(13H)-one,
N-(4-chlorophenyl)-N'-(2,3,13,14,15,16,17,18,19,20-decahydro-15,19-dimethyl-14-oxo-11,7-metheno-7H-12-oxa-2,3,5,6,15,19-hexaazacyclooctadec[1,2,3-cd]inden-10-yl)-urea,
4-[[(2,3,13,14,15,16,17,18,19,20-decahydro-15,19-dimethyl-14-oxo-11,7-metheno-7H-12-oxa-2,3,5,6,15,19-hexaazacyclooctadec[1,2,3-cd]inden-10-yl)oxy]acetyl]-morpholine,
N-cyclohexyl-2-[(2,3,13,14,15,16,17,18,19,20-decahydro-15,19-dimethyl-14-oxo-7,11-metheno-11H-12-oxa-2,3,5,6,15,19-hexaazacyclooctadec[1,2,3-cd]inden-10-yl)oxy]-acetamide, 2,3,15,16,17,18,19,20-octahydro-10-(2-methoxyethoxy)-15,19-dimethyl-7,11-metheno-11H-12-oxa-2,3,5,6,15,19-hexaazacyclooctadec[1,2,3-cd]inden-14(13H)-one, 2,3,15,16,17,18,19,20-octahydro-15,19-dimethyl-11,7-metheno-7H-12-oxa-2,3,5,6,15,19-hexaazacyclooctadec[1,2,3-cd]inden-14(13H)-one, N-cyclopropyl-2-[(2,3,13,14,15,16,17,18,19,20-decahydro-15,19-dimethyl-14-oxo-11,7-metheno-7H-12-oxa-2,3,5,6,15,19-hexaazacyclooctadec[1,2,3-cd]inden-10-yl)oxy]-acetamide, N-(cyclopropylmethyl)-N'-(2,3,13,14,15,16,17,18,19,20-decahydro-15,19-dimethyl-14-oxo-11,7-metheno-7H-12-oxa-2,3,5,6,15,19-hexaazacyclooctadec[1,2,3-cd]inden-10-yl)-urea, 2,3,15,16,17,18,19,20-octahydro-10-[2-(2-methoxyethoxy)ethoxy]-15,19-dimethyl-11,7-metheno-7H-12-oxa-2,3,5,6,15,19-hexaazacyclooctadec[1,2,3-cd]inden-14(13H)-one, 2,3,15,16,17,18,19,20-octahydro-10-(2-methoxyethoxy)-15-methyl-11,7-metheno-7H-12-oxa-2,3,5,6,15,19-hexaazacyclooctadec[1,2,3-cd]inden-14(13H)-one, 2-[(2,3,13,14,15,16,17,18,19,20-decahydro-15,19-dimethyl-14-oxo-11,7-metheno-7H-12-oxa-2,3,5,6,15,19-hexaazacyclooctadec[1,2,3-cd]inden-10-yl)oxy]-N-(4-methoxyphenyl)-acetamide, 10-(3-ethoxypropoxy)-2,3,15,16,17,18,19,20-octahydro-15,19-dimethyl-11,7-metheno-7H-12-oxa-2,3,5,6,15,19-hexaazacyclooctadec[1,2,3-cd]inden-14(13H)-one, 2-[(2,5,13,14,15,16,17,18,19,20-decahydro-15,19-dimethyl-14-oxo-11,7-metheno-7H-12-oxa-2,3,5,6,15,19-hexaazacyclooctadec[1,2,3-cd]inden-10-yl)oxy]-N-(3,4,5-trimethoxyphenyl)-acetamide, 10-(difluoromethoxy)-2,3,15,16,17,18,19,20-octahydro-15,19-dimethyl-11,7-metheno-7H-12-oxa-2,3,5,6,15,19-hexaazacyclooctadec[1,2,3-cd]inden-14(13H)-one, 10-bromo-2,3,15,16,17,18,19,20-octahydro-15,19-dimethyl-11,7-metheno-7H-12-oxa-2,3,5,6,15,19-hexaazacyclooctadec[1,2,3-cd]inden-14(13H)-one, 2,3,15,16,17,18,19,20-octahydro-15,19-dimethyl-10-[2-(1-methylethoxy)ethoxy]-7,11-metheno-11H-12-oxa-2,3,5,6,15,19-hexaazacyclooctadec[1,2,3-cd]inden-14(13H)-one, 2,3,15,16,17,18,19,20-octahydro-10-(3-methoxypropoxy)-15,19-dimethyl-7,11-metheno-11H-12-oxa-2,3,5,6,15,19-hexaazacyclooctadec[1,2,3-cd]inden-14(13H)-one, 10-[2-[ethyl(2-methoxyethyl)amino]ethoxy]-2,3,15,16,17,18,19,20-octahydro-15,19-dimethyl-11,7-metheno-7H-12-oxa-2,3,5,6,15,19-hexaazacyclooctadec[1,2,3-cd]inden-14(13H)-one, 2,3,15,16,17,18,19,20-octahydro-10-[3-(4-methoxyphenoxy)propoxy]-15,19-dimethyl-11,7-metheno-7H-12-oxa-2,3,5,6,15,19-hexaazacyclooctadec[1,2,3-cd]inden-14(13H)-one, 10-[2-[(4-chlorophenyl)amino]ethoxy]-2,3,15,16,17,18,19,20-octahydro-15,19-dimethyl-11,7-metheno-7H-12-oxa-2,3,5,6,15,19-hexaazacyclooctadec[1,2,3-cd]inden-14(13H)-one, 2,3,15,16,17,18,19,20-octahydro-10-[2-[2-methoxyethyl)(phenylmethyl)amino]ethoxy]-15,19-dimethyl-7,11-metheno-11H-12-oxa-2,3,5,6,15,19-hexaazacyclooctadec[1,2,3-cd]inden-14(13H)-one, 2,3,15,16,17,18,19,20-octahydro-10-(2-hydroxyethoxy)-15,19-dimethyl-11,7-metheno-7H-12-oxa-2,3,5,6,15,19-hexaazacyclooctadec[1,2,3-cd]inden-14(13H)-one, N-(4-chlorophenyl)-2-[(2,3,13,14,15,16,17,18,19,20-decahydro-15,19-dimethyl-14-oxo-11,7-metheno-7H-12-oxa-2,3,5,6,15,19-hexaazacyclooctadec[1,2,3-cd]inden-10-yl)oxy]-acetamide, 10-[2-(4-chlorophenoxy)ethoxy]-2,3,15,16,17,18,19,20-octahydro-15,19-dimethyl-11,7-metheno-7H-12-oxa-2,3,5,6,15,19-hexaazacyclooctadec[1,2,3-cd]inden-14(13H)-one, 10-(2-ethoxyethoxy)-2,3,15,16,17,18,19,20-octahydro-15-methyl-7,11-metheno-11H-12-oxa-2,3,5,6,15,19-hexaazacyclooctadec[1,2,3-cd]inden-14(13H)-one, 10-[3-[(4-chlorophenyl)amino]propoxy]-2,3,15,16,17,18,19,20-octahydro-15,19-dimethyl-7,11-metheno-11H-12-oxa-2,3,5,6,15,19-hexaazacyclooctadec[1,2,3-cd]inden-14(13H)-one, 2,3,15,16,17,18,19,20-octahydro-15,19-dimethyl-10-(1-pyrrolidinyl)-11,7-metheno-7H-12-oxa-2,3,5,6,15,19-hexaazacyclooctadec[1,2,3-cd]inden-14(13H)-one, 2,3,15,16,17,18,19,20-octahydro-15,19-dimethyl-10-[2-[(1-methyl-1H-imidazol-2-yl)thio]ethoxy]-7,11-metheno-11H-12-oxa-2,3,5,6,15,19-hexaazacyclooctadec[1,2,3-cd]inden-14(13H)-one, and 10-(2-ethoxyethoxy)-2,3,15,16,17,18,19,20-octahydro-2,15,19-trimethyl-7,11-metheno-11H-12-oxa-2,3,5,6,15,19-hexaazacyclooctadec[1,2,3-cd]inden-14(13H)-one, and the N-oxide forms, the pharmaceutically acceptable addition salts, the quaternary amines and the stereochemically isomeric forms of such compounds.

8. A compound as claimed in claim 1 selected from:

2,6,13,14,15,16,18,19,20,21,22,23-dodecahydro-10-methoxy-18,22-dimethyl-17H-7,11-metheno-12-oxa-2,3,5,6,18,22-hexaazacycloheneicos[1,2,3-cd]inden-17-one, 2,6,14,15,17,18,19,20,21,22-decahydro-10-methoxy-17,21-dimethyl-7,11-metheno-11H-12-oxa-2,3,5,6,17,21-hexaazacycloeicos[1,2,3-cd]inden-16(13H)-one, 10-chloro-2,6,14,15,16,17,19,20,21,22,23,24-dodecahydro-19,23-dimethyl-7,11-metheno-11H-12-oxa-2,3,5,6,19,23-hexaazacyclodocos[1,2,3-cd]inden-18(13H)-one, 2,6,15,16,17,18,19,20-octahydro-10-methoxy-15,19-dimethyl-7,11-metheno-11H-12-oxa-2,3,5,6,15,19-hexaazacyclooctadec[1,2,3-cd]inden-14(13H)-one, 2,14,15,17,18,19,20,21-octahydro-10-methoxy-17,20-dimethyl-6H-11,7-metheno-12-oxa-2,3,5,6,17,20-hexaazacyclononadec[1,2,3-cd]inden-16(13H)-one, 19-ethyl-2,6,15,16,17,18,19,20-octahydro-10-methoxy-15-methyl-7,11-metheno-11H-12-oxa-2,3,5,6,15,19-hexaazacyclooctadec[1,2,3-cd]inden-14(13H)-one, 2,6,15,16,17,18,19,20-octahydro-15,19-dimethyl-9-(trifluoromethyl)-11,7-metheno-7H-12-oxa-2,3,5,6,15,19-hexaazacyclooctadec[1,2,3-cd]inden-14(13H)-one, 2,15,16,17,18,19-hexahydro-15,18-dimethyl-6H-11,7-metheno-12-oxa-2,3,5,6,15,18-hexaazacycloheptadec[1,2,3-cd]inden-14(13H)-one, 2,15,16,17,18,19-hexahydro-10-methoxy-15,18-dimethyl-6H-7,11-metheno-12-oxa-2,3,5,6,15,18-hexaazacycloheptadec[1,2,3-cd]inden-14(13H)-one, 10-chloro-2,6,15,16,17,18,19,20-octahydro-15,19-dimethyl-7,11-metheno-11H-12-oxa-2,3,5,6,15,19-hexaazacyclooctadec[1,2,3-cd]inden-14(13H)-one, 10-ethoxy-2,6,15,16,17,18,19,20-octahydro-15,19-dimethyl-7,11-metheno-11H-12-oxa-2,3,5,6,15,19-hexaazacyclooctadec[1,2,3-cd]inden-14(13H)-one, 2,6,15,16,17,18,19,20-octahydro-15,19-dimethyl-10-(phenylmethoxy)-7,11-metheno-11H-12-oxa-2,3,5,6,15,19-hexaazacyclooctadec[1,2,3-cd]inden-14(13H)-one, 2,6,15,16,17,18,19,20-octahydro-10-methoxy-15-methyl-7,11-metheno-11H-12-oxa-2,3,5,6,15,19-hexaazacyclooctadec[1,2,3-cd]inden-14(13H)-one, 2,6,15,16,17,18,19,20-octahydro-10-methoxy-15-methyl-19-(phenylmethyl)-7,11-metheno-11H-12-oxa-2,3,5,6,15,19-hexaazacyclooctadec[1,2,3-cd]inden-14(13H)-one, 19-(cyclopropylmethyl)-2,6,15,16,17,18,19,20-octahydro-10-methoxy-15-methyl-7,11-metheno-11H-12-oxa-2,3,5,6,15,19-hexaazacyclooctadec[1,2,3-cd]inden-14(13H)-one, N-(2,6,13,14,15,16,17,18,19,20-decahydro-15,19-dimethyl-14-oxo-11,7-metheno-7H-12-oxa-2,3,5,6,15,19-hexaazacyclooctadec[1,2,3-cd]inden-10-yl)-N'-(4-methoxyphenyl)-urea, 2,6,15,16,17,18,19,20-octahydro-10-methoxy-19-methyl-15-(1-methylethyl)-7,11-metheno-11H-12-oxa-2,3,5,6,15,19-hexaazacyclooctadec[1,2,3-cd]inden-14(13H)-one, 15-cyclohexyl-2,6,15,16,17,18,19,20-octahydro-10-methoxy-19-methyl-7,11-metheno-11H-12-oxa-2,3,5,6,15,19-hexaazacyclooctadec[1,2,3-cd]inden-14(13H)-one, N-cyclohexyl-N'-(2,6,13,14,15,16,17,18,19,20-decahydro-15,19-dimethyl-14-oxo-11,7-metheno-7H-12-oxa-2,3,5,6,15,19-hexaazacyclooctadec[1,2,3-cd]inden-10-yl)-urea, N-(3-chlorophenyl)-N'-(2,6,13,14,15,16,17,18,19,20-decahydro-15,19-dimethyl-14-oxo-11,7-metheno-7H-12-oxa-2,3,5,6,15,19-hexaazacyclooctadec[1,2,3-cd]inden-10-yl)-urea, N-cyclopentyl-N'-(2,6,13,14,15,16,17,18,19,20-decahydro-15,19-dimethyl-14-oxo-11,7-metheno-7H-12-oxa-2,3,5,6,15,19-hexaazacyclooctadec[1,2,3-cd]inden-10-yl)-urea and 10-(cyclopropylmethoxy)-2,6,15,16,17,18,19,20-octahydro-15,19-dimethyl-7,11-metheno-11H-12-oxa-2,3,5,6,15,19-hexaazacyclooctadec[1,2,3-cd]inden-14(13H)-one, and the N-oxide forms, the pharmaceutically acceptable addition salts, the quaternary amines and the stereochemically isomeric forms of such compounds.

9. A pharmaceutical composition comprising a compound as claimed in claim 1 and a pharmaceutically acceptable carrier or diluent.

10. A method of treating a cell proliferative disease in a warm-blooded animal in which the cell proliferative disease is selected from lung cancer, breast cancer, liver cancer, ovarian cancer, prostate cancer, pancreatic cancer, colorectal cancer, colon, rectal or stomach cancer, papillary carcinomas, papillary thyroid cancer, squamous cell cancers of the head and neck, oesophageal cancers, oropharyngeal cancer, and acute myelogenous leukaemia (AML), which comprises administering to the said animal an effective amount of a compound as claimed in claim 1.

* * * * *